US012735717B2

(12) United States Patent
Christensen et al.

(10) Patent No.: US 12,735,717 B2
(45) Date of Patent: Sep. 15, 2026

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: CERES, INC., Thousand Oaks, CA (US)

(72) Inventors: Cory Christensen, Zionsville, IN (US); Bonnie Hund, Pueblo, CO (US)

(73) Assignee: CERES, INC., Thousand Oaks, CA (US)

( * ) Notice: Subject to any disclaimer, the term of this patent is extended or adjusted under 35 U.S.C. 154(b) by 308 days.

(21) Appl. No.: 18/666,709

(22) Filed: May 16, 2024

(65) Prior Publication Data

US 2024/0318195 A1 Sep. 26, 2024

Related U.S. Application Data

(60) Division of application No. 18/049,501, filed on Oct. 25, 2022, now Pat. No. 12,024,713, which is a division of application No. 16/829,740, filed on Mar. 25, 2020, now Pat. No. 11,542,521, which is a division of application No. 14/273,492, filed on May 8, 2014, now Pat. No. 10,689,661, which is a continuation of application No. 12/863,773, filed as application No. PCT/US2009/031609 on Jan. 21, 2009, now abandoned.

(60) Provisional application No. 61/022,786, filed on Jan. 22, 2008.

(51) Int. Cl.
*A01H 5/00* (2018.01)
*A01H 1/00* (2006.01)
*C12N 15/82* (2006.01)

(52) U.S. Cl.
CPC ........... *C12N 15/8273* (2013.01); *A01H 1/00* (2013.01); *A01H 1/12* (2021.01); *A01H 1/1225* (2021.01); *A01H 5/00* (2013.01)

(58) Field of Classification Search
None
See application file for complete search history.

(56) References Cited

U.S. PATENT DOCUMENTS

| | | | |
|---|---|---|---|
| 11,542,521 | B2 | 1/2023 | Christensen |
| 11,761,013 | B2 | 9/2023 | Christensen et al. |
| 12,024,713 | B2 | 7/2024 | Christensen et al. |
| 2006/0057724 | A1 | 3/2006 | Alexandrov et al. |
| 2006/0150283 | A1 | 7/2006 | Alexandrov |
| 2007/0039067 | A1 | 2/2007 | Feldmann |
| 2007/0214517 | A1 | 9/2007 | Alexandrov et al. |
| 2010/0192237 | A1 | 7/2010 | Ren et al. |
| 2013/0042367 | A1 | 2/2013 | Nadzan et al. |
| 2020/0239904 | A1 | 7/2020 | Christensen et al. |

FOREIGN PATENT DOCUMENTS

| | | |
|---|---|---|
| EP | 1033405 | 9/2000 |
| WO | 2007044988 | 4/2007 |

OTHER PUBLICATIONS

Dissmeyer et al, "T-Loop Phosphorylation of Arabidopsis CDKA;1 is required for its function and can be partially substituted by an aspartate residue,". The Plant Cell vol. 19:972-985; Mar. 2007.
Friedberg, "Automated protein function prediction- the genomic challenge," Briefings in Bioinformatics; vol. 7. No. 3. 225-242; Jan. 2006.
Guerois et al., "Predicting changes in the stability of proteins and protein complexes: A study of more than 1000 mutations", J. Mol. Biol.; 320; 369-287; 2002.
Kumar et al., "Predicting the effects of coding non-synonymous variants on protein function using the SIFT algorithm," www.nature.com/natureprotocols; Nature Protocols; vol. 4 No. 8; 2009.
Ng et al., Predicting the effects of amino acid substitutions on protein function, Annual Review Genom. Hum. Genet; 7:61-80; 2006.
Reva et al., Predicting the functional impact of protein mutations: application to cancergenomics,: Nucleic Acids Research; vol. 39. No 17.; e118; Jul. 2011.
Rivera et al., Genomic evidence for two functionally distinct gene classes, Proc. Natl. Acad. Sci.; vol. 95; 6239-6244; May 1998.
Sandhya et al., "CUSP: an algorithm to distinguish structurally conserved and unconserved regions in protein domain alignments and its application in the study of large length variations," BMC Structural Biol: 8:28; May 2008.
Churchman, et al., SIAMESE, A plant-specific cell cycle regulator, controls endoreplication onset in *Arabidopsis thaliana*, The Plant Cell, 2006, 18(11): 3145-3157.
Gong, et al., "RNA helicase-like protein as an early regulator of transcription factor for plant chilling and freezing tolerance", PNAS, vol. 99, No. 17, Aug. 20, 2002, pp. 11507-11512.
Low, et al., Conformational switch upon phosphorylation: human CDK inhibitor p19INK4d between the native and partially folded state, ACS Chemical Biology, 2008, 4(1): 53-63.
NCBI GenBank Acession AAM6430, 5, Jan. 27, 2006.
Salaita, et al., "Identification and characterization of mutants capable of seed germination at 10° C from activation-tagged lines of *Arabidopsis thaliana*", Journal of Experimental Botany, vol. 56, No. 418, Aug. 2005, pp. 2059-2069.
Yi, et al., "The pepper transcription factor CaPF1 confers pathogen and freezing tolerance in *Arabidopsis*", Plant Physiology, vol. 136, No. 1, Sep. 3, 2004, pp. 2862-2874.

(Continued)

*Primary Examiner* — Phuong T Bui
(74) *Attorney, Agent, or Firm* — Dentons US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased cold tolerance levels and plant products produced from plants having increased cold tolerance levels.

9 Claims, 18 Drawing Sheets

Specification includes a Sequence Listing.

(56) References Cited

OTHER PUBLICATIONS

Churchman et al. SIAMESE, a plant-specific cell cycle regulator, controls endoreplication onset in *Arabidopsis thaliana*. The Plant Cell. 2006. 18:3145-3157.
Peres et al. Novel plant-specific cyclin-dependent kinase inhibitors induced by biotic and abiotic stresses. Journal of Biological Chemistry. 2007. 282(35):25588-25596.
GenBank Accession No. Q9LZ60. SIAMESE-related 3. published Feb. 17, 2016. pp. -3.
GenBank Accession No. BX833341. published Feb. 6, 2004. pp 1-2.
Feldmann et al., Published Applications Database, US Publication No. 20070039067, Feb. 15, 2007, SEQ ID No. 56571.
USPTO: Non-Final Office Action regarding U.S. Appl. No. 16/829,755, dated Feb. 7, 2023.

FIGURE 2 (Continued)

| | | | | | | |
|---|---|---|---|---|---|---|
| SEQ-ID-NO-20 | FSDFDRLI-- | DFEFPNSF-- | -----NHHQNN | AGGDSLVPVQ | TKTEPLPLTN | 217 |
| SEQ-ID-NO-32 | FSEMDPFL-- | DFDYSNSF-- | ------QNNNS | AGNDSVVPVQ | KPSLAPPLIN | 215 |
| SEQ-ID-NO-28 | FCEMDPFL-- | DFEYQNSMDG | RYKQSHGGGG | AGADSVVPVQ | NKPAPLPVID | 228 |
| SEQ-ID-NO-22 | FSDMDPFI-- | DFEYQDSF-- | ---QQHDG-- | -AMDSVVPVQ | TKPATISMIN | 209 |
| SEQ-ID-NO-40 | FSELDPYL-- | SVELPRFQ-- | ---------- | -HADSVVPNG | AGAAV----- | 184 |
| SEQ-ID-NO-44 | YADSDPYL-- | DLDFARSM-- | ---------- | ---DDIKAIG | VQNGPP---- | 191 |
| SEQ-ID-NO-58 | FPDSDAYL-- | DLDFVRSM-- | ---------- | ---DGIKAIG | VPVAPS---- | 191 |
| SEQ-ID-NO-71 | FADSDKYLGV | DLDFARSM-- | ---------- | ---DGIKAIG | VPVAPP---- | 205 |

| | | | | | | |
|---|---|---|---|---|---|---|
| SEQ-ID-NO-20 | NDH------C | FDIDFCRS-- | -KLSAF-TYP | SQSVSHSVST | SSIEYGVVPD | 257 |
| SEQ-ID-NO-32 | NHHHHQSETC | FDVDFCRS-- | -KLSSF-NYP | SNSLSQSVSS | SSLDVGVVPD | 261 |
| SEQ-ID-NO-28 | HKN------C | FDIDFCRS-- | -KLTSFSSYP | SQSLSHSVSS | SSLDVGVVPD | 269 |
| SEQ-ID-NO-22 | NEN------C | FDVDFCRS-- | -KFPTF-SYQ | TKSQSHSVSS | SSLEVGVVPD | 249 |
| SEQ-ID-NO-40 | ---------- | -ELDFTCGIG | VKHSSYSSYT | ATSLAHSCSS | S--EVGVVPE | 221 |
| SEQ-ID-NO-44 | ---------- | -ELDITGG-- | -KL----FYS | DHSMNHSVSS | S--EAAVVPD | 221 |
| SEQ-ID-NO-58 | ---------- | -ELDVAGG-- | -AL----FYP | EHSMNHSMST | S--EVAVVPD | 221 |
| SEQ-ID-NO-71 | ---------- | -ELDIAAG-- | -AF----YYP | EHSMNHSVSS | S--EVAVVPD | 235 |

| | | | | | | |
|---|---|---|---|---|---|---|
| SEQ-ID-NO-20 | GNTNNS---- | ---------- | -----VNRST | ITSSTTGG-- | ---------- | 276 |
| SEQ-ID-NO-32 | GNTVSDMSYS | FGR------N | SSDSSGIVVV | SGNSVGQG-- | ---------- | 293 |
| SEQ-ID-NO-28 | GNSMSDISYP | FGRSMNTYTD | ------PSMPI | SGSTTNQA-- | ---------- | 302 |
| SEQ-ID-NO-22 | GNSVSDISYT | LGRTMG---D | PSA--PIWAA | TANNQAPP-- | ---------- | 282 |
| SEQ-ID-NO-40 | AFGGSGSGGG | SFELDFTRPK | PQAYMPYTGT | PQSHSVPSAD | VEVVPERGDL | 271 |
| SEQ-ID-NO-44 | AAAGGG---- | ---------- | ---------- | ------APM-- | ---------- | 230 |
| SEQ-ID-NO-58 | ALSAGG---- | ---------- | ---------- | -APAPAPS-- | ---------- | 234 |
| SEQ-ID-NO-71 | VLAGG----- | ---------- | ---------- | ------VPA-- | ---------- | 243 |

| | | | | | | |
|---|---|---|---|---|---|---|
| SEQ-ID-NO-20 | -----DHQASS | MDREARVLRY | REKRKNRKFE | KTIRYASRKA | YAESRPRIKG | 322 |
| SEQ-ID-NO-32 | -----ATQLCG | MDREARVLRY | REKRKNRKFE | KTIRYASRKA | YAETRPRIKG | 339 |
| SEQ-ID-NO-28 | -----AAQLAG | IDREARVLRY | REKRKNRKFE | KTIRYASRKA | YAETRPRIKG | 348 |
| SEQ-ID-NO-22 | -----QAQVGG | MDREARVLRY | REKRKNRKFE | KTIRYASRKA | YAESRPRIKG | 328 |
| SEQ-ID-NO-40 | AAVRPVPLMG | ESREARLMRY | REKRKNRRFE | KTIRYASRKA | YAETRPRIKG | 321 |
| SEQ-ID-NO-44 | -----PVVSRG | REREARLMRY | REKRKSRRFE | KTIRYASRKA | YAETRPRIKG | 276 |
| SEQ-ID-NO-58 | --VAVVASKG | KEREARLMRY | REKRKNRRFQ | KTIRYASRKA | YAETRPRIKG | 282 |
| SEQ-ID-NO-71 | --V-PVASRG | KEREARLMRY | REKRKNRRFD | KTIRYASRKA | YAETRPRIKG | 290 |

FIGURE 3

| | | | | | | |
|---|---|---|---|---|---|---|
| SEQ ID NO 79 | ---------- | ---------MA | SATIRN---- | ---------- | ---------- | 8 |
| SEQ ID NO 88 | ---------- | ---------MD | YSSTKELP-- | PAGAWWSR-- | ---------ET | 20 |
| SEQ ID NO 81 | -MGKKGKAAA | RERREERRRE | VTLLRAVPYE | PHQRWWDGLA | PA-------RA | 43 |
| SEQ ID NO 82 | -MGKKGKEAA | RERREQRRRE | VTLLRAVPYE | PHQRWWDGLA | PPPPPPPGRA | 49 |
| SEQ ID NO 83 | -MGKKGKEAA | RERREQRRRE | VTLLRAVPYE | PHQRWWDGLA | PP-PPPPGRA | 48 |
| SEQ ID NO 90 | -MTNK--EKA | RERREKRMQE | ISLLRTIPYS | DHHRWWSC-- | ---------EN | 37 |
| SEQ ID NO 86 | -MGHK--E-- | KSRKDKRLQE | ISLLRTIPYS | DHQRWWSK-- | ---------ET | 35 |
| SEQ ID NO 74 | MSGKK--ERN | KERREKRLQE | ISLLRTIPYS | DHQRWWSQ-- | ---------ET | 38 |
| SEQ ID NO 85 | -MGSK--EPA | KEKREKRLQE | ISLLRTIPYS | DHQRWWSS-- | ---------ET | 37 |

| | | | | | | |
|---|---|---|---|---|---|---|
| SEQ ID NO 79 | -AVVTGANKG | IGFGICKQLV | SNGITVVLTA | RDEKRGLEAV | EKL-----KEF | 53 |
| SEQ ID NO 88 | VAVVTGANRG | IGHALAARLA | EHGLTVVLTA | RDGARGEAAA | APL-----RAR | 66 |
| SEQ ID NO 81 | VAVVTGASRG | IGYEISRQLA | RHGLHVVLAS | RDAARGRDAA | EGI----LREE | 90 |
| SEQ ID NO 82 | VAVVTGANRG | IGYEAARQLA | THGLHVVLTS | RDAARGRDAA | EQIRAAAGKP | 99 |
| SEQ ID NO 83 | VAVVTGANRG | IGYEAARQLA | THGLHVVLTS | RDAARGRDAT | EQIRAAAGKP | 98 |
| SEQ ID NO 90 | VAVVTGSNRG | IGFEIARQLA | VHGLTVVLTA | RNVNAGLEAV | KSLR--HQEE | 85 |
| SEQ ID NO 86 | IAVVTGGNRG | IGFEISRQLA | DHGVTVVLTS | RDASVGVESI | KVL-----QEG | 81 |
| SEQ ID NO 74 | VAVVTGANRG | IGFEIARQLA | GHGLTVILTS | RNISVGIEAT | KAL-----QEG | 84 |
| SEQ ID NO 85 | VAVVTGGNRG | IGFEIARQLA | DHGLSVILTS | RESSAGLEAA | NVL-----REL | 83 |

| | | | | | | |
|---|---|---|---|---|---|---|
| SEQ ID NO 79 | GVSDQVVFHQ | LDVTDPKSIE | SLANFIKTQF | GKLDILVNNA | GIHGAYVDRD | 103 |
| SEQ ID NO 88 | GLA--VAFRR | LDVSDAASVA | EFAAWLRDAV | GGLDILVNNA | A--------- | 105 |
| SEQ ID NO 81 | GTS--AEWRQ | LDVADAASVE | AFAAWTARTH | GGIHVLINNA | G--------- | 129 |
| SEQ ID NO 82 | GVS--VEWRQ | LDVTDAASVE | GFATWVERTH | GGVHVLVNNA | G--------- | 138 |
| SEQ ID NO 83 | GVS--VEWRQ | LDVTDAASVE | GFATWVERTH | GGVHVLVNNA | G--------- | 137 |
| SEQ ID NO 90 | GLK--VYFHQ | LDVTDSSSIR | EFGCWLKQTF | GGLDILVNNA | G--------- | 124 |
| SEQ ID NO 86 | GLD--VHCHQ | LDILDSSSVN | EFAEWLKEEY | GGLDILVNNA | G--------- | 120 |
| SEQ ID NO 74 | GFS--YDVHQ | LDILDGESIS | AFVEWIKQKY | GGIDILVNNA | G--------- | 123 |
| SEQ ID NO 85 | GLS--VDFHQ | LDVLDSLSIK | TFAEWIQQTY | GGLDVLVNNA | G--------- | 122 |

| | | | | | | |
|---|---|---|---|---|---|---|
| SEQ ID NO 79 | ALAAAGEKVA | NVDWRKISTE | NFEAAEACIR | TNYYGVKLMC | EALIPLLELS | 153 |
| SEQ ID NO 88 | ---------- | -VSFNELDTN | SVEHAETVLR | TNFYGAKMLT | EALLPLFRQS | 144 |
| SEQ ID NO 81 | ---------- | -VNFNRGADN | SVEFAEQVIE | TNYFGTRRMI | EAMLPLLKPS | 168 |
| SEQ ID NO 82 | ---------- | -VNFNRGADN | SVEFAEQVTE | TNYFGTKRMI | EAMMPLMITS | 177 |
| SEQ ID NO 83 | ---------- | -VNFNRGADN | SVEFAEQVIE | TNYFGTKRMI | EAMMPLMITS | 176 |
| SEQ ID NO 90 | ---------- | -VNYNLGSDN | TVEFAETVIS | TNYQGTKNMT | KAMIPLMRPS | 163 |
| SEQ ID NO 86 | ---------- | -VNSNMGSDN | SVENARKCIE | TNYYGTKRMI | EAMIPLMKPS | 159 |
| SEQ ID NO 74 | ---------- | -VNYNLGFDN | SVEFARQVVD | TNYYGTKNMI | KAMIPVMKPS | 162 |
| SEQ ID NO 85 | ---------- | -VNYNMGSDN | SVENAKNVVD | TNYYGIKNVT | EALIPLMRPS | 161 |

FIGURE 3 (Continued)

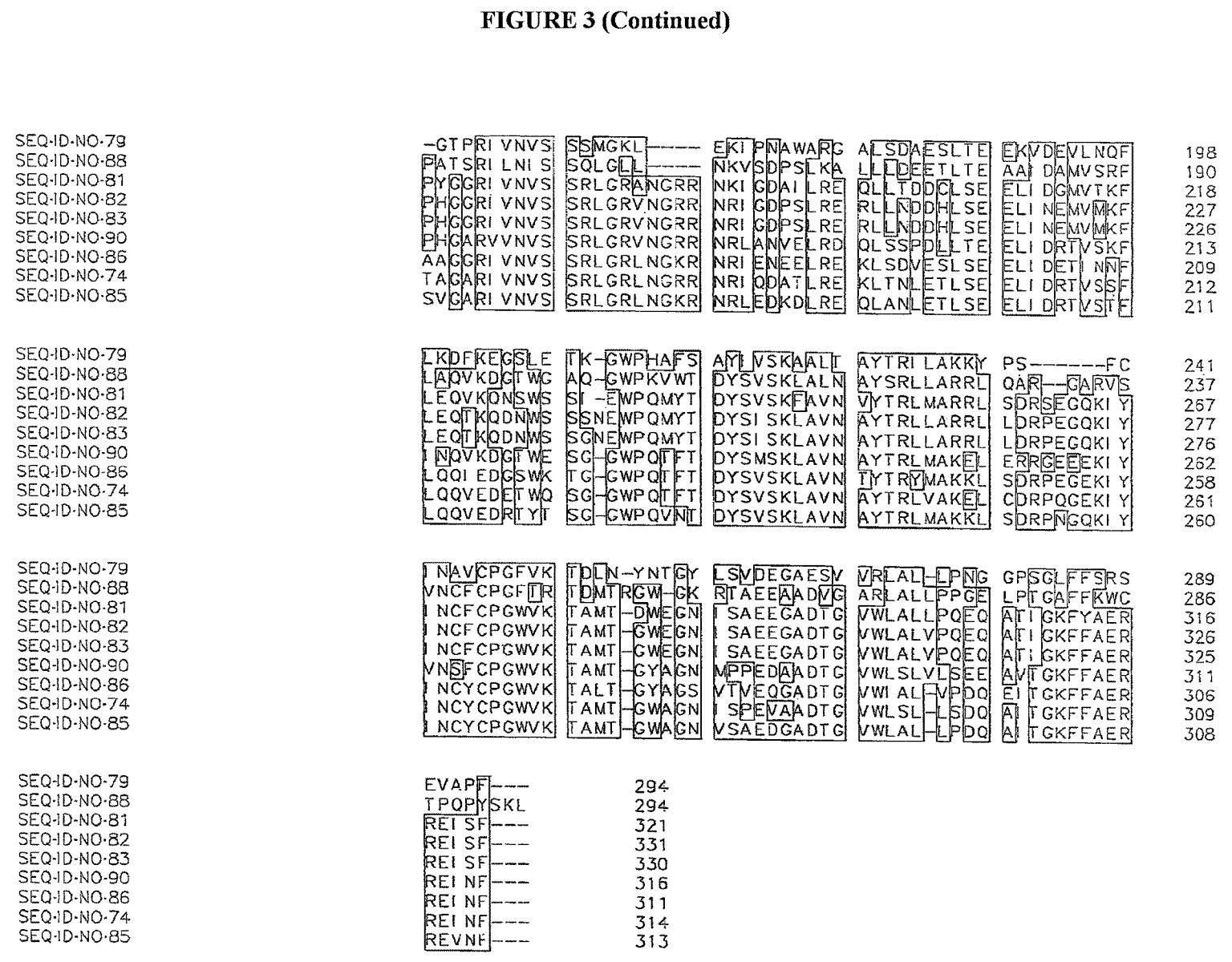

```
SEQ-ID-NO-79  -GTPRI VNVS SSMGKL---- EKI PNAWARG ALSDAESLTE EKVDEVLNQF  198
SEQ-ID-NO-88  PATSRI LNI S SQLGLL---- NKVSDPSLKA LLLDEETLTE AAI DAMVSRF  190
SEQ-ID-NO-81  PYGGRI VNVS SRLGRANGRR NKI GDAI LRE QLLTDDCLSE ELI DGMVTKF  218
SEQ-ID-NO-82  PHGGRI VNVS SRLGRVNGRR NRI GDPSLRE RLLNDDHLSE ELI NEMVMKF  227
SEQ-ID-NO-83  PHGGRI VNVS SRLGRVNGRR NRI GDPSLRE RLLNDDHLSE ELI NEMVMKF  226
SEQ-ID-NO-90  PHGARVVNVS SRLGRVNGRR NRLANVELRD QLSSPDLLTE ELI DRTVSKF  213
SEQ-ID-NO-86  AAGGRI VNVS SRLGRLNGKR NRI ENEELRE KLSDVESLSE ELI DETI NNF  209
SEQ-ID-NO-74  TAGARI VNVS SRLGRLNGRR NRI QDATLRE KLTNLETLSE ELI DRTVSSF  212
SEQ-ID-NO-85  SVGARI VNVS SRLGRLNGKR NRLEDKDLRE QLANLETLSE ELI DRTVSTF  211

SEQ-ID-NO-79  LKDFKEGSLE TK-GWPHAFS AYLVSKAALT AYTRI LAKKY PS------FC  241
SEQ-ID-NO-88  LAQVKDGTWG AQ-GWPKVWT DYSVSKLALN AYSRLLARRL QAR--GARVS  237
SEQ-ID-NO-81  LEQVKQNSWS SI -EWPQMYT DYSVSKFAVN VYTRLMARRL SDRSEGQKI Y  267
SEQ-ID-NO-82  LEQTKQDNWS SSNEWPQMYT DYSI SKLAVN AYTRLLARRL LDRPEGQKI Y  277
SEQ-ID-NO-83  LEQTKQDNWS SGNEWPQMYT DYSI SKLAVN AYTRLLARRL LDRPEGQKI Y  276
SEQ-ID-NO-90  I NQVKDGTWE SG-GWPQTFT DYSMSKLAVN AYTRLMAKEL ERRGEEEKI Y  262
SEQ-ID-NO-86  LQQI EDGSWK TG-GWPQTFT DYSVSKLAVN TYTRYMAKKL SDRPEGEKI Y  258
SEQ-ID-NO-74  LQQVEDETWQ SG-GWPQTFT DYSVSKLAVN AYTRLVAKEL CDRPQGEKI Y  261
SEQ-ID-NO-85  LQQVEDRTYT SG-GWPQVNT DYSVSKLAVN AYTRLMAKKL SDRPNGQKI Y  260

SEQ-ID-NO-79  I NAVCPGFVK TDLN-YNTGY LSVDEGAESV VRLAL-LPNG GPSGLFFSRS  289
SEQ-ID-NO-88  VNCFCPGFTR TDMTRGW-GK RTAEEAADVG ARLALLPPGE LPTGAFFKWC  286
SEQ-ID-NO-81  I NCFCPGWVK TAMT-DWEGN I SAEEGADTG VWLALLPQEQ ATI GKFYAER  316
SEQ-ID-NO-82  I NCFCPGWVK TAMT-GWEGN I SAEEGADTG VWLALVPQEQ ATI GKFFAER  326
SEQ-ID-NO-83  I NCFCPGWVK TAMT-GWEGN I SAEEGADTG VWLALVPQEQ ATI GKFFAER  325
SEQ-ID-NO-90  VNSFCPGWVK TAMT-GYAGN MPPEDAADTG VWLSLVLSEE AVTGKFFAER  311
SEQ-ID-NO-86  I NCYCPGWVK TALT-GYAGS VTVEQGADTG VWI AL-VPDQ EI TGKFFAER  306
SEQ-ID-NO-74  I NCYCPGWVK TAMT-GWAGN I SPEVAADTG VWLSL-LSDQ AI TGKFFAER  309
SEQ-ID-NO-85  I NCYCPGWVK TAMT-GWAGN VSAEDGADTG VWLAL-LPDQ AI TGKFFAER  308

SEQ-ID-NO-79  EVAPF---  294
SEQ-ID-NO-88  TPQPYSKL  294
SEQ-ID-NO-81  REI SF---  321
SEQ-ID-NO-82  REI SF---  331
SEQ-ID-NO-83  REI SF---  330
SEQ-ID-NO-90  REI NF---  316
SEQ-ID-NO-86  REI NF---  311
SEQ-ID-NO-74  REI NF---  314
SEQ-ID-NO-85  REVNF---  313
```

FIGURE 5 (Continued)

```
SEQ-ID-NO-143  TDQQLDQHLP LFNLPHKILC KVVNVELRAE TDSDEVYAQI MLQPQTEQ--  101
SEQ-ID-NO-123  MNQVADSQMR LYDLPSKLLC RVLNVELKAE QDTDEVYAQV MLMPEPEQ--  105
SEQ-ID-NO-121  TNQVGEQRMQ LYNLPWKILC EVMNVELKAE PDTDEVYAQL TLLPELKRQE  123
SEQ-ID-NO-120  TNQVGEQRMQ LYNLPWKILC EVMNVELKAE PDTDEVYAQL TLLPELKQQE  124
SEQ-ID-NO-124  TNQVGEQRMQ LYNLPWKILC EVMNVELKAE PDTDEVYAQL TLLPESKQQE  107
SEQ-ID-NO-125  TNQVGEQRMQ LYNLPWKILC EVMNVELKAE PDTDEVYAQL TLLPESKQQE  123
SEQ-ID-NO-126  TNQVGEQRMQ LYNLPWKILC EVMNVELKAE PDTDEVYAQL TLLPESKQQE  124
SEQ-ID-NO-114  TNQVADQQMP LYNLLPKILC RVVNVQLKAE PDTDEVFAQV TLLPEHNQ--  136
SEQ-ID-NO-116  TNQVADQQMP LYNLLPKILC RVVNVQLKAE PDTDEVFAQV TLLPEHNQ--  136
SEQ-ID-NO-119  TNQAAEQQMP LYDLPSKILC RVINVDLKAE ADTDEVYAQI TLLPEPVQ--  137
SEQ-ID-NO-118  TNQAAEQQMP LYDLPSKLLC RVINVDLKAE ADTDEVYAQI TLLPEANQ--  142
SEQ-ID-NO-112  TNQAAEQQMP LYDLPSKLLC RVINVDLKAE ADTDEVYAQI TLLPEANQ--  142
SEQ-ID-NO-117  TNQAAEQQMP LYDLPSKLLC RVINVDLKAE ADTDEVYAQI TLLPEANQ--  142
SEQ-ID-NO-134  ---AGGGCDV PVALPPHVAC RVVDVELCAD PATDEVYARL AMVAEGEIFE  98
SEQ-ID-NO-136  CDGGGMSAPA PPRVPPHVVC RVVDVELRAD AATDEVYARL ALVAMDTMFG  101
SEQ-ID-NO-131  ---APDFSAA IYGLPPHVFC RILDVKLHAE TTTDEVYAQV SLLPESEDIE  130
SEQ-ID-NO-132  ---APDFSAA IYGLPPHVFC RILDVKLHAE TTTDEVYAQV SLLPESEDIE  130
SEQ-ID-NO-128  ---APDFSAA IYGLPPHVFC RILDVKLHAE TTTDEVYAQV SLLPESEDIE  130
SEQ-ID-NO-127  LGDAPAAAAA AAAVPPHVFC RVVDVTLLAD AATDEVYAQL SLVPEKEEVA  117
SEQ-ID-NO-138  LGDAPAAAAA AAAVPPHVFC RVVDVTLLAD AATDEVYAQL SLVPEKEEVA  117

SEQ-ID-NO-143  -------SEP TSPDPEPPEP ERCNI-HSFC KTLTASDTST H-GLSVLRRH  142
SEQ-ID-NO-123  ---NEMAVEK TTPTS-GPVQ ARPPV-RSFC KTLTASDTST HGGFSVLRRH  150
SEQ-ID-NO-121  ---DNGSTEE EVPSAPAAGH VRPRV-HSFC KTLTASDTST HGGFSVLRRH  169
SEQ-ID-NO-120  ---DNGSTEE EVPSAPAAGH VRPRV-HSFC KTLTASDTST HGGFSVLRRH  170
SEQ-ID-NO-124  ---DNGSTEE EVPSAPAAGH VRPRV-HSFC KTLTASDTST HGGFSVLRRH  153
SEQ-ID-NO-125  ---DNGSTEE EVPSAPAAGH VRPRV-HSFC KTLTASDTST HGGFSVLRRH  169
SEQ-ID-NO-126  ---DNGSTEE EVPSAPAAGH VRPRV-HSFC KTLTASDTST HGGFSVLRRH  170
SEQ-ID-NO-114  ---DESVLEK EPPPPPPP-- -RFHV-HSFC KTLTASDTST HGGFSVLRRH  179
SEQ-ID-NO-116  ---DESVLEK EPPPPPPP-- -RFHV-HSFC KTLTASDTST HGGFSVLRRH  179
SEQ-ID-NO-119  ---DENSIEK EAPPPPPP-- -RFQV-HSFC KTLTASDTST HGGFSVLRRH  180
SEQ-ID-NO-118  ---DENAIEK EAPLPPPP-- -RFQV-HSFC KTLTASDTST HGGFSVLRRH  185
SEQ-ID-NO-112  ---DENAIEK EAPLPPPP-- -RFQV-HSFC KTLTASDTST HGGFSVLRRH  185
SEQ-ID-NO-117  ---DENAIEK EAPLPPPP-- -RFQV-HSFC KTLTASDTST HGGFSVLRRH  185
SEQ-ID-NO-134  KNMGGGRFEG EDDMEDGDGE RKSRMLHMFC KTLTASDTST HGGFSVPRRA  148
SEQ-ID-NO-136  RNINDGETEE KNGEEEDGDG EKKHASHMFC KTLTASDTST HGGFSVPRRA  151
SEQ-ID-NO-131  RKVREGI DV DGGEEDYEVL KRSNTPHMFC KTLTASDTST HGGFSVPRRA  180
SEQ-ID-NO-132  RKVREGI DV DGGEEDYEVL KRSNTPHMFC KTLTASDTST HGGFSVPRRA  180
SEQ-ID-NO-128  RKVREGI DV DGGEEDYEVL KRSNTPHMFC KTLTASDTST HGGFSVPRRA  180
SEQ-ID-NO-127  RRADDG---- EGEDGDGMKQ RFARMPHMFC KTLTASDTST HGGFSVPRRA  163
SEQ-ID-NO-138  RRADDG---- EGEDGDGMKQ RFARMPHMFC KTLTASDTST HGGFSVPRRA  163
```

FIGURE 5 (Continued)

| | | | | | | |
|---|---|---|---|---|---|---|
| SEQ·ID·NO·143 | AEECLPQLDM | TQNPPWQELV | AKDLHGNEWH | FRHIFRGQPR | RHLLTTGWSV | 192 |
| SEQ·ID·NO·123 | ADECLPPLDM | TQSPPTQELV | AKDLHSMDWR | FRHIFRGQPR | RHLLQSGWSV | 200 |
| SEQ·ID·NO·121 | ADECLPPLDM | SRQPPTQELV | AKDLHGVEWR | FRHIFRGQPR | RHLLQSGWSV | 219 |
| SEQ·ID·NO·120 | ADECLPPLDM | SRQPPTQELV | AKDLHGVEWR | FRHIFRGQPR | RHLLQSGWSV | 220 |
| SEQ·ID·NO·124 | ADECLPPLDM | SRQPPTQELV | AKDLHGVEWR | FRHIFRGQPR | RHLLQSGWSV | 203 |
| SEQ·ID·NO·125 | ADECLPPLDM | SRQPPTQELV | AKDLHGVEWR | FRHIFRGQPR | RHLLQSGWSV | 219 |
| SEQ·ID·NO·126 | ADECLPPLDM | SRQPPTQELV | AKDLHGVEWR | FRHIFRGQPR | RHLLQSGWSV | 220 |
| SEQ·ID·NO·114 | ADECLPPLDM | SRQPPTQELV | AKDLHGNEWR | FRHIFRGQPR | RHLLQSGWSV | 229 |
| SEQ·ID·NO·116 | ADECLPPLDM | SRQPPTQELV | AKDLHGNEWR | FRHIFRGQPR | RHLLQSGWSV | 229 |
| SEQ·ID·NO·119 | ADECLPPLDM | SRQPPTQELV | AKDLHASEWR | FRHIFRGQPR | RHLLQSGWSV | 230 |
| SEQ·ID·NO·118 | ADECLPPLDM | SRQPPTQELV | AKDLHANEWR | FRHIFRGQPR | RHLLQSGWSV | 235 |
| SEQ·ID·NO·112 | ADECLPPLDM | SRQPPTQELV | AKDLHANEWR | FRHIFRGQPR | RHLLQSGWSV | 235 |
| SEQ·ID·NO·117 | ADECLPPLDM | SRQPPTQELV | AKDLHANEWR | FRHIFRGQPR | RHLLQSGWSV | 235 |
| SEQ·ID·NO·134 | AEDCFPPLDY | QQIRPSQELV | AKDLHGAKWR | FRHIYRGQPR | RHLLTTGWSS | 198 |
| SEQ·ID·NO·136 | AEDCFPPLDY | EQLRPSQELI | AKDLHGMKWR | FRHIYRGQPR | RHLLTTGWSS | 201 |
| SEQ·ID·NO·131 | AEDCFPPLDY | SQPRPSQELL | ARDLHGLEWR | FRHIYRGQPR | RHLLTTGWSA | 230 |
| SEQ·ID·NO·132 | AEDCFPPLDY | SQPRPSQELL | ARDLHGLEWR | FRHIYRGQPR | RHLLTTGWSA | 230 |
| SEQ·ID·NO·128 | AEDCFPPLDY | SQPRPSQELL | ARDLHGLEWR | FRHIYRGQPR | RHLLTTGWSA | 230 |
| SEQ·ID·NO·127 | AEDCFPPLDY | SQQRPSQELV | AKDLHSTEWR | FRHIYRGQPR | RHLLTTGWSA | 213 |
| SEQ·ID·NO·138 | AEDCFPPLDY | SQQRPSQELV | AKDLHGTEWR | FRHIYRGQPR | RHLLTTGWSA | 213 |

| | | | | | | |
|---|---|---|---|---|---|---|
| SEQ·ID·NO·143 | FVSSKRLVAG | DAFIFLRGEN | GELRVGVRRL | MRQLNNMPSS | VISSHSMHLG | 242 |
| SEQ·ID·NO·123 | FVSSKRLVAG | DAFIFLRGEN | GELRVGVRRA | MRQLSNVPSS | VISSQSMHLG | 250 |
| SEQ·ID·NO·121 | FVSAKRLVAG | DAFIFLRGEN | GELRVGVRRA | MRQQTNVPSS | VISSHSMHLG | 269 |
| SEQ·ID·NO·120 | FVSAKRLVAG | DAFIFLRGEN | GELRVGVRRA | MRQQTNVPSS | VISSHSMHLG | 270 |
| SEQ·ID·NO·124 | FVSAKRLVAG | DAFIFLRGEN | GELRVGVRRA | MRQQTNVPSS | VISSHSMHLG | 253 |
| SEQ·ID·NO·125 | FVSAKRLVAG | DAFIFLRGEN | GELRVGVRRA | MRQQTNVPSS | VISSHSMHLG | 269 |
| SEQ·ID·NO·126 | FVSAKRLVAG | DAFIFLRGEN | GELRVGVRRA | MRQQTNVPSS | VISSHSMHLG | 270 |
| SEQ·ID·NO·114 | FVSSKRLVAG | DAFIFLRGEN | GELRVGVRRA | MRQQGNVPSS | VISSHSMHLG | 279 |
| SEQ·ID·NO·116 | FVSSKRLVAG | DAFIFLRGEN | GELRVGVRRA | MRQQGNVPSS | VISSHSMHLG | 279 |
| SEQ·ID·NO·119 | FVSSKRLVAG | DAFIFLRGEN | GELRVGVRRA | MRQQGNVPSS | VISSHSMHLG | 280 |
| SEQ·ID·NO·118 | FVSSKRLVAG | DAFIFLRGEN | GELRVGVRRA | MRQQGNVPSS | VISSHSMHLG | 285 |
| SEQ·ID·NO·112 | FVSSKRLVAG | DAFIFLRGEN | GELRVGVRRA | MRQQGNVPSS | VISSHSMHLG | 285 |
| SEQ·ID·NO·117 | FVSSKRLVAG | DAFIFLRGEN | GELRVGVRRA | MRQQGNVPSS | VISSHSMHLG | 285 |
| SEQ·ID·NO·134 | FVNKKKLVSG | DAVLFLRGDD | GELRLGVRRA | IQLKNEALLK | AFNSNSSKIH | 248 |
| SEQ·ID·NO·136 | FINKKKLVSG | DAVLFLRGND | GELRLGVRRA | VQLKNEALLE | AVNCTDSKLL | 251 |
| SEQ·ID·NO·131 | FVNKKKLVSG | DAVLFLRGDD | GKLRLGVRRA | SQIEGTAALS | AQYNQNMNHN | 280 |
| SEQ·ID·NO·132 | FVNKKKLVSG | DAVLFLRGDD | GKLRLGVRRA | SQIEGTAALS | AQYNQNMNHN | 280 |
| SEQ·ID·NO·128 | FVNKKKLVSG | DAVLFLRGDD | GKLRLGVRRA | SQIEGTAALS | AQYNQNMNHN | 280 |
| SEQ·ID·NO·127 | FVNKKKLVSG | DAVLFLRGDD | GELRLGVRRA | AQLKNGSAFP | ALYNQCSNLG | 263 |
| SEQ·ID·NO·138 | FVNKKKLVSG | DAVLFLRGDD | GELRLGVRRA | AQLKNGSAFP | ALYNQCSNLG | 263 |

FIGURE 5 (Continued)

```
SEQ-ID-NO-143  VLATASHAIS TGTLFSVFYK PRTSRSEFVV SVNKYLEAKN HKMSVGMRFK  292
SEQ-ID-NO-123  VLATAWHAIN TKSMFTVYYK PRTSPSEFII PYDQYMESVK NNYSVGMRFR  300
SEQ-ID-NO-121  VLATAWHAVN TGTMFTVYYK PRTSPAEFVV PYDRYMESLK RNYSIGMRFK  319
SEQ-ID-NO-120  VLATAWHAVN TGTMFTVYYK PRTSPAEFVV PYDRYMESLK RNYSIGMRFK  320
SEQ-ID-NO-124  VLATAWHAVN TGTMFTVYYK PRTSPAEFVV PYDRYMESLK QNYSIGMRFK  303
SEQ-ID-NO-125  VLATAWHAVN TGTMFTVYYK PRTSPAEFVV PYDRYMESLK QNYSIGMRFK  319
SEQ-ID-NO-126  VLATAWHAVN TGTMFTVYYK PRTSPAEFVV PYDRYMESLK QNYSIGMRFK  320
SEQ-ID-NO-114  VLATAWHAVS TGTLFTVYYK PRTSPAEFIV PFDQYMESVK NNYSIGMRFK  329
SEQ-ID-NO-116  VLATAWHAVS TGTLFTVYYK PRTSPAEFIV PFDQYMESVK NNYSIGMRFK  329
SEQ-ID-NO-119  VLATAWHAIS TGTMFTVYYK PRTSPSEFIV PFDQYIESVK INYSIGMRFK  330
SEQ-ID-NO-118  VLATAWHAIS TGTMFTVYYK PRTSPSEFIV PFDQYMESVK NNYSIGMRFK  335
SEQ-ID-NO-112  VLATAWHAIS TGTMFTVYYK PRTSPSEFIV PFDQYMESVK NNYSIGMRFK  335
SEQ-ID-NO-117  VLATAWHAIS TGTMFTVYYK PRTSPSEFIV PFDQYMESVK NNYSIGMRFK  335
SEQ-ID-NO-134  TLSAVANSLK HRSVFHICYN PRAAASEFIV PYWKFLKSLN RPFCIGMRFK  298
SEQ-ID-NO-136  MLSAVANSLD NRSIFHICFN PRVGASEFIV PYCKFLKSLN YPFSVGTRFK  301
SEQ-ID-NO-131  NFSEVAHAIS THSVFSISYN PKASWSNFII PAPKFLKVVD YPFCIGMRFK  330
SEQ-ID-NO-132  NFSEVAHAIS THSVFSISYN PKASWSNFII PAPKFLKVVD YPFCIGMRFK  330
SEQ-ID-NO-128  NFSEVAHAIS THSVFSISYN PKASWSNFII PAPKFLKVVD YPFCIGMRFK  330
SEQ-ID-NO-127  TLANVAHAVA TESVFNIYYN PRLSQSEFIV PYWKFMKSLS QPFSVGLRFK  313
SEQ-ID-NO-138  TLANVAHAVA TESVFNIYYN PRLSQSEFIV PYWKFMKSLS QPFSVGLRFK  313

SEQ-ID-NO-143  MRFEGDESPE RRFSGLIIGM GCMPANSTSP WANSEWRSLK VQWDEPSAIL  342
SEQ-ID-NO-123  MRFEGEEAPE QRFTGTIIGS E---NLDPV- WPESSWRSLK VRWDEPSTIP  346
SEQ-ID-NO-121  MRFESEEAPE QRFTGTIVGM G---DSDPAG WPESKWRSLK VRWDEASSIP  366
SEQ-ID-NO-120  MRFEGEEAPE QRFTGTIVGM G---DSDPAG WPESKWRSLK VRWDEASSIP  367
SEQ-ID-NO-124  MRFEGEEAPE QRFTGTIVGM G---DSDPAG WPESKWRSLK VRWDEASSIP  350
SEQ-ID-NO-125  MRFEGEEAPE QRFTGTIVGM G---DSDPAG WPESKWRSLK VRWDEASSIP  366
SEQ-ID-NO-126  MRFEGEEAPE QRFTGTIVGM G---DSDPAG WPESKWRSLK VRWDEASSIP  367
SEQ-ID-NO-114  MRFEGEEAPE QRFTGTIVGI E---DADPGR WKNSKWRCLK VRWDETSTMP  376
SEQ-ID-NO-116  MRFEGEEAPE QRFTGTIVGI E---DADPGR WKNSKWRCLK VRWDETSTMP  376
SEQ-ID-NO-119  MRFEGEEAPE QRFTGTIVGI E---DSDPTR WAKSKWRSLK VRWDETTSIP  377
SEQ-ID-NO-118  MRFEGEEAPE QRFTGTIVGI E---ESDPTR WPKSKWRSLK VRWDETSSIP  382
SEQ-ID-NO-112  MRFEGEEAPE QRFTGTIVGI E---ESDPTR WPKSKWRSLK VRWDETSSIP  382
SEQ-ID-NO-117  MRFEGEEAPE QRFTGTIVGI E---ESDPTR WPKSKWRSLK VRWDETSSIP  382
SEQ-ID-NO-134  IQYGSEDVNE RR-SGMITGI N---EVDPIR WTGSKWKSLQ VRWEDGTDCN  344
SEQ-ID-NO-136  VGCENEDANE RSF-GLIIGI S---EVDPIH WPGSKWKSLL IKWDGATKYS  347
SEQ-ID-NO-131  ARVESEDASE RRSPGIISGI S---DLDPIR WPGSKWRCLL VRWDDIVANG  377
SEQ-ID-NO-132  ARVESEDASE RRSPGIISGI S---DLDPIR WPGSKWRCLL VRWDDIVANG  377
SEQ-ID-NO-128  ARVESEDASE RRSPGIISGI S---DLDPIR WPGSKWRCLL VRWDDIVANG  377
SEQ-ID-NO-127  MRYESEDATE RRYTGIITGS G---DTDPM- WHGSKWKCLL VRWDDDAEFR  359
SEQ-ID-NO-138  MRYESEDASE RRYTGIITGS G---DTDPM- WHGSKWKCLL VRWDDDAEFR  359
```

FIGURE 5 (Continue)

| | | | | | | |
|---|---|---|---|---|---|---|
| SEQ·ID·NO·143 | RPDRVSPWEV | EPLN-RTNPQ | PPQPPLRNKR | ARP-------P | ASPSIAPELA | 385 |
| SEQ·ID·NO·123 | RPDRVSPWKI | EPAS-SPP-V | NPLPLSRVKR | PRPNAPPASP | ESPILTKEAA | 394 |
| SEQ·ID·NO·121 | RPERVSPWQI | EPAV-SPPPV | NPLPVPRTKR | LRPNATALPA | DSSAIAKEAA | 415 |
| SEQ·ID·NO·120 | RPERVSPWQI | EPAV-SPPPV | NPLPVPRTKR | LRPNATALPA | DSSAIAKEAA | 416 |
| SEQ·ID·NO·124 | RPERVSPWQI | EPAV-SPPPV | NPLPVPRTKR | LRPNATALPA | DSSAIAKEAA | 399 |
| SEQ·ID·NO·125 | RPERVSPWQI | EPAV-SPPPV | NPLPVPRTKR | LRPNATALPA | DSSAIAKEAA | 415 |
| SEQ·ID·NO·126 | RPERVSPWQI | EPAV-SPPPV | NPLPVPRTKR | LRPNATALPA | DSSAIAKEAA | 416 |
| SEQ·ID·NO·114 | RPERVSPWKI | EPAL-APPAL | NPLPLPRPKR | PRANMVPSSP | DSSVLTRD-- | 423 |
| SEQ·ID·NO·116 | RPERVSPWKI | EPAL-APPAL | NPLPLPRPKR | PRANMVPSSP | DSSVLTRDGS | 425 |
| SEQ·ID·NO·119 | RPDRVSPWKI | EPAL-SPPAL | SPVPMPRPKR | PRSNLASSTP | DSSMRIREGS | 426 |
| SEQ·ID·NO·118 | RPDRVSPWKV | EPAL-APPAL | SPVPMPRPKR | PRSNIAPSSP | DSSMLTREGT | 431 |
| SEQ·ID·NO·112 | RPDRVSPWKV | EPAL-APPAL | SPVPMPRPKR | PRSNIAPSSP | DSSMLTREGT | 431 |
| SEQ·ID·NO·117 | RPDRVSPWKV | EPAL-APPAL | SPVPMPRPKR | PRSNIAPSSP | DSSMLTREGT | 431 |
| SEQ·ID·NO·134 | SQNRLSPWDI | EIVGGSVSIA | QSLSASSSKR | TKLC-PQGNV | DVPTLYGNVR | 393 |
| SEQ·ID·NO·136 | HQNRVSPWDI | EGVGSSVSVT | HRLSSSVSKR | TKLCFPPSDL | DTPILDGNGR | 397 |
| SEQ·ID·NO·131 | HQQRVSPWEI | EPSG-SISNS | GSFVTTGPKR | SRIGFSSGKP | DIPVSEGIRA | 426 |
| SEQ·ID·NO·132 | HQQRVSPWEI | EPSG-SISNS | GSFVTTGPKR | SRIGISSGKP | DIPVSEGIRA | 426 |
| SEQ·ID·NO·128 | HQQRVSPWEI | EPSG-SISNS | GSFVTTGPKR | SRIGFSSGKP | DIPVSEGIRA | 426 |
| SEQ·ID·NO·127 | RPNRVSPWEI | ELT--SSVSG | SHLSTPHSKR | LKPCLPHVNP | EYMVPRGGGC | 407 |
| SEQ·ID·NO·138 | RPNRVSPWEI | ELT--SSVSG | SHLSTPHSKR | LKPCLPHVNP | EYMVPRGGGC | 407 |

| | | | | | | |
|---|---|---|---|---|---|---|
| SEQ·ID·NO·143 | PVFG------ | ---------- | ---------- | ---------- | ------FW--- | 391 |
| SEQ·ID·NO·123 | TKVDTDPAQA | QRSQNSTVLQ | GQEQMTLRSN | LTESNDSDVT | AHKPMMW--- | 441 |
| SEQ·ID·NO·121 | TKVVVESEP- | --NGTQRTFQ | TQENATPKSG | FGNSSELE-S | AQKSIMR--- | 458 |
| SEQ·ID·NO·120 | TKVVVESEP- | --NGTQRTFQ | TQENATPKSG | FGNSSELE-S | AQKSIMR--- | 459 |
| SEQ·ID·NO·124 | TKVVVESEP- | --NGTQRTFQ | TQENATPKSG | FGNSSELE-S | AQKSIMR--- | 442 |
| SEQ·ID·NO·125 | TKVVVESEP- | --NGTQRTFQ | TQENATPKSG | FGNSSELE-S | AQKSIMR--- | 458 |
| SEQ·ID·NO·126 | TKVVVESEP- | --NGTQRTFQ | TQENATPKSG | FGNSSELE-S | AQKSIMR--- | 459 |
| SEQ·ID·NO·114 | -----DPPSA | --SGFSRVLQ | GQEFSTLRGT | FAESNESN-A | AEKSVMW--- | 462 |
| SEQ·ID·NO·116 | FKVTADPPSA | --SGFSRVLQ | GQEFSTLRGT | FAESNESN-A | AEKSVMW--- | 469 |
| SEQ·ID·NO·119 | SKANMDPLPA | --SGLSRVLQ | GQEYPTLRTK | HVESVECD-A | PENSVVW--- | 470 |
| SEQ·ID·NO·118 | TKANMDPLPA | --SGLSRVLQ | GQEYSTLRTK | HTESVECD-A | PENSVVW--- | 475 |
| SEQ·ID·NO·112 | TKANMDPLPA | --SGLSRVLQ | GQEYSTLRTK | HTESVECD-A | PENSVVW--- | 475 |
| SEQ·ID·NO·117 | TKANMDPLPA | --SGLSRVLQ | GQEYSTLRTK | HTESVECD-A | PENSVVW--- | 475 |
| SEQ·ID·NO·134 | PDSVGA---- | --DKLPRVLQ | GQELMGSGTH | ---------- | ---------- | 417 |
| SEQ·ID·NO·136 | PDSVET---- | --ERFHRVLQ | GQELVHSSIH | GAAC------ | ---------- | 425 |
| SEQ·ID·NO·131 | TDFEES---- | --LRFQRVLQ | GQEIF----- | ---------- | ---------- | 445 |
| SEQ·ID·NO·132 | TDFEES---- | --LRFQRVLQ | GQEIF----- | ---------- | ---------- | 445 |
| SEQ·ID·NO·128 | TDFEES---- | --LRFQRVLQ | GQEIF----- | ---------- | ---------- | 445 |
| SEQ·ID·NO·127 | PDFAES---- | --AQFHKVLQ | GQELLGFKSH | GGTAAATSQP | CEARHLQYID | 451 |
| SEQ·ID·NO·138 | PDFAES---- | --AQFHKVLQ | GQELLGFKSH | GGTAAATSQP | CEARHLQYID | 451 |

FIGURE 5 (Continued)

```
SEQ-ID-NO-143  V---SPVVTV ASVGHDPPPP ALSVDAESDQ LSQPSHANKA TDAPAASSDR  533
SEQ-ID-NO-123  APNNHLSSPM AATHEPMLQT PSSLNQLQPV QTD----CIP EVSVSTAGTA  665
SEQ-ID-NO-121  KSEPSKSPSS V-VYDGTPQT PGATEWRRPD VTEVEKCSDP SKAMKPLDTP  696
SEQ-ID-NO-120  KSEPLKSPSS V-VYDGTPQT PGATEWRRPD VTEVEKCSDP SKAMKPLDTP  697
SEQ-ID-NO-124  KSEPLKSPSS V-VYDGTPQT PGATEWRRPD VTEVEKCSDP SKAMKPLDTP  680
SEQ-ID-NO-125  KSEPLKSPSS V-VYDGTPQT PGATEWRRPD VTEVEKCSDP SKAMKPLDTP  696
SEQ-ID-NO-126  KSEPLKSPSS V-VYDGTPQT PGATEWRRPD VTEVEKCSDP SKAMKPLDTP  697
SEQ-ID-NO-114  ----PVAPEA AGTTITMNEP LSHIQPVSHQ LTFESDQKSE QSKGSKMTDE  691
SEQ-ID-NO-116  ----PVAPEA AGTTITMNEP LSHIQPVSHQ LTFESDQKSE QSKGSKMTDE  698
SEQ-ID-NO-119  ----NGTDTT LSQRNNLNDP AGPTQMASPK VQDL---SDQ SKGSKSTNDH  697
SEQ-ID-NO-118  ----NGTDST MSQRNNLNDA AGLTQIASPK VQDL---SDQ SKGSKSTNDH  708
SEQ-ID-NO-112  ----NGTDST MSQRNNLNDA AGLTQIASPK VQDL---SDQ SKGSKSTNDH  708
SEQ-ID-NO-117  ----NGTDST MSQRNNLNDA AGLTQIASPK VQDL---SDQ SKGSKSTNDH  708
SEQ-ID-NO-134  SPSSAAVPPQ LWLASKSNEE AANGSQLNP- -------FGI RKVPGDGAAK  583
SEQ-ID-NO-136  E---VHSPSS VLMFNQTMVP HAELDGATN- ---REEVHGS RYLSSNAIGR  577
SEQ-ID-NO-131  V---SSSPSS V-LFTNSNSP NGRLEDHHG- ---------- ----------  545
SEQ-ID-NO-132  V---SSSPSS V-LLTNSNSP NGRLEDHHG- ---------- ----------  545
SEQ-ID-NO-128  V---SSSPSS V-LLTNSNSP NGRLEDHHG- ---------- ----------  545
SEQ-ID-NO-127  ----SSSPPS VLMFQQANSK MPRLEFGHGQ LDKHENDRRV RFGPSEGIER  602
SEQ-ID-NO-138  ----SSSPPS VLMFQQANSK MPRLEFGHGQ LDKHENDRRV RFGPSEGIER  602

SEQ-ID-NO-143  SPNETESRQ- ---------- ---------- -ARSCTKVLM QGVAVGRAVD  561
SEQ-ID-NO-123  TENEKSGQQ- -----AQQSS KDVQSKTQVA STRSCTKVHK QGVALGRSVD  709
SEQ-ID-NO-121  QPDSVPEKPS SQQASSQQAS RNMSCKSQGV STRSCKKVHK QGIALGRSVD  746
SEQ-ID-NO-120  QPDSVPEKPS -----SQQAS RNMSCKSQGV STRSCKKVHK QGIALGRSVD  742
SEQ-ID-NO-124  QPDSVPEKPS -----SQQAS RNMSCKSQGV STRSCKKVHK QGIALGRSVD  725
SEQ-ID-NO-125  QPDSVPEKPS -----SQQAS RNMSCKSQGV STRSCKKVHK QGIALGRSVD  741
SEQ-ID-NO-126  QPDSVPEKPS -----SQQAS RNMSCKSQGV STRSCKKVHK QGIALGRSVD  742
SEQ-ID-NO-114  NENEKPFQA- -----GHLRT KDNHCKAQNG STRSCTKVHK QGIALGRSVD  735
SEQ-ID-NO-116  NENEKPFQA- -----GHLRT KDNHCKAQNG STRSCTKVHK QGIALGRSVD  742
SEQ-ID-NO-119  REQGRPFPV- -----SKPHP KDVQTKTN-- SCRSCTKVQK QGIALGRSVD  739
SEQ-ID-NO-118  REQGRPFQT- -----NNPHP KDAQTKTN-- SSRSCTKVHK QGIALGRSVD  750
SEQ-ID-NO-112  REQGRPFQT- -----NNPHP KDAQTKTN-- SSRSCTKVHK QGIALGRSVD  750
SEQ-ID-NO-117  REQGRPFQT- -----NNPHP KDAQTKTN-- SSRSCTKVHK QGIALGRSVD  750
SEQ-ID-NO-134  LGDGAAKLG- ---------- ---------- ---------- ---SDGRKVA  599
SEQ-ID-NO-136  EAEPWPSME- -----QQRAS VNGSEPLDTT EASAPARNAE SG-SVGRGVG  620
SEQ-ID-NO-131  ---------- ---------- ---------- ---------- ---------G  546
SEQ-ID-NO-132  ---------- ---------- ---------- ---------- ---------G  546
SEQ-ID-NO-128  ---------- ---------- ---------- ---------- ---------G  546
SEQ-ID-NO-127  REQRIPLQP- -----YPTSG EVIDGQVTVE KSHSPGRHGK DG-PDNKAVG  645
SEQ-ID-NO-138  REQRIPLQP- -----YPTSG EVIDGQVTVE KSHSPGRHGK DG-PDNKAVG  645
```

FIGURE 5 (Continued)

| | | |
|---|---|---|
| SEQ-ID-NO-143 | ESDVPQSDSD NSAPVSADKD | 676 |
| SEQ-ID-NO-123 | ---------- ---------- | 808 |
| SEQ-ID-NO-121 | CLSTSSLNSE NC-------- | 857 |
| SEQ-ID-NO-120 | CLSTSSLNSE NC-------- | 853 |
| SEQ-ID-NO-124 | CLSTSSLNSE NC-------- | 836 |
| SEQ-ID-NO-125 | CLSTSSLNSE NC-------- | 852 |
| SEQ-ID-NO-126 | CLSTSSLNSE NC-------- | 853 |
| SEQ-ID-NO-114 | LPLPSACSPM NC-------- | 845 |
| SEQ-ID-NO-116 | LPLPSACSPM NC-------- | 852 |
| SEQ-ID-NO-119 | ASNPSLSSAG NS-------- | 848 |
| SEQ-ID-NO-118 | ASNPSLSSAG NS-------- | 859 |
| SEQ-ID-NO-112 | ASNPSLSSAG NS-------- | 859 |
| SEQ-ID-NO-117 | ASNPSLSSAG NS-------- | 859 |
| SEQ-ID-NO-134 | LCAAPLGI-- ---------- | 660 |
| SEQ-ID-NO-136 | LCAAPLGI-- ---------- | 680 |
| SEQ-ID-NO-131 | MRDMLLDIAL ---------- | 608 |
| SEQ-ID-NO-132 | MRDMLLDIAL ---------- | 608 |
| SEQ-ID-NO-128 | MRDMLLDIAL ---------- | 608 |
| SEQ-ID-NO-127 | LDVGVGALIM ---------- | 719 |
| SEQ-ID-NO-138 | LDVGVGALIM ---------- | 719 |

SEQUENCE LISTING

```
Sequence total quantity: 260
SEQ ID NO: 1            moltype = DNA  length = 621
FEATURE                 Location/Qualifiers
misc_feature            1..621
                        note = Ceres SEEDLINE ID no.ME00327
misc_feature            1..621
                        note = Inplanta Sequence
misc_feature            1..621
                        note = Encodes the peptide sequence at SEQ ID NO. 2
source                  1..621
```

```
                       mol_type = other DNA
                       organism = Arabidopsis thaliana
SEQUENCE: 1
actagttagt tgaaatggag gctttcaagc ttcggatcca acgcacgtaa tctctctctc  60
tctctctctt ctctcttttt tctttctctc ttctttctct ctgtaaaact tgtctaatgg  120
cagagatctg ctgcgtcaaa gagatccaag aagaagacgt ggagaagatc cgattaccga  180
cccgacccga attagacatt cctgtctctg atcacgaaga tccaacggtc aacgaagaag  240
aagggtgcaa gactccaaca tcgtccgatc acaagattcc ggaggtgaag tatacgttat  300
gtccaccggc tccgagaaaa ccaaaaccga atcgatcttc cggtacgaaa cggaaattaa  360
cgccggttaa tgttcttaac cgcataccga ttgatctgag ccgtgagatc gagatgttct  420
tcgaggattt ggaccgtagg atcaagaagt cacggaaaca ataagaagat tattgcctta  480
attggtaatg atcgttcatt tctaattcat gactgtgtgg tggtaatttg atcctttgaa  540
tttttcttca ttttttttt cttttttttt tcgttttctg tataattaat tagctaataa  600
caataagaaa atttatgtac c                                          621

SEQ ID NO: 2           moltype = AA  length = 115
FEATURE                Location/Qualifiers
REGION                 1..115
                       note = misc_feature - Ceres SEEDLINE ID no.ME00327
REGION                 1..115
                       note = misc_feature - Bit score of 224.6 for hmm based on
                        sequences of FIGURE 1.
source                 1..115
                       mol_type = protein
                       organism = Arabidopsis thaliana
SEQUENCE: 2
MAEICCVKEI QEEDVEKIRL PTRPELDIPV SDHEDPTVNE EEGCKTPTSS DHKIPEVKYT  60
LCPPAPRKPK PNRSSGTKRK LTPVNVLNRI PIDLSREIEM FFEDLDRRIK KSRKQ       115

SEQ ID NO: 3           moltype = DNA  length = 992
FEATURE                Location/Qualifiers
misc_feature           1..992
                       note = Ceres CLONE ID no.1897908
misc_feature           1..992
                       note = Encodes the peptide sequence at SEQ ID NO 4
source                 1..992
                       mol_type = other DNA
                       organism = Gossypium hirsutum
SEQUENCE: 3
gggttgtcaa agccttttct ctgtctctca tctttgcctt ctctttctca tttcgcagct  60
aaattccaaa ctaaaatcca agatagaaaa agaaattcag agaacaatca aggaagatgg  120
tgatgtgatg aattaaaaaa aagaaaaacc ctctggcatt ttcgtttcct atatatcaaa  180
taccaagctt cttctctttg tttttctagg cttttttttc ctgctggtac ttgtactgtc  240
ttttccttca tttgcttgca attttcataa tttgatccct ctctctaatc tttaaattct  300
ttgtcttcat catttcttca tatcctaggt tgattttgga cttccatgta ctcaaaatta  360
aaaccagttc cattcatggg tgtctcaact accatggaac tcagtttctt ggttaggcct  420
cctctagaat tcaatgaaga ttgtggaact gcaactaatg ttaaacaaga agaagaagaa  480
gagaagagca agttggtgat gatgggtaca tctgaatctg aggtggttgc tgctgctaat  540
gatgatcaag atgaaaacga caacgatggg ttcaagactc ctacttcgtt cgaccataaa  600
atcccagccg ccaccatcct caagtgccca cctgcaccaa ggaaaccaaa atccctcccc  660
attatatcgt caccagcaaa acgaaaatcg cttcgcagga gaatcctact tgatttgacg  720
aaagagatcg agtctttgtt ccctccagct cttattgcag atctagggaa caagattaag  780
aaagtcagac aaggaagtga cttcaaatga tatgatatat atatacatat atacatacaa  840
atataactat atatgtatca tgtatttatt tgaagaattt taattatgtt atttgttttc  900
atcatccaag accatcacat ctatgttcag tttcattgat gtgtttttta tttggtgttt  960
ctatcagatc taaaaccata taaagacttt gc                              992

SEQ ID NO: 4           moltype = AA  length = 154
FEATURE                Location/Qualifiers
REGION                 1..154
                       note = misc_feature - Ceres CLONE ID no.1897908
REGION                 1..154
                       note = misc_feature - Bit score of 132.4 for hmm based on
                        sequences of FIGURE 1.
REGION                 1..154
                       note = misc_feature - Functional Homolog Of Ceres SEEDLINE
                        ID no. ME00327 at SEQ ID NO. 2
source                 1..154
                       mol_type = protein
                       organism = Gossypium hirsutum
SEQUENCE: 4
MYSKLKPVPF MGVSTTMELS FLVRPPLEFN EDCGTATNVK QEEEEEKSKL VMMGTSESEV  60
VAAANDDQDE NDNDGFKTPT SFDHKIPAAT ILKCPPAPRK PKSLPIISSP AKRKSLRRRI  120
LLDLTKEIES LFPPALIADL GNKIKKVRQG SDFK                            154

SEQ ID NO: 5           moltype = DNA  length = 1175
FEATURE                Location/Qualifiers
misc_feature           1..1175
                       note = Ceres CLONE ID no.1938030
```

-continued

```
misc_feature            1..1175
                        note = Encodes the peptide sequence at SEQ ID NO 6
source                  1..1175
                        mol_type = other DNA
                        organism = Gossypium hirsutum
SEQUENCE: 5
aaaagtgggt tgtcaaagcc ttttctctgt ctctcatctt tgctttctct ttctcatttc  60
gcagctaaat tccaaactaa aatccaagat agaaaaagaa attcagagag caatcaagga  120
agatggtgat gtgatgaatt aaaaaaaaaa actttggcat tttcgtttac tatatatcaa  180
ataacaagct tcttctcttt gtttttctag gctttttttt tcctgctggt acttgaactg  240
tcttttcctt catttgcttg caattttcat aagttgatcc ctctctctca tctttaaatt  300
ctttgtcctt caccatttct tcatatccta ggttgatttt ggacttccat gtactcaaaa  360
ttaaaaccag ttccattcat gggtgtctca agtaccatgg aactcagttt cttggttagg  420
cctcctctag aattcaatga agattgtgga actgcaacta atgttaaaca ggaagaagaa  480
gaagagaaga gcaagttggt gacgatgggt acatctgaat ctgaggtggt tgctgctgct  540
aatgattatc aagatgaaaa cgacaacgat gggttcaaga ccaacgatgg gttcaagact  600
cctacttcat tggaccataa aatcccagcc gccgccatcc tcaagtgccc acctgcacca  660
aggaaaccaa aatccctccc cattatatcg tcaccagcaa aacgaaaatc tcttcgcagg  720
agaatcctgc ttgatttgac gaaagagatc gagtctttgt tccctccagc tcttattgca  780
gatctaggga acaagattaa gaaagtcaga caaggaagtg acttcaaatg acatgataca  840
tatacatata tacatacata caaatataac tatatatgtg tcatgtattt atttgaagaa  900
ttttaattat gttatttgtt ttcatcatcc tagaccatca cttctatgtt cagtttcatt  960
ggtgtgtttt ttatttggtg tttctatcag atctaaaacc atacaaagac tttgcaaaat  1020
ggatcaaagc aagtacaaag tgagtgatgt gattcatgga ttttagcatt gggttcttta  1080
ctttcttttt cttttggctg cactcttaac ctagctaaaa gatgaacttt tgaggtttga  1140
ttttaaattt aattagagct acatataatt atacg                             1175

SEQ ID NO: 6            moltype = AA  length = 160
FEATURE                 Location/Qualifiers
REGION                  1..160
                        note = misc_feature - Ceres CLONE ID no.1938030
REGION                  1..160
                        note = misc_feature - Bit score of 131.1 for hmm based on
                         sequences of FIGURE 1.
REGION                  1..160
                        note = misc_feature - Functional Homolog Of Ceres SEEDLINE
                         ID no. ME00327 at SEQ ID NO. 2
source                  1..160
                        mol_type = protein
                        organism = Gossypium hirsutum
SEQUENCE: 6
MYSKLKPVPF MGVSSTMELS FLVRPPLEFN EDCGTATNVK QEEEEEKSKL VTMGTSESEV  60
VAAANDYQDE NDNDGFKTND GFKTPTSLDH KIPAAAILKC PPAPRKPKSL PIISSPAKRK  120
SLRRRILLDL TKEIESLFPP ALIADLGNKI KKVRQGSDFK                       160

SEQ ID NO: 7            moltype = DNA  length = 781
FEATURE                 Location/Qualifiers
misc_feature            1..781
                        note = Ceres CLONE ID no.1915941
misc_feature            1..781
                        note = Encodes the peptide sequence at SEQ ID NO 8
source                  1..781
                        mol_type = other DNA
                        organism = Gossypium hirsutum
SEQUENCE: 7
tcgctcgctc gctgggttaa aactgtttcg tcctattttc tctcttaact gtagaaacaa  60
agtctggaat tgtacaactc caccaggggg aaggatggtg atttgatgat ttaccatatt  120
gctttatgtt atacattctc atcgcttttt atctgtttgc actaatgtat gtagaattgc  180
ggctgcctgc aggtttccct tgtcggtatc tcgagttcag agacggccgt agtcaaaggt  240
ggtgaagaag gaatggaatt cgacattctg aaacgacccc taccggtgaa gtgccaaact  300
acaacctctt cttcttttc acccggtaaa caacaaaaag aagaaggaga aatcaacgtt  360
aaagcagctg gtgaggggaa ggaagagaag aaagaaaaga attccaagga aatagatgat  420
gatgatgatg atgggtttaa aactccaaca tctacggatt ccaaaatccc agctgagccg  480
aaacaatgcc cgcctgcacc tagaaaaccc aagccaaata aaagaaaagc atcatcgcct  540
accaatggtt caaccgcagt caggaatccg ctactgctgg atctttcgga agagctcgag  600
tccttgagtc acaaggtcaa gaaaaaaact cgaacacaag agcagcaata atttttattc  660
attgttagcg gtattaagta cacacccatc aaacattaat aacttaattc tttatttgta  720
tttatgggag ttcattgttt ttgctgacgg tgaagatcat gatgatattg aagcttatga  780
c                                                                  781

SEQ ID NO: 8            moltype = AA  length = 132
FEATURE                 Location/Qualifiers
REGION                  1..132
                        note = misc_feature - Ceres CLONE ID no.1915941
REGION                  1..132
                        note = misc_feature - Bit score of 254.1 for hmm based on
                         sequences of FIGURE 1.
REGION                  1..132
                        note = misc_feature - Functional Homolog Of Ceres SEEDLINE
```

```
                       ID no. ME00327 at SEQ ID NO. 2
source                 1..132
                       mol_type = protein
                       organism = Gossypium hirsutum
SEQUENCE: 8
MEFDILKRPL PVKCQTTTSS SFSPGKQQKE EGEINVKAAG EGKEEKKEKN SKEIDDDDDD  60
GFKTPTSTDS KIPAEPKQCP PAPRKPKPNK RKASSPTNGS TAVRNPLLLD LSEELESLSH  120
KVKKKTRTQE QQ                                                     132

SEQ ID NO: 9           moltype = DNA  length = 483
FEATURE                Location/Qualifiers
misc_feature           1..483
                       note = Ceres ANNOT ID no.1461830
misc_feature           1..483
                       note = Encodes the peptide sequence at SEQ ID NO 10
source                 1..483
                       mol_type = other DNA
                       organism = Populus balsamifera
                       sub_species = trichocarpa
SEQUENCE: 9
atggggtttt ccaactctga gatgtttttc tctgagaaag atctgaatcc catggaattc  60
aatttccttg tgagatctgc attagaactt ggagatgact gtgaaattgt accccaagat  120
cttcatcagg aaaaagaagt acttgaaaaa gaagaaaagc aagaagacga atgcgagata  180
tcggtgccta ctttgaagat aaaactgccg tctgtagaag cattccaaat tgaagatgat  240
aaagatgacg atgatgatgg gttcaagact ccaacttctt tggatcgcaa aattcctgtc  300
atttttcaat gtccgcccgc acccagaaaa cctaaatcac tcccatcagc caaacgaaaa  360
tcgcctcaac ggagagtctt acttgatctg tccaatgaga tcgaatcctt gtttcctcca  420
gctcttgctg gggatcttgg tggcaagatt aagaaagtta gacaaggcaa tgacaccaag  480
taa                                                               483

SEQ ID NO: 10          moltype = AA  length = 143
FEATURE                Location/Qualifiers
REGION                 1..143
                       note = misc_feature - Ceres ANNOT ID no.1461830
REGION                 1..143
                       note = misc_feature - Bit score of 305.4 for hmm based on
                        sequences of FIGURE 1.
REGION                 1..143
                       note = misc_feature - Functional Homolog Of Ceres SEEDLINE
                        ID no. ME00327 at SEQ ID NO. 2
source                 1..143
                       mol_type = protein
                       note = subspecies = trichocarpa
                       organism = Populus balsamifera
SEQUENCE: 10
MEFNFLVRSA LELGDDCEIV PQDLHQEKEV LEKEEKQEDE CEISVPTLKI KLPSVEAFQI  60
EDDKDDDDDG FKTPTSLDRK IPVIFQCPPA PRKPKSLPSA KRKSPQRRVL LDLSNEIESL  120
FPPALAGDLG GKIKKVRQGN DTK                                         143

SEQ ID NO: 11          moltype = DNA  length = 561
FEATURE                Location/Qualifiers
misc_feature           1..561
                       note = Ceres ANNOT ID no.1439985
misc_feature           1..561
                       note = Encodes the peptide sequence at SEQ ID NO 12
source                 1..561
                       mol_type = other DNA
                       organism = Populus balsamifera
                       sub_species = trichocarpa
SEQUENCE: 11
atggctgacc cgataaagag tgaacctcat tctcaaagcg aaggtttttc tgccatgttc  60
tcggaatcga aaccattttc gttaacgggg ttgcctaact ctcagatttt tttctctgag  120
aaagatccga atcctaagga attcaatttc cttgtgagac ccacgttaga acttggagat  180
gacggtgaaa ctgtacctca agagcttcat caggaaaaag aagttgaaga agaaggaaag  240
caagaagata aatgcgagat ctcggtacct actttgaaga taaaattccc atctttagga  300
gctttccaaa ttgaagatag tgatcatggt gatggttcga agactccaac ttcttcggat  360
tgcaaaatcc ctgtcatttt tcaatgtccg cctgcaccta taaaacctaa atcacttcca  420
tcaaccaaac gaaaatcgcc tcgacggaga gtcttacttg atctgtccaa cgaggttgaa  480
actttgtttc ccccagctct tgctgcaaat cttggtggca agattaagaa agttagacaa  540
ggcaacgaca gtaccaaata a                                           561

SEQ ID NO: 12          moltype = AA  length = 168
FEATURE                Location/Qualifiers
REGION                 1..168
                       note = misc_feature - Ceres ANNOT ID no.1439985
REGION                 1..168
                       note = misc_feature - Bit score of 220.9 for hmm based on
                        sequences of FIGURE 1.
REGION                 1..168
```

-continued

```
                      note = misc_feature - Functional Homolog Of Ceres SEEDLINE
                       ID no. ME00327 at SEQ ID NO. 2
source                1..168
                      mol_type = protein
                      note = subspecies = trichocarpa
                      organism = Populus balsamifera
SEQUENCE: 12
MFSESKPFSL TGLPNSQIFF SEKDPNPKEF NFLVRPTLEL GDDGETVPQE LHQEKEVEEE  60
GKQEDKCEIS VPTLKIKFPS LGAFQIEDSD HGDGSKTPTS SDCKIPVIFQ CPPAPIKPKS  120
LPSTKRKSPR RRVLLDLSNE VETLFPPALA ANLGGKIKKV RQGNDSTK              168

SEQ ID NO: 13         moltype = AA  length = 115
FEATURE               Location/Qualifiers
REGION                1..115
                      note = misc_feature - Public GI ID no.15241794
REGION                1..115
                      note = misc_feature - Bit score of 218.0 for hmm based on
                       sequences of FIGURE 1.
REGION                1..115
                      note = misc_feature - Functional Homolog Of Ceres SEEDLINE
                       ID no. ME00327 at SEQ ID NO. 2
source                1..115
                      mol_type = protein
                      organism = Arabidopsis thaliana
SEQUENCE: 13
MAEICCVKEI QEEDVEKIRL PTRPELDIPD SDHEDPTVNE EEGCKTPTSS DHKIPEVKYT  60
LCPPAPRKPK PNRSSGTKRK LTPVNVVNRI PIDLSREIEM FFEDLDRRIK KSRKQ       115

SEQ ID NO: 14         moltype = DNA  length = 678
FEATURE               Location/Qualifiers
misc_feature          1..678
                      note = Ceres CLONE ID no.1080942
misc_feature          1..678
                      note = Encodes the peptide sequence at SEQ ID NO 15
source                1..678
                      mol_type = other DNA
                      organism = Brassica napus
SEQUENCE: 14
ctaagaagat ttgttcagtg cacacgacaa aacacaaaaa caaaaccttc aagaacaact  60
ccatttaaat atctataaag aaatgaatct tgatttaata caagatctgc ccatgctgaa  120
gttcccatca cccatcaaga tcccatccaa caacaccaac agagatgatg acggcagcag  180
cggcggctgc accactccca cttcctccga ccacaagatt cctccctcca ccgccactac  240
tcctcctcct ccgcctcaga aacgccgccc acctccgtcg ccatcatgtt tcatcagatc  300
ttgcaagagg aagcttttga cgccatcaaa ggttgagatc atcgtcaaca aagatgagat  360
cgaacggttc ttctcctctg tttacaatca ctcaacgacg tcatccccca caacaaccac  420
caccaaaaag gctctcgcgg tggttaggcg acggagaagt ttccgttctt gttcacgaag  480
atgatcaata attggagtta accacaataa agttaaaggt tccttcattt cggtaacttt  540
ttatttattt tatgtaacga ttctcaactt tacacgtcga cccactctat aaatatacat  600
gtgctatcga tcgttggaat ctttcttttc ttaatagctt catgaattat gtaaatgttc  660
aataaattta tatttgct                                                678

SEQ ID NO: 15         moltype = AA  length = 133
FEATURE               Location/Qualifiers
REGION                1..133
                      note = misc_feature - Ceres CLONE ID no.1080942
REGION                1..133
                      note = misc_feature - Bit score of 274.7 for hmm based on
                       sequences of FIGURE 1.
REGION                1..133
                      note = misc_feature - Functional Homolog Of Ceres SEEDLINE
                       ID no. ME00327 at SEQ ID NO. 2
source                1..133
                      mol_type = protein
                      organism = Brassica napus
SEQUENCE: 15
MNLDLIQDLP MLKFPSPIKI PSNNTNRDDD GSSGGCTTPT SSDHKIPPST ATTPPPPPQK  60
RRPPPSPSCF IRSCKRKLLT PSKVEIIVNK DEIERFFSSV YNHSTTSSPT TTTTKKALAV  120
VRRRRSFRSC SRR                                                     133

SEQ ID NO: 16         moltype = DNA  length = 623
FEATURE               Location/Qualifiers
misc_feature          1..623
                      note = Ceres CLONE ID no.1073190
misc_feature          1..623
                      note = Encodes the peptide sequence at SEQ ID NO 17
source                1..623
                      mol_type = other DNA
                      organism = Glycine max
SEQUENCE: 16
```

-continued

```
aacaagtttt ctacatccac acaaaaaagg ttttccaaac ataagcacac atttacagac  60
atggatgatc ttgagttatt acaagatctg tcccaattca acttcccagc aaccatcaag  120
atcccatcta aaacctctaa agacaacaaa gacggcgatg gtgataacga cgagggcttt  180
agctgcagca cacccacatc tcaagaacac aagattcctt ctgtccacga ttctccacct  240
cccccgccga gaaaacctcg tgcactgcct tcaaaaccgt cgcctacggc ggctctggtg  300
ataagatcgt gtaagaggaa gctcttagtg tcggctcctg agattatcat gaacaaggaa  360
gagattgacc gtttcttctc ctctgtctat agtgacacgt caacgacggc taaacggcgg  420
agacgttatc tttattgtgc gcgaagatga gcctttagtt caagatttac attttctaca  480
gttttactgg aaatatataa attaaaaacc ttattataag tattttaatt ttcaaaatgg  540
atggataatt ttctgtagcc gcatattaat tccgcatgga ggggtcgttg ttgtaaattc  600
cgtaataaat gaaatttaat tcc                                         623

SEQ ID NO: 17          moltype = AA  length = 129
FEATURE                Location/Qualifiers
REGION                 1..129
                       note = misc_feature - Ceres CLONE ID no.1073190
REGION                 1..129
                       note = misc_feature - Bit score of 272.3 for hmm based on
                        sequences of FIGURE 1.
REGION                 1..129
                       note = misc_feature - Functional Homolog Of Ceres SEEDLINE
                        ID no. ME00327 at SEQ ID NO. 2
source                 1..129
                       mol_type = protein
                       organism = Glycine max
SEQUENCE: 17
MDDLELLQDL SQFNFPATIK IPSKTSKDNK DGDGDNDEGF SCSTPTSQEH KIPSVHDSPP  60
PPPRKPRALP SKPSPTAALV IRSCKRKLLV SAPEIIMNKE EIDRFFSSVY SDTSTTAKRR  120
RRYLYCARR                                                         129

SEQ ID NO: 18          moltype = DNA  length = 1377
FEATURE                Location/Qualifiers
misc_feature           1..1377
                       note = Ceres SEEDLINE ID no.ME04315
misc_feature           1..1377
                       note = Expected Sequence
misc_feature           1..1377
                       note = Encodes the peptide sequence at SEQ ID NO. 20
source                 1..1377
                       mol_type = other DNA
                       organism = Arabidopsis thaliana
SEQUENCE: 18
aaaaaacttc aaagagagag agagagagag ttttgtgaac tcaagaaaat aaaaaaagtt  60
atagttaatg ggattcggct tagagagtat caaatcaatc tccggcggat ggggcgcggc  120
ggcgcgttcc tgtgacgctt gtaaatcagt taccgccgcc gtgttctgtc gagttgactc  180
agctttctta tgcatagcat gtgacacaag aatccattcc ttcactcgcc acgagcgcgt  240
gtgggtttgt gaagtttgtg aacaagctcc cgccgccgtc acttgcaaag ccgacgccgc  300
cgctctttgc gtcacttgtg atgccgatat tcactctgct aatcctctcg ctagccgtca  360
cgaacgtgtc cccgtcgaaa ctttcttcga ctcagccgaa accgccgtcg ccaaaatctc  420
agcttcttcg actttggta tccttggctc atccaccacc gttgatttaa ccgctgttcc  480
ggttatggct gatgatctcg gtttatgtcc gtggttactt cctaatgatt tcaacgaacc  540
ggctaaaatc gaaatcggaa ctgaaaacat gaaaggttct tctgacttta tgttttctga  600
tttcgatcgg cttattgatt tcgagtttcc gaattcgttc aatcatcatc aaaacaacgc  660
cggaggagat agtcttgttc cggttcagac gaaaacagag cctctcccgt taactaacaa  720
tgatcattgc ttcgatattg atttctgcag atcaaagctc tctgctttca cttacccttc  780
tcaatcagtc agccacagtg tttcgacttc ttctattgaa tacggtgtag ttcctgacgg  840
aaacacaaac aactctgtta accggagcac gatcactagc tcgacgactg gtggtgatca  900
tcaagcgagc tctatggata gagaagctag ggttttgagg tacagagaga agagaaagaa  960
caggaaattt gagaagacga ttcgttacgc ttcgaggaaa gcttatgcag agtcacggcc  1020
aaggatcaaa ggccggtttg cgaaaagaac agagacagaa aacgacgaca ttttccttag  1080
tcatgtttat gcttcagcag cacacgcaca gtacggtgtc gtaccaacgt tctgattcga  1140
atctacggtg gataaacaat caacctgaag acttcatatc ttccaccgtt gatttacagt  1200
cggtgtataa taagtatagt gagtcttacc gtagacaaac atcttatcct ctttaccgtt  1260
ttaattactt ttttttacg cgctctcact gccactgtaa ctcttttttt tttcttccta  1320
tatatgtatg cttattttta tttagaaaat gttatgaaat catataattt ggtaatc     1377

SEQ ID NO: 19          moltype = DNA  length = 1377
FEATURE                Location/Qualifiers
misc_feature           1..1377
                       note = Ceres SEEDLINE ID no.ME04315
misc_feature           1..1377
                       note = Inplanta Sequence
misc_feature           1..1377
                       note = Encodes the peptide sequence at SEQ ID NO. 20
source                 1..1377
                       mol_type = other DNA
                       organism = Arabidopsis thaliana
SEQUENCE: 19
aaaaaacttc aaagagagag agagagagag ttttgtgaac tcaagaaaat aaaaaaagtt  60
```

-continued

```
atagttaatg ggattcggct tagagagtat caaatcaatc tccggcggat ggggcgcggc  120
ggcgcgttcc tgtgacgctt gtaaatcagt taccgccgcc gtgttctgtc gagttgactc  180
agctttctta tgcatagcat gtgacacaag aatccattcc ttcactcgcc acgagcgcgt  240
gtgggtttgt gaagtttgtg aacaagctcc cgccgccgtc acttgcaaag ccgacgccgc  300
cgctctttgc gtcacttgtg atgccgatat tcactctgct aatcctctcg ctagccgtca  360
cgaacgtgtc cccgtcgaaa ctttcttcga ctcagccgaa accgccgtcg ccaaaatctc  420
agcttcttcg acttttggta tccttggctc atccaccacc gttgatttaa ccgctgttcc  480
ggttatggct gatgatctcg gtttatgtcc gtggttactt cctaatgatt tcaacgaacc  540
ggctaaaatc gaaatcggaa ctgaaaacat gaaaggttct tctgacttta tgttttctga  600
tttcgatcgg cttattgatt tcgagtttcc gaattcgttc aatcatcatc aaaacaacgc  660
cggaggagat agtcttgttc cggttcagac gaaaacagag cctctcccgt taactaacaa  720
tgatcattgc ttcgatattg atttctgcag atcaaagctc tctgctttca cttacccttc  780
tcaatcagtc agccacagtg tttcgacttc ttctattgaa tacggtgtag ttcctgacgg  840
aaacacaaac aactctgtta accggagcac gatcactagc tcgacgactg gtggtgatca  900
tcaagcgagc tctatggata gagaagctag ggttttgagg tacagagaga agagaaagaa  960
caggaaattt gagaagacga ttcgttacgc ttcgaggaaa gcttatgcag agtcacggcc  1020
aaggatcaaa ggccggtttg cgaaaagaac agagacagaa aacgacgaca ttttccttag  1080
tcatgtttat gcttcagcag cacacgcaca gtacggtgtc gtaccaacgt tctgattcga  1140
atctacggtg gataaacaat caacctgaag acttcatatc ttccaccgtt gatttacagt  1200
cggtgtataa taagtatagt gagtcttacc gtagacaaac atcttatcct ctttaccgtt  1260
ttaattactt ttttttacg cgctctcact gccactgtaa ctcttttttt tttcttccta  1320
tatatgtatg cttattttta tttaaaaaat gttatgaaat catataattt ggtaatc     1377
```

```
SEQ ID NO: 20          moltype = AA  length = 355
FEATURE                Location/Qualifiers
REGION                 1..355
                       note = misc_feature - Ceres SEEDLINE ID no.ME04315
REGION                 1..355
                       note = misc_feature - Bit score of 860.9 for hmm based on
                        sequences of FIGURE 2.
REGION                 285..329
                       note = misc_feature - Pfam Name: CCT Pfam Description: CCT
                        motif
REGION                 56..103
                       note = misc_feature - Pfam Name: zf-B_box Pfam Description:
                        B-box zinc finger
source                 1..355
                       mol_type = protein
                       organism = Arabidopsis thaliana
SEQUENCE: 20
MGFGLESIKS ISGGWGAAAR SCDACKSVTA AVFCRVDSAF LCIACDTRIH SFTRHERVWV  60
CEVCEQAPAA VTCKADAAAL CVTCDADIHS ANPLASRHER VPVETFFDSA ETAVAKISAS  120
STFGILGSST TVDLTAVPVM ADDLGLCPWL LPNDFNEPAK IEIGTENMKG SSDFMFSDFD  180
RLIDFEFPNS FNHHQNNAGG DSLVPVQTKT EPLPLTNNDH CFDIDFCRSK LSAFTYPSQS  240
VSHSVSTSSI EYGVVPDGNT NNSVNRSTIT SSTTGGDHQA SSMDREARVL RYREKRKNRK  300
FEKTIRYASR KAYAESRPRI KGRFAKRTET ENDDIFLSHV YASAAHAQYG VVPTF       355
```

```
SEQ ID NO: 21          moltype = DNA  length = 1541
FEATURE                Location/Qualifiers
misc_feature           1..1541
                       note = Ceres CLONE ID no.1842825
misc_feature           1..1541
                       note = Encodes the peptide sequence at SEQ ID NO 22
source                 1..1541
                       mol_type = other DNA
                       organism = Gossypium hirsutum
SEQUENCE: 21
aagagcaaac tgtggcacta ctccatgtat actcccaaaa tctctaaaaa gggaaatact  60
agtcctttcg agggcaactg aaagaggaga aaaaaaaatc tattggtttt gatttgtgag  120
gatggtaatc gatacaacca acgtcaaggg acttacggga cgctggggca tggcagcaaa  180
gacatgcgac acatgtaaat cagcggcagc ggctattttc tgtcgttctg attccgcttt  240
tatgtgcctc agctgcgatt ccaggatcca ctctgctaat gacaagcttg tttcttgtcg  300
tcacgagagg gtgtggatgt gtgaggtgtg cgagcaggcc ccagctgccg tcacttgcaa  360
ggccgacgcc gctgcccttt gcgtcgcctg cgattccgac atccactctg ctaatccttt  420
ggctcgtcgc cacgagcgtg tccctgtcca gcctttcttt gactctgctg attccatcgt  480
caaatcttct tctttcagct tccttgtgcc gactgatcct aatactggtt ctaattgtca  540
acaagaagat gtagagacag gttcttggct gttgcccaat cccaaactca ccatggaaac  600
taaccaagtc aaaacagggg attttttctt ctccgacatg gatccgttta ttgattttga  660
gtaccaggat tcgtttcaac agcatgacgg agctatggac agcgtagttc cagttcagac  720
caaaccagct acaatttcaa tgatcaacaa tgaaaattgt ttcgatgttg atttctgtcg  780
atccaagttc cctactttca gctaccagac aaagtctcaa agccatagtg tttcatcatc  840
gtcgctcgag gtaggagtag ttccagatgg gaactccgtg tcggatatct catatacttt  900
gggacggacc atgggtgacc caagcgcacc aatctgggca gctacagcca ataaccaagc  960
accacctcag gcccaagtcg gtggaatgga tcgagaagct agagttctaa ggtacagaga  1020
gaagagaaag aacagaaaat ttgagaaaac aatccgctac gcttcgagaa aggcatacgc  1080
cgagtcaagg ccaaggatca aaggccgttt cgccaaaaga aatgaaaccg acaacgaagt  1140
tgaccacatg tataactcgg cttcttccgc tgctaccgca gcagctttca tgtacgataa  1200
ccagtacggc atcgtcccat ccttttgagg atgtcatgaa tgaatctgat tcagatggaa  1260
acaagaattg ttggctgtaa tattcaactg tgatatatat atccagcaag tagaatcaac  1320
```

-continued

```
taccctaagg aaaacaaatg atgtagcttt taattatggt tattgatgta aaaatagtgt  1380
atccatgagc tattgatttg cagggattca ttcaagttga ttaactgcag aataagatgg  1440
aaaagtcctg caaaatctga aacaaagccc ttccactttt tctctagagg gcttcttctg  1500
tgattctgtt atctagaagt aaaagttttt cttggttttt c                      1541

SEQ ID NO: 22          moltype = AA  length = 368
FEATURE                Location/Qualifiers
REGION                 1..368
                       note = misc_feature - Ceres CLONE ID no.1842825
REGION                 1..368
                       note = misc_feature - Bit score of 932.9 for hmm based on
                        sequences of FIGURE 2.
REGION                 291..335
                       note = misc_feature - Pfam Name: CCT Pfam Description: CCT
                        motif
REGION                 62..109
                       note = misc_feature - Pfam Name: zf-B_box Pfam Description:
                        B-box zinc finger
REGION                 1..368
                       note = misc_feature - Functional Homolog Of Ceres SEEDLINE
                        ID no. ME04315 at SEQ ID NO. 20
source                 1..368
                       mol_type = protein
                       organism = Gossypium hirsutum
SEQUENCE: 22
MVIDTTNVKG LTGRWGMAAK TCDTCKSAAA AIFCRSDSAF MCLSCDSRIH SANDKLVSCR  60
HERVWMCEVC EQAPAAVTCK ADAAALCVAC DSDIHSANPL ARRHERVPVQ PFFDSADSIV  120
KSSSFSFLVP TDPNTGSNCQ QEDVETGSWL LPNPKLTMET NQVKTGDFFF SDMDPFIDFE  180
YQDSFQQHDG AMDSVVPVQT KPATISMINN ENCFDVDFCR SKFPTFSYQT KSQSHSVSSS  240
SLEVGVVPDG NSVSDISYTL GRTMGDPSAP IWAATANNQA PPQAQVGGMD REARVLRYRE  300
KRKNRKFEKT IRYASRKAYA ESRPRIKGRF AKRNETDNEV DHMYNSASSA ATAAAFMYDN  360
QYGIVPSF                                                           368

SEQ ID NO: 23          moltype = DNA  length = 1332
FEATURE                Location/Qualifiers
misc_feature           1..1332
                       note = Ceres CLONE ID no.1834027
misc_feature           1..1332
                       note = Encodes the peptide sequence at SEQ ID NO 24
source                 1..1332
                       mol_type = other DNA
                       organism = Gossypium hirsutum
SEQUENCE: 23
ttaaaatcaa taacaaacac ttcaaaccct ccacgtttga tccaaacata atattttttt  60
atttccattg ctttgatttg attcgcgatt atgggaatcg aaataagcgg cggcacgatc  120
attccaggag gttgggggc  cgccgccatg gctgtcgcgg ctaagacatg cgacgcatgt  180
aaatcatcgg cggcagctat cttttgtcgt actgattggg tctttttatg cttgaattgt  240
gattccaatt tccattccgg tcacgaaagg gtgtctatgt gtgaagtttg cgaacaagct  300
ccggcggctg tcacttgtaa agccgacgcg gcggctcttt gtgtcacttg cgacgccgat  360
atccattcag cgaacccact ggctcgccgt cacgaacgtg tacccatcga acctttctac  420
gactccgctg attccatcgt caaatcttcc ccttttagct tccttgtgcc gacgacggat  480
cataatggta ctaattgtaa acaagaaatt gaatctaaca aaggggattt ttttttcaca  540
gaaatggatc ggtttatcga tttcgggtac ccgaattcat ctcaacatct tcatgatgcc  600
gccatggata gcgttgttcc agttcaaact ccaaaaccag tcattccact gatcaacgat  660
ggaagctgtt tcgatacttt cagctatcaa actcaatcat ctctcagtca tagcgtttca  720
tcatcgtcgc ttgaagtaga aacagttcca gatgggaatt accacgcaac acaagtgggt  780
ggttcaatcg atcgagaagc tagggtttta aggtacaaag agaagagaaa gaacaggaaa  840
ttcgagaaga caatacgata cgcttcaaga aaggcttacg ctgaatcaag accaagaatc  900
aaaggtcgat ttgctaaaag aacagaaacc cacaacgatg atgttgatca catgttcaat  960
aactcttctt tcgctgttgg tcctgctggt ttcatggcgg aaacagacta tggtgtcgtt  1020
ccatcgtttt gaatgttgat gttttatgtt tggtttaatc tgtaatgtat taaattattt  1080
aatccaattt ccagcaaagt agaaataacc ttatggccat tgaaaatcaa ggaagaaaga  1140
tgcttagttc tttgattaat cattaaagtt tctgatgtat aaaaaacagt gtatcggtgg  1200
agttcgtcgt atgttcgcca tggttgattt gcaggattcc tgcaagggag atatattagt  1260
tttcataaaa atgtttattt caatctctga ataaaaccag atatatggta agtaaatgct  1320
tcaatttagt tc                                                      1332

SEQ ID NO: 24          moltype = AA  length = 313
FEATURE                Location/Qualifiers
REGION                 1..313
                       note = misc_feature - Ceres CLONE ID no.1834027
REGION                 1..313
                       note = misc_feature - Bit score of 543.8 for hmm based on
                        sequences of FIGURE 2.
REGION                 235..279
                       note = misc_feature - Pfam Name: CCT Pfam Description: CCT
                        motif
REGION                 64..106
                       note = misc_feature - Pfam Name: zf-B_box Pfam Description:
```

-continued

```
                         B-box zinc finger
REGION                  1..313
                        note = misc_feature - Functional Homolog Of Ceres SEEDLINE
                         ID no. ME04315 at SEQ ID NO. 20
source                  1..313
                        mol_type = protein
                        organism = Gossypium hirsutum
SEQUENCE: 24
MGIEISGGTI IPGGWGAAAM AVAAKTCDAC KSSAAAIFCR TDWVFLCLNC DSNFHSGHER  60
VSMCEVCEQA PAAVTCKADA AALCVTCDAD IHSANPLARR HERVPIEPFY DSADSIVKSS  120
PFSFLVPTTD HNGTNCKQEI ESNKGDFFFT EMDRFIDFGY PNSSQHLHDA AMDSVVPVQT  180
PKPVIPLIND GSCFDTFSYQ TQSSLSHSVS SSSLEVETVP DGNYHATQVG GSIDREARVL  240
RYKEKRKNRK FEKTIRYASR KAYAESRPRI KGRFAKRTET HNDDVDHMFN NSSFAVGPAG  300
FMAETDYGVV PSF                                                     313

SEQ ID NO: 25           moltype = DNA  length = 1226
FEATURE                 Location/Qualifiers
misc_feature            1..1226
                        note = Ceres CLONE ID no.1837064
misc_feature            1..1226
                        note = Encodes the peptide sequence at SEQ ID NO 26
source                  1..1226
                        mol_type = other DNA
                        organism = Gossypium hirsutum
SEQUENCE: 25
gattccaaag atctcacccc atcaactgaa atggctgcaa agcattcgga cgcctgtaaa  60
ccaacagcta ccgatccaga ttttatgtgc ctgagttatg attcttccac cgccatccat  120
ggctgcattg ggagggtgtt gatgtgcgac gtttgcgagc aagttccggc tgcgttcact  180
tgcaaagccg atgccgccgc gctttgtgtc gcttgtgatg ccgatattca ctccgctaat  240
catttggctc gtcgtcacta ccgtgtcccg atcgaccctt ttcttggtcc acaaaaagag  300
gatgtagtag tgatgggttc ttggtctttg ttacctggtt tcaatcataa actggttgaa  360
acagaggatt tggggatttc agaaatggat ccatttattg atttggagta ccaggatgga  420
tatcatgttt tacagcatca taatttaggt atggaaagct tagttccagt tcagatcgaa  480
ccggcaacaa cagttccagt ggtcaacccct attcacttct gccaatctca gtctctcagc  540
catagtgtat cgtcatcctc ggttgagtta ggtgatggga attctttatc agatatctca  600
tgcccattaa gaggtaccac aactgatcca agcatactca tatgcaacaa ccaagtagac  660
caagttggtt caatggatcg agtggctcgg gttttgaggt acagagaaaa gagaaagaag  720
agaaaatttg agaaaacagt tcgttacgct tcacgaaaag cctacgctga atcaagaccg  780
agaatcaaag gtcgtttcgt taaaagaact caaatccata accgagttga ccatctctgt  840
aactcggcaa catcaccatc atcatcaaca acgacatccc acacgcatta ctacggtatc  900
gtcccatctt ttttatgaaa gggaaacgtg gaaaaatgaa accaaaaaat ttaattttag  960
tgatgatatt gtaaaattcc actagtttat gtagcaagta gaataataat cccaagtcca  1020
ttaagattga ggaagatatt atgtaaccca aataacggtg atgtttttgg tagccgttga  1080
tatttggggc ttttagggtt atacgcaagc agatgttaga gttctaagaa ctgatatttt  1140
gcttgcagtt ctgaaaaaaa tgaagccctt ttcaccattt ttattgagag gggcttcttt  1200
tgtttttatg ttactaaagt ttgacc                                       1226

SEQ ID NO: 26           moltype = AA  length = 295
FEATURE                 Location/Qualifiers
REGION                  1..295
                        note = misc_feature - Ceres CLONE ID no.1837064
REGION                  1..295
                        note = misc_feature - Bit score of 317.3 for hmm based on
                         sequences of FIGURE 2.
REGION                  217..261
                        note = misc_feature - Pfam Name: CCT Pfam Description: CCT
                         motif
REGION                  34..81
                        note = misc_feature - Pfam Name: zf-B_box Pfam Description:
                         B-box zinc finger
REGION                  1..295
                        note = misc_feature - Functional Homolog Of Ceres SEEDLINE
                         ID no. ME04315 at SEQ ID NO. 20
source                  1..295
                        mol_type = protein
                        organism = Gossypium hirsutum
SEQUENCE: 26
MAAKHSDACK PTATDPDFMC LSYDSSTAIH GCIGRVLMCD VCEQVPAAFT CKADAAALCV  60
ACDADIHSAN HLARRHYRVP IDPFLGPQKE DVVVMGSWSL LPGFNHKLVE TEDLGISEMD  120
PFIDLEYQDG YHVLQHHNLG MESLVPVQIE PATTVPVVNP IHFCQSQSLS HSVSSSSVEL  180
GDGNSLSDIS CPLRGTTTDP SILICNNQVD QVGSMDRVAR VLRYREKRKK RKFEKTVRYA  240
SRKAYAESRP RIKGRFVKRT QIHNRVDHLC NSATSPSSST TTSHTHYYGI VPSFL       295

SEQ ID NO: 27           moltype = DNA  length = 1155
FEATURE                 Location/Qualifiers
misc_feature            1..1155
                        note = Ceres ANNOT ID no.1482536
misc_feature            1..1155
                        note = Encodes the peptide sequence at SEQ ID NO 28
```

-continued

```
source                  1..1155
                        mol_type = other DNA
                        organism = Populus balsamifera
                        sub_species = trichocarpa
SEQUENCE: 27
atgggaattg aagttgagag cttaaagaac ttgaccggag gatggagtgt tgcggctaaa  60
cgttgcgact cgtgcaaaac ggcagctgca gctgcgtttt gccgggcgga ctctgctttt  120
ttgtgtctga attgtgacac caagattcac catagtgggg tgaacagcaa gatcatgtca  180
aggcacgagc gtgtgtggat gtgtgaggtt tgcgagcaag cacccgctgc ggttacctgt  240
aaggctgatg cagctgctct ttgtgttact tgtgatgctg acatccactc tgctaaccct  300
cttgctcgcc gtcatgaacg agtccccgtg gagccttttt atgactctgc tgaatcaatt  360
gttaagactt cctcggcgtt taattttcta gtgcctggtg atcaaaatgg tgtgtctgca  420
tatgatcata acgatgagat cgagggtgtt tcgtggttgt tgcacggtaa tcacacaaca  480
catgacctta ataccaagat caacatcgag aatcctgttg tcaagactgg agatatgttt  540
ttctgtgaaa tggatccctt tcttgatttt gagtatcaga attcgatgga tgggaggtac  600
aagcagagtc atggtggggg tggtgctgga gctgatagcg ttgtgcctgt gcaaaacaaa  660
ccagctccgc ttcccgtgat cgatcataaa aactgctttg atattgattt ctgtagatcg  720
aaactcacct ctttcagcag ctacccctct cagtccctta gccacagcgt ttcttcgtct  780
tccctcgatg ttggtgttgt tcctgatggg aattctatgt ccgatatttc gtatcccttc  840
ggccgaagca tgaatactta taccgatcca agcatgccca tctcaggttc cactacaaat  900
caagcagcag ctcagttagc tgggattgac cgcgaagcta gagttttgag gtacagagag  960
aaaagaaaga accgtaaatt cgaaaaaacc atacggtatg cttcacgtaa agcttacgca  1020
gaaaccaggc caagaatcaa aggccgattc gcgaagcgaa ccgaaatgga atccgatatg  1080
gacaccctat ataactctcc gagctctgtc cctttcctgg ccgatactca ttacggtgtc  1140
gttccctcgt tttga                                                   1155

SEQ ID NO: 28           moltype = AA  length = 384
FEATURE                 Location/Qualifiers
REGION                  1..384
                        note = misc_feature - Ceres ANNOT ID no.1482536
REGION                  1..384
                        note = misc_feature - Bit score of 969.7 for hmm based on
                         sequences of FIGURE 2.
REGION                  311..355
                        note = misc_feature - Pfam Name: CCT Pfam Description: CCT
                         motif
REGION                  63..110
                        note = misc_feature - Pfam Name: zf-B_box Pfam Description:
                         B-box zinc finger
REGION                  1..384
                        note = misc_feature - Functional Homolog Of Ceres SEEDLINE
                         ID no. ME04315 at SEQ ID NO. 20
source                  1..384
                        mol_type = protein
                        note = subspecies = trichocarpa
                        organism = Populus balsamifera
SEQUENCE: 28
MGIEVESLKN LTGGWSVAAK RCDSCKTAAA AAFCRADSAF LCLNCDTKIH HSGVNSKIMS  60
RHERVWMCEV CEQAPAAVTC KADAAALCVT CDADIHSANP LARRHERVPV EPFYDSAESI  120
VKTSSAFNFL VPGDQNGVSA YDHNDEIEGV SWLLHGNHTT HDLNTKINIE NPVVKTGDMF  180
FCEMDPFLDF EYQNSMDGRY KQSHGGGGAG ADSVVPVQNK PAPLPVIDHK NCFDIDFCRS  240
KLTSFSSYPS QSLSHSVSSS SLDVGVVPDG NSMSDISYPF GRSMNTYTDP SMPISGSTTN  300
QAAAQLAGID REARVLRYRE KRKNRKFEKT IRYASRKAYA ETRPRIKGRF AKRTEMESDM  360
DTLYNSPSSV PFLADTHYGV VPSF                                         384

SEQ ID NO: 29           moltype = AA  length = 355
FEATURE                 Location/Qualifiers
REGION                  1..355
                        note = misc_feature - Public GI ID no.18424009
REGION                  1..355
                        note = misc_feature - Bit score of 856.7 for hmm based on
                         sequences of FIGURE 2.
REGION                  285..329
                        note = misc_feature - Pfam Name: CCT Pfam Description: CCT
                         motif
REGION                  56..103
                        note = misc_feature - Pfam Name: zf-B_box Pfam Description:
                         B-box zinc finger
REGION                  1..355
                        note = misc_feature - Functional Homolog Of Ceres SEEDLINE
                         ID no. ME04315 at SEQ ID NO. 20
source                  1..355
                        mol_type = protein
                        organism = Arabidopsis thaliana
SEQUENCE: 29
MGFGLESIKS ISGGWGAAAR SCDACKSVTA AVFCRVDSAF LCIACDTRIH SFTRHERVWV  60
CEVCEQAPAA VTCKADAAAL CVSCDADIHS ANPLASRHER VPVETFFDSA ETAVAKISAS  120
STFGILGSST TVDLTAVPVM ADDLGLCPWL LPNDFNEPAK IEIGTENMKG SSDFMFSDFD  180
RLIDFEFPNS FNHHQNNAGG DSLVPVQTKT EPLPLTNNDH CFDIDFCRSK LSAFTYPSQS  240
```

```
VSHSVSTSSI EYGVVPDGNT NNSVNRSTIT SSTTGGDHQA SSMDREARVL RYREKRKNRK  300
FEKTIRYASR KAYAESRPRI KGRFAKRTET ENDDIFLSHV YASAAHAQYG VVPTF       355

SEQ ID NO: 30          moltype = AA  length = 351
FEATURE                Location/Qualifiers
REGION                 1..351
                       note = misc_feature - Public GI ID no.9759262
REGION                 1..351
                       note = misc_feature - Bit score of 833.0 for hmm based on
                        sequences of FIGURE 2.
REGION                 281..325
                       note = misc_feature - Pfam Name: CCT Pfam Description: CCT
                        motif
REGION                 56..103
                       note = misc_feature - Pfam Name: zf-B_box Pfam Description:
                        B-box zinc finger
REGION                 1..351
                       note = misc_feature - Functional Homolog Of Ceres SEEDLINE
                        ID no. ME04315 at SEQ ID NO. 20
source                 1..351
                       mol_type = protein
                       organism = Arabidopsis thaliana
SEQUENCE: 30
MGFGLESIKS ISGGWGAAAR SCDACKSVTA AVFCRVDSAF LCIACDTRIH SFTRHERVWV  60
CEVCEQAPAA VTCKADAAAL CVSCDADIHS ANPLASRHER VPVETFFDSA ETAVAKISAS  120
STFGILGSST TVDLTAVPVM ADDLGLCPWL LPNDFNEPAK IEIGTENMKG SSDFMFSDFD  180
RLIDFEFPNS FNHHQNNAGG DSLVPVQTKT EPLPLTNNDH CFDIDFCRSK LSAFTYPSQS  240
VSTSSIEYGV VPDGNTNNSV NRSTITSSTT GGDHQASSMD REARVLRYRE KRKNRKFEKT  300
IRYASRKAYA ESRPRIKGRF AKRTETENDD IFLSHVYASA AHAQYGVVPT F           351

SEQ ID NO: 31          moltype = DNA  length = 1428
FEATURE                Location/Qualifiers
misc_feature           1..1428
                       note = Ceres CLONE ID no.463157
misc_feature           1..1428
                       note = Encodes the peptide sequence at SEQ ID NO 32
source                 1..1428
                       mol_type = other DNA
                       organism = Glycine max
SEQUENCE: 31
aactcactca ctcattcaag tcgctaatcc tagttccttc aactcctcgc tggcaacaac  60
agcagtacta ccattagccg cgtttttcaa aagtgatttt cgagaattag cgatgggaat  120
tgaaagagga ggcttcaagg gattcaggag cgcctggagc gtgccgccca agccgtgcga  180
ttcctgcaag ctggcctcgg cggcgctttt ctgccgcccc gattccgcgt ttctctgcat  240
cgcctgcgat tccaacattc actgctcgaa caaactcgcg tcgcgccacg agcgcgtgtg  300
gatgtgtgag gtgtgcgagc aggcacccgc tgctgtcacg tgcaaggccg acgccgccgc  360
cctctgcgtc acgtgtgact ccgacatcca ctccgcgaac cccctcgcgc aacgccacga  420
gcgcgtcccc gtggaacctt tctttgactc cgctgagtcc atagtgaaag cctctgctgc  480
cgccaccttc gggttcattg tcccatccga cgacggcggc gcctccgacg ctttcgcccc  540
cgatgactcc gacgccgccg cgtggctcat cccgaaccct aatttcgggt ccaagctcat  600
ggacgccccc gaaatcaagt ccaaggagat attcttctct gaaatggacc ccttcctcga  660
ttttgattac tcaaactcct tccaaaacaa caacagcgcc ggaaacgaca gcgtcgttcc  720
agttcaaaaa ccctctctcg cccctcccct aatcaataat caccaccacc accaatcaga  780
aacttgcttc gacgtcgatt tttgtcgctc gaagctctcc tcctttaact acccttccaa  840
ttctcttagc caaagcgttt cgtcgtcgtc gcttgatgtt ggagtggtgc cggacgggaa  900
cacggtgtca gacatgtcgt attcttttgg tcggaacagt tcggattcga gtgggattgt  960
tgttgtgtca ggaaatagtg tggggcaagg tgcgacgcag ttgtgtggaa tggatcggga  1020
agcgagggta ctgcgataca gagagaaaag gaagaaccga aaattcgaga agacaattcg  1080
atacgcatcg cgaaaagcat atgcggaaac ccggcccagg ataaaaggcc gcttcgccaa  1140
acgaacagaa attgactcgg atgtggagcg tctctatagc cctggccctg cggtgctcat  1200
gctggacact ccatacggcg tcgtaccatc gttttagtta atttcaaaat gaagaaacga  1260
tggagtgcat gaatcttaga ataatgatta gcgattctgt gggattgtta ggggaaaaag  1320
gtgaagaatc gaatcggtac gaacgtgatt cttagctgga gcgcgatggg ggaagattat  1380
tgtgaagatt tgtctcgatc gaccagaaaa gcccgtttac tttttatg               1428

SEQ ID NO: 32          moltype = AA  length = 374
FEATURE                Location/Qualifiers
REGION                 1..374
                       note = misc_feature - Ceres CLONE ID no.463157
REGION                 1..374
                       note = misc_feature - Bit score of 912.7 for hmm based on
                        sequences of FIGURE 2.
REGION                 302..346
                       note = misc_feature - Pfam Name: CCT Pfam Description: CCT
                        motif
REGION                 60..107
                       note = misc_feature - Pfam Name: zf-B_box Pfam Description:
                        B-box zinc finger
REGION                 1..374
```

-continued

```
                        note = misc_feature - Functional Homolog Of Ceres SEEDLINE
                         ID no. ME04315 at SEQ ID NO. 20
source                  1..374
                        mol_type = protein
                        organism = Glycine max
SEQUENCE: 32
MGIERGGFKG FRSAWSVPPK PCDSCKLASA ALFCRPDSAF LCIACDSNIH CSNKLASRHE  60
RVWMCEVCEQ APAAVTCKAD AAALCVTCDS DIHSANPLAQ RHERVPVEPF FDSAESIVKA  120
SAAATFGFIV PSDDGGASDA FAPDDSDAAA WLIPNPNFGS KLMDAPEIKS KEIFFSEMDP  180
FLDFDYSNSF QNNNSAGNDS VVPVQKPSLA PPLINNHHHH QSETCFDVDF CRSKLSSFNY  240
PSNSLSQSVS SSSLDVGVVP DGNTVSDMSY SFGRNSSDSS GIVVVSGNSV GQGATQLCGM  300
DREARVLRYR EKRKNRKFEK TIRYASRKAY AETRPRIKGR FAKRTEIDSD VERLYSPGPA  360
VLMLDTPYGV VPSF                                                  374

SEQ ID NO: 33           moltype = DNA  length = 1556
FEATURE                 Location/Qualifiers
misc_feature            1..1556
                        note = Ceres CLONE ID no.685991
misc_feature            1..1556
                        note = Encodes the peptide sequence at SEQ ID NO 34
source                  1..1556
                        mol_type = other DNA
                        organism = Triticum aestivum
SEQUENCE: 33
aacttttgct tcgccgtgga agggatcgtc gtagctggct tagcttgctg ctttgcttcc  60
aagtgttgct gctggtggtg ctgtggtagt gtggtgtgag gtgtgatgga gctgcagggg  120
ctggggaggt actggggcgt gggcggcagg aggtgcgggt cgtgccgggg gtcgccggcg  180
gcggtgcact gccggacgtg cgatgggggc agtggggacg gggcgtacct gtgcgcgggc  240
tgtggcgagg ggcacgcgcg ggcggggcac gagagggtgt gggtctgcga ggtgtgcgag  300
ctcgcgccgg ccgcggtcac ctgcaaggcc gacgccgccg cgctctgcgc cgcctgcgac  360
gccgacatcc accacgccaa cccgctcgcg cgccgccacg agcgcgtccc cgtgcagccc  420
atcgggtcct cgtcacccga ggggcaggag caggagcagg atgcgttcgt gatgtcgttc  480
ggcggctcgg tcgacgggga gaagcagcag aaccccgtgg tgaacctgaa cgacgctctg  540
gaggccggcg ccggcgggaa ggagaacgtg aagctggact tcctgttcgc ggacatgatg  600
gaccctttct tcggctccga gctcccgcgc ttcccgcacg ccgacagcgt tgtccccagc  660
ggcggcgcgg tggagctgga cttcggtggc gtcgccgccc ccgtcgtcgt ctccaacccg  720
tcctacagct cctacacggc ggcgtcgctc ggtggaagtg gctcgtcgtc ggaggtcggc  780
ttggtgccgg acgcgatctg tggccgaggc ggcggcatca tcgagctgga cttcgcacag  840
tccaaggccg cgtacctgcc ctacaccccc acaccaagcc acagtaccgt ctcctcggtg  900
gatgttgggt cggtgccgga gcggagcgac agcgccgtcg cggcggcgac gccggcgacg  960
ggggagggga gggaggcgcg tctgatgcgg taccgcgaga agcgcaagaa ccggcggttc  1020
gagaagacca tccggtacgc gtcccggaag gcctacgccg agagcaggcc gcgcgtcaag  1080
ggccgcttcg ccaagcgcgc cgacgacgcg gacaccgacg ccgtcgcggc ggccacgatc  1140
accacgccgg ggccatgcgt gctcgacttc ggcagctacg gcgtcgtgcc caccttctga  1200
ggcggcgcct gatttcgtgt ccatttcctc cggcgagcgt gccggctggg tgcctaatta  1260
aatccggcac cgccatggcc ggcacgagcg cgccgacgtg catgcgtcgt gttccctctt  1320
gtataattgc atgtaatgtt tttcgagctg gctgatcgct ggctggcgtg tagtatactg  1380
taatcaacat gcacgcacgc acgcacgcat gttttgctag aactagaata atacagatag  1440
ttctagttga ctagtctact accctgtacc ctttccctgg gctagcttga tgccaaatta  1500
ggctagggca atgtaacgtg tttgctggaa cagcttagtt ctagttttgg atccgc      1556

SEQ ID NO: 34           moltype = AA  length = 364
FEATURE                 Location/Qualifiers
REGION                  1..364
                        note = misc_feature - Ceres CLONE ID no.685991
REGION                  1..364
                        note = misc_feature - Bit score of 464.6 for hmm based on
                         sequences of FIGURE 2.
REGION                  289..333
                        note = misc_feature - Pfam Name: CCT Pfam Description: CCT
                         motif
REGION                  56..103
                        note = misc_feature - Pfam Name: zf-B_box Pfam Description:
                         B-box zinc finger
REGION                  1..364
                        note = misc_feature - Functional Homolog Of Ceres SEEDLINE
                         ID no. ME04315 at SEQ ID NO. 20
source                  1..364
                        mol_type = protein
                        organism = Triticum aestivum
SEQUENCE: 34
MELQGLGRYW GVGGRRCGSC RGSPAAVHCR TCDGGSGDGA YLCAGCGEGH ARAGHERVWV  60
CEVCELAPAA VTCKADAAAL CAACDADIHH ANPLARRHER VPVQPIGSSS PEGQEQEQDA  120
FVMSFGGSVD GEKQQNPVVN LNDALEAGAG GKENVKLDFL FADMMDPFFG SELPRFPHAD  180
SVVPSGGAVE LDFGGVAAPV VVSNPSYSSY TAASLGGSGS SSEVGLVPDA ICGRGGGIIE  240
LDFAQSKAAY LPYTPTPSHS TVSSVDVGSV PERSDSAVAA ATPATGEGRE ARLMRYREKR  300
KNRRFEKTIR YASRKAYAES RPRVKGRFAK RADDADTDAV AAATITTPGP CVLDFGSYGV  360
VPTF                                                             364
```

-continued

```
SEQ ID NO: 35           moltype = DNA  length = 1442
FEATURE                 Location/Qualifiers
misc_feature            1..1442
                        note = Ceres CLONE ID no.702632
misc_feature            1..1442
                        note = Encodes the peptide sequence at SEQ ID NO 36
source                  1..1442
                        mol_type = other DNA
                        organism = Triticum aestivum
SEQUENCE: 35
acctcagatc aatcactctt ccctcccact actcccaccg cgttcacccg ccattgcctg  60
tcgaagctac gagattagtt actagtatga tggagctgcg caagtactgg ggcgtggggg  120
ggaggaggtg cggggcgtgc gagggggcgg cgccggcggc ggtgcactgc cgggattgcg  180
ccgggtacct gtgcacgggg tgcgacgcgc ggccggcgca cgcgcgggct ggccacgagc  240
gcgtctgggt gtgcgaggtc tgcgaggtca gccccgcggc cgtgacgtgc aaggccgacg  300
ccgccgtgct ctgcgccgtg tgcgacgccg acatccacca cgccaacccg ctcgccgagc  360
gccacgtgcg cgtgcccatc gcgcccatct gctcccccga ggccgccgcg gtggcggccg  420
aggccatgat gttctgtggc gccggtgacg gcgaggcgcg ggcggatcag gacgacgtgc  480
ccgagcagct gcaccaacac ggggggatgc tgaaacctca acgtggaggc cggcaaggag  540
ggccggaaga tggactacct cttctccgac ctcgtcgacc cctacctcgc tgtcgacttt  600
acgcgcttcg cccacgctga cagcgtcgtg cccagcggcg tcgccaccgg cgccgtaccc  660
gccgtcgtgg acctggactt cgcgtgcggg atcggcgcca agccgccggc gacctacagc  720
tcctcgtaca cggccaacgc ctccggcgcg cacagcggct cttcatcgga ggtcagcgtg  780
gtgccggagg ccatctgcgg cggcgtcggg agcttcgaga tcgacttcac ccggcccaag  840
ccgcagccgt acatgcccgc gtacaccgcg gcaccgccga gccatggggt gagcgcgcag  900
caggcgtggc cggtggacat ggggtacttg acggtgccgg agcgtccggt ggcggtgacc  960
ggggagggca gggtggcgag gctgatgcgg taccgggaga agaggaagaa ccgccggttc  1020
gagaagacca tccggtacgc gtccaggaag gcctacgccg agtcgcggcc gcgcgtcaag  1080
ggccgcttcg ccaagcgcac cgaccaggac gccgacggcg acgacgtgga cgcggaggcc  1140
catgccgtgc cgtcttccac gtcctacttg ctcgactttg gctacggcgt cgtgccgtcc  1200
ttctgatccg ccggcccggc gccccggccg gcggccttgt acttgtacca ttgatgcatg  1260
tacagtagta cgtaggggac tagtaatcca tccatgtact cctcctgagc tagttcgatc  1320
gcgcttttga tgtactagta atactgtaaa ctgtaacagt agtagtactt tggccaatat  1380
gctcgtttat ttttggatgg ccgaaactag tagcccaaac atttggatca tcaatcatta  1440
tt                                                                 1442

SEQ ID NO: 36           moltype = AA  length = 372
FEATURE                 Location/Qualifiers
REGION                  1..372
                        note = misc_feature - Ceres CLONE ID no.702632
REGION                  1..372
                        note = misc_feature - Bit score of 497.8 for hmm based on
                         sequences of FIGURE 2.
REGION                  295..339
                        note = misc_feature - Pfam Name: CCT Pfam Description: CCT
                         motif
REGION                  51..98
                        note = misc_feature - Pfam Name: zf-B_box Pfam Description:
                         B-box zinc finger
REGION                  1..372
                        note = misc_feature - Functional Homolog Of Ceres SEEDLINE
                         ID no. ME04315 at SEQ ID NO. 20
source                  1..372
                        mol_type = protein
                        organism = Triticum aestivum
SEQUENCE: 36
MMELRKYWGV GGRRCGACEG AAPAAVHCRD CAGYLCTGCD ARPAHARAGH ERVWVCEVCE  60
VSPAAVTCKA DAAVLCAVCD ADIHHANPLA ERHVRVPIAP ICSPEAAAVA AEAMMFCGAG  120
DGEARADQDD VPEQLHQHGG MLNLNVEAGK EGRKMDYLFS DLVDPYLAVD FTRFAHADSV  180
VPSGVATGAV PAVVDLDFAC GIGAKPPATY SSSYTANASG AHSGSSSEVS VVPEAICGGV  240
GSFEIDFTRP KPQPYMPAYT AAPPSHGVSA QQAWPVDMGY LTVPERPVAV TGEGRVARLM  300
RYREKRKNRR FEKTIRYASR KAYAESRPRV KGRFAKRTDQ DADGDDVDAE AHAVPSSTSY  360
LLDFGYGVVP SF                                                      372

SEQ ID NO: 37           moltype = DNA  length = 1345
FEATURE                 Location/Qualifiers
misc_feature            1..1345
                        note = Ceres CLONE ID no.1559496
misc_feature            1..1345
                        note = Encodes the peptide sequence at SEQ ID NO 38
source                  1..1345
                        mol_type = other DNA
                        organism = Zea mays
SEQUENCE: 37
ctgacacccg tggcatccct ctcgtgactc ccggagcgga ggcatggaca ccgcggcgga  60
gctggagctg gggctggagt tggagcagaa gccggcggcg gggtactgga gcgtggtggg  120
cgcgcgccct tgcgacgcgt gcgccgcgga gccggcgcgg ctgcactgcc gcgcggacgg  180
cgcgttcctg tgccccggct gcgacgcccg ggcgcacggc gccgggtcgc gccacgcgcg  240
cgtctggctg tgcgaggtct gcgagcacgc ccccgccgtc gtcacctgcc gcgccgacgc  300
```

-continued

```
cgccgcgctc tgcgccgcct gcgacgccga catccactcg gccaacccgc tcgcgcgccg  360
ccacgagcgc ctccccatcg cccctctctt cggcgcgctc gcggacgcgc cgcagccctt  420
cccgtccccg gccctcgctg ccgccgcggg ggccgaggcc ccggccccga ccccggctca  480
gggtgaagcg gtggcggaag actacgggag cagcgaggcc gaggcggcgt cgtggttgct  540
ccccgagccc gacaacagcc acgaggacag cgccgccgac acgttcttcg cggagtcgga  600
cgcgtacctc ggcgccgacc tcgacttcgc ccggtgcatg gacggcgtca aggccatcgg  660
cgtgccggtc gcgccgcccg agctggacat cggtgccggc agcttttgct accccgaaca  720
ctccatgaac cacattttgt cgtcatcctc ggaggtggcg gtggtaccgg acgcgcaggc  780
ggccggtctg ccggtggtgg tggtggtgag cagaggggag gagcgggagg cgcggctgat  840
gcggtaccgt gagaagcgca agaaccgccg gttcgacaag accatccgct acgcgtcccg  900
caaggcgtac gccgagacgc ggccgcgcat caagggccgc ttcgccaagc gccgttccgc  960
ggagggcgag gacgaggcgc tggagcacga ggaagggcg tgcttctcgc ccgcggggtc  1020
ggcgcccgcc gcgtcggacg gcgtcgtccc gtccttgtgt tgaggggaga agacgacgac  1080
gaccccggca gacggctgct taactttgcc agctctgtcg accctgaacc ttttttttt  1140
ccctccccca ccttctctct tttgatcgag gggttgccag ctctggatct gaaactctga  1200
acgcatggga cgcgagctgt gtgtagcatg aataactgcg tagtttgttg gatggacgaa  1260
ctcaatcgcg ctcgcatgga atggaactct tgtaatccac cctttgtaca ttaccatcta  1320
gagttgctcc ttttttccat gagcc                                    1345
```

```
SEQ ID NO: 38          moltype = AA  length = 339
FEATURE                Location/Qualifiers
REGION                 1..339
                       note = misc_feature - Ceres CLONE ID no.1559496
REGION                 1..339
                       note = misc_feature - Bit score of 612.0 for hmm based on
                        sequences of FIGURE 2.
REGION                 261..305
                       note = misc_feature - Pfam Name: CCT Pfam Description: CCT
                        motif
REGION                 70..112
                       note = misc_feature - Pfam Name: zf-B_box Pfam Description:
                        B-box zinc finger
REGION                 1..339
                       note = misc_feature - Functional Homolog Of Ceres SEEDLINE
                        ID no. ME04315 at SEQ ID NO. 20
source                 1..339
                       mol_type = protein
                       organism = Zea mays
SEQUENCE: 38
MDTAAELELG LELEQKPAAG YWSVVGARPC DACAAEPARL HCRADGAFLC PGCDARAHGA  60
GSRHARVWLC EVCEHAPAVV TCRADAAALC AACDADIHSA NPLARRHERL PIAPLFGALA  120
DAPQPFPSPA LAAAAGAEAP APTPAQGEAV AEDYGSSEAE AASWLLPEPD NSHEDSAADT  180
FFAESDAYLG ADLDFARCMD GVKAIGVPVA PPELDIGAGS FCYPEHSMNH ILSSSSEVAV  240
VPDAQAAGLP VVVVVSRGEE REARLMRYRE KRKNRRFDKT IRYASRKAYA ETRPRIKGRF  300
AKRRSAEGED EALEHEEGAC FSPAGSAPAA SDGVVPSLC                     339
```

```
SEQ ID NO: 39          moltype = DNA  length = 1490
FEATURE                Location/Qualifiers
misc_feature           1..1490
                       note = Ceres CLONE ID no.1674443
misc_feature           1..1490
                       note = Encodes the peptide sequence at SEQ ID NO 40
source                 1..1490
                       mol_type = other DNA
                       organism = Zea mays
SEQUENCE: 39
gctgcgctgc ctccctccac tactacgcca gccactctgc cttccctccc ccaccaccac  60
aagaaccgct tcaccattgc cgcgccgcgt ccagctgagc ctcctcttag ccgcgccagc  120
caggagaagg cgcgcgcgca cacctgctgc ttggtgaccg cgttcgatgg agctgcacaa  180
gtactggggc gtggggggcc ggcggtgcgg cagctgcgag ggggccccgg cggcggtgca  240
ctgccgcacg tgcgttggtg gatccttcct ctgcacgacg tgcgacgccc gccccgcgca  300
cgcgcgcctg ggccacgagc gcgtgtggat gtgcgaggtc tgcgagctgg cccccgccgc  360
cgtcacgtgc aaggccgacg ccgccgtgct ctgcgccgct tgcgactccg acatccacga  420
cgccaacccg ctggcccggc gccacgcgcg ggtccccgtc gcccccatcg gctccgaggc  480
cgccgccgcg gccgtggagg ccatgctgtt cgggaccggc gaggcggccg cttccgaggc  540
cgacgagcag cacgcggcgg ccgagcacgc gcacgcgcac gcgctgaacc tcaacgtgga  600
ggccaaggac atgaagctgg actacctctt ctctgaactg gatccctacc tcagcgtcga  660
gatcccgcgc ttccagcacg ctgacagcgt cgtccccaac ggcgccggcg ctgccgtcga  720
gctggacttc acgtgcggca tcggcgttaa gcactcctcc tacagctcct acacggccac  780
ctccctcgct catagcggct cctcgtcgga ggttggcgtg gtgccagagg ccttcggcgg  840
cagcggcagc ggcggcggga gctttgagct cgacttcaca aggcccaagc ctcaggccta  900
catgccatac accgggactc cccagagcca cagcgtgcca tccgcggacg tggaggtggt  960
gccggagcgg ggagacttgg ctgcggtgag gccggtgccg ctgatggggg agagcaggga  1020
ggcgcgcctg atgcggtacc gtgagaaaag gaagaacagg cgcttcgaga agaccatccg  1080
gtacgcgtcc cggaaggcct acgccgagac gcggccgcga atcaagggcc ggtttgccaa  1140
gcgtgctgac cacgacgggg acgccgacgc cgacgacgct gaggccgagg ccgaggccga  1200
ggccgccgtg ccgatgtcat atgtgctcga cttcggctac ggcgtcgtac cgagcttttg  1260
atgtgcccgg gcccaacacg cgcgcacatg gccggccgcg cgcttgaacc ggcatggcac  1320
gccgctgcgc gcgcgccttg tacttgtatc gatcgatgta tagggaggag tagtaatccc  1380
```

-continued

```
atgtactctc tttttgagca agctcttgcg taaactagtg atgtataatt tgtactacta  1440
gtaagaaact gcagtagccg ctgctaatgg atcaccaatc tataccgcgc            1490

SEQ ID NO: 40          moltype = AA  length = 364
FEATURE                Location/Qualifiers
REGION                 1..364
                       note = misc_feature - Ceres CLONE ID no.1674443
REGION                 1..364
                       note = misc_feature - Bit score of 815.7 for hmm based on
                        sequences of FIGURE 2.
REGION                 284..328
                       note = misc_feature - Pfam Name: CCT Pfam Description: CCT
                        motif
REGION                 51..98
                       note = misc_feature - Pfam Name: zf-B_box Pfam Description:
                        B-box zinc finger
REGION                 1..364
                       note = misc_feature - Functional Homolog Of Ceres SEEDLINE
                        ID no. ME04315 at SEQ ID NO. 20
source                 1..364
                       mol_type = protein
                       organism = Zea mays
SEQUENCE: 40
MELHKYWGVG GRRCGSCEGA PAAVHCRTCV GGSFLCTTCD ARPAHARLGH ERVWMCEVCE  60
LAPAAVTCKA DAAVLCAACD SDIHDANPLA RRHARVPVAP IGSEAAAAAV EAMLFGTGEA  120
AASEADEQHA AAEHAHAHAL NLNVEAKDMK LDYLFSELDP YLSVEIPRFQ HADSVVPNGA  180
GAAVELDFTC GIGVKHSSYS SYTATSLAHS GSSSEVGVVP EAFGGSGSGG GSFELDFTRP  240
KPQAYMPYTG TPQSHSVPSA DVEVVPERGD LAAVRPVPLM GESREARLMR YREKRKNRRF  300
EKTIRYASRK AYAETRPRIK GRFAKRADHD GDADADDAEA EAEAEAAVPM SYVLDFGYGV  360
VPSF                                                              364

SEQ ID NO: 41          moltype = DNA  length = 1449
FEATURE                Location/Qualifiers
misc_feature           1..1449
                       note = Ceres CLONE ID no.1828897
misc_feature           1..1449
                       note = Encodes the peptide sequence at SEQ ID NO 42
source                 1..1449
                       mol_type = other DNA
                       organism = Panicum virgatum
SEQUENCE: 41
gcgcgcgctc cctcccctcc cctcctccca ccagcccacc accaccacaa gcaccgcgtc  60
gtccacacca cctgccattg ccgcgccgag ctcagcctct agctgcgcca ggagggcgcc  120
cgcctccctc cctgccgacg ccggtgtgat ggagctgcac aagtactggg gcgtgggggg  180
ccgccggtgc ggcggctgcg aggcggcccc ggcggcggtg cactgccgct cgtgccccgc  240
cgggggcgcg ttcctctgca cggcgtgcga cgcgcgcccg gggcacgcgc atctgggcca  300
cgagcgcgtg tggatgtgcg aggtctgcga gctggcgccc gccgccgtca cgtgcaaggc  360
cgacgccgcc gtgctctgcg ccgcctgcga cgccgacatc cacgacgcca acccgctggc  420
gcgccgccac gcacgcgtcc ccgtcgcgcc catcggctcg gaggccgcgg ccgccgccgt  480
ggaggccatg ctgttcggga ccggcgagcc ggccgcgtcc gaggccgagg agccgcagaa  540
cgcggcggcc gggcacaacc accagcacgc gctgaacctc aacgtggagg ccaaggacat  600
gaagctggac tacctctttt ccgacctgga cccctacctc agcgtcgata tcccgcgctt  660
ccagcacgcc gacagcgtcg tccccagcgg cgtcggcgcc ggagcagccg gcgccgtcga  720
gctggacttc acgtgcggca tcggcgtcga gccctccggg gggggggggg ggggggggac  780
atccctcgcc cacagcggct cctcttctga ggtcggcgtg gtgccagagg ccttctgcgg  840
cggggggggg agcttcgagc tcgacttcac aaggcccaag cctcaagcct acatgccgta  900
caccgcgact cctcagagtc acagcgtgtc gtcggtggac gtggaggtgg tgccggagcg  960
gggggacatg atggcggcgg cgaggccggt gccgctggtg ggggagagcc gggaggcgcg  1020
gctgatgcgc taccgggaga agcggaagaa ccggcggttc gagaagacca tccggtacgc  1080
gtcccggaag gcctacgccg agatgcggcc gcggatcaag ggccggttcg ccaagcgcgc  1140
cgaccacgac gccgacgccg acgacgccga ggccgaggcc gaggccgccg tgccgtcgcc  1200
ggcgtcgtac gtgctcgact tcggctacgg cgtcgtgccc agcttctgat cgacgacgat  1260
cgtctcgctc gttccacgcg cggcgcgctt gacccggcac cggcgcgcgc gccttgtact  1320
tgtatcgatg catgtatagg ggaggaatag taatcccatg tactctcgtc ttggagctgc  1380
gctagccctg cgtacgtacg ctagtgatgt ataatttgta caacccagta ttttgccctg  1440
tacccgctc                                                         1449

SEQ ID NO: 42          moltype = AA  length = 366
FEATURE                Location/Qualifiers
REGION                 1..366
                       note = misc_feature - Ceres CLONE ID no.1828897
REGION                 1..366
                       note = misc_feature - Bit score of 667.9 for hmm based on
                        sequences of FIGURE 2.
REGION                 288..332
                       note = misc_feature - Pfam Name: CCT Pfam Description: CCT
                        motif
REGION                 52..99
                       note = misc_feature - Pfam Name: zf-B_box Pfam Description:
```

```
                        B-box zinc finger
REGION                  1..366
                        note = misc_feature - Functional Homolog Of Ceres SEEDLINE
                         ID no. ME04315 at SEQ ID NO. 20
source                  1..366
                        mol_type = protein
                        organism = Panicum virgatum
SEQUENCE: 42
MELHKYWGVG GRRCGGCEAA PAAVHCRSCP AGGAFLCTAC DARPGHAHLG HERVWMCEVC  60
ELAPAAVTCK ADAAVLCAAC DADIHDANPL ARRHARVPVA PIGSEAAAAA VEAMLFGTGE  120
PAASEAEEPQ NAAAGHNHQH ALNLNVEAKD MKLDYLFSDL DPYLSVDIPR FQHADSVVPS  180
GVGAGAAGAV ELDFTCGIGV EPSGGGGGGG TSLAHSGSSS EVGVVPEAFC GGGGSFELDF  240
TRPKPQAYMP YTATPQSHSV SSVDVEVVPE RGDMMAAARP VPLVGESREA RLMRYREKRK  300
NRRFEKTIRY ASRKAYAEMR PRIKGRFAKR ADHDADADDA EAEAEAAVPS PASYVLDFGY  360
GVVPSF                                                            366

SEQ ID NO: 43           moltype = AA  length = 332
FEATURE                 Location/Qualifiers
REGION                  1..332
                        note = misc_feature - Public GI ID no.125540249
REGION                  1..332
                        note = misc_feature - Bit score of 624.0 for hmm based on
                         sequences of FIGURE 2.
REGION                  261..305
                        note = misc_feature - Pfam Name: CCT Pfam Description: CCT
                         motif
REGION                  72..114
                        note = misc_feature - Pfam Name: zf-B_box Pfam Description:
                         B-box zinc finger
REGION                  1..332
                        note = misc_feature - Functional Homolog Of Ceres SEEDLINE
                         ID no. ME04315 at SEQ ID NO. 20
source                  1..332
                        mol_type = protein
                        note = subspecies = indica
                        organism = Oryza sativa
SEQUENCE: 43
MEAVEDKAMV GVGGAVAAGY SSSSWGLGTR ACDSCGGEAA RLYCRADGAF LCARCDARAH  60
GAGSRHARVW LCEVCEHAPA AVTCRADAAA LCAACDADIH SANPLARRHE RLPVAPFFGP  120
LADAPQPFTF SQAAADAAGA REEDADDDRS NEAEAASWLL PEPDDNSHED SAAAADAFFA  180
DTGAYLGVDL DFARSMDGIK AIGVPVAPPE LDLTAGSLFY PEHSMAHSLS SSEVAIVPDA  240
LSAGAAAPPM VVVVASKGKE REARLMRYRE KRKNRRFDKT IRYASRKAYA ETRPRIKGRF  300
AKRTADADDD DEAPCSPAFS ALAASDGVVP SF                               332

SEQ ID NO: 44           moltype = AA  length = 331
FEATURE                 Location/Qualifiers
REGION                  1..331
                        note = misc_feature - Public GI ID no.116310719
REGION                  1..331
                        note = misc_feature - Bit score of 733.5 for hmm based on
                         sequences of FIGURE 2.
REGION                  239..283
                        note = misc_feature - Pfam Name: CCT Pfam Description: CCT
                         motif
REGION                  62..104
                        note = misc_feature - Pfam Name: zf-B_box Pfam Description:
                         B-box zinc finger
REGION                  1..331
                        note = misc_feature - Functional Homolog Of Ceres SEEDLINE
                         ID no. ME04315 at SEQ ID NO. 20
source                  1..331
                        mol_type = protein
                        note = subspecies = indica
                        organism = Oryza sativa
SEQUENCE: 44
MEGDDKSAVV GGAYWGLAAR ACDACGGEAA RLFCRADAAF LCAGCDARAH GPGSRHARVW  60
LCEVCEHAPA AVTCRADAAA LCAACDADIH SANPLARRHE RLPVAPFFGA LADAPKPGSG  120
AHGGDAAAAD DDGSNDAEAA SWLLPEPDHG QKDGAVGATD ELYADSDPYL DLDFARSMDD  180
IKAIGVQNGP PELDITGGKL FYSDHSMNHS VSSSEAAVVP DAAAGGGAPM PVVSRGRERE  240
ARLMRYREKR KSRRFEKTIR YASRKAYAET RPRIKGRFAK RTKGGAGADA DADADGEDEE  300
MYSSAAAAVA ALMAPGGSDA DYGVDGVVPT F                                331

SEQ ID NO: 45           moltype = AA  length = 370
FEATURE                 Location/Qualifiers
REGION                  1..370
                        note = misc_feature - Public GI ID no.125556324
REGION                  1..370
                        note = misc_feature - Bit score of 608.3 for hmm based on
                         sequences of FIGURE 2.
```

-continued

```
REGION                 294..338
                       note = misc_feature - Pfam Name: CCT Pfam Description: CCT
                        motif
REGION                 50..97
                       note = misc_feature - Pfam Name: zf-B_box Pfam Description:
                        B-box zinc finger
REGION                 1..370
                       note = misc_feature - Functional Homolog Of Ceres SEEDLINE
                        ID no. ME04315 at SEQ ID NO. 20
source                 1..370
                       mol_type = protein
                       note = subspecies = indica
                       organism = Oryza sativa
SEQUENCE: 45
MELRKYWGVG GRRCGACEAS PAAVHCRGCG GVYLCTACDA RPGHARAAHE RVWVCEVCEV  60
APAAVTCKAD AAVLCAACDA DIHDANPLAR RHARVPVAPI GSAAAAAVAA EAMLFGVAAA  120
GAEAEAVEEK AAAEHHHHQQ RQQHGALNLN VEAKDMKLDY LFSDLDPYLN VEFARFPHAD  180
SVVPNGAGAG AAIELDFTCG LGVGVGGAKQ SYSSYTATDL AHSGSSSEVG VVPEAMCGGG  240
GAIDLDFTRP KPQPYMPYTA TPPPSHSVVS AQMSSSVVDV GVVPERAAAM GEGREARLMR  300
YREKRKNRRF EKTIRYASRK AYAETRPRIK GRFAKRADHD ADDADADADD PAAVPSSYML  360
DFGYGVVPSF                                                         370

SEQ ID NO: 46          moltype = AA  length = 347
FEATURE                Location/Qualifiers
REGION                 1..347
                       note = misc_feature - Public GI ID no.125538317
REGION                 1..347
                       note = misc_feature - Bit score of 444.3 for hmm based on
                        sequences of FIGURE 2.
REGION                 279..323
                       note = misc_feature - Pfam Name: CCT Pfam Description: CCT
                        motif
REGION                 55..102
                       note = misc_feature - Pfam Name: zf-B_box Pfam Description:
                        B-box zinc finger
REGION                 1..347
                       note = misc_feature - Functional Homolog Of Ceres SEEDLINE
                        ID no. ME04315 at SEQ ID NO. 20
source                 1..347
                       mol_type = protein
                       note = subspecies = indica
                       organism = Oryza sativa
SEQUENCE: 46
MELGLGRYWG VGGRRCGACA VAPAAVHCRT CDGGGGGGGY LCAGCDAEHG RAGHERVWVC  60
EVCELAPAAV TCKADAAALC AACDSDIHDA NPLARRHERV PGHPIGSSAA PPPDALLLGG  120
ENDAAAAVDG GGGGKEVKLD FLFADFMDPY LGGSPELARF PHADSVVPNH NGSAGPAMEL  180
GFAGGGGAAV KPSYSSYTAA SLGNSGSSSE VGLVPDAICG GGGGGIIELD FAQSKAAYLP  240
YASTPSHSMS SSMDMGVAAP EMSDGAAAAA GRAYAAEGRA ARLMRYREKR KNRRFEKTIR  300
YASRKAYAET RPRVKGRFAK RADDHDAAAP PPQIMLDFAG YGVVPTF                347

SEQ ID NO: 47          moltype = AA  length = 332
FEATURE                Location/Qualifiers
REGION                 1..332
                       note = misc_feature - Public GI ID no.115447239
REGION                 1..332
                       note = misc_feature - Bit score of 623.8 for hmm based on
                        sequences of FIGURE 2.
REGION                 261..305
                       note = misc_feature - Pfam Name: CCT Pfam Description: CCT
                        motif
REGION                 72..114
                       note = misc_feature - Pfam Name: zf-B_box Pfam Description:
                        B-box zinc finger
REGION                 1..332
                       note = misc_feature - Functional Homolog Of Ceres SEEDLINE
                        ID no. ME04315 at SEQ ID NO. 20
source                 1..332
                       mol_type = protein
                       note = subspecies = japonica
                       organism = Oryza sativa
SEQUENCE: 47
MEAVEDKAMV GVGGAVAAGY SSSSWGLGTR ACDSCGGEAA RLYCRADGAF LCARCDARAH  60
GAGSRHARVW LCEVCEHAPA AVTCRADAAA LCAACDADIH SANPLARRHE RLPVAPFFGP  120
LADAPQPFPF SQAAADAAAA REEDADDDRS NEAEAASWLL PEPDDNSHED SAAAADAFFA  180
DTGAYLGVDL DFARSMDGIK AIGVPVAPPE LDLTAGSLFY PEHSMAHSLS SSEVAIVPDA  240
LSAGSAAPPM VVVVASKGKE REARLMRYRE KRKNRRFDKT IRYASRKAYA ETRPRIKGRF  300
AKRTADADDD DEAPCSPAFS ALAASDGVVP SF                                332

SEQ ID NO: 48          moltype = AA  length = 333
```

-continued

```
FEATURE                Location/Qualifiers
REGION                 1..333
                       note = misc_feature - Public GI ID no.115459216
REGION                 1..333
                       note = misc_feature - Bit score of 726.7 for hmm based on
                        sequences of FIGURE 2.
REGION                 239..283
                       note = misc_feature - Pfam Name: CCT Pfam Description: CCT
                        motif
REGION                 62..104
                       note = misc_feature - Pfam Name: zf-B_box Pfam Description:
                        B-box zinc finger
REGION                 1..333
                       note = misc_feature - Functional Homolog Of Ceres SEEDLINE
                        ID no. ME04315 at SEQ ID NO. 20
source                 1..333
                       mol_type = protein
                       note = subspecies = japonica
                       organism = Oryza sativa
SEQUENCE: 48
MEGDDKSAVV GGAYWGLAAR ACDACGGEAA RLFCRADAAF LCAGCDARAH GPGSRHARVW  60
LCEVCEHAPA AVTCRADAAA LCAACDADIH SANPLARRHE RLPVAPFFGA LADAPKPGSG  120
AHGGDAAAAD DDGSNDAEAA SWLLPEPDHG QKDGAVGATD ELYADSDPYL DLDFARSMDD  180
IKAIGVQNGP PELDITGGKL FYSDHSMNHS VSSSEAAVVP DAAAGGGAPM PVVSRGRERE  240
ARLMRYREKR KSRRFEKTIR YASRKAYAET RPRIKGRFAK RTKGGAGADA DADADADGED  300
EEMYSSAAAA VAALMAPGGS DADYGVDGVV PTF                               333

SEQ ID NO: 49          moltype = AA  length = 370
FEATURE                Location/Qualifiers
REGION                 1..370
                       note = misc_feature - Public GI ID no.115469296
REGION                 1..370
                       note = misc_feature - Bit score of 607.4 for hmm based on
                        sequences of FIGURE 2.
REGION                 294..338
                       note = misc_feature - Pfam Name: CCT Pfam Description: CCT
                        motif
REGION                 50..97
                       note = misc_feature - Pfam Name: zf-B_box Pfam Description:
                        B-box zinc finger
REGION                 1..370
                       note = misc_feature - Functional Homolog Of Ceres SEEDLINE
                        ID no. ME04315 at SEQ ID NO. 20
source                 1..370
                       mol_type = protein
                       note = subspecies = japonica
                       organism = Oryza sativa
SEQUENCE: 49
MELRKYWGVG GRRCGACEAS PAAVHCRGCG GVYLCTACDA RPGHARAAHE RVWVCEVCEV  60
APAAVTCKAD AAVLCAACDA DIHDANPLAR RHARVPVAPI GSAAAAAVAA EAMLFGVAAA  120
GAEAEAVEDK AAAEHHHHQQ RQQHGALNLN VEAKDMKLDY LFSDLDPYLN VEFARFPHAD  180
SVVPNGAGAG AAIELDFTCG LGVGVGGAKQ SYSSYTATDL AHSGSSSEVG VVPEAMCGGG  240
GAIDLDFTRP KPQPYMPYTA TPPPSHSVVS AQMSSSVVDV GVVPERAAAM GEGREARLMR  300
YREKRKNRRF EKTIRYASRK AYAETRPRIK GRFAKRADHD ADDADADADD PAAVPSSYML  360
DFGYGVVPSF                                                         370

SEQ ID NO: 50          moltype = AA  length = 332
FEATURE                Location/Qualifiers
REGION                 1..332
                       note = misc_feature - Public GI ID no.125582846
REGION                 1..332
                       note = misc_feature - Bit score of 505.9 for hmm based on
                        sequences of FIGURE 2.
REGION                 261..305
                       note = misc_feature - Pfam Name: CCT Pfam Description: CCT
                        motif
REGION                 27..71
                       note = misc_feature - Pfam Name: zf-B_box Pfam Description:
                        B-box zinc finger
REGION                 1..332
                       note = misc_feature - Functional Homolog Of Ceres SEEDLINE
                        ID no. ME04315 at SEQ ID NO. 20
source                 1..332
                       mol_type = protein
                       note = subspecies = japonica
                       organism = Oryza sativa
SEQUENCE: 50
MEAVEDKAMV GVGGAVAAGY SSSSWGLGTR ACDSCGGEAA RLYCRADGAF LCARCDARAH  60
GAGSRHARVW LCEVCEHAPA RRHVPGGRRG AVRRLRRRHH SANPLARRHE RLPVAPFFGP  120
```

-continued

```
LADAPQPFPF SQAAADAAAA REEDADDDRS NEAEAASWLL PEPDDNSHED SAAAADAFFA  180
DTGAYLGVDL DFARSMDGIK AIGVPVAPPE LDLTAGSLFY PEHSMAHSLS SSEVAIVPDA  240
LSAGSAAPPM VVVVASKGKE REARLMRYRE KRKNRRFDKT IRYASRKAYA ETRPRIKGRF  300
AKRTADADDD DEAPCSPAFS ALAASDGVVP SF                                332

SEQ ID NO: 51          moltype = AA  length = 375
FEATURE                Location/Qualifiers
REGION                 1..375
                       note = misc_feature - Public GI ID no.92875402
REGION                 1..375
                       note = misc_feature - Bit score of 812.8 for hmm based on
                        sequences of FIGURE 2.
REGION                 298..342
                       note = misc_feature - Pfam Name: CCT Pfam Description: CCT
                        motif
REGION                 60..107
                       note = misc_feature - Pfam Name: zf-B_box Pfam Description:
                        B-box zinc finger
REGION                 1..375
                       note = misc_feature - Functional Homolog Of Ceres SEEDLINE
                        ID no. ME04315 at SEQ ID NO. 20
source                 1..375
                       mol_type = protein
                       organism = Medicago truncatula
SEQUENCE: 51
MGIERGGLKS LRGGWSVPPK LCDSCKLTPA ALFCRSDSAF LCINCDSTIH SANKLSSRHE  60
RVWMCEVCEQ APASVTCKAD AAALCVTCDS DIHSANPLAR RHERVPVEPF FDSAESVVKS  120
SSAAAAAAAS FNFVVPTDDG YGQDDAEAAA WLIPNPNFGS KLNETQDIKT REMFFSDMDP  180
FLDFDYSNNF QNNNCSNAMN DSVVPVQTKP TPAPMMNHNS EGCFDIDFCR SKLSSFNYPS  240
HSISHSVSSS SLDVGVVPDG NTVSEISYNF GSESMVSGGV NSSNQGVQGA TQLCGMDREA  300
RVMRYREKRK NRKFEKTIRY ASRKAYAETR PRIKGRFAKR TEIDSDVDRL YNPADPLSVP  360
SSMLMDCPYG VVPTF                                                   375

SEQ ID NO: 52          moltype = AA  length = 307
FEATURE                Location/Qualifiers
REGION                 1..307
                       note = misc_feature - Public GI ID no.3341723
REGION                 1..307
                       note = misc_feature - Bit score of 395.2 for hmm based on
                        sequences of FIGURE 2.
REGION                 1..48
                       note = misc_feature - Pfam Name: zf-B_box Pfam Description:
                        B-box zinc finger
REGION                 241..285
                       note = misc_feature - Pfam Name: CCT Pfam Description: CCT
                        motif
REGION                 1..307
                       note = misc_feature - Functional Homolog Of Ceres SEEDLINE
                        ID no. ME04315 at SEQ ID NO. 20
source                 1..307
                       mol_type = protein
                       organism = Raphanus sativus
SEQUENCE: 52
MASRLCDSCR SAAATLYCRA DAAFLCGECD GKIHTANKLA SRHERVLLCQ ICEQAPAHVT  60
CEADAAALCV TCDRDIHSAN PLSRRHERVS VTPFYDAPAQ GGSPATTKSA ASSNLFGEDA  120
DVSMEAVSWL LPNPSVKEGV VVEIPNLFAD LDYSAVDPKM EASENSSGND GVVPVQTKAL  180
FLNEDYFNFD VSASKTTFPH GYSCINQTVS STSLEVPLVP EGGAVTTTNA TPAVQLSPAE  240
REARVLRYRE KRKNRKFEKT IRYASRKAYA EVRPRIKGRF AKRTDSRVND GGGDVGVYGG  300
FGVVPSF                                                            307

SEQ ID NO: 53          moltype = AA  length = 329
FEATURE                Location/Qualifiers
REGION                 1..329
                       note = misc_feature - Public GI ID no.4091806
REGION                 1..329
                       note = misc_feature - Bit score of 506.4 for hmm based on
                        sequences of FIGURE 2.
REGION                 1..48
                       note = misc_feature - Pfam Name: zf-B_box Pfam Description:
                        B-box zinc finger
REGION                 268..312
                       note = misc_feature - Pfam Name: CCT Pfam Description: CCT
                        motif
REGION                 1..329
                       note = misc_feature - Functional Homolog Of Ceres SEEDLINE
                        ID no. ME04315 at SEQ ID NO. 20
source                 1..329
                       mol_type = protein
                       organism = Malus x domestica
```

-continued

```
SEQUENCE: 53
MASKLCDSCQ SATATLFCRA DSAFLCVNCD SKIHAANKLA SRHPRVWLCE VCEQAPAHVT  60
CKADDAALCV TCDRDIHSAN PLSSRHDRVP VTPFYDSVNS AANSVPVVKS VVNFLDDRYL  120
SDVDGETEVS REEAEAASWL LPNPKAMENP DLNSGQYLFQ EMDPYLDLDY GHVDPKLEEA  180
QEQNSCGADG VVPVQSKNMQ PLLVNDQSFE LDFSAGSKPF VYGYHHARCL SQSVSSSSMD  240
ISVVPDGNAV TAAVETSQPA VQLSSVDRVA RVLRYREKRK NRKFEKTIRY ASRKAYAETR  300
PRIKGRFAKR TEVEIEAERM CRYGVVPSF                                   329

SEQ ID NO: 54           moltype = AA  length = 312
FEATURE                 Location/Qualifiers
REGION                  1..312
                        note = misc_feature - Public GI ID no.60459257
REGION                  1..312
                        note = misc_feature - Bit score of 400.3 for hmm based on
                         sequences of FIGURE 2.
REGION                  1..48
                        note = misc_feature - Pfam Name: zf-B_box Pfam Description:
                         B-box zinc finger
REGION                  245..289
                        note = misc_feature - Pfam Name: CCT Pfam Description: CCT
                         motif
REGION                  1..312
                        note = misc_feature - Functional Homolog Of Ceres SEEDLINE
                         ID no. ME04315 at SEQ ID NO. 20
source                  1..312
                        mol_type = protein
                        organism = Pisum sativum
SEQUENCE: 54
MATKLCDSCK STKATLFCRS DSAFLCITCD SNIQAANKLA SRHHRVTLCE VCEQAPAHVT  60
CKADAAALCV SCDHDIHSAN PPASRHERIP LNTFHHNSKQ QFFSESDPDA DVSTEEAEAA  120
SWLLQTPANP KGPDLNSSHY SFTEIDATDL NFVCVDAKTD SPEQHSPGTA DGVVPVQSHS  180
KTVTEHYSDI NNDFSTSKPF TYNYNHSVSS SSLEVGVVPD GNVMSEMSYC GYGRTEAVQI  240
TAADREARVM RYREKRKNRR FEKTIRYASR KAYAETRPRI KGRFAKRTDL NMNVNLIGED  300
ESYDGYGVVP SC                                                     312

SEQ ID NO: 55           moltype = DNA  length = 1283
FEATURE                 Location/Qualifiers
misc_feature            1..1283
                        note = Ceres CLONE ID no.1756710
misc_feature            1..1283
                        note = Encodes the peptide sequence at SEQ ID NO 56
source                  1..1283
                        mol_type = other DNA
                        organism = Panicum virgatum
SEQUENCE: 55
agcagccact acaagctgcc gtgccgagtg agctagtgag cgagcgagct cccggcgcgc  60
gatggagggt gacaagaagt cggcgggcgg ggccccggcc tactggggcc tgggcgcgcg  120
gccctgcgac gagtgcggcg ccgaggcggc gcggctctac tgccgcgcgg acgcggcgtt  180
cctctgcgcc gggtgcgacg cgcgcgcgca cggcgccggg tcgcgccacg cccgcgtctg  240
gctgtgcgag gtctgcgagc acgcgccggc cgccgtcacg tgccgcgcgg acgccgccgc  300
gctctgcgcc tcctgcgacg ccgacatcca ctccgccaac ccgctcgcgc gccgccacga  360
gcgccagacc gtggcgccct tctacggcgc gctcgccgac gcgcccaagc ccttcgcctc  420
gtcggtggcc gtgcccaaag cggccgacga cgacggaagc aacgaggccg aggcggcgtc  480
gtggctcctc cccgagcccg accacgggca caaggaaggc gccacgacgg aggtgttctt  540
cgcggactcc gacccgtacc tcgacctcga cttcgcgcgc accatggacg acatcaaggc  600
catcggcgcc cagaacggcc ccgccggcgc cgagctcgac ctcaccggcg ccaagctctt  660
ctactccgac cactccatga actacagcgt gtcgtcgtcg gaggcagcgg tggtgcccga  720
cgcggcggcg ggcgcggcgc ccgtcgtgcc tgtggtgagc aggggcctgg agcgggaggc  780
ccggctgatg cggtaccggg agaagcgcaa gagccggcgg ttcgagaaga cgatccggta  840
cgcgtcccgc aaggcgtacg cggagacgcg gccgcgcatc aagggccggt tcgccaagcg  900
caccccgggg cccggcgcgg acggggagga cccgctggag gagcacgagg aggagatgta  960
ctcctccgcc gcggccgccg tggccgcgct catggccccc ggcggcgccg acgccgacta  1020
cggcgtcgtg cccacgtatt gatcggcgcc ggcctgctgt acactagcta gcctcgacct  1080
ctcggggctg taatttttgc tgcatgcctt gcatgcaaaa agctgccgtg tagcattgat  1140
tacctgtaat atgattccac ggaagccatg aggctggact tccaagctct tcttcctccc  1200
taatgattcc gtcatgtacg gatgtatatt attattattt atcacgaact gctgctaatc  1260
tgcaactgta atttctaatt agc                                         1283

SEQ ID NO: 56           moltype = AA  length = 326
FEATURE                 Location/Qualifiers
REGION                  1..326
                        note = misc_feature - Ceres CLONE ID no.1756710
REGION                  1..326
                        note = misc_feature - Bit score of 628.3 for hmm based on
                         sequences of FIGURE 2.
REGION                  238..282
                        note = misc_feature - Pfam Name: CCT Pfam Description: CCT
                         motif
REGION                  62..104
```

-continued

```
                        note = misc_feature - Pfam Name: zf-B_box Pfam Description:
                         B-box zinc finger
REGION                  1..326
                        note = misc_feature - Functional Homolog Of Ceres SEEDLINE
                         ID no. ME04315 at SEQ ID NO. 20
source                  1..326
                        mol_type = protein
                        organism = Panicum virgatum
SEQUENCE: 56
MEGDKKSAGG APAYWGLGAR PCDECGAEAA RLYCRADAAF LCAGCDARAH GAGSRHARVW  60
LCEVCEHAPA AVTCRADAAA LCASCDADIH SANPLARRHE RQTVAPFYGA LADAPKPFAS  120
SVAVPKAADD DGSNEAEAAS WLLPEPDHGH KEGATTEVFF ADSDPYLDLD FARTMDDIKA  180
IGAQNGPAGA ELDLTGAKLF YSDHSMNYSV SSSEAAVVPD AAAGAAPVVP VVSRGLEREA  240
RLMRYREKRK SRRFEKTIRY ASRKAYAETR PRIKGRFAKR TPGPGADGED PLEEHEEEMY  300
SSAAAAVAAL MAPGGADADY GVVPTY                                       326

SEQ ID NO: 57           moltype = DNA  length = 1398
FEATURE                 Location/Qualifiers
misc_feature            1..1398
                        note = Ceres CLONE ID no.907473
misc_feature            1..1398
                        note = Encodes the peptide sequence at SEQ ID NO 58
source                  1..1398
                        mol_type = other DNA
                        organism = Triticum aestivum
SEQUENCE: 57
gtttttaact cgacttagcc aagtttggca aacgaacagg ccccgtggcc ccgcccccgc  60
gcgacagcga ccgggcgccc gaagtgtctc gcgctcgccc acggcacccg agcggagccc  120
ccgcccctac catgtgctct ccctgcccgc agacccctca aaacccaccc gcgcccgcac  180
ccaggcaccg agcacccagc agaaagaaac gcaccaaatc tttatcccct gccctcagca  240
gtgccgacct gagcgccgga gatctgcggc gagcgagatg aaagtggagg agcagacggt  300
ggtgggagga ggaggagggg ggctctgggg gctggccggg cggccgtgcg acacgtgcgc  360
cgtggacgcg gcgcggctct actgccggtc ggacggcgcc tacctctgcg ccgggtgcga  420
cgcgcgcgct cacggggccg gctcccgcca cgcgcgcgtc tggctctgcg aggtctgcga  480
gcacgcgccc gccgcggtca cctgccgcgc cgacgccgcc gcgctctgcg ccacgtgcga  540
cgccgacatc cactccgcca acccgctcgc cagccggcac gagcgcctcc ccgtcacgcc  600
tttcttcggc gcgctcgccg acccgcccca gcccgccccc tccccgtcct ccgccgccgc  660
gacgcaggag gacgcggacg acgacgggag caacgaggcc gaggcggcct cctggcttct  720
tcccgagcct ggcgatagcc ccgaggacag caccgctacc ttcttccctg actcggacgc  780
gtacctcgat ctggacttcg tccggtctat ggacgggatc aaggccatcg ggtgcccgt  840
cgccccttcc gagctcgacg tcgccggcgg cgctctcttc taccccgaac actccatgaa  900
ccacagcatg tcaacgtccg aggtcgcggt ggtgccggac gcgctgtcag ccggcggggc  960
cccggcgccg gcgccgtcgg tggcggtggt ggctagcaag gggaaggagc gggaggcccg  1020
gctgatgcgg taccgggaga agcgcaagaa ccggaggttc cagaagacca tccgctacgc  1080
gtcccgcaag gcgtacgccg agacgcggcc gcgcatcaag ggccggttcg ccaagcgcac  1140
cgccgaggac gacgcgctgg agcgggacgg gccgttctcg cccgcgtcgt cggcgcacct  1200
ggcgtcggac ggtgactacg gcgtcgtgcc gtccttctga ggagaccggc gacggcgacg  1260
gcgactctgc tgtagttttg gcgcgcgcat ccatccgagt gcgctcgcgt gcggtggctg  1320
cgacgcgcgc tccgtgtaac attgaataat ctgtacagtt ttgttccatg ggattagtgc  1380
cgtgaccgtg ccgacctg                                                1398

SEQ ID NO: 58           moltype = AA  length = 320
FEATURE                 Location/Qualifiers
REGION                  1..320
                        note = misc_feature - Ceres CLONE ID no.907473
REGION                  1..320
                        note = misc_feature - Bit score of 719.5 for hmm based on
                         sequences of FIGURE 2.
REGION                  245..289
                        note = misc_feature - Pfam Name: CCT Pfam Description: CCT
                         motif
REGION                  64..106
                        note = misc_feature - Pfam Name: zf-B_box Pfam Description:
                         B-box zinc finger
REGION                  1..320
                        note = misc_feature - Functional Homolog Of Ceres SEEDLINE
                         ID no. ME04315 at SEQ ID NO. 20
source                  1..320
                        mol_type = protein
                        organism = Triticum aestivum
SEQUENCE: 58
MKVEEQTVVG GGGGGLWGLA GRPCDTCAVD AARLYCRSDG AYLCAGCDAR AHGAGSRHAR  60
VWLCEVCEHA PAAVTCRADA AALCATCDAD IHSANPLASR HERLPVTPFF GALADPPQPA  120
PSPSSAAATQ EDADDDGSNE AEAASWLLPE PGDSPEDSTA TFFPDSDAYL DLDFVRSMDG  180
IKAIGVPVAP SELDVAGGAL FYPEHSMNHS MSTSEVAVVP DALSAGGAPA PAPSVAVVAS  240
KGKEREARLM RYREKRKNRR FQKTIRYASR KAYAETRPRI KGRFAKRTAE DDALERDGPF  300
SPASSAHLAS DGDYGVVPSF                                              320

SEQ ID NO: 59           moltype = AA  length = 340
```

-continued

```
FEATURE                 Location/Qualifiers
REGION                  1..340
                        note = misc_feature - Public GI ID no.4091804
REGION                  1..340
                        note = misc_feature - Bit score of 486.8 for hmm based on
                         sequences of FIGURE 2.
REGION                  1..48
                        note = misc_feature - Pfam Name: zf-B_box Pfam Description:
                         B-box zinc finger
REGION                  279..323
                        note = misc_feature - Pfam Name: CCT Pfam Description: CCT
                         motif
REGION                  1..340
                        note = misc_feature - Functional Homolog Of Ceres SEEDLINE
                         ID no. ME04315 at SEQ ID NO. 20
source                  1..340
                        mol_type = protein
                        organism = Malus x domestica
SEQUENCE: 59
MALKLCDSCK SATGTLFCRA DSAFLCVNCD SKIHAANKLA SRHARVWLCE VCEQAPAHVT  60
CKADDAALCV TCDRDIHSAN PLSHADERVP VTPFYDSVNS ATDSVPAVKS AVNFLNDRYF  120
SDVDGEIEAR REEAEAASWL LPNPKAMENP DLNSGQYLFP EMDPYMDLDY GHVDPKLEDA  180
QEQNSCITDG VVPEQSKNMQ PQLVNDHSFE IDFSAASKPF VYGYHHAQCL RQSVSSSSMD  240
VSIVPDDNAM TDDSNPYNKS MTSAVESSHP AVQLSSADRE ARVLRYREKR KNRKFEKTIR  300
YASRKAYAET RPRIKGRFAK RTEVEIEAEP MCRYGIVPSF                        340

SEQ ID NO: 60           moltype = AA  length = 323
FEATURE                 Location/Qualifiers
REGION                  1..323
                        note = misc_feature - Public GI ID no.21667487
REGION                  1..323
                        note = misc_feature - Bit score of 599.5 for hmm based on
                         sequences of FIGURE 2.
REGION                  236..280
                        note = misc_feature - Pfam Name: CCT Pfam Description: CCT
                         motif
REGION                  61..103
                        note = misc_feature - Pfam Name: zf-B_box Pfam Description:
                         B-box zinc finger
REGION                  1..323
                        note = misc_feature - Functional Homolog Of Ceres SEEDLINE
                         ID no. ME04315 at SEQ ID NO. 20
source                  1..323
                        mol_type = protein
                        note = subspecies = vulgare
                        organism = Hordeum vulgare
SEQUENCE: 60
MEGEEKPVVG GAYWGVGARA CDSCATEAAR LFCRADAAFL CAGCDARAHG SGSRHARVWL  60
CEVCEHAPAA VTCKADAAVL CASCDADIHA ANPLARRHER VPVAPFFGAA ADAHKPFPSS  120
GAQAGAAASA EDDGSNDAEA ASWLLPEPDH KDGANGATAD VFFADSDHYL DLDFARSMDD  180
IKAISVQLNG QPEIDLNGGN KGFYSDHSMN HSLSSSEAAV VPDAAAAPVV SRGREREARL  240
MRYREKRKSR RFEKTIRYAS RKAYAETRPR VKGRFAKRTG TADADALEEH EEMYSSAAAA  300
VAALMAPGPD HDYGVDGVVP TLV                                          323

SEQ ID NO: 61           moltype = AA  length = 325
FEATURE                 Location/Qualifiers
REGION                  1..325
                        note = misc_feature - Public GI ID no.21655154
REGION                  1..325
                        note = misc_feature - Bit score of 678.1 for hmm based on
                         sequences of FIGURE 2.
REGION                  250..294
                        note = misc_feature - Pfam Name: CCT Pfam Description: CCT
                         motif
REGION                  70..112
                        note = misc_feature - Pfam Name: zf-B_box Pfam Description:
                         B-box zinc finger
REGION                  1..325
                        note = misc_feature - Functional Homolog Of Ceres SEEDLINE
                         ID no. ME04315 at SEQ ID NO. 20
source                  1..325
                        mol_type = protein
                        note = subspecies = vulgare
                        organism = Hordeum vulgare
SEQUENCE: 61
MKVEEQTVVG GGGGAGQGGA GFWGLAGRPC DTCAVDAARL YCRLDGAYLC AGCDARAHGA  60
GSRHARVWLC EVCEHAPAAV TCRADAAALC ATCDADIHSA NPLASRHLLL PTPFFGALAD  120
PPQPVPSPSS AAATQEDAED DGSNEAEAAS WLLPEPGDSP EDSAATFFAD SDAYLDLDFV  180
RSMDGIKAIG VPVAPSELDL AGGTLFYPEH SMNHSMSTSE VAVVPDALSA GGAPAPAPSV  240
```

-continued

```
AVVASKGKER EARLMRYREK RKNRRFQKTI RYASRKAYAE TRPRIKGRFA KRTAEDDALE  300
QDGPFSPASS AHLASDGDYG VVPSF                                        325

SEQ ID NO: 62          moltype = AA  length = 391
FEATURE                Location/Qualifiers
REGION                 1..391
                       note = misc_feature - Public GI ID no.45544883
REGION                 1..391
                       note = misc_feature - Bit score of 432.4 for hmm based on
                        sequences of FIGURE 2.
REGION                 322..366
                       note = misc_feature - Pfam Name: CCT Pfam Description: CCT
                        motif
REGION                 52..99
                       note = misc_feature - Pfam Name: zf-B_box Pfam Description:
                        B-box zinc finger
REGION                 1..391
                       note = misc_feature - Functional Homolog Of Ceres SEEDLINE
                        ID no. ME04315 at SEQ ID NO. 20
source                 1..391
                       mol_type = protein
                       organism = Solanum lycopersicum
SEQUENCE: 62
MLKKENSNNW ARVCDSCHSA TCTVYCRADS AYLCAGCDAR IHTASLMASR HERVWVCEAC  60
ERAPAAFLCK ADAASLCASC DADIHSANPL ARRHHRVPIM PIPGTIYGPP AVHTITGGSM  120
MIGGTTGEGT EDDGFLSLNQ DADDTTIDEE DEDEAASWLL LNPPVKNNNK NNNYGMLFGG  180
EVVDDYLDLA EYGGDSQFND QYSVNQQQQH YSVPQKSYVE DSVVPVQNGQ RKSLILYQTP  240
QQQQSHHLNF QLGMEYDNSN TGYGYPASLS HSVSISSMDV SVVPESAQSE TSNSHPRPPK  300
GTIDLFSGPP IQIPPQLTPM DREARVLRYR EKKKNRKFEK TIRYASRKAY AETRPRIKGR  360
FAKRTDVEAE VDQMFSTQLM TDSNYGIVPS F                                 391

SEQ ID NO: 63          moltype = AA  length = 376
FEATURE                Location/Qualifiers
REGION                 1..376
                       note = misc_feature - Public GI ID no.21655166
REGION                 1..376
                       note = misc_feature - Bit score of 528.8 for hmm based on
                        sequences of FIGURE 2.
REGION                 297..341
                       note = misc_feature - Pfam Name: CCT Pfam Description: CCT
                        motif
REGION                 51..98
                       note = misc_feature - Pfam Name: zf-B_box Pfam Description:
                        B-box zinc finger
REGION                 1..376
                       note = misc_feature - Functional Homolog Of Ceres SEEDLINE
                        ID no. ME04315 at SEQ ID NO. 20
source                 1..376
                       mol_type = protein
                       note = subspecies = vulgare
                       organism = Hordeum vulgare
SEQUENCE: 63
MMELRKYWGV GGRRCGGCEG AAPAAVHCRD CAGYLCTGCD ARPAHARAGH ERVWVCEVCE  60
VSPAAVTCKA DAAVLCAACD ADIHHANPLA ERHVRVPIAP IGSPEAAAVA AEAMMLCGAG  120
DGDARADPDE VHDQLHHHGH GGMLNLNVEA GKEGGKMDYL FSDLVDPYLA VDFTRFAHAD  180
SVVPNGVATA AVPAVVDLDF ACGIGAKPPP SYSSSYTANG SGAHSGSSSE VGVVPEAIHG  240
GAGSFELDFT RPKPQAYMPA YTPAPPSHGV GMQQASAVDM GYLTVPERPV AVTGEGRVAR  300
LMRYREKRKN RRFEKTIRYA SRKAYAESRP RVKGRFAKRA DQDADGDGDD LDAEAHAVPS  360
STSYLLDFGY GVVPSF                                                  376

SEQ ID NO: 64          moltype = AA  length = 417
FEATURE                Location/Qualifiers
REGION                 1..417
                       note = misc_feature - Public GI ID no.10946337
REGION                 1..417
                       note = misc_feature - Bit score of 351.2 for hmm based on
                        sequences of FIGURE 2.
REGION                 348..392
                       note = misc_feature - Pfam Name: CCT Pfam Description: CCT
                        motif
REGION                 77..119
                       note = misc_feature - Pfam Name: zf-B_box Pfam Description:
                        B-box zinc finger
REGION                 1..417
                       note = misc_feature - Functional Homolog Of Ceres SEEDLINE
                        ID no. ME04315 at SEQ ID NO. 20
source                 1..417
                       mol_type = protein
                       organism = Ipomoea nil
```

-continued

```
SEQUENCE: 64
MLKEESCEVL DLDVTIGSSS GSRSGNKQNW ARVCDICRSA ACSVYCRADL AYLCGGCDAR  60
VHGANTVAGR HERVLVCEAC ESAPATVICK ADAASLCAAC DSDIHSANPL ARRHHRVPIL  120
PISGTLYGPP TSNPCRESSM MVGLTGDAAE EDNGFLTQDA EETTMDEDED EAASWLLLNP  180
NPNPNPNPVK SNNSTNMCKG GNNNNNEMSC AVEAVDAYLD LAEFSSCHNN LFEDKYSINQ  240
QQNYSVPQRN MSYRGDSIVP NHGKNQFHYT QGLQQHNHHA IFNCKEWNMR ILTRDMVSIS  300
SMDVGVVPES TLSDTSISHS RASKGTIDLF SGPPIQMPPQ LQLSQMDREA RVLRYREKKK  360
TRKFEKTIRY ASRKAYAETR PRIKGRFAKR TDVDTEVDQI FYAPLMAESG YGIVPSF     417

SEQ ID NO: 65          moltype = AA  length = 381
FEATURE                Location/Qualifiers
REGION                 1..381
                       note = misc_feature - Public GI ID no.90657642
REGION                 1..381
                       note = misc_feature - Bit score of 456.0 for hmm based on
                        sequences of FIGURE 2.
REGION                 312..356
                       note = misc_feature - Pfam Name: CCT Pfam Description: CCT
                        motif
REGION                 59..106
                       note = misc_feature - Pfam Name: zf-B_box Pfam Description:
                        B-box zinc finger
REGION                 1..381
                       note = misc_feature - Functional Homolog Of Ceres SEEDLINE
                        ID no. ME04315 at SEQ ID NO. 20
source                 1..381
                       mol_type = protein
                       organism = Cleome spinosa
SEQUENCE: 65
MLKEERTSGG ETGENNWARI CDTCRSAACT VYCRADSAYL CTSCDARVHA ANHVASRHER  60
VWVCESCERA PAAFLCKADA ASLCAACDAE IHSANPLARR HHRVPILPIS GSMSGPMANH  120
HPSETAMTDT ENDMVVGREE AEDEDEDDEE AASWLLLNPG KNSGNNNNQN NGFFFDGEAD  180
EYLDLVEYNS SMENQFSDQY SQYHQDCGVP QKSFGGDGVV PLQVEESRGQ LHHEQQSFQL  240
AITYGSPGAL YGSYNGSMNH SVSMSSMDIV VVPESTASDM AVVSQLRAPK GTTDLLIGPP  300
IQMMPQLSPM DREARVLRYR EKKKTRKFEK TIRYASRKAY AETRPRIKGR FAKRTDIEAE  360
VDQAFSTTLM QESGYGIVPS F                                            381

SEQ ID NO: 66          moltype = DNA  length = 155
FEATURE                Location/Qualifiers
misc_feature           1..155
                       note = 000HORDEUM
misc_feature           1..155
                       note = Homolog Of Ceres SEEDLINE ID no. ME00572 at SEQ ID
                        NO. 111
source                 1..155
                       mol_type = other DNA
                       organism = Hordeum vulgare
                       sub_species = vulgare
SEQUENCE: 66
tcctcgtgtc agaattaacg ttcttgacct tgtaaggcct tttcttgacc ttgtaaggcc  60
ctcccctaac gtttctcctg gtgtctccaa cctcacactt tctttcccct ttctatccct  120
cctgagctat tccctatttt gtacgtctac aatct                             155

SEQ ID NO: 67          moltype = DNA  length = 161
FEATURE                Location/Qualifiers
misc_feature           1..161
                       note = 000PICEA
misc_feature           1..161
                       note = Homolog Of Ceres SEEDLINE ID no. ME00572 at SEQ ID
                        NO. 111
source                 1..161
                       mol_type = other DNA
                       organism = Picea sp.
SEQUENCE: 67
atcaccccaa actgagcctt tcttgacctt gtaagacctt ttcttgacct tgtaagacca  60
gccatagaat cccgagaaca aggtcgctca actctcaaac aatcttcttc taattagtct  120
atccctcctg agctatttac agttgagttt caagttcttc c                      161

SEQ ID NO: 68          moltype = AA  length = 409
FEATURE                Location/Qualifiers
REGION                 1..409
                       note = misc_feature - Public GI ID no.45544887
REGION                 1..409
                       note = misc_feature - Bit score of 383.3 for hmm based on
                        sequences of FIGURE 2.
REGION                 340..384
                       note = misc_feature - Pfam Name: CCT Pfam Description: CCT
                        motif
REGION                 59..106
```

```
                        note = misc_feature - Pfam Name: zf-B_box Pfam Description:
                         B-box zinc finger
REGION                  1..409
                        note = misc_feature - Functional Homolog Of Ceres SEEDLINE
                         ID no. ME04315 at SEQ ID NO. 20
source                  1..409
                        mol_type = protein
                        organism = Solanum lycopersicum
SEQUENCE: 68
MLKKENSGGL DGSSNYWARV CDSCRSVTCT IYCQADSAYL CADCDARIHA ASLVTSRHKR  60
VWVCEACERA PAAFLCKADA ASLCASCDAD IHSANPLAHR HHRIPIITIP GTLYGPPAVE  120
TVGGDSMMIS GSTGEGTEDD GFLSLTQDAD DTIIDEEDED EDEAASWLLL NHPVKNNNKN  180
NVNNNNNQTN NYDMLFGGEV VDDYLDLAEY GGDSQFNDQY NVNQQQQYF VPQMSYGGDS  240
VVPVQDGQGK PLIFYQQQQQ QQQSHHQNFQ LGMEYDNSNT RLGLPASMSH SVSVVSMDVS  300
VVPESALCET SNSQPRPQKG TIELFSGHPI QIPLLTPMDR EARVLRYREK KKNRKFEKTI  360
RYASRKAYAE TRPRIKGRFA KRTDVEAEVD QMFSTQLMTD SSYRIVPSF             409

SEQ ID NO: 69           moltype = AA  length = 376
FEATURE                 Location/Qualifiers
REGION                  1..376
                        note = misc_feature - Public GI ID no.47606678
REGION                  1..376
                        note = misc_feature - Bit score of 188.5 for hmm based on
                         sequences of FIGURE 2.
REGION                  307..351
                        note = misc_feature - Pfam Name: CCT Pfam Description: CCT
                         motif
REGION                  34..66
                        note = misc_feature - Pfam Name: zf-B_box Pfam Description:
                         B-box zinc finger
REGION                  1..376
                        note = misc_feature - Functional Homolog Of Ceres SEEDLINE
                         ID no. ME04315 at SEQ ID NO. 20
source                  1..376
                        mol_type = protein
                        organism = Lolium temulentum
SEQUENCE: 69
MNSNSSSTIY EEAVGQEGSW SRLCDGCCMV PSVVYCHADS AYLCASCDVR IHSANRVASR  60
HERVCLSKAH EHAPALLQCR TDAVASCAAY EAQAHYANLL AGMHQCVPVV SHPATAIPAA  120
SLLAEAAVTT TILSCKEEEA FWLLLSKNSA NQNCSGDNRS SSTYFGEVDE YFDLVGYNSY  180
YDSRMNNNQA QYGMQEQQHL QPMQKEYAEK EGSECVVPSQ FATVSKPQQS GYALVGSEQA  240
ASMTAGVSVY TDSVNNSISF SSMEGGIVPD NTVVDLPYSI IPTPAGASSL HSGPPLQMPL  300
HFSSMDREAK VLRYKEKKKT RTFEKTTRYA TKKAYAEARP RIKGRFAKIS EAEMEVDQLF  360
SAAALSDSSY STVPWF                                                 376

SEQ ID NO: 70           moltype = DNA  length = 1350
FEATURE                 Location/Qualifiers
misc_feature            1..1350
                        note = Ceres CLONE ID no.1755065
misc_feature            1..1350
                        note = Encodes the peptide sequence at SEQ ID NO 71
source                  1..1350
                        mol_type = other DNA
                        organism = Panicum virgatum
SEQUENCE: 70
aaccatttcc gacgcagaac ccccgggggc cggaatccgt gacacccacc cggaggagag  60
cagagcagag gcatcaggca tggccgccgc ggtggagctg gagcagaagc cggcggtggg  120
gtactggggc gtggccggcg cgcggccctg cgacgcgtgc gccgcggagc cggcgcggct  180
gcactgccgc gcggacggcg cgttcctgtg ccccgggtgc gacgcccgcg cgcacggcgc  240
cgggtcgcgc cacgcgcgcg tctggctctg cgaggtctgt gagcacgctc ccgccgccgt  300
cacgtgccgc gccgacgccg ccgcgctctg cgcggcctgc gacgccgaca tccactcggc  360
caacccgctc gcgcgccgcc acgagcggct ccccgtcgcg cccttcttcg gcgcgctcgc  420
cgacgcgccg cagccgttcc cgtccgcggc cttcgccacc gcgggggggcc agtcccaggg  480
ggacgcggcg gcggcggcgg cggcggacga cgacgggagc aacgaggccg aggccgcctc  540
atggctcctc cccgagcccg acaccagcca cgaggacagc gcagccgcca ccgacgcctt  600
cttcgcggac tccgacaagt acctcggcgt cgacctcgac ttcgcccggt ccatggacgg  660
catcaaggcc atcggcgtcc cggtcgcgcc gccggagctg gacatcgccg ctggcgcttt  720
ctactacccc gaacactcca tgaaccatag cgtgtcgtca tcagaggtgg cggtcgtgcc  780
ggacgtgctg gcgggcggcg tcccggcggt gccggtggcg agccggggga aggagcggga  840
agcgcggctg atgcggtacc gcgagaagcg caagaaccgg cggttcgaca agaccatccg  900
gtacgcgtcc cgcaaggcgt acgccgagac gcggccgcgc atcaagggcc gcttcgccaa  960
gcgctgctcc gccgaggccg aggacgagga cgaggcgctg ctggagcacg aggaaggggc  1020
gtgcttctcg cccgcggtgt cggcccccgc ggcctcggac ggcgtcgtcc cgtccttctg  1080
ctaaggggga cgacgggtgg cggccgcgcc tcctcctcct ccccggctcc caggcggcaa  1140
ccccttaatt ttgccgactc tgaatcgacc cccaacgcat gccaacatgc gaatgcgatg  1200
cgcgcgctcc gtgtagcata ataattgtac agcagctcgt ccgacgcaac gagctcaatc  1260
gcggtcgcac ggaacgcctg taatcctcct caccatccgt gtaatccagc cttgtacatt  1320
accatctaga ggtgtttgtg cttctcttgc                                  1350
```

```
SEQ ID NO: 71          moltype = AA  length = 334
FEATURE                Location/Qualifiers
REGION                 1..334
                       note = misc_feature - Ceres CLONE ID no.1755065
REGION                 1..334
                       note = misc_feature - Bit score of 736.3 for hmm based on
                        sequences of FIGURE 2.
REGION                 253..297
                       note = misc_feature - Pfam Name: CCT Pfam Description: CCT
                        motif
REGION                 64..106
                       note = misc_feature - Pfam Name: zf-B_box Pfam Description:
                        B-box zinc finger
REGION                 1..334
                       note = misc_feature - Functional Homolog Of Ceres SEEDLINE
                        ID no. ME04315 at SEQ ID NO. 20
source                 1..334
                       mol_type = protein
                       organism = Panicum virgatum
SEQUENCE: 71
MAAAVELEQK PAVGYWGVAG ARPCDACAAE PARLHCRADG AFLCPGCDAR AHGAGSRHAR  60
VWLCEVCEHA PAAVTCRADA AALCAACDAD IHSANPLARR HERLPVAPFF GALADAPQPF  120
PSAAFATAGG QSQGDAAAAA AADDDGSNEA EAASWLLPEP DTSHEDSAAA TDAFFADSDK  180
YLGVDLDFAR SMDGIKAIGV PVAPPELDIA AGAFYYPEHS MNHSVSSSEV AVVPDVLAGG  240
VPAVPVASRG KEREARLMRY REKRKNRRFD KTIRYASRKA YAETRPRIKG RFAKRCSAEA  300
EDEDEALLEH EEGACFSPAV SAPAASDGVV PSFC                            334

SEQ ID NO: 72          moltype = DNA  length = 166
FEATURE                Location/Qualifiers
misc_feature           1..166
                       note = 000SORGHUM
misc_feature           1..166
                       note = Homolog Of Ceres SEEDLINE ID no. ME00572 at SEQ ID
                        NO. 111
source                 1..166
                       mol_type = other DNA
                       organism = Sorghum bicolor
SEQUENCE: 72
tggtttcgca aggtgaggtc ttcttgacct tgcaagacct tttcttgacc ttgtaagacc  60
caactctgcg acatctcttt cctgtcttac accttcctct tcattcttac ttcttttcta  120
tgtctatccc ttatgagctg tgttgagcta tgttaggtcc tagtta                166

SEQ ID NO: 73          moltype = DNA  length = 154
FEATURE                Location/Qualifiers
misc_feature           1..154
                       note = 000TRITICUM
misc_feature           1..154
                       note = Homolog Of Ceres SEEDLINE ID no. ME00572 at SEQ ID
                        NO. 111
source                 1..154
                       mol_type = other DNA
                       organism = Triticum aestivum
SEQUENCE: 73
tcctcatgcc agaattaatg ttcttgacct tgtaaggcct tttcttgacc ttgtaaggcc  60
ctccccttac gtttctccgg gtgtctccaa cctcacactt tctccccccct tctatccctc  120
ctgagctatc tccatgcata ttttgtctag caat                            154

SEQ ID NO: 74          moltype = AA  length = 314
FEATURE                Location/Qualifiers
REGION                 1..314
                       note = misc_feature - Ceres CLONE ID no.1844076
REGION                 1..314
                       note = misc_feature - Bit score of 824.2 for hmm based on
                        sequences of FIGURE 3.
REGION                 38..173
                       note = misc_feature - Pfam Name: adh_short Pfam
                        Description: short chain dehydrogenase
source                 1..314
                       mol_type = protein
                       organism = Arabidopsis thaliana
SEQUENCE: 74
MSGKKERNKE RREKRLQEIS LLRTIPYSDH QRWWSQETVA VVTGANRGIG FEIARQLAGH  60
GLTVILTSRN ISVGIEATKA LQEGGFSYDV HQLDILDGES ISAFVEWIKQ KYGGIDILVN  120
NAGVNYNLGF DNSVEFARQV VDTNYYGTKN MIKAMIPVMK PSTAGARIVN VSSRLGRLNG  180
RRNRIQDATL REKLTNLETL SEELIDRTVS SFLQQVEDET WQSGGWPQTF TDYSVSKLAV  240
NAYTRLVAKE LCDRPQGEKI YINCYCPGWV KTAMTGWAGN ISPEVAADTG VWLSLLSDQA  300
ITGKFFAERR EINF                                                  314

SEQ ID NO: 75          moltype = DNA  length = 1167
```

-continued

```
FEATURE                Location/Qualifiers
misc_feature           1..1167
                       note = Ceres CLONE ID no.35974
misc_feature           1..1167
                       note = Encodes the peptide sequence at SEQ ID NO 76
source                 1..1167
                       mol_type = other DNA
                       organism = Arabidopsis thaliana
SEQUENCE: 75
acacccaaac acgcgacgcg agcgaaagaa gacgatgacg aacaaggaga aagctcgaga  60
gagaagggag aaaaaaatgc aggagatctc tctccttcga actattcctt actctgacca  120
ccataggtgg tggtcttgtg aaaatgtagc agtagtgact ggttcaaacc gcgggattgg  180
attcgagatt gcaagacagc ttgcggttca cggattgacg gttgttctta cagctagaaa  240
cgtgaatgct ggtcttgaag cagttaaatc tttgaggcac caagaagaag gtctcaaggt  300
ttattttcat caacttgatg tcacagactc ttcctcgatt agagagtttg gttgctggct  360
taagcaaaca tttggaggtt tagatattct cgtgaataat gcaggtgtta actacaatct  420
cggctcagat aatacggttg aatttgctga aacagttata tctactaact accaaggaac  480
caaaaacatg acaaaagcta tgataccctt gatgagacca tctcctcatg gcgctcgtgt  540
agtcaatgtt agttctcggc taggtagagt aaatggaaga cgtaatagac tggcaaatgt  600
agagttgaga gatcagctaa gcagtccaga tttgctgacc gaggaactta tagacagaac  660
tgtctctaaa ttcatcaacc aagtaaaaga cggaacttgg gaatcaggcg ggtggcctca  720
gacattcact gactactcca tgtctaagct tgcagtcaat gcttacacga gactaatggc  780
aaaagaactt gagagacgag gagaggaaga gaagatttat gttaacagct tttgccctgg  840
ttgggtgaag actgcgatga ctggctacgc cggaaatatg ccacctgaag atgcagctga  900
tactggagtt tggcttagcc tggtcctttc cgaagagtca gtaaccggaa aattcttcgc  960
agagagacgt gagatcaact tctgagggtt gttgaatgtt tgtaaacgtt ggaatagatt  1020
gtgtcgtctt cgtttagtgc catagtttta gtcaaaggtt tacaaaatca attgtaattg  1080
gtaagtgaat ggttgtagtc atgatacgcg tcagatttgc cacaaaacta ggagtttata  1140
atttaaatat aattaatttt taattgc                                     1167

SEQ ID NO: 76          moltype = AA  length = 316
FEATURE                Location/Qualifiers
REGION                 1..316
                       note = misc_feature - Ceres CLONE ID no.35974
REGION                 1..316
                       note = misc_feature - Bit score of 817.6 for hmm based on
                        sequences of FIGURE 3.
REGION                 37..174
                       note = misc_feature - Pfam Name: adh_short Pfam
                        Description: short chain dehydrogenase
REGION                 1..316
                       note = misc_feature - Functional Homolog Of Full Length
                        Ceres SEEDLINE ID no.ME17294 at SEQ ID NO. 74
source                 1..316
                       mol_type = protein
                       organism = Arabidopsis thaliana
SEQUENCE: 76
MTNKEKARER REKKMQEISL LRTIPYSDHH RWWSCENVAV VTGSNRGIGF EIARQLAVHG  60
LTVVLTARNV NAGLEAVKSL RHQEEGLKVY FHQLDVTDSS SIREFGCWLK QTFGGLDILV  120
NNAGVNYNLG SDNTVEFAET VISTNYQGTK NMTKAMIPLM RPSPHGARVV NVSSRLGRVN  180
GRRNRLANVE LRDQLSSPDL LTEELIDRTV SKFINQVKDG TWESGGWPQT FTDYSMSKLA  240
VNAYTRLMAK ELERRGEEEK IYVNSFCPGW VKTAMTGYAG NMPPEDAADT GVWLSLVLSE  300
ESVTGKFFAE RREINF                                                 316

SEQ ID NO: 77          moltype = AA  length = 304
FEATURE                Location/Qualifiers
REGION                 1..304
                       note = misc_feature - Public GI ID no.10176876
REGION                 1..304
                       note = misc_feature - Bit score of 730.9 for hmm based on
                        sequences of FIGURE 3.
REGION                 23..160
                       note = misc_feature - Pfam Name: adh_short Pfam
                        Description: short chain dehydrogenase
REGION                 1..304
                       note = misc_feature - Functional Homolog Of Full Length
                        Ceres SEEDLINE ID no.ME17294 at SEQ ID NO. 74
source                 1..304
                       mol_type = protein
                       organism = Arabidopsis thaliana
SEQUENCE: 77
MQEISLLRTI PYSDHHRWWS CENVAVVTGS NRGIGFEIAR QLAVHGLTVV LTARNVNAGL  60
EAVKSLRHQE EGLKVYFHQL DVTDSSSIRE FGCWLKQTFG GLDILVNNAG VNYNLGSDNT  120
VEFAETVIST NYQGTKNMTK AMIPLMRPSP HGARVVNVSS RLENLVEIHE LQRLANVELR  180
DQLSSPDLLT EELIDRTVSK FINQVKDGTW ESGGWPQTFT DYSMSKLAVN AYTRLMAKEL  240
ERRGEEEKIY VNSFCPGWVK TAMTGYAGNM PPEDAADTGV WLSLVLSEEA VTGKFFAERR  300
EINF                                                              304

SEQ ID NO: 78          moltype = DNA  length = 1164
```

-continued

```
FEATURE                 Location/Qualifiers
misc_feature            1..1164
                        note = Ceres CLONE ID no.473040
misc_feature            1..1164
                        note = Encodes the peptide sequence at SEQ ID NO 79
source                  1..1164
                        mol_type = other DNA
                        organism = Glycine max
SEQUENCE: 78
acttcttaaa actggtatct gatttacaaa aggttacaaa cttctcttgc ataaagaatg  60
gcatcagcaa caataaggaa tgcagttgtc acgggagcaa acaaagggat aggatttgga  120
atatgcaagc aattggtttc taatggcatc acagtggtgc taacagcaag ggatgagaaa  180
aggggtcttg aagctgttga aaagctgaaa gagtttggtg tgtctgatca agtggtgttt  240
catcagcttg atgtgactga ccctaaaagc attgaatccc ttgcaaattt catcaaaacc  300
cagtttggaa aacttgatat cttggtgaat aatgcaggaa ttcatggagc atatgttgac  360
cgtgatgctt tagctgctgc tggggaaaaa gttgccaatg ttgattggag aaaaatctca  420
actgaaaatt ttgaagctgc cgaagcaggc attagaacaa attactatgg agtcaaatta  480
atgtgtgaag cacttattcc ccttctagaa ttgtcaggca caccaaggat tgtcaatgtt  540
tcctcctcca tggggaagtt ggagaaaata ccaaatgcat gggctagagg agccctaagt  600
gatgctgaga gcctaacaga agaaaaggtg gatgaggttt tgaatcagtt tctaaaagat  660
tttaaagagg gttcattaga aaccaaaggg tggccacatg ctttttctgc atatatagtc  720
tcaaaagctg ctttgactgc ctacacaagg attcttgcta agaagtaccc atctttctgc  780
atcaatgctg tttgccctgg ctttgtgaaa acagatctca actacaatac tggctatctt  840
agtgttgatg aaggtgctga aagtgttgta aggttggctc tgctacctaa tggaggtcct  900
tctggtctat tcttttctcg aagtgaagtg gcaccattct gatccaaaga ctgttgtgta  960
cttgaagagg ataaataata agcatggttt catgataaga catgtatcaa atttgtacct  1020
agcacaacaa gaaaataagc cacatgtctg atcactgatg gctgcccatc attgatgaga  1080
acaaccctat agtgaattct agatattaca atgacattac taatttgaga aatctaattt  1140
tggatataaa gatatctgtt tgtc                                         1164

SEQ ID NO: 79           moltype = AA  length = 294
FEATURE                 Location/Qualifiers
REGION                  1..294
                        note = misc_feature - Ceres CLONE ID no.473040
REGION                  1..294
                        note = misc_feature - Bit score of 656.1 for hmm based on
                         sequences of FIGURE 3.
REGION                  7..168
                        note = misc_feature - Pfam Name: adh_short Pfam
                         Description: short chain dehydrogenase
REGION                  1..294
                        note = misc_feature - Functional Homolog Of Full Length
                         Ceres SEEDLINE ID no.ME17294 at SEQ ID NO. 74
source                  1..294
                        mol_type = protein
                        organism = Glycine max
SEQUENCE: 79
MASATIRNAV VTGANKGIGF GICKQLVSNG ITVVLTARDE KRGLEAVEKL KEFGVSDQVV  60
FHQLDVTDPK SIESLANFIK TQFGKLDILV NNAGIHGAYV DRDALAAAGE KVANVDWRKI  120
STENFEAAEA GIRTNYYGVK LMCEALIPLL ELSGTPRIVN VSSSMGKLEK IPNAWARGAL  180
SDAESLTEEK VDEVLNQFLK DFKEGSLETK GWPHAFSAYI VSKAALTAYT RILAKKYPSF  240
CINAVCPGFV KTDLNYNTGY LSVDEGAESV VRLALLPNGG PSGLFFSRSE VAPF        294

SEQ ID NO: 80           moltype = DNA  length = 2073
FEATURE                 Location/Qualifiers
misc_feature            1..2073
                        note = Ceres CLONE ID no.922223
misc_feature            1..2073
                        note = Encodes the peptide sequence at SEQ ID NO 81
source                  1..2073
                        mol_type = other DNA
                        organism = Triticum aestivum
SEQUENCE: 80
gtaaacaagc ccatggactc ttattttctc tttatgttgg gcttaatgtt cttggggcta  60
tggttccgag ttctcaaaaa aaaaagttcg attccggcga acacagtaca gcagagggag  120
cgagagatgg ggaagaaggg caaggcggcg gcaagggagc gccgggagga gcggcggcgg  180
gaagtcacgc tcctccgcgc cgtaccctac gagccccacc agcggtggtg ggacggcctc  240
gcgccggcgc gcgccgtggc ggtggtgacg ggggccagcc gcggcatcgg ctacgagatc  300
tcccgccagc tcgcgcgcca cggcctccac gtcgtcctcg cctcgcgcga cgccgcgcgg  360
ggcagggacg ccgcggaggg gatcctccgc gaggagggca cgagcgcgga gtggcggcag  420
ctcgacgtgg cggacgccgc gtcggtcgag gccttcgccg cctggacggc gcggacccac  480
ggcggcatcc atgtccttat taacaatgca ggtgtaaact tcaacagagg agcagataac  540
tctgttgaat ttgcagagca agtaattgag acaaattatt ttggtacaag gcggatgatt  600
gaagccatgc taccattact gaaaccttct ccgtatggtg gccggatagt gaatgtgagc  660
tcaaggcttg gcagggccaa tggcagacgc aataaaatcg gcgatgcgat cctaagagag  720
caactattaa ctgatgattg cttatctgag gaattgattg atgggatggt cactaaattc  780
cttgaacaag tgaagcaaaa tagttggtcc tccattgagt ggcctcagat gtacacggac  840
tattcggtct caaagtttgc tgttaatgtg tatacaagac tcatggcaag gaggttatct  900
gacaggtctg aaggccaaaa gatttacatt aactgtttct gtcctggctg ggtaaagact  960
```

-continued

```
gccatgactg attgggaagg gaacatttca gccgaagaag gtgctgatac tggagtgtgg  1020
cttgctctgt taccccagga acaagcaaca attggaaagt tctatgctga gagacgcgag  1080
ataagcttct gaggtgatcg gaatggtgga tatgcgagtg ggagtggtac atttaaccat  1140
atgtatttaa ttaaagtttt aaactatgta ggtgatcgga atggtggata tgcgagtggg  1200
agtggcatgt tcatgaagag caatccacat gattggcaga ctccagcatg gttttcgagt  1260
cgcgactcat gcgagttgct ctggggcagc gactcggaag aagtcgagcc tgcgttgtga  1320
ctagtcatga ctcagagtcg cgagtcgata ctaagctgag ttgaccatat ttttgcgact  1380
catagactag tcgtcgacta gtcgcaacta gtcgagcgac tcgaaatcca tggactccag  1440
tcggtcaaag agcattgagt cttcacactg atggaaggcc atgctctcta attttgtcaa  1500
taaatgatgc agtaccagat gctttcagac gatactcaga cgacgttgcc catcagaccg  1560
tttgttaatt agattcacgt caatctcatg gtgtagagtc tgcgtcggct gcacatcggc  1620
cataccatgt cgtgtgtaca tcaatttcgt gaagttgctg gaaacaggga aatgttcacc  1680
aggcccacca ccactagtcc acaacggcag taagcaggca tggcatgctg gactgctgca  1740
ccgaatatat gattaggctg gatctcaagc aactccactg tcagattctc tcattatctt  1800
ccaagtagag gtggaatcct tatgacccaa tggatgagag cgatgcaacg ctgcctcacc  1860
cacgcatgca gaagatcgat atgtttggga acgaaccggt cggcctacct tgggaattct  1920
ggagctatag tcatggctag gccgccattc atggaccgga gactacatgt cttgcagtat  1980
attgttctga ttttgccgcc acctgcatat gtgtggtaca tactttgtta tgttcgtgtt  2040
tgtatgcaat ggttggatcg tgtgatttgc tgg                               2073

SEQ ID NO: 81           moltype = AA  length = 321
FEATURE                 Location/Qualifiers
REGION                  1..321
                        note = misc_feature - Ceres CLONE ID no.922223
REGION                  1..321
                        note = misc_feature - Bit score of 823.6 for hmm based on
                         sequences of FIGURE 3.
REGION                  43..179
                        note = misc_feature - Pfam Name: adh_short Pfam
                         Description: short chain dehydrogenase
REGION                  1..321
                        note = misc_feature - Functional Homolog Of Full Length
                         Ceres SEEDLINE ID no.ME17294 at SEQ ID NO. 74
source                  1..321
                        mol_type = protein
                        organism = Triticum aestivum
SEQUENCE: 81
MGKKGKAAAR ERREERRREV TLLRAVPYEP HQRWWDGLAP ARAVAVVTGA SRGIGYEISR  60
QLARHGLHVV LASRDAARGR DAAEGILREE GTSAEWRQLD VADAASVEAF AAWTARTHGG  120
IHVLINNAGV NFNRGADNSV EFAEQVIETN YFGTRRMIEA MLPLLKPSPY GGRIVNVSSR  180
LGRANGRRNK IGDAILREQL LTDDCLSEEL IDGMVTKFLE QVKQNSWSSI EWPQMYTDYS  240
VSKFAVNVYT RLMARRLSDR SEGQKIYINC FCPGWVKTAM TDWEGNISAE EGADTGVWLA  300
LLPQEQATIG KFYAERREIS F                                           321

SEQ ID NO: 82           moltype = AA  length = 331
FEATURE                 Location/Qualifiers
REGION                  1..331
                        note = misc_feature - Public GI ID no.125528967
REGION                  1..331
                        note = misc_feature - Bit score of 831.3 for hmm based on
                         sequences of FIGURE 3.
REGION                  49..188
                        note = misc_feature - Pfam Name: adh_short Pfam
                         Description: short chain dehydrogenase
REGION                  1..331
                        note = misc_feature - Functional Homolog Of Full Length
                         Ceres SEEDLINE ID no.ME17294 at SEQ ID NO. 74
source                  1..331
                        mol_type = protein
                        note = subspecies = indica
                        organism = Oryza sativa
SEQUENCE: 82
MGKKGKEAAR ERREQRRREV TLLRAVPYEP HQRWWDGLAP PPPPPPGRAV AVVTGANRGI  60
GYEAARQLAT HGLHVVLTSR DAARGRDAAE QIRAAAGKPG VSVEWRQLDV TDAASVEGFA  120
TWVERTHGGV HVLVNNAGVN FNRGADNSVE FAEQVTETNY FGTKRMIEAM MPLMITSPHG  180
GRIVNVSSRL GRVNGRRNRI GDPSLRERLL NDDHLSEELI NEMVMKFLEQ TKQDNWSSSN  240
EWPQMYTDYS ISKLAVNAYT RLLARRLLDR PEGQKIYINC FCPGWVKTAM TGWEGNISAE  300
EGADTGVWLA LVPQEQATIG KFFAERREIS F                                331

SEQ ID NO: 83           moltype = AA  length = 330
FEATURE                 Location/Qualifiers
REGION                  1..330
                        note = misc_feature - Public GI ID no.125573200
REGION                  1..330
                        note = misc_feature - Bit score of 834.6 for hmm based on
                         sequences of FIGURE 3.
REGION                  48..187
                        note = misc_feature - Pfam Name: adh_short Pfam
                         Description: short chain dehydrogenase
```

```
REGION                  1..330
                        note = misc_feature - Functional Homolog Of Full Length
                         Ceres SEEDLINE ID no.ME17294 at SEQ ID NO. 74
source                  1..330
                        mol_type = protein
                        note = subspecies = japonica
                        organism = Oryza sativa
SEQUENCE: 83
MGKKGKEAAR ERREQRRREV TLLRAVPYEP HQRWWDGLAP PPPPPGRAVA VVTGANRGIG  60
YEAARQLATH GLHVVLTSRD AARGRDATEQ IRAAAGKPGV SVEWRQLDVT DAASVEGFAT  120
WVERTHGGVH VLVNNAGVNF NRGADNSVEF AEQVIETNYF GTKRMIEAMM PLMITSPHGG  180
RIVNVSSRLG RVNGRRNRIG DPSLRERLLN DDHLSEELIN EMVMKFLEQT KQDNWSSGNE  240
WPQMYTDYSI SKLAVNAYTR LLARRLLDRP EGQKIYINCF CPGWVKTAMT GWEGNISAEE  300
GADTGVWLAL VPQEQATIGK FFAERREISF                                 330

SEQ ID NO: 84           moltype = DNA  length = 942
FEATURE                 Location/Qualifiers
misc_feature            1..942
                        note = Ceres ANNOT ID no.1527409
misc_feature            1..942
                        note = Encodes the peptide sequence at SEQ ID NO 85
source                  1..942
                        mol_type = other DNA
                        organism = Populus balsamifera
                        sub_species = trichocarpa
SEQUENCE: 84
atgggaagta aagagccagc aaaggaaaag agagaaaaaa gactccaaga aatttctctt  60
ctccgtacca ttccttactc tgatcatcaa aggtggtggt catcagaaac tgttgctgtg  120
gtgaccggtg gaaatagagg aataggattt gagattgcga ggcaacttgc agaccatgga  180
ttgtctgtta tcctgacatc acgagaaagt agcgcaggcc ttgaagctgc caatgtcttg  240
cgagagttgg gtttgagtgt ggacttccat caacttgatg tcttagattc tttatccatc  300
aaaacgtttg ctgagtggat acaacaaact tacggcggat tagatgtttt ggtgaataat  360
gctggtgtta attacaatat ggggtctgac aattctgttg aaaatgccaa gaatgttgtt  420
gatacaaact attatggtat caaaaatgtc actgaagctc tgattccttt gatgagacct  480
tcttctgtag gtgctcgtat tgttaatgta agttcacggc ttggaagact aaatggcaaa  540
cgaaacagac ttgaagacaa agatttgaga gagcaactgg ctaacctgga aacactttca  600
gaggaactca ttgataggac ggtgtctact ttcctacaac aagtagaaga ccgcacatat  660
acatcaggtg gatggcctca ggtgaacact gattactcgg tgtcaaaact tgcagttaat  720
gcttatacta ggctaatggc aaagaaactg tccgatcggc ctaatggtca gaagatctat  780
ataaactgct actgcccagg gtgggtgaag acagctatga caggctgggc tggtaatgta  840
tcagctgagg atggagctga cacaggagta tggctggccc tgcttccaga ccaagcaatc  900
acagggaaat tttttgctga gagacgtgag gtaaacttct ga                   942

SEQ ID NO: 85           moltype = AA  length = 313
FEATURE                 Location/Qualifiers
REGION                  1..313
                        note = misc_feature - Ceres ANNOT ID no.1527409
REGION                  1..313
                        note = misc_feature - Bit score of 836.2 for hmm based on
                         sequences of FIGURE 3.
REGION                  37..172
                        note = misc_feature - Pfam Name: adh_short Pfam
                         Description: short chain dehydrogenase
REGION                  1..313
                        note = misc_feature - Functional Homolog Of Full Length
                         Ceres SEEDLINE ID no.ME17294 at SEQ ID NO. 74
source                  1..313
                        mol_type = protein
                        note = subspecies = trichocarpa
                        organism = Populus balsamifera
SEQUENCE: 85
MGSKEPAKEK REKRLQEISL LRTIPYSDHQ RWWSSETVAV VTGGNRGIGF EIARQLADHG  60
LSVILTSRES SAGLEAANVL RELGLSVDFH QLDVLDSLSI KTFAEWIQQT YGGLDVLVNN  120
AGVNYNMGSD NSVENAKNVV DTNYYGIKNV TEALIPLMRP SSVGARIVNV SSRLGRLNGK  180
RNRLEDKDLR EQLANLETLS EELIDRTVST FLQQVEDRTY TSGGWPQVNT DYSVSKLAVN  240
AYTRLMAKKL SDRPNGQKIY INCYCPGWVK TAMTGWAGNV SAEDGADTGV WLALLPDQAI  300
TGKFFAERRE VNF                                                   313

SEQ ID NO: 86           moltype = AA  length = 311
FEATURE                 Location/Qualifiers
REGION                  1..311
                        note = misc_feature - Public GI ID no.92871098
REGION                  1..311
                        note = misc_feature - Bit score of 828.1 for hmm based on
                         sequences of FIGURE 3.
REGION                  35..170
                        note = misc_feature - Pfam Name: adh_short Pfam
                         Description: short chain dehydrogenase
REGION                  1..311
```

```
                       note = misc_feature - Functional Homolog Of Full Length
                        Ceres SEEDLINE ID no.ME17294 at SEQ ID NO. 74
source                 1..311
                       mol_type = protein
                       organism = Medicago truncatula
SEQUENCE: 86
MGHKEKSRKD KRLQEISLLR TIPYSDHQRW WSKETIAVVT GGNRGIGFEI SRQLADHGVT  60
VVLTSRDASV GVESIKVLQE GGLDVHCHQL DILDSSSVNE FAEWLKEEYG GLDILVNNAG  120
VNSNMGSDNS VENARKCIET NYYGTKRMIE AMIPLMKPSA AGGRIVNVSS RLGRLNGKRN  180
RIENEELREK LSDVESLSEE LIDETINNFL QQIEDGSWKT GGWPQTFTDY SVSKLAVNTY  240
TRYMAKKLSD RPEGEKIYIN CYCPGWVKTA LTGYAGSVTV EQGADTGVWI ALVPDQEITG  300
KFFAERREIN F                                                       311

SEQ ID NO: 87          moltype = DNA  length = 1171
FEATURE                Location/Qualifiers
misc_feature           1..1171
                       note = Ceres CLONE ID no.1831117
misc_feature           1..1171
                       note = Encodes the peptide sequence at SEQ ID NO 88
source                 1..1171
                       mol_type = other DNA
                       organism = Panicum virgatum
SEQUENCE: 87
ctcccacccg cgctcccagc acgcccaccg tcgcctaccc cgtctccagc tcgatggact  60
actcgagcac caaggagtta cctccggccg gggcctggtg gtcgagggag acggtggccg  120
tggtgacggg cgcgaaccgg ggcatcgggc acgccctcgc cgcgcgcctg gcggagcacg  180
ggctcaccgt ggtgctcacc gcgcgggacg gcgcgcgcgg ggaggccgcc gcggccccgc  240
tccgcgcgcg cgggctcgcc gtcgccttcc gcaggctcga cgtctccgac gccgcctccg  300
tcgccgagtt cgccgcctgg ctccgcgacg ccgtcggcgg cctcgacatc ctggtgaaca  360
acgccgccgt gtccttcaac gagatcgaca ccaactcggt ggagcacgcc gagacggtcc  420
tccggaccaa cttctacggc gccaagatgc tcacggaagc gctcctgccg ctgttccggc  480
agtccccggc caccagcagg atcctcaaca tcagctcgca gctcggcctt ctcaacaagg  540
tgagcgaccc gtccctgaag gcgttgctgc tggacgagga gaccctgacg gaggcggcga  600
tcgacgccat ggtgtcgcgg ttcctggcgc aggtgaagga cgggacgtgg ggcgcgcagg  660
gttggcccaa ggtgtggacg gactactcgg tctccaagct ggccctgaac gcctactccc  720
ggctgctggc gcggcggctg caggcgcgcg gcgcccgcgt gagcgtcaac tgcttctgcc  780
ccgggttcac gcgcaccgac atgaccaggg gctgggggaa gcgcaccgcc gaggaggcgg  840
ccgacgtcgg cgcgcggctc gcgctgctgc cgcccggcga gctccccacg ggggccttct  900
tcaagtggtg cacgccgcag ccctactcca agctgtgacc tgccgagcca cgccgccggc  960
ccgcgcgccc cggccatggc ggccgcagga gtatgtagcg ttggtttagc tgcttctagt  1020
tactttcaat gcagacaaga agccgatcga gtagtgtctc ttagcagtct ggctttctgc  1080
caaggtgctt tggttgagca atgcaaccaa accatgtcag cgatcaatgt actatgcgtg  1140
cttagccgtg caagatttag gtcaacttcc g                                 1171

SEQ ID NO: 88          moltype = AA  length = 294
FEATURE                Location/Qualifiers
REGION                 1..294
                       note = misc_feature - Ceres CLONE ID no.1831117
REGION                 1..294
                       note = misc_feature - Bit score of 671.6 for hmm based on
                        sequences of FIGURE 3.
REGION                 20..160
                       note = misc_feature - Pfam Name: adh_short Pfam
                        Description: short chain dehydrogenase
REGION                 1..294
                       note = misc_feature - Functional Homolog Of Full Length
                        Ceres SEEDLINE ID no.ME17294 at SEQ ID NO. 74
source                 1..294
                       mol_type = protein
                       organism = Panicum virgatum
SEQUENCE: 88
MDYSSTKELP PAGAWWSRET VAVVTGANRG IGHALAARLA EHGLTVVLTA RDGARGEAAA  60
APLRARGLAV AFRRLDVSDA ASVAEFAAWL RDAVGGLDIL VNNAAVSFNE IDTNSVEHAE  120
TVLRTNFYGA KMLTEALLPL FRQSPATSRI LNISSQLGLL NKVSDPSLKA LLLDEETLTE  180
AAIDAMVSRF LAQVKDGTWG AQGWPKVWTD YSVSKLALNA YSRLLARRLQ ARGARVSVNC  240
FCPGFTRTDM TRGWGKRTAE EAADVGARLA LLPPGELPTG AFFKWCTPQP YSKL        294

SEQ ID NO: 89          moltype = DNA  length = 951
FEATURE                Location/Qualifiers
misc_feature           1..951
                       note = Ceres ANNOT ID no.857222
misc_feature           1..951
                       note = Encodes the peptide sequence at SEQ ID NO 90
source                 1..951
                       mol_type = other DNA
                       organism = Arabidopsis thaliana
SEQUENCE: 89
atgacgaaca aggagaaagc tcgagagaga agggagaaaa gaatgcagga gatctctctc  60
cttcgaacta ttccttactc tgaccaccat aggtggtggt cttgtgaaaa tgtagcagta  120
```

```
gtgactggtt caaaccgcgg gattggattc gagattgcaa gacagcttgc ggttcacgga  180
ttgacggttg ttcttacagc tagaaacgtg aatgctggtc ttgaagcagt taaatctttg  240
aggcaccaag aagaaggtct caaggtttat tttcatcaac ttgatgtcac agactcttcg  300
tcgattagag agtttggttg ctggcttaag caaacatttg gaggtttaga tattctcgtg  360
aataatgcag gtgttaacta caatctcggc tcagataata cggttgaatt tgctgaaaca  420
gttatatcta ctaactacca aggaaccaaa aacatgacaa aagctatgat acccttgatg  480
agaccatctc ctcatggcgc tcgtgtagtc aatgttagtt ctcggctagg tagagtaaat  540
ggaagacgta atagactggc aaatgtagag ttgagagatc agctaagcag tccagatttg  600
ctgaccgagg aacttataga cagaactgtc tctaaattca tcaaccaagt aaaagacgga  660
acttgggaat caggcgggtg gcctcagaca ttcactgact actccatgtc taagcttgca  720
gtcaatgctt acacgagact aatggcaaaa gaacttgaga gacgaggaga ggaagagaag  780
atttatgtta acagctttg ccctggttgg gtgaagactg cgatgactgg ctacgccgga  840
aatatgccac ctgaagatgc agctgatact ggagtttggc ttagcctggt cctttccgaa  900
gaggcagtaa ccggaaaatt cttcgcagag agacgtgaga tcaacttctg a           951
```

```
SEQ ID NO: 90          moltype = AA  length = 316
FEATURE                Location/Qualifiers
REGION                 1..316
                       note = misc_feature - Ceres ANNOT ID no.857222
REGION                 1..316
                       note = misc_feature - Bit score of 823.3 for hmm based on
                        sequences of FIGURE 3.
REGION                 37..174
                       note = misc_feature - Pfam Name: adh_short Pfam
                        Description: short chain dehydrogenase
REGION                 1..316
                       note = misc_feature - Functional Homolog Of Full Length
                        Ceres SEEDLINE ID no.ME17294 at SEQ ID NO. 74
source                 1..316
                       mol_type = protein
                       organism = Arabidopsis thaliana
SEQUENCE: 90
MTNKEKARER REKRMQEISL LRTIPYSDHH RWWSCENVAV VTGSNRGIGF EIARQLAVHG  60
LTVVLTARNV NAGLEAVKSL RHQEEGLKVY FHQLDVTDSS SIREFGCWLK QTFGGLDILV  120
NNAGVNYNLG SDNTVEFAET VISTNYQGTK NMTKAMIPLM RPSPHGARVV NVSSRLGRVN  180
GRRNRLANVE LRDQLSSPDL LTEELIDRTV SKFINQVKDG TWESGGWPQT FTDYSMSKLA  240
VNAYTRLMAK ELERRGEEEK IYVNSFCPGW VKTAMTGYAG NMPPEDAADT GVWLSLVLSE  300
EAVTGKFFAE RREINF                                                 316
```

```
SEQ ID NO: 91          moltype = DNA  length = 1213
FEATURE                Location/Qualifiers
misc_feature           1..1213
                       note = Expected Sequence
misc_feature           1..1213
                       note = Encodes the peptide sequence at SEQ ID NO. 93
source                 1..1213
                       mol_type = other DNA
                       organism = Triticum aestivum
SEQUENCE: 91
acacggctgt ggtttcaatt ttatttcatc tctatccaat tgagtgatgg aacggctgag  60
agtagtggtg cctaattgcc tgagctgtat tgagttctga atattcatgt tcaaaaaatt  120
cctactacca tgcatagaag tctgaatatt tagcagaaaa tagcttggac atgggcagtc  180
taaaaatgat attcagtttc atacatgtga gactatgata cataggttct gcacaaagca  240
aggaggaaac cgatatgcaa tgagtggtta ggtgctgata ctggcagatt tttgtctgaa  300
tatctctggt aacccagcta cagattaaca atgcaggtgt aaacttcaac agaggagcag  360
ataactctgt tgaatttgca gagcaagtaa ttgagacaaa ttattttggt acaaagcgga  420
tgattgaagc catgctacca ttactgaaac cttctccgta tggtggccgg atagtgaatg  480
taagctcaag gcttggtagg gccaatggca ggcgcaataa aatcggcgat gcgatcctaa  540
gagagcaact attaactgat gattgcttat ctgaagaatt gatttgatgg gattgtcact  600
aaattccttg aacaagtgaa gcaaaatagt tggtcctcca ttgagtggcc tcagatgtac  660
acggactatt ctatytcaaa gcttgctgtt aatgtgtata caagactcat ggctaagagg  720
cttgctgaca ggtytgaagg ccaaaagatt tacattaact gtttctgtcc tggctgggta  780
aagactgcca tgactgattg ggaagggaac atttmagycg aagaaggtgc tgatactgga  840
gtgtggcttg mtctgttacc ccaggcacaa gcaacaattg gaaagttcta tgctgagaga  900
cgcgagataa gcttctgagg tgactagtct tgtccatact tttgctccag ctagacagct  960
acaagttgaa attttccata gttttgcccc cagctataag tagagaaaag ccatgaccca  1020
aggttcgtat gttcaaattg ctttgtgtta cttgcaccta ttggcataga agtgatacat  1080
gcttactttt atctatgtcc tcttaaaggg cttgtggttt gctttttatt ttgcacgtta  1140
gctgaagagc agtagaactg agatgtgttc ccatttcctc tgatatttaa tgcagtaacg  1200
gatccatctt tct                                                    1213
```

```
SEQ ID NO: 92          moltype = DNA  length = 1212
FEATURE                Location/Qualifiers
misc_feature           1..1212
                       note = Inplanta Sequence
misc_feature           1..1212
                       note = Encodes the peptide sequence at SEQ ID NO. 93
source                 1..1212
                       mol_type = other DNA
```

```
                         organism = Triticum aestivum
SEQUENCE: 92
acacggctgt ggtttcaatt ttatttcatc tctatccaat tgagtgatgg aacggctgag  60
agtagtggtg cctaattgcc tgagctgtat tgagttctga atattcatgt tcaaaaaatt  120
cctactacca tgcatagaag tctgaatatt tagcagaaaa tagcttggac atgggcagtc  180
taaaaatgat attcagtttc atacatgtga gactatgata cataggttct gcacaaagca  240
aggaggaaac cgatatgcaa tgagtggtta ggtgctgata ctggcagatt tttgtctgaa  300
tatctctggt aacccagcta cagattaaca atgcaggtgt aaacttcaac agaggagcag  360
ataactctgt tgaatttgca gagcaagtaa ttgagacaaa ttattttggt acaaagcgga  420
tgattgaagc catgctacca ttactgaaac cttctccgta tggtggccgg atagtgaatg  480
taagctcaag gcttggtagg gccaatggca ggcgcaataa aatcggcgat gcgatcctaa  540
gagagcaact attaactgat gattgcttat ctgaggaatt gattggtggg attgtcacta  600
aattccttga acaagtgaag caaaatagtt ggtcctccat tgagtggcct cagatgtaca  660
cggactattc tatctcaaag cttgctgtta atgtgtatac aagactcatg gctaagaggc  720
ttgctgacag gtctgaaggc caaaagattt acattaactg tttctgtcct ggctgggtaa  780
agactgccat gactgattgg gaagggaaca tttcagccga agaaggtgct gatactggag  840
tgtggcttgc tctgttaccc caggcacaag caacaattgg aaagttctat gctgagagac  900
gcgagataag cttctgaggt gactagtctt gtccatactt ttactccagc tagacagcta  960
caagttgaaa ttttccatag ttttgccccc agctataagt agagaaaagc catgacccaa  1020
ggttcgtatg ttcaaattgc tttgtgttac ttgcacctat tggcatagaa gtgatacatg  1080
cttactttta tctatgtcct cttaaagggc ttgtggtttg ctttttattt tgcacgttag  1140
ctgaagagca gtagaactga gatgtgttcc catttcctct gatatttaat gcagtaacgg  1200
atccatcttt ct                                                    1212

SEQ ID NO: 93            moltype = AA  length = 165
FEATURE                  Location/Qualifiers
REGION                   1..165
                         note = misc_feature - Functional Homolog Of Ceres SEEDLINE
                          ID no.ME17294 at SEQ ID NO. 93
REGION                   1..165
                         note = misc_feature - Bit score of 449.7 for hmm based on
                          sequences of FIGURE 4.
source                   1..165
                         mol_type = protein
                         organism = Triticum aestivum
SEQUENCE: 93
MIEAMLPLLK PSPYGGRIVN VSSRLGRANG RRNKIGDAIL REQLLTDDCL SEELIGGIVT  60
KFLEQVKQNS WSSIEWPQMY TDYSISKLAV NVYTRLMAKR LADRSEGQKI YINCFCPGWV  120
KTAMTDWEGN ISAEEGADTG VWLALLPQAQ ATIGKFYAER REISF                165

SEQ ID NO: 94            moltype = DNA  length = 1171
FEATURE                  Location/Qualifiers
misc_feature             1..1171
                         note = Ceres CLONE ID no.1831117
misc_feature             1..1171
                         note = Encodes the peptide sequence at SEQ ID NO 95
source                   1..1171
                         mol_type = other DNA
                         organism = Panicum virgatum
SEQUENCE: 94
ctcccacccg cgctcccagc acgcccaccg tcgcctaccc cgtctccagc tcgatggact  60
actcgagcac caaggagtta cctccggccg gggcctggtg gtcgagggag acggtggccg  120
tggtgacggg cgcgaaccgg ggcatcgggc acgccctcgc cgcgcgcctg gcggagcacg  180
ggctcaccgt ggtgctcacc gcgcgggacg gcgcgcgcgg ggaggccgcc gcggccccgc  240
tccgcgcgcg cgggctcgcc gtcgccttcc gcaggctcga cgtctccgac gccgcctccg  300
tcgccgagtt cgccgcctgg ctccgcgacg ccgtcggcgg cctcgacatc ctggtgaaca  360
acgccgccgt gtccttcaac gagatcgaca ccaactcggt ggagcacgcc gagacggtcc  420
tccggaccaa cttctacggc gccaagatgc tcacggaagc gctcctgccg ctgttccggc  480
agtccccggc caccagcagg atcctcaaca tcagctcgca gctcggcctt ctcaacaagg  540
tgagcgaccc gtccctgaag gcgttgctgc tggacgagga gaccctgacg gaggcggcga  600
tcgacgccat ggtgtcgcgg ttcctggcgc aggtgaagga cgggacgtgg ggcgcgcagg  660
gttggcccaa ggtgtggacg gactactcgg tctccaagct ggccctgaac gcctactccc  720
ggctgctggc gcggcggctg caggcgcgcg gcgcccgcgt gagcgtcaac tgcttctgcc  780
ccgggttcac gcgcaccgac atgaccaggg gctgggggaa gcgcaccgcc gaggaggcgg  840
ccgacgtcgg cgcgcggctc gcgctgctgc cgcccggcga gctccccacg ggggccttct  900
tcaagtggtg cacgccgcag ccctactcca agctgtgacc tgccgagcca cgccgccggc  960
ccgcgcgccc cggccatggc ggccgcagga gtatgtagcg ttggtttagc tgcttctagt  1020
tactttcaat gcagacaaga agccgatcga gtagtgtctc ttagcagtct ggctttctgc  1080
caaggtgctt tggttgagca atgcaaccaa accatgtcag cgatcaatgt actatgcgtg  1140
cttagccgtg caagatttag gtcaacttcc g                               1171

SEQ ID NO: 95            moltype = AA  length = 163
FEATURE                  Location/Qualifiers
REGION                   1..163
                         note = misc_feature - Ceres CLONE ID no.1831117
REGION                   1..163
                         note = misc_feature - Bit score of 411.8 for hmm based on
                          sequences of FIGURE 4.
REGION                   1..163
```

```
                        note = misc_feature - Functional Homolog Of Ceres SEEDLINE
                         ID no.ME17294 at SEQ ID NO. 93
source                  1..163
                        mol_type = protein
                        organism = Panicum virgatum
SEQUENCE: 95
MLTEALLPLF RQSPATSRIL NISSQLGLLN KVSDPSLKAL LLDEETLTEA AIDAMVSRFL  60
AQVKDGTWGA QGWPKVWTDY SVSKLALNAY SRLLARRLQA RGARVSVNCF CPGFTRTDMT  120
RGWGKRTAEE AADVGARLAL LPPGELPTGA FFKWCTPQPY SKL                   163

SEQ ID NO: 96           moltype = AA  length = 164
FEATURE                 Location/Qualifiers
REGION                  1..164
                        note = misc_feature - Public GI ID no.92871098
REGION                  1..164
                        note = misc_feature - Truncated
REGION                  1..164
                        note = misc_feature - Bit score of 389.1 for hmm based on
                         sequences of FIGURE 4.
REGION                  1..164
                        note = misc_feature - Functional Homolog Of Ceres SEEDLINE
                         ID no.ME17294 at SEQ ID NO. 93
source                  1..164
                        mol_type = protein
                        organism = Medicago truncatula
SEQUENCE: 96
MIEAMIPLMK PSAAGGRIVN VSSRLGRLNG KRNRIENEEL REKLSDVESL SEELIDETIN  60
NFLQQIEDGS WKTGGWPQTF TDYSVSKLAV NTYTRYMAKK LSDRPEGEKI YINCYCPGWV  120
KTALTGYAGS VTVEQGADTG VWIALVPDQE ITGKFFAERR EINF                  164

SEQ ID NO: 97           moltype = DNA  length = 1243
FEATURE                 Location/Qualifiers
misc_feature            1..1243
                        note = Ceres CLONE ID no.1844076
misc_feature            1..1243
                        note = Truncated
misc_feature            1..1243
                        note = Encodes the peptide sequence at SEQ ID NO 98
source                  1..1243
                        mol_type = other DNA
                        organism = Gossypium hirsutum
SEQUENCE: 97
atttcagtcc aataactttc ctagacctta tttgcgtttc agctccgtgc atccatttac  60
tttctccttc tccattttga ctcgtcacct caaaattgcc ccacacctga aagacggagc  120
aaacactagg atatgtcagg gaaaaaggaa agaaacaagg agagaagaga aaagagactc  180
caagagattt cacttctcag gaccattcct tattctgatc atcaaaggtg gtggtcacaa  240
gaaactgttg cagttgtaac tggtgctaat agaggaatcg ggtttgagat tgcaagacaa  300
cttgccgggc atggattgac agtaatacta acatcaagga acattagtgt cggcattgaa  360
gcaaccaagg ccttacaaga agggggtttc agttatgatg ttcatcagct tgatatcttg  420
gatggtgaat caatttcagc gtttgttgaa tggataaaac aaaaatacgg tggcattgat  480
atcctggtga ataatgcagg tgttaactac aacctcgggt tcgataattc tgtggaattc  540
gcacgacagg tagttgacac caattattat ggcactaaaa atatgattaa agcaatgata  600
ccagtaatga aaccttccac tgctggtgct cgtatcgtta atgtaagctc acggctaggc  660
agactaaacg gccgccgcaa tagaattcaa gatgcaactt tgagagaaaa actaactaat  720
ttggaaactc tctcagagga attgattgat agaacagtgt ctagtttctt acaacaagtt  780
gaagatgaaa cttggcaatc aggcggatgg cctcaaacat tcactgatta ctctgtatct  840
aaacttgctg tcaatgctta caccagactg gtggccaaag aactctgcga tcgaccacaa  900
ggcgaaaaga tatatatcaa ctgttattgt ccaggatggg tgaagactgc aatgacaggt  960
tgggcaggca atatttctcc tgaggttgca gctgacactg gagtctggct ttccttgctt  1020
tctgaccaag caataactgg aaagtttttt gcagagagac gagaaatcaa cttttgagta  1080
aattaagttc tgcattgtag agtcaaaaat ttgttctatt cttgaagatt cgatgaaaca  1140
gttgaaagta acttgtttta gaagcaattt ggcccatacg tagcaccaaa ctaaaaccga  1200
acatatgaat caatgctgct ttctgtctaa ccttaaaaga ccc                   1243

SEQ ID NO: 98           moltype = AA  length = 164
FEATURE                 Location/Qualifiers
REGION                  1..164
                        note = misc_feature - Ceres CLONE ID no.1844076
REGION                  1..164
                        note = misc_feature - Bit score of 438.0 for hmm based on
                         sequences of FIGURE 4.
REGION                  1..164
                        note = misc_feature - Truncated
REGION                  1..164
                        note = misc_feature - Functional Homolog Of Ceres SEEDLINE
                         ID no.ME17294 at SEQ ID NO. 93
source                  1..164
                        mol_type = protein
                        organism = Gossypium hirsutum
```

-continued

```
SEQUENCE: 98
MIKAMIPVMK PSTAGARIVN VSSRLGRLNG RRNRIQDATL REKLTNLETL SEELIDRTVS  60
SFLQQVEDET WQSGGWPQTF TDYSVSKLAV NAYTRLVAKE LCDRPQGEKI YINCYCPGWV  120
KTAMTGWAGN ISPEVAADTG VWLSLLSDQA ITGKFFAERR EINF                   164

SEQ ID NO: 99          moltype = DNA  length = 1167
FEATURE                Location/Qualifiers
misc_feature           1..1167
                       note = Ceres CLONE ID no.35974
misc_feature           1..1167
                       note = Encodes the peptide sequence at SEQ ID NO 100
source                 1..1167
                       mol_type = other DNA
                       organism = Arabidopsis thaliana
SEQUENCE: 99
acacccaaac acgcgacgcg agcgaaagaa gacgatgacg aacaaggaga aagctcgaga  60
gagaagggag aaaaaaatgc aggagatctc tctccttcga actattcctt actctgacca  120
ccataggtgg tggtcttgtg aaaatgtagc agtagtgact ggttcaaacc gcgggattgg  180
attcgagatt gcaagacagc ttgcggttca cggattgacg gttgttctta cagctagaaa  240
cgtgaatgct ggtcttgaag cagttaaatc tttgaggcac caagaagaag gtctcaaggt  300
ttattttcat caacttgatg tcacagactc ttcctcgatt agagagtttg gttgctggct  360
taagcaaaca tttggaggtt tagatattct cgtgaataat gcaggtgtta actacaatct  420
cggctcagat aatacggttg aatttgctga aacagttata tctactaact accaaggaac  480
caaaaacatg acaaaagcta tgataccctt gatgagacca tctcctcatg gcgctcgtgt  540
agtcaatgtt agttctcggc taggtagagt aaatggaaga cgtaatagac tggcaaatgt  600
agagttgaga gatcagctaa gcagtccaga tttgctgacc gaggaactta tagacagaac  660
tgtctctaaa ttcatcaacc aagtaaaaga cggaacttgg gaatcaggcg ggtggcctca  720
gacattcact gactactcca tgtctaagct tgcagtcaat gcttacacga gactaatggc  780
aaaagaactt gagagacgag gagaggaaga gaagatttat gttaacagct tttgccctgg  840
ttgggtgaag actgcgatga ctggctacgc cggaaatatg ccacctgaag atgcagctga  900
tactggagtt tggcttagcc tggtcctttc cgaagagtca gtaaccggaa aattcttcgc  960
agagagacgt gagatcaact tctgagggtt gttgaatgtt tgtaaacgtt ggaatagatt  1020
gtgtcgtctt cgtttagtgc catagtttta gtcaaaggtt tacaaaatca attgtaattg  1080
gtaagtgaat ggttgtagtc atgatacgcg tcagatttgc cacaaaacta ggagtttata  1140
atttaaatat aattaatttt taattgc                                      1167

SEQ ID NO: 100         moltype = AA  length = 165
FEATURE                Location/Qualifiers
REGION                 1..165
                       note = misc_feature - Ceres CLONE ID no.35974
REGION                 1..165
                       note = misc_feature - Bit score of 357.4 for hmm based on
                        sequences of FIGURE 4.
REGION                 1..165
                       note = misc_feature - Truncated
REGION                 1..165
                       note = misc_feature - Functional Homolog Of Ceres SEEDLINE
                        ID no.ME17294 at SEQ ID NO. 93
source                 1..165
                       mol_type = protein
                       organism = Arabidopsis thaliana
SEQUENCE: 100
MTKAMIPLMR PSPHGARVVN VSSRLGRVNG RRNRLANVEL RDQLSSPDLL TEELIDRTVS  60
KFINQVKDGT WESGGWPQTF TDYSMSKLAV NAYTRLMAKE LERRGEEEKI YVNSFCPGWV  120
KTAMTGYAGN MPPEDAADTG VWLSLVLSEE SVTGKFFAER REINF                  165

SEQ ID NO: 101         moltype = AA  length = 165
FEATURE                Location/Qualifiers
REGION                 1..165
                       note = misc_feature - Public GI ID no.110737329
REGION                 1..165
                       note = misc_feature - Bit score of 355.4 for hmm based on
                        sequences of FIGURE 4.
REGION                 1..165
                       note = misc_feature - Functional Homolog Of Ceres SEEDLINE
                        ID no.ME17294 at SEQ ID NO. 93
source                 1..165
                       mol_type = protein
                       organism = Arabidopsis thaliana
SEQUENCE: 101
MTKAMIPLMR PSPHGARVVN VSSRLGRVNG RRNRLANVEL RDQLSSPDLL TEELIDRTVS  60
KFINQVKDGT WESGGWPQTF TDYPMSKLAV NAYTRLMAKE LERRGEEEKI YVNSFCPGWV  120
KTAMTGYAGN MPPEDAADTG VWLSLVLSEE AVTGKFFAER REINF                  165

SEQ ID NO: 102         moltype = AA  length = 167
FEATURE                Location/Qualifiers
REGION                 1..167
                       note = misc_feature - Public GI ID no.10176876
REGION                 1..167
```

```
                         note = misc_feature - Bit score of 316.9 for hmm based on
                          sequences of FIGURE 4.
REGION                   1..167
                         note = misc_feature - Truncated
REGION                   1..167
                         note = misc_feature - Functional Homolog Of Ceres SEEDLINE
                          ID no.ME17294 at SEQ ID NO. 93
source                   1..167
                         mol_type = protein
                         organism = Arabidopsis thaliana
SEQUENCE: 102
MTKAMIPLMR PSPHGARVVN VSSRLENLVE IHELQRLANV ELRDQLSSPD LLTEELIDRT  60
VSKFINQVKD GTWESGGWPQ TFTDYSMSKL AVNAYTRLMA KELERRGEEE KIYVNSFCPG  120
WVKTAMTGYA GNMPPEDAAD TGVWLSLVLS EEAVTGKFFA ERREINF                167

SEQ ID NO: 103           moltype = DNA  length = 1164
FEATURE                  Location/Qualifiers
misc_feature             1..1164
                         note = Ceres CLONE ID no.473040
misc_feature             1..1164
                         note = Encodes the peptide sequence at SEQ ID NO 104
source                   1..1164
                         mol_type = other DNA
                         organism = Glycine max
SEQUENCE: 103
acttcttaaa actggtatct gatttacaaa aggttacaaa cttctcttgc ataaagaatg  60
gcatcagcaa caataaggaa tgcagttgtc acgggagcaa acaaagggat aggatttgga  120
atatgcaagc aattggtttc taatggcatc acagtggtgc taacagcaag ggatgagaaa  180
aggggtcttg aagctgttga aaagctgaaa gagtttggtg tgtctgatca agtggtgttt  240
catcagcttg atgtgactga ccctaaaagc attgaatccc ttgcaaattt catcaaaacc  300
cagtttggaa aacttgatat cttggtgaat aatgcaggaa ttcatggagc atatgttgac  360
cgtgatgctt tagctgctgc tggggaaaaa gttgccaatg ttgattggag aaaaatctca  420
actgaaaatt ttgaagctgc cgaagcaggc attagaacaa attactatgg agtcaaatta  480
atgtgtgaag cacttattcc ccttctagaa ttgtcaggca caccaaggat tgtcaatgtt  540
tcctcctcca tggggaagtt ggagaaaata ccaaatgcat gggctagagg agccctaagt  600
gatgctgaga gcctaacaga agaaaaggtg gatgaggttt tgaatcagtt tctaaaagat  660
tttaaagagg gttcattaga aaccaaaggg tggccacatg ctttttctgc atatatagtc  720
tcaaaagctg ctttgactgc ctacacaagg attcttgcta agaagtaccc atctttctgc  780
atcaatgctg tttgccctgg ctttgtgaaa acagatctca actacaatac tggctatctt  840
agtgttgatg aaggtgctga aagtgttgta aggttggctc tgctacctaa tggaggtcct  900
tctggtctat tcttttctcg aagtgaagtg gcaccattct gatccaaaga ctgttgtgta  960
cttgaagagg ataaataata agcatggttt catgataaga catgtatcaa atttgtacct  1020
agcacaacaa gaaaataagc cacatgtctg atcactgatg gctgcccatc attgatgaga  1080
acaaccctat agtgaattct agatattaca atgacattac taatttgaga aatctaattt  1140
tggatataaa gatatctgtt tgtc                                        1164

SEQ ID NO: 104           moltype = AA  length = 153
FEATURE                  Location/Qualifiers
REGION                   1..153
                         note = misc_feature - Ceres CLONE ID no.473040
REGION                   1..153
                         note = misc_feature - Bit score of 360.8 for hmm based on
                          sequences of FIGURE 4.
REGION                   1..153
                         note = misc_feature - Truncated
REGION                   1..153
                         note = misc_feature - Functional Homolog Of Ceres SEEDLINE
                          ID no.ME17294 at SEQ ID NO. 93
source                   1..153
                         mol_type = protein
                         organism = Glycine max
SEQUENCE: 104
MCEALIPLLE LSGTPRIVNV SSSMGKLEKI PNAWARGALS DAESLTEEKV DEVLNQFLKD  60
FKEGSLETKG WPHAFSAYIV SKAALTAYTR ILAKKYPSFC INAVCPGFVK TDLNYNTGYL  120
SVDEGAESVV RLALLPNGGP SGLFFSRSEV APF                              153

SEQ ID NO: 105           moltype = DNA  length = 2073
FEATURE                  Location/Qualifiers
misc_feature             1..2073
                         note = Ceres CLONE ID no.922223
misc_feature             1..2073
                         note = Encodes the peptide sequence at SEQ ID NO 106
source                   1..2073
                         mol_type = other DNA
                         organism = Triticum aestivum
SEQUENCE: 105
gtaaacaagc ccatggactc ttattttctc tttatgttgg gcttaatgtt cttggggcta  60
tggttccgag ttctcaaaaa aaaaagttcg attccggcga acacagtaca gcagagggag  120
cgagagatgg ggaagaaggg caaggcggcg gcaagggagc gccgggagga gcggcggcgg  180
```

```
gaagtcacgc tcctccgcgc cgtaccctac gagccccacc agcggtggtg ggacggcctc  240
gcgccggcgc gcgccgtggc ggtggtgacg ggggccagcc gcggcatcgg ctacgagatc  300
tcccgccagc tcgcgcgcca cggcctccac gtcgtcctcg cctcgcgcga cgccgcgcgg  360
ggcagggacg ccgcggaggg gatcctccgc gaggagggca cgagcgcgga gtggcggcag  420
ctcgacgtgg cggacgccgc gtcggtcgag gccttcgccg cctggacggc gcggacccac  480
ggcggcatcc atgtccttat taacaatgca ggtgtaaact tcaacagagg agcagataac  540
tctgttgaat ttgcagagca agtaattgag acaaattatt ttggtacaag gcggatgatt  600
gaagccatgc taccattact gaaaccttct ccgtatggtg gccggatagt gaatgtgagc  660
tcaaggcttg gcagggccaa tggcagacgc aataaaatcg gcgatgcgat cctaagagag  720
caactattaa ctgatgattg cttatctgag gaattgattg atgggatggt cactaaattc  780
cttgaacaag tgaagcaaaa tagttggtcc tccattgagt ggcctcagat gtacacggac  840
tattcggtct caaagtttgc tgttaatgtg tatacaagac tcatggcaag gaggttatct  900
gacaggtctg aaggccaaaa gatttacatt aactgtttct gtcctggctg ggtaaagact  960
gccatgactg attgggaagg gaacatttca gccgaagaag gtgctgatac tggagtgtgg  1020
cttgctctgt taccccagga acaagcaaca attggaaagt tctatgctga gagacgcgag  1080
ataagcttct gaggtgatcg gaatggtgga tatgcgagtg ggagtggtac atttaaccat  1140
atgtatttaa ttaaagtttt aaactatgta ggtgatcgga atggtggata tgcgagtggg  1200
agtggcatgt tcatgaagag caatccacat gattggcaga ctccagcatg gttttcgagt  1260
cgcgactcat gcgagttgct ctggggcagc gactcggaag aagtcgagcc tgcgttgtga  1320
ctagtcatga ctcagagtcg cgagtcgata ctaagctgag ttgaccatat ttttgcgact  1380
catagactag tcgtcgacta gtcgcaacta gtcgagcgac tcgaaatcca tggactccag  1440
tcggtcaaag agcattgagt cttcacactg atggaaggcc atgctctcta attttgtcaa  1500
taaatgatgc agtaccagat gctttcagac gatactcaga cgacgttgcc catcagaccg  1560
tttgttaatt agattcacgt caatctcatg gtgtagagtc tgcgtcggct gcacatcggc  1620
cataccatgt cgtgtgtaca tcaatttcgt gaagttgctg gaaacaggga aatgttcacc  1680
aggcccacca ccactagtcc acaacggcag taagcaggca tggcatgctg gactgctgca  1740
ccgaatatat gattaggctg gatctcaagc aactccactg tcagattctc tcattatctt  1800
ccaagtagag gtggaatcct tatgacccaa tggatgagag cgatgcaacg ctgcctcacc  1860
cacgcatgca gaagatcgat atgtttggga acgaaccggt cggcctacct tgggaattct  1920
ggagctatag tcatggctag gccgccattc atggaccgga gactacatgt cttgcagtat  1980
attgttctga ttttgccgcc acctgcatat gtgtggtaca tactttgtta tgttcgtgtt  2040
tgtatgcaat ggttggatcg tgtgatttgc tgg                               2073

SEQ ID NO: 106          moltype = AA  length = 165
FEATURE                 Location/Qualifiers
REGION                  1..165
                        note = misc_feature - Ceres CLONE ID no.922223
REGION                  1..165
                        note = misc_feature - Bit score of 455.9 for hmm based on
                         sequences of FIGURE 4.
REGION                  1..165
                        note = misc_feature - Truncated
REGION                  1..165
                        note = misc_feature - Functional Homolog Of Ceres SEEDLINE
                         ID no.ME17294 at SEQ ID NO. 93
source                  1..165
                        mol_type = protein
                        organism = Triticum aestivum
SEQUENCE: 106
MIEAMLPLLK PSPYGGRIVN VSSRLGRANG RRNKIGDAIL REQLLTDDCL SEELIDGMVT  60
KFLEQVKQNS WSSIEWPQMY TDYSVSKFAV NVYTRLMARR LSDRSEGQKI YINCFCPGWV  120
KTAMTDWEGN ISAEEGADTG VWLALLPQEQ ATIGKFYAER REISF                  165

SEQ ID NO: 107          moltype = AA  length = 166
FEATURE                 Location/Qualifiers
REGION                  1..166
                        note = misc_feature - Public GI ID no.125528967
REGION                  1..166
                        note = misc_feature - Bit score of 452.6 for hmm based on
                         sequences of FIGURE 4.
REGION                  1..166
                        note = misc_feature - Truncated
REGION                  1..166
                        note = misc_feature - Functional Homolog Of Ceres SEEDLINE
                         ID no.ME17294 at SEQ ID NO. 93
source                  1..166
                        mol_type = protein
                        note = subspecies = indica
                        organism = Oryza sativa
SEQUENCE: 107
MIEAMMPLMI TSPHGGRIVN VSSRLGRVNG RRNRIGDPSL RERLLNDDHL SEELINEMVM  60
KFLEQTKQDN WSSSNEWPQM YTDYSISKLA VNAYTRLLAR RLLDRPEGQK IYINCFCPGW  120
VKTAMTGWEG NISAEEGADT GVWLALVPQE QATIGKFFAE RREISF                 166

SEQ ID NO: 108          moltype = AA  length = 158
FEATURE                 Location/Qualifiers
REGION                  1..158
                        note = misc_feature - Public GI ID no.115442007
REGION                  1..158
```

```
                      note = misc_feature - Truncated
REGION                1..158
                      note = misc_feature - Bit score of 417.1 for hmm based on
                       sequences of FIGURE 4.
REGION                1..158
                      note = misc_feature - Functional Homolog Of Ceres SEEDLINE
                       ID no.ME17294 at SEQ ID NO. 93
source                1..158
                      mol_type = protein
                      note = subspecies = japonica
                      organism = Oryza sativa
SEQUENCE: 108
MITSPHGGRI VNVSSRLGRV NGRRNRIGDP SLRERLLNDD HLSEELINEM VMKFLEQTKQ  60
DNWSSGNEWP QMYTDYSISK LAVNAYTRLL ARRLLDRPEG QKIYINCFCP GWVKTAMTGW  120
EGNISAEEGA DTGVWLALVP QEQATIGKFF AERREISF                          158

SEQ ID NO: 109        moltype = DNA  length = 951
FEATURE               Location/Qualifiers
misc_feature          1..951
                      note = Ceres ANNOT ID no.857222
misc_feature          1..951
                      note = Encodes the peptide sequence at SEQ ID NO 110
source                1..951
                      mol_type = other DNA
                      organism = Arabidopsis thaliana
SEQUENCE: 109
atgacgaaca aggagaaagc tcgagagaga agggagaaaa gaatgcagga gatctctctc  60
cttcgaacta ttccttactc tgaccaccat aggtggtggt cttgtgaaaa tgtagcagta  120
gtgactggtt caaaccgcgg gattggattc gagattgcaa gacagcttgc ggttcacgga  180
ttgacggttg ttcttacagc tagaaacgtg aatgctggtc ttgaagcagt taaatctttg  240
aggcaccaag aagaaggtct caaggtttat tttcatcaac ttgatgtcac agactcttcg  300
tcgattagag agtttggttg ctggcttaag caaacatttg gaggtttaga tattctcgtg  360
aataatgcag gtgttaacta caatctcggc tcagataata cggttgaatt tgctgaaaca  420
gttatatcta ctaactacca aggaaccaaa aacatgacaa aagctatgat acccttgatg  480
agaccatctc ctcatggcgc tcgtgtagtc aatgttagtt ctcggctagg tagagtaaat  540
ggaagacgta atagactggc aaatgtagag ttgagagatc agctaagcag tccagatttg  600
ctgaccgagg aacttataga cagaactgtc tctaaattca tcaaccaagt aaaagacgga  660
acttgggaat caggcgggtg gcctcagaca ttcactgact actccatgtc taagcttgca  720
gtcaatgctt acacgagact aatggcaaaa gaacttgaga gacgaggaga ggaagagaag  780
atttatgtta acagcttttg ccctggttgg gtgaagactg cgatgactgg ctacgccgga  840
aatatgccac ctgaagatgc agctgatact ggagtttggc ttagcctggt cctttccgaa  900
gaggcagtaa ccggaaaatt cttcgcagag agacgtgaga tcaacttctg a           951

SEQ ID NO: 110        moltype = AA  length = 165
FEATURE               Location/Qualifiers
REGION                1..165
                      note = misc_feature - Ceres ANNOT ID no.857222
REGION                1..165
                      note = misc_feature - Truncated
REGION                1..165
                      note = misc_feature - Bit score of 401.6 for hmm based on
                       sequences of FIGURE 4.
REGION                1..165
                      note = misc_feature - Functional Homolog Of Ceres SEEDLINE
                       ID no.ME17294 at SEQ ID NO. 93
source                1..165
                      mol_type = protein
                      organism = Arabidopsis thaliana
SEQUENCE: 110
MTKAMIPLMR PSPHGARVVN VSSRLGRVNG RRNRLANVEL RDQLSSPDLL TEELIDRTVS  60
KFINQVKDGT WESGGWPQTF TDYSMSKLAV NAYTRLMAKE LERRGEEEKI YVNSFCPGWV  120
KTAMTGYAGN MPPEDAADTG VWLSLVLSEE AVTGKFFAER REINF                  165

SEQ ID NO: 111        moltype = DNA  length = 557
FEATURE               Location/Qualifiers
misc_feature          1..557
                      note = Ceres SEEDLINE ID no. ME00572
misc_feature          1..557
                      note = Inplanta Sequence
source                1..557
                      mol_type = other DNA
                      organism = Arabidopsis thaliana
SEQUENCE: 111
atcccaccgt ttcttaagac tctctctctc tttctgtttt ctatttctct ctctctcaaa  60
tgaaagagag agaagagctc ccatggatga aaatagcgag accgaagttt ctccaaggca  120
ttaaggaaaa cataacctcc gtgatgcata gagattattg gatccgctgt gctgagacat  180
tgagtttttc ttcggcattc cagtttcaat gataaagggg tgttatccta tctgagcttt  240
tagtcggatt ttttcttttc aattattgtg ttttatctag atgatgcatt tcattattct  300
ctttttcttg accttgtaag gccttttctt gaccttgtaa gaccccatct ctttctaaac  360
```

```
gttttattat tttctcgttt tacagattct attctatctc ttctcaatat agaatagata  420
tctatctcta cctctaattc gttcgagtca ttttctccta ccttgtctat ccctcctgag  480
ctaatctcca catatatctt ttgtttgtta ttgatgtatg gttgacataa attcaataaa  540
gaagttgacg tttttcc                                                  557

SEQ ID NO: 112          moltype = AA  length = 859
FEATURE                 Location/Qualifiers
REGION                  1..859
                        note = misc_feature - Ceres LOCUS ID no. AT5G62000
REGION                  1..859
                        note = misc_feature - Is Acted Upon By Ceres SEEDLINE ID
                         no. ME00572 at SEQ ID NO. 111
REGION                  1..859
                        note = misc_feature - Bit score of 2157.8 for hmm based on
                         sequences of FIGURE 5.
REGION                  163..268
                        note = misc_feature - Pfam Name: B3 Pfam Description: B3
                         DNA binding domain
REGION                  290..372
                        note = misc_feature - Pfam Name: Auxin_resp Pfam
                         Description: Auxin response factor
source                  1..859
                        mol_type = protein
                        organism = Arabidopsis thaliana
SEQUENCE: 112
MASSEVSMKG NRGGDNFSSS GFSDPKETRN VSVAGEGQKS NSTRSAAAER ALDPEAALYR  60
ELWHACAGPL VTVPRQDDRV FYFPQGHIEQ VEASTNQAAE QQMPLYDLPS KLLCRVINVD  120
LKAEADTDEV YAQITLLPEA NQDENAIEKE APLPPPPRFQ VHSFCKTLTA SDTSTHGGFS  180
VLRRHADECL PPLDMSRQPP TQELVAKDLH ANEWRFRHIF RGQPRRHLLQ SGWSVFVSSK  240
RLVAGDAFIF LRGENGELRV GVRRAMRQQG NVPSSVISSH SMHLGVLATA WHAISTGTMF  300
TVYYKPRTSP SEFIVPFDQY MESVKNNYSI GMRFKMRFEG EEAPEQRFTG TIVGIEESDP  360
TRWPKSKWRS LKVRWDETSS IPRPDRVSPW KVEPALAPPA LSPVPMPRPK RPRSNIAPSS  420
PDSSMLTREG TTKANMDPLP ASGLSRVLQG QEYSTLRTKH TESVECDAPE NSVVWQSSAD  480
DDKVDVVSGS RRYGSENWMS SARHEPTYTD LLSGFGTNID PSHGQRIPFY DHSSSPSMPA  540
KRILSDSEGK FDYLANQWQM IHSGLSLKLH ESPKVPAATD ASLQGRCNVK YSEYPVLNGL  600
STENAGGNWP IRPRALNYYE EVVNAQAQAQ AREQVTKQPF TIQEETAKSR EGNCRLFGIP  660
LTNNMNGTDS TMSQRNNLND AAGLTQIASP KVQDLSDQSK GSKSTNDHRE QGRPFQTNNP  720
HPKDAQTKTN SSRSCTKVHK QGIALGRSVD LSKFQNYEEL VAELDRLFEF NGELMAPKKD  780
WLIVYTDEEN DMMLVGDDPW QEFCCMVRKI FIYTKEEVRK MNPGTLSCRS EEEAVVGEGS  840
DAKDAKSASN PSLSSAGNS                                                859

SEQ ID NO: 113          moltype = DNA  length = 2538
FEATURE                 Location/Qualifiers
misc_feature            1..2538
                        note = Ceres ANNOT ID no.1527370
misc_feature            1..2538
                        note = Encodes the peptide sequence at SEQ ID NO. 114
source                  1..2538
                        mol_type = other DNA
                        organism = Populus balsamifera
                        sub_species = trichocarpa
SEQUENCE: 113
atggcttctt cagagatttc agcgaaagct aacagtggaa acattagagg aggaggagag  60
agcttcactt ctggttacag tgaagccatg gaagggcaga aaaatcattc tactcatcca  120
agttcagcta gagttgtaga tgctgaaacg gcgctgtata atgagctatg gcatgcttgt  180
gctggtcctt tagtgactgt acctcgtgaa ggagatcgtg tgttttattt ccctcaagga  240
catatagagc aggtggaggc atcaacgaat caggtagcag accagcagat gccgctgtat  300
aatcttctac cgaagatctt atgtcgtgtg gttaatgttc agttgaaggc tgaaccagat  360
actgatgagg tgtttgcgca agtgactctg cttcctgagc acaaccaaga tgagagtgtg  420
ttggagaagg agcctcctcc acctccacca ccgcgatttc atgtacattc attttgtaaa  480
accctgactg cttcggatac cagtactcat ggtggatttt cggttcttag aagacatgca  540
gatgaatgtc ttccaccttt ggatatgtca aggcagcctc caacacagga attggttgcc  600
aaggatttgc atggaaatga atggcgtttc cgacacattt ttcggggcca accacggagg  660
cacttgcttc agagtggatg gagcgtgttt gttagctcca aaaggcttgt tgcgggtgat  720
gcgtttatat ttctaagagg tgagaatgga gaacttcgag ttggtgttag acgtgcaatg  780
agacagcagg gtaatgttcc atcatctgtc atatccagcc acagcatgca tcttggggtg  840
cttgctacag catggcatgc tgtttcaacg gggaccctgt tcactgttta ttacaagcca  900
aggacaagtc ctgcagagtt cattgtcccc tttgatcaat acatggagtc tgtcaagaat  960
aattattcca tagggatgag gtttaaaatg agatttgaag gagaagaagc tcctgagcaa  1020
agatttactg gcactattgt tggaattgaa gatgccgatc ccgggaggtg gaagaattct  1080
aaatggaggt gccttaaggt gagatgggat gaaacttcta ccatgcctcg gccagagaga  1140
gtttcaccat ggaaaattga gcctgctcta gcacctcctg cactaaatcc tcttccattg  1200
cccaggccta aaaggcctcg agcaaacatg gtgccctcat cccctgactc ctcagttctt  1260
actagagatg accctccatc agcaagtgga ttttcaaggg tcttgcaagg tcaagaattc  1320
tcgaccttga gaggcacttt tgcagagagc aatgagtcca atgctgctga aaagtctgtt  1380
atgtggccat cctcagcaga tgatgagaag atcgatgtgt tatctacttc aagaagattt  1440
ggatcagaga ggtggatgtc ctctgcgagg catgaaccaa cctgcacaga tttgctatct  1500
ggctttggga caaattctga ttcattccat gggtttggtg ccccgtttgt tgaccaaact  1560
gccgtggctg ctaatccaac gaagaaacac ttgtcagatc aagggcagtt taacttgctt  1620
```

-continued

```
gccagcccgt ggtccataat gtcctcgggt ctcttgctaa agttgtcaga gtcaaataca  1680
aaggttccag tacaaggcag cgatgtaaca tatcaagcac gggcaaatgt gtttagtgag  1740
tatcctgtgc ttcaaggtca tagagttgag cagtcgcata aaaactggat gatgcatccc  1800
ccgccatctc attttgataa tcatgctaat tcgagagagt taatgcccaa acctgttttg  1860
atgcaagaac atgattctgg aaaatccctg gaaggaaact gcaagctctt tgggattcct  1920
ttgaaaatta gtaaacctgt tgcaccagag gcagcaggga ccacaatcac gatgaacgaa  1980
ccactgagtc atatccaacc tgtgagtcac caacttacat ttgaatctga tcagaagtca  2040
gaacaatcca aaggttcgaa gatgactgat gaaaatgaaa acgagaaacc attccaagct  2100
ggtcatttgc gaacaaagga caaccatgga aaagcacaaa atggctcaac caggagttgt  2160
acgaaggttc acaagcaggg gattgcactt ggtaggtctg ttgatcttgc caagttcaat  2220
aactatgatg agttgattgc tgaattggac aggctgtttg aatttaatgg tgaattaatg  2280
gctccccaaa agaattggct gattgtgtac acagacgatg aggatgatat gatgcttgtt  2340
ggagatgatc cctggcagga atttgttggc atggttagga agatagttat ttacaccaaa  2400
gaggaggcac agaagattaa accaggcgcc ttgaattcaa agggcgttga gaatccaatg  2460
gatatggagg gtgaggatga tgccaaggaa gccaaacatc tgccacttcc ttcagcatgt  2520
agccctatga attgttag                                                 2538

SEQ ID NO: 114         moltype = AA  length = 845
FEATURE                Location/Qualifiers
REGION                 1..845
                       note = misc_feature - Ceres ANNOT ID no.1527370
REGION                 1..845
                       note = misc_feature - Bit score of 2089.3 for hmm based on
                        sequences of FIGURE 5.
REGION                 157..262
                       note = misc_feature - Pfam Name: B3 Pfam Description: B3
                        DNA binding domain
REGION                 284..366
                       note = misc_feature - Pfam Name: Auxin_resp Pfam
                        Description: Auxin response factor
REGION                 1..845
                       note = misc_feature - Is Acted Upon By Ceres SEEDLINE ID
                        no. ME00572 at SEQ ID NO. 111
source                 1..845
                       mol_type = protein
                       note = subspecies = trichocarpa
                       organism = Populus balsamifera
SEQUENCE: 114
MASSEISAKA NSGNIRGGGE SFTSGYSEAM EGQKNHSTHP SSARVVDAET ALYNELWHAC  60
AGPLVTVPRE GDRVFYFPQG HIEQVEASTN QVADQQMPLY NLLPKILCRV VNVQLKAEPD  120
TDEVFAQVTL LPEHNQDESV LEKEPPPPPP PRFHVHSFCK TLTASDTSTH GGFSVLRRHA  180
DECLPPLDMS RQPPTQELVA KDLHGNEWRF RHIFRGQPRR HLLQSGWSVF VSSKRLVAGD  240
AFIFLRGENG ELRVGVRRAM RQQGNVPSSV ISSHSMHLGV LATAWHAVST GTLFTVYYKP  300
RTSPAEFIVP FDQYMESVKN NYSIGMRFKM RFEGEEAPEQ RFTGTIVGIE DADPGRWKNS  360
KWRCLKVRWD ETSTMPRPER VSPWKIEPAL APPALNPLPL PRPKRPRANM VPSSPDSSVL  420
TRDDPPSASG FSRVLQGQEF STLRGTFAES NESNAAEKSV MWPSSADDEK IDVLSTSRRF  480
GSERWMSSAR HEPTCTDLLS GFGTNSDSFH GFGAPFVDQT AVAANPTKKH LSDQGQFNLL  540
ASPWSIMSSG LLLKLSESNT KVPVQGSDVT YQARANVFSE YPVLQGHRVE QSHKNWMMHP  600
PPSHFDNHAN SRELMPKPVL MQEHDSGKSL EGNCKLFGIP LKISKPVAPE AAGTTITMNE  660
PLSHIQPVSH QLTFESDQKS EQSKGSKMTD ENENEKPFQA GHLRTKDNHG KAQNGSTRSC  720
TKVHKQGIAL GRSVDLAKFN NYDELIAELD RLFEFNGELM APQKNWLIVY TDDEDDMMLV  780
GDDPWQEFVG MVRKIVIYTK EEAQKIKPGA LNSKGVENPM DMEGEDDAKE AKHLPLPSAC  840
SPMNC                                                              845

SEQ ID NO: 115         moltype = DNA  length = 2637
FEATURE                Location/Qualifiers
misc_feature           1..2637
                       note = Ceres ANNOT ID no.1473961
misc_feature           1..2637
                       note = Encodes the peptide sequence at SEQ ID NO. 116
source                 1..2637
                       mol_type = other DNA
                       organism = Populus balsamifera
                       sub_species = trichocarpa
SEQUENCE: 115
atggcttctt cagagatttc agcgaaagct aacagtggaa acattagagg aggaggagag  60
agcttcactt ctggttacag tgaagccatg gaagggcaga aaaatcattc tactcatcca  120
agttcagcta gagttgtaga tgctgaaacg gcgctgtata atgagctatg gcatgcttgt  180
gctggtcctt tagtgactgt acctcgtgaa ggagatcgtg tgttttattt ccctcaagga  240
catatagagc aggtggaggc atcaacgaat caggtagcag accagcagat gccgctgtat  300
aatcttctac cgaagatctt atgtcgtgtg gttaatgttc agttgaaggc tgaaccagat  360
actgatgagg tgtttgcgca agtgactctg cttcctgagc acaaccaaga tgagagtgtg  420
ttggagaagg agcctcctcc acctccacca ccgcgatttc atgtacattc attttgtaaa  480
accctgactg cttcggatac cagtactcat ggtggatttt cggttcttag aagacatgca  540
gatgaatgtc ttccaccttt ggatatgtca aggcagcctc caacacagga attggttgcc  600
aaggatttgc atggaaatga atggcgtttc cgacacattt ttcggggtaa tcatctcata  660
ctcgaacaat caacttgcat tcaagatgcc agttgcttaa tatgcacaat gatttcaatg  720
ccaggccaac cacggaggca cttgcttcag agtggatgga gcgtgtttgt tagctccaaa  780
aggcttgttg cgggtgatgc gtttatattt ctaagaggtg agaatggaga acttcgagtt  840
```

-continued

```
ggtgttagac gtgcaatgag acagcagggt aatgttccat catctgtcat atccagccac  900
agcatgcatc ttggggtgct tgctacagca tggcatgctg tttcaacggg gaccctgttc  960
actgtttatt acaagccaag gacaagtcct gcagagttca ttgtcccctt tgatcaatac  1020
atggagtctg tcaagaataa ttattccata gggatgaggt ttaaaatgag atttgaagga  1080
gaagaagctc ctgagcaaag atttactggc actattgttg gaattgaaga tgccgatccc  1140
gggaggtgga agaattctaa atggaggtgc cttaaggtga gatgggatga aacttctacc  1200
atgcctcggc cagagagagt ttcaccatgg aaaattgagc ctgctctagc acctcctgca  1260
ctaaatcctc ttccattgcc caggcctaaa aggcctcgag caaacatggt gccctcatcc  1320
cctgactcct cagttcttac tagagatggt tcattcaaag taactgcaga ccctccatca  1380
gcaagtggat tttcaagggt cttgcaaggt caagaattct cgaccttgag aggcactttt  1440
gcagagagca atgagtccaa tgctgctgaa aagtctgtta tgtggccatc ctcagcagat  1500
gatgagaaga tcgatgtgtt atctacttca agaagatttg gatcagagag gtggatgtcc  1560
tctgcgaggc atgaaccaac ctgcacagat ttgctatctg gctttgggac aaattctgat  1620
tcattccatg ggtttggtgc cccgtttgtt gaccaaactg ccgtggctgc taatccaacg  1680
aagaaacact tgtcagatca agggcagttt aacttgcttg ccagcccgtg gtccataatg  1740
tcctcgggtc tcttgctaaa gttgtcagag tcaaatacaa aggttccagt acaaggcagc  1800
gatgtaacat atcaagcacg ggcaaatgtg tttagtgagt atcctgtgct tcaaggtcat  1860
agagttgagc agtcgcataa aaactggatg atgcatcccc cgccatctca ttttgataat  1920
catgctaatt cgagagagtt aatgcccaaa cctgttttga tgcaagaaca tgattctgga  1980
aaatccctgg aaggaaactg caagctcttt gggattcctt tgaaaattag taaacctgtt  2040
gcaccagagg cagcagggac cacaatcacg atgaacgaac cactgagtca tatccaacct  2100
gtgagtcacc aacttacatt tgaatctgat cagaagtcag aacaatccaa aggttcgaag  2160
atgactgatg aaaatgaaaa cgagaaacca ttccaagctg gtcatttgcg aacaaaggac  2220
aaccatggaa aagcacaaaa tggctcaacc aggagttgta cgaaggttca caagcagggg  2280
attgcacttg gtaggtctgt tgatcttgcc aagttcaata actatgatga gttgattgct  2340
gaattggaca ggctgtttga atttaatggt gaattaatgg ctccccaaaa gaattggctg  2400
attgtgtaca cagacgatga ggatgatatg atgcttgttg gagatgatcc ctggcaggaa  2460
tttgttggca tggttaggaa gatagttatt tacaccaaag aggaggcaca gaagattaaa  2520
ccaggcgcct tgaattcaaa gggcgttgag aatccaatgg atatggaggg tgaggatgat  2580
gccaaggaag ccaaacatct gccacttcct tcagcatgta gccctatgaa ttgttag     2637
```

```
SEQ ID NO: 116          moltype = AA  length = 852
FEATURE                 Location/Qualifiers
REGION                  1..852
                        note = misc_feature - Ceres ANNOT ID no.1473961
REGION                  1..852
                        note = misc_feature - Bit score of 2110.3 for hmm based on
                         sequences of FIGURE 5.
REGION                  157..262
                        note = misc_feature - Pfam Name: B3 Pfam Description: B3
                         DNA binding domain
REGION                  284..366
                        note = misc_feature - Pfam Name: Auxin_resp Pfam
                         Description: Auxin response factor
REGION                  1..852
                        note = misc_feature - Is Acted Upon By Ceres SEEDLINE ID
                         no. ME00572 at SEQ ID NO. 111
source                  1..852
                        mol_type = protein
                        note = subspecies = trichocarpa
                        organism = Populus balsamifera
SEQUENCE: 116
MASSEISAKA NSGNIRGGGE SFTSGYSEAM EGQKNHSTHP SSARVVDAET ALYNELWHAC  60
AGPLVTVPRE GDRVFYFPQG HIEQVEASTN QVADQQMPLY NLLPKILCRV VNVQLKAEPD  120
TDEVFAQVTL LPEHNQDESV LEKEPPPPPP PRFHVHSFCK TLTASDTSTH GGFSVLRRHA  180
DECLPPLDMS RQPPTQELVA KDLHGNEWRF RHIFRGQPRR HLLQSGWSVF VSSKRLVAGD  240
AFIFLRGENG ELRVGVRRAM RQQGNVPSSV ISSHSMHLGV LATAWHAVST GTLFTVYYKP  300
RTSPAEFIVP FDQYMESVKN NYSIGMRFKM RFEGEEAPEQ RFTGTIVGIE DADPGRWKNS  360
KWRCLKVRWD ETSTMPRPER VSPWKIEPAL APPALNPLPL PRPKRPRANM VPSSPDSSVL  420
TRDGSFKVTA DPPSASGFSR VLQGQEFSTL RGTFAESNES NAAEKSVMWP SSADDEKIDV  480
LSTSRRFGSE RWMSSARHEP TCTDLLSGFG TNSDSFHGFG APFVDQTAVA ANPTKKHLSD  540
QGQFNLLASP WSIMSSGLLL KLSESNTKVP VQGSDVTYQA RANVFSEYPV LQGHRVEQSH  600
KNWMMHPPPS HFDNHANSRE LMPKPVLMQE HDSGKSLEGN CKLFGIPLKI SKPVAPEAAG  660
TTITMNEPLS HIQPVSHQLT FESDQKSEQS KGSKMTDENE NEKPFQAGHL RTKDNHGKAQ  720
NGSTRSCTKV HKQGIALGRS VDLAKFNNYD ELIAELDRLF EFNGELMAPQ KNWLIVYTDD  780
EDDMMLVGDD PWQEFVGMVR KIVIYTKEEA QKIKPGALNS KGVENPMDME GEDDAKEAKH  840
LPLPSACSPM NC                                                     852
```

```
SEQ ID NO: 117          moltype = AA  length = 859
FEATURE                 Location/Qualifiers
REGION                  1..859
                        note = misc_feature - Public GI ID no.62319853
REGION                  1..859
                        note = misc_feature - Bit score of 2155.3 for hmm based on
                         sequences of FIGURE 5.
REGION                  163..268
                        note = misc_feature - Pfam Name: B3 Pfam Description: B3
                         DNA binding domain
REGION                  290..372
```

-continued

```
                        note = misc_feature - Pfam Name: Auxin_resp Pfam
                         Description: Auxin response factor
REGION                  1..859
                        note = misc_feature - Is Acted Upon By Ceres SEEDLINE ID
                         no. ME00572 at SEQ ID NO. 111
source                  1..859
                        mol_type = protein
                        organism = Arabidopsis thaliana
SEQUENCE: 117
MASSEVSMKG NRGGDNFSSS GFSDPKETRN VSVAGEGQKS NSTRSAAAER ALDPEAALYR  60
ELWHACAGPL VTVPRQDDRV FYFPQGHIEQ VEASTNQAAE QQMPLYDLPS KLLCRVINVD  120
LKAEADTDEV YAQITLLPEA NQDENAIEKE APLPPPPRFQ VHSFCKTLTA SDTSTHGGFS  180
VLRRHADECL PPLDMSRQPP TQELVAKDLH ANEWRFRHIF RGQPRRHLLQ SGWSVFVSSK  240
RLVAGDAFIF LRGENGELRV GVRRAMRQQG NVPSSVISSH SMHLGVLATA WHAISTGTMF  300
TVYYKPRTSP SEFIVPFDQY MESVKNNYSI GMRFKMRFEG EEAPEQRFTG TIVGIEESDP  360
TRWPKSKWRS LKVRWDETSS IPRPDRVSPW KVEPALAPPA LSPVPMPRPK RPRSNIAPSS  420
PDSSMLTREG TTKANMDPLP ASGLSRVLQG QEYSTLRTKH TESVECDAPE NSVVWQSSAD  480
DDKVDVVSGS RRYGSENWMS SARHEPTYTD LLSGFGTNID PSHGQRIPFY DHSSSPSMPA  540
KRILSDSEGK FDYLANQWQM IHSGLSLKLH ESPKVPAATD ASLQGRCNVK YSEYPVLNGL  600
STENAGGNWP IRPRALNYYE EVVNAQAQAQ AREQVTKQPF TIQEETAKSR EGNCRLFGIP  660
LTNNMNGTDS TMSQRNNLND AAGLTQIASP KVQDLSDQSK GSKSTNDHRE QGRPFQTNNP  720
HPKDAQTKTN SSRSCTKVHK QGIALGRSVD LSKFQNYEEL VAELDRLFEF NGELMAPKKD  780
WLIVYTDEEN DMMLVGDDPW QEFCCMVRKI FIYTKEEVRK MNPGTVSCRS EEEAVVGEGS  840
DAKDAKSASN PSLSSAGNS                                                859

SEQ ID NO: 118          moltype = AA  length = 859
FEATURE                 Location/Qualifiers
REGION                  1..859
                        note = misc_feature - Public GI ID no.62319903
REGION                  1..859
                        note = misc_feature - Bit score of 2157 for hmm based on
                         sequences of FIGURE 5.
REGION                  163..268
                        note = misc_feature - Pfam Name: B3 Pfam Description: B3
                         DNA binding domain
REGION                  290..372
                        note = misc_feature - Pfam Name: Auxin_resp Pfam
                         Description: Auxin response factor
REGION                  1..859
                        note = misc_feature - Is Acted Upon By Ceres SEEDLINE ID
                         no. ME00572 at SEQ ID NO. 111
source                  1..859
                        mol_type = protein
                        organism = Arabidopsis thaliana
SEQUENCE: 118
MASSEVSMKG NRGGDNFSSS GFSDPKETRN VSVAGEGQKS NSTRSAAAER ALDPEAALYR  60
ELWHACAGPL VTVPRQDDRV FYFPQGHIEQ VEASTNQAAE QQMPLYDLPS KLLCRVINVD  120
LKAEADTDEV YAQITLLPEA NQDENAIEKE APLPPPPRFQ VHSFCKTLTA SDTSTHGGFS  180
VLRRHADECL PPLDMSRQPP TQELVAKDLH ANEWRFRHIF RGQPRRHLLQ SGWSVFVSSK  240
RLVAGDAFIF LRGENGELRV GVRRAMRQQG NVPSSVISSH SMHLGVLATA WHAISTGTMF  300
TVYYKPRTSP SEFIVPFDQY MESVKNNYSI GMRFKMRFEG EEAPEQRFTG TIVGIEESDP  360
TRWPKSKWRS LKVRWDETSS IPRPDRVSPW KVEPALAPPA LSPVPMPRPK RPRSNIAPSS  420
PDSSMLTREG TTKANMDPLP ASGLSRVLQG QEYSTLRTKH TESVECDAPE NSVVWQSSAD  480
DDKVDVVSGS RRYGSENWMS SARHEPTYTD LLSGFGTNID PSHGQRIPFY DHSSSPSMPA  540
KRILSDSEGK FDYLANQWQM IHSGLSLKLH ESPKVPAATD ASLQGRCNVK YSEYPALNGL  600
STENAGGNWP IRPRALNYYE EVVNAQAQAQ AREQVTKQPF TIQEETAKSR EGNCRLFGIP  660
LTNNMNGTDS TMSQRNNLND AAGLTQIASP KVQDLSDQSK GSKSTNDHRE QGRPFQTNNP  720
HPKDAQTKTN SSRSCTKVHK QGIALGRSVD LSKFQNYEEL VAELDRLFEF NGELMAPKKD  780
WLIVYTDEEN DMMLVGDDPW QEFCCMVRKI FIYTKEEVRK MNPGTLSCRS EEEAVVGEGS  840
DAKDAKSASN PSLSSAGNS                                                859

SEQ ID NO: 119          moltype = AA  length = 848
FEATURE                 Location/Qualifiers
REGION                  1..848
                        note = misc_feature - Public GI ID no.47716275
REGION                  1..848
                        note = misc_feature - Bit score of 2099.9 for hmm based on
                         sequences of FIGURE 5.
REGION                  158..263
                        note = misc_feature - Pfam Name: B3 Pfam Description: B3
                         DNA binding domain
REGION                  285..367
                        note = misc_feature - Pfam Name: Auxin_resp Pfam
                         Description: Auxin response factor
REGION                  1..848
                        note = misc_feature - Is Acted Upon By Ceres SEEDLINE ID
                         no. ME00572 at SEQ ID NO. 111
source                  1..848
                        mol_type = protein
```

```
                         organism = Brassica napus
SEQUENCE: 119
MASSEVSMKG NRGRGENFSS AGYSDPTVAG EAQKTQSNRS VAAERVVDPE AALYRELWHA  60
CAGPLVTVPR QDDRVFYFPQ GHIEQVEAST NQAAEQQMPL YDLPSKILCR VINVDLKAEA  120
DTDEVYAQIT LLPEPVQDEN SIEKEAPPPP PRFQVHSFC KTLTASDTST HGGFSVLRRH  180
ADECLPPLDM SRQPPTQELV AKDLHASEWR FRHIFRGQPR RHLLQSGWSV FVSSKRLVAG  240
DAFIFLRGEN GELRVGVRRA MRQQGNVPSS VISSHSMHLG VLATAWHAIS TGTMFTVYYK  300
PRTSPSEFIV PFDQYTESVK INYSIGMRFK MRFEGEEAPE QRFTGTIVGI EDSDPTRWAK  360
SKWRSLKVRW DETTSIPRPD RVSPWKIEPA LSPPALSPVP MPRPKRPRSN LASSTPDSSM  420
RIREGSSKAN MDPLPASGLS RVLQGQEYPT LRTKHVESVE CDAPENSVVW QSSTDDDKVD  480
VISASRRYEN WISSGRHGPT CTDLLSGFGT NIEPPHGHQI PFYDRLSSPP SVAARKILSD  540
QDGKFEYLAN QWMMHSGLSL KLHESPKVPA ASDASFQGIG NPNYGEYALP RAVTTENAAG  600
NWPIRPRALN YFEEAVHAQA REHVTKRPAV VQEEAAKPRD GNCRLFGIPL VNNVNGTDTT  660
LSQRNNLNDP AGPTQMASPK VQDLSDQSKG SKSTNDHREQ GRPFPVSKPH PKDVQTKTNS  720
CRSCTKVQKQ GIALGRSVDL SKFQNYEELV TELDRLFEFN GELMAPKKDW LIVYTDDEND  780
MMLVGDDPWQ EFCCMVRKIF IYTKEEVRKM NPGTLCCRNE EEPVVGEGSD AKDAKSASNP  840
SLSSAGNS                                                          848

SEQ ID NO: 120          moltype = AA  length = 853
FEATURE                 Location/Qualifiers
REGION                  1..853
                        note = misc_feature - Public GI ID no.125534572
REGION                  1..853
                        note = misc_feature - Bit score of 2096 for hmm based on
                         sequences of FIGURE 5.
REGION                  148..253
                        note = misc_feature - Pfam Name: B3 Pfam Description: B3
                         DNA binding domain
REGION                  275..357
                        note = misc_feature - Pfam Name: Auxin_resp Pfam
                         Description: Auxin response factor
REGION                  1..853
                        note = misc_feature - Is Acted Upon By Ceres SEEDLINE ID
                         no. ME00572 at SEQ ID NO. 111
source                  1..853
                        mol_type = protein
                        note = subspecies = indica
                        organism = Oryza sativa
SEQUENCE: 120
MATAEVGGGG GEGDAAAAAV ARAGGGGGGG GGGGEDALFT ELWSACAGPL VTVPRVGEKV  60
FYFPQGHIEQ VEASTNQVGE QRMQLYNLPW KILCEVMNVE LKAEPDTDEV YAQLTLLPEL  120
KQQEDNGSTE EEVPSAPAAG HVRPRVHSFC KTLTASDTST HGGFSVLRRH ADECLPPLDM  180
SRQPPTQELV AKDLHGVEWR FRHIFRGQPR RHLLQSGWSV FVSAKRLVAG DAFIFLRGEN  240
GELRVGVRRA MRQQTNVPSS VISSHSMHLG VLATAWHAVN TGTMFTVYYK PRTSPAEFVV  300
PYDRYMESLK RNYSIGMRFK MRFEGEEAPE QRFTGTIVGM GDSDPAGWPE SKWRSLKVRW  360
DEASSIPRPE RVSPWQIEPA VSPPPVNPLP VPRTKRLRPN ATALPADSSA IAKEAATKVV  420
VESEPNGTQR TFQTQENATP KSGFGNSSEL ESAQKSIMRP SGFDREKNNT PIQWKLGSDG  480
WMQMSKPESY SEMLSGFQPP KDVQTPQGFC SLPEQITAGH SNFWHTVNAQ YQDQQSNHNM  540
FPSSWSFMPP NTRLGLNKQN YSMIQEAGVL SQRPGNTKFG NGVYAALPGR GTEQYSGGWF  600
GHMMPNSHMD DTQPRLIKPK PLVVAHGDVQ KAKGASCKLF GIHLDSPAKS EPLKSPSSVV  660
YDGTPQTPGA TEWRRPDVTE VEKCSDPSKA MKPLDTPQPD SVPEKPSSQQ ASRNMSCKSQ  720
GVSTRSCKKV HKQGIALGRS VDLTKFNGYE ELIAELDDMF DFNGELKGPK KEWMVVYTDN  780
EGDMMLVGDD PWIEFCDMVH KIFIYTREEV QRMNPGTLNS RSEDSHANSM ERGSVGREMR  840
GCLSTSSLNS ENC                                                    853

SEQ ID NO: 121          moltype = AA  length = 857
FEATURE                 Location/Qualifiers
REGION                  1..857
                        note = misc_feature - Public GI ID no.26251300
REGION                  1..857
                        note = misc_feature - Bit score of 2070.6 for hmm based on
                         sequences of FIGURE 5.
REGION                  147..252
                        note = misc_feature - Pfam Name: B3 Pfam Description: B3
                         DNA binding domain
REGION                  274..356
                        note = misc_feature - Pfam Name: Auxin_resp Pfam
                         Description: Auxin response factor
REGION                  1..857
                        note = misc_feature - Is Acted Upon By Ceres SEEDLINE ID
                         no. ME00572 at SEQ ID NO. 111
source                  1..857
                        mol_type = protein
                        note = subspecies = indica
                        organism = Oryza sativa
SEQUENCE: 121
MATAEVGGGG GEGDAAAAAV ARAGGGGGGG GGGEDALFTE LWSACAGPLV TVPRVGEKEF  60
YFPQGHIEQV EASTNQVGEQ RMQLYNLPWK ILCEVMNVEL KAEPDTDEVY AQLTLLPELK  120
RQEDNGSTEE EVPSAPAAGH VRPRVHSFCK TLTASDTSTH GGFSVLRRHA DECLPPLDMS  180
```

-continued

```
RQPPTQELVA KDLHGVEWRF RHIFRGQPRR HLLQSGWSVF VSAKRLVAGD AFIFLRGENG  240
ELRVGVRRAM RQQTNVPSSV ISSHSMHLGV LATAWHAVNT GTMFTVYYKP RTSPAEFVVP  300
YDRYMESLKR NYSIGMRFKM RFESEEAPEQ RFTGTIVGMG DSDPAGWPES KWRSLKVRWD  360
EASSIPRPER VSPWQIEPAV SPPPVNPLPV PRTKRLRPNA TALPADSSAI AKEAATKVVV  420
ESEPNGTQRT FQTQENATPK SGFGNSSELE SAQKSIMRPS GFDREKNNTP IQWKLGSDGR  480
MQMSKPESYS EMLSGFQPPK DVQTPQGFCS LPEQITAGHS NFWHTVNAQY QDQQSNHNMF  540
PSSWSFMPPN TRLGLNKQNY SMIQEAGVLS QRPGNTKFGN GVYAALPGRG TEQYSGGWFG  600
LMMPNSHMDD TQPRLIKPKP LVVAHGDVQK AKGASCKLFG IHLDSPAKSE PSKSPSSVVY  660
DGTPQTPGAT EWRRPDVTEV EKCSDPSKAM KPLDTPQPDS VPEKPSSQQA SSQQASRNMS  720
CKSQGVSTRS CKKVHKQGIA LGRSVDLTKF NGYEELIAEL DDMFDFNGEL KGPKKEWMVV  780
YTDNEGDMML VGDDPWIEFC DMVHKIFIYT REEVQRMNPG TLNLRSEDSH ANSMERGSVG  840
REMRGCLSTS SLNSENC                                                857

SEQ ID NO: 122          moltype = AA  length = 853
FEATURE                 Location/Qualifiers
REGION                  1..853
                        note = misc_feature - Public GI ID no.125528952
REGION                  1..853
                        note = misc_feature - Bit score of 1880.3 for hmm based on
                         sequences of FIGURE 5.
REGION                  123..228
                        note = misc_feature - Pfam Name: B3 Pfam Description: B3
                         DNA binding domain
REGION                  250..331
                        note = misc_feature - Pfam Name: Auxin_resp Pfam
                         Description: Auxin response factor
REGION                  1..853
                        note = misc_feature - Is Acted Upon By Ceres SEEDLINE ID
                         no. ME00572 at SEQ ID NO. 111
source                  1..853
                        mol_type = protein
                        note = subspecies = indica
                        organism = Oryza sativa
SEQUENCE: 122
MAPPPPPQGS STGDPLYDEL WHACAGPLVT VPRVGDLVFY FPQGHIEQVE ASMNQVADSQ  60
MRLYDLPSKL LCRVLNVELK AEQDTDEVYA QVMLMPEPEQ NEMAVEKTTP TSGPVQARPP  120
VRSFCKTLTA SDTSTHGGFS VLRRHADECL PPLDMTQSPP TQELVAKDLH SMDWRFRHIF  180
RGQPRRHLLQ SGWSVFVSSK RLVAGDAFIF LRGENGELRV GVRRAMRQLS NVPSSVISSQ  240
SMHLGVLATA WHAINTKSMF TVYYKPRTSP SEFIIPYDQY MESVKNNYSV GMRFRMRFEG  300
EEAPEQRFTG TIIGSENLDP VWPESSWRSL KVRWDEPSTI PRPDRVSPWK IEPASSPPVN  360
PLPLSRVKRP RPNAPPASPE SPILTKEAAT KVDTDPAQAQ RSQNSTVLQG QEQMTLRSNL  420
TESNDSDVTA HKPMMWSPSP NAAKAHPLTF QQRPPMDNWM QLGRRETDFK DVRSGSQSFG  480
DSPGFFMQNF DEAPNRLTSF KNQFQDQGSA RHFSDPYYYV SPQPSLTVES STQMHTDSKE  540
LHFWNGQSTV YGNSRDRPQN FRFEQNSSSW LNQSFARPEQ PRVIRPHASI APVELEKTEG  600
SGFKIFGFKV DTTNAPNNHL SSPMAATHEP MLQTPSSLNQ LQPVQTDCIP EVSVSTAGTA  660
TENEKSGQQA QQSSKDVQSK TQVASTRSCT KHMKFFLLVV DMLKFSFCKF LAKSQFYPLC  720
GMVHKQGVAL GRSVDLSKFS NYDELKAELD KMFEFDGELV SSNKNWQIVY TDNEGDMMLV  780
GDDPWEEFCS IVRKIYIYTK EEVQKMNSKS NAPRKDDSSE NEKGSVKRDD TRDGGVLQKA  840
ASASVLSILR YSS                                                    853

SEQ ID NO: 123          moltype = AA  length = 808
FEATURE                 Location/Qualifiers
REGION                  1..808
                        note = misc_feature - Public GI ID no.115441981
REGION                  1..808
                        note = misc_feature - Bit score of 1951.3 for hmm based on
                         sequences of FIGURE 5.
REGION                  128..233
                        note = misc_feature - Pfam Name: B3 Pfam Description: B3
                         DNA binding domain
REGION                  255..336
                        note = misc_feature - Pfam Name: Auxin_resp Pfam
                         Description: Auxin response factor
REGION                  1..808
                        note = misc_feature - Is Acted Upon By Ceres SEEDLINE ID
                         no. ME00572 at SEQ ID NO. 111
source                  1..808
                        mol_type = protein
                        note = subspecies = japonica
                        organism = Oryza sativa
SEQUENCE: 123
MPPAAMAPPP PPQGSSTGDP LYDELWHACA GPLVTVPRVG DLVFYFPQGH IEQVEASMNQ  60
VADSQMRLYD LPSKLLCRVL NVELKAEQDT DEVYAQVMLM PEPEQNEMAV EKTTPTSGPV  120
QARPPVRSFC KTLTASDTST HGGFSVLRRH ADECLPPLDM TQSPPTQELV AKDLHSMDWR  180
FRHIFRGQPR RHLLQSGWSV FVSSKRLVAG DAFIFLRGEN GELRVGVRRA MRQLSNVPSS  240
VISSQSMHLG VLATAWHAIN TKSMFTVYYK PRTSPSEFII PYDQYMESVK NNYSVGMRFR  300
MRFEGEEAPE QRFTGTIIGS ENLDPVWPES SWRSLKVRWD EPSTIPRPDR VSPWKIEPAS  360
SPPVNPLPLS RVKRPRPNAP PASPESPILT KEAATKVDTD PAQAQRSQNS TVLQGQEQMT  420
LRSNLTESND SDVTAHKPMM WSPSPNAAKA HPLTFQQRPP MDNWMQLGRR ETDFKDVRSG  480
```

```
SQSFGDSPGF FMQNFDEAPN RLTSFKNQFQ DQGSARHFSD PYYYVSPQPS LTVESSTQMH  540
TDSKELHFWN GQSTVYGNSR DRPQNFRFEQ NSSSWLNQSF ARPEQPRVIR PHASIAPVEL  600
EKTEGSGFKI FGFKVDTTNA PNNHLSSPMA ATHEPMLQTP SSLNQLQPVQ TDCIPEVSVS  660
TAGTATENEK SGQQAQQSSK DVQSKTQVAS TRSCTKVHKQ GVALGRSVDL SKFSNYDELK  720
AELDKMFEFD GELVSSNKNW QIVYTDNEGD MMLVGDDPWE EFCSIVRKIY IYTKEEVQKM  780
NSKSNAPRKD DSSENEKGHL PMPNKSDN                                    808

SEQ ID NO: 124         moltype = AA  length = 836
FEATURE                Location/Qualifiers
REGION                 1..836
                       note = misc_feature - Public GI ID no.23893346
REGION                 1..836
                       note = misc_feature - Bit score of 2065.7 for hmm based on
                        sequences of FIGURE 5.
REGION                 131..236
                       note = misc_feature - Pfam Name: B3 Pfam Description: B3
                        DNA binding domain
REGION                 258..340
                       note = misc_feature - Pfam Name: Auxin_resp Pfam
                        Description: Auxin response factor
REGION                 1..836
                       note = misc_feature - Is Acted Upon By Ceres SEEDLINE ID
                        no. ME00572 at SEQ ID NO. 111
source                 1..836
                       mol_type = protein
                       note = subspecies = japonica
                       organism = Oryza sativa
SEQUENCE: 124
MATAEVGGGG GGGGGGGEDA LFTELWSACA GPLVTVPRVG EKVFYFPQGH IEQVEASTNQ  60
VGEQRMQLYN LPWKILCEVM NVELKAEPDT DEVYAQLTLL PESKQQEDNG STEEEVPSAP  120
AAGHVRPRVH SFCKTLTASD TSTHGGFSVL RRHADECLPP LDMSRQPPTQ ELVAKDLHGV  180
EWRFRHIFRG QPRRHLLQSG WSVFVSAKRL VAGDAFIFLR GENGELRVGV RRAMRQQTNV  240
PSSVISSHSM HLGVLATAWH AVNTGTMFTV YYKPRTSPAE FVVPYDRYME SLKQNYSIGM  300
RFKMRFEGEE APEQRFTGTI VGMGDSDPAG WPESKWRSLK VRWDEASSIP RPERVSPWQI  360
EPAVSPPPVN PLPVPRTKRL RPNATALPAD SSAIAKEAAT KVVVESEPNG TQRTFQTQEN  420
ATPKSGFGNS SELESAQKSI MRPSGFDREK NNTPIQWKLG SDGRMQMSKP ESYSEMLSGF  480
QPPKDVQIPQ GFWSLPEQIT AGHSNFWHTV NAQYQDQQSN HNMFPSSWSF MPPNTRLGLN  540
KQNYSMIQEA GVLSQRPGNT KFGNGVYAAL PGRGTEQYSG GWFGHMMPNS HMDDTQPRLI  600
KPKPLVVAHG DVQKAKGASC KLFGIHLDSP AKSEPLKSPS SVVYDGTPQT PGATEWRRPD  660
VTEVEKCSDP SKAMKPLDTP QPDSVPEKPS SQQASRNMSC KSQGVSTRSC KKVHKQGIAL  720
GRSVDLTKFN GYEELIAELD DMFDFNGELK GPKKEWMVVY TDNEGDMMLV GDDPWIEFCD  780
MVHKIFIYTR EEVQRMNPGT LNSRSEDSHA NSMERGSVGR EMRGCLSTSS LNSENC      836

SEQ ID NO: 125         moltype = AA  length = 852
FEATURE                Location/Qualifiers
REGION                 1..852
                       note = misc_feature - Public GI ID no.115485689
REGION                 1..852
                       note = misc_feature - Bit score of 2092.5 for hmm based on
                        sequences of FIGURE 5.
REGION                 147..252
                       note = misc_feature - Pfam Name: B3 Pfam Description: B3
                        DNA binding domain
REGION                 274..356
                       note = misc_feature - Pfam Name: Auxin_resp Pfam
                        Description: Auxin response factor
REGION                 1..852
                       note = misc_feature - Is Acted Upon By Ceres SEEDLINE ID
                        no. ME00572 at SEQ ID NO. 111
source                 1..852
                       mol_type = protein
                       note = subspecies = japonica
                       organism = Oryza sativa
SEQUENCE: 125
MATAEVGGGG GEGDAAAAAV ARGGGGGGGG GGGEDALFTE LWSACAGPLV TVPRVGEKVF  60
YFPQGHIEQV EASTNQVGEQ RMQLYNLPWK ILCEVMNVEL KAEPDTDEVY AQLTLLPESK  120
QQEDNGSTEE EVPSAPAAGH VRPRVHSFCK TLTASDTSTH GGFSVLRRHA DECLPPLDMS  180
RQPPTQELVA KDLHGVEWRF RHIFRGQPRR HLLQSGWSVF VSAKRLVAGD AFIFLRGENG  240
ELRVGVRRAM RQQTNVPSSV ISSHSMHLGV LATAWHAVNT GTMFTVYYKP RTSPAEFVVP  300
YDRYMESLKQ NYSIGMRFKM RFEGEEAPEQ RFTGTIVGMG DSDPAGWPES KWRSLKVRWD  360
EASSIPRPER VSPWQIEPAV SPPPVNPLPV PRTKRLRPNA TALPADSSAI AKEAATKVVV  420
ESEPNGTQRT FQTQENATPK SGFGNSSELE SAQKSIMRPS GFDREKNNTP IQWKLGSDGR  480
MQMSKPESYS EMLSGFQPPK DVQIPQGFCS LPEQITAGHS NFWHTVNAQY QDQQSNHNMF  540
PSSWSFMPPN TRLGLNKQNY SMIQEAGVLS QRPGNTKFGN GVYAALPGRG TEQYSGGWFG  600
HMMPNSHMDD TQPRLIKPKP LVVAHGDVQK AKGASCKLFG IHLDSPAKSE PLKSPSSVVY  660
DGTPQTPGAT EWRRPDVTEV EKCSDPSKAM KPLDTPQPDS VPEKPSSQQA SRNMSCKSQG  720
VSTRSCKKVH KQGIALGRSV DLTKFNGYEE LIAELDDMFD FNGELKGPKK EWMVVYTDNE  780
GDMMLVGDDP WIEFCDMVHK IFIYTREEVQ RMNPGTLNSR SEDSHANSME RGSVGREMRG  840
CLSTSSLNSE NC                                                     852
```

```
SEQ ID NO: 126          moltype = AA  length = 853
FEATURE                 Location/Qualifiers
REGION                  1..853
                        note = misc_feature - Public GI ID no.108864435
REGION                  1..853
                        note = misc_feature - Bit score of 2094.3 for hmm based on
                         sequences of FIGURE 5.
REGION                  148..253
                        note = misc_feature - Pfam Name: B3 Pfam Description: B3
                         DNA binding domain
REGION                  275..357
                        note = misc_feature - Pfam Name: Auxin_resp Pfam
                         Description: Auxin response factor
REGION                  1..853
                        note = misc_feature - Is Acted Upon By Ceres SEEDLINE ID
                         no. ME00572 at SEQ ID NO. 111
source                  1..853
                        mol_type = protein
                        note = subspecies = japonica
                        organism = Oryza sativa
SEQUENCE: 126
MATAEVGGGG GEGDAAAAAV ARAGGGGGGG GGGGEDALFT ELWSACAGPL VTVPRVGEKV  60
FYFPQGHIEQ VEASTNQVGE QRMQLYNLPW KILCEVMNVE LKAEPDTDEV YAQLTLLPES  120
KQQEDNGSTE EEVPSAPAAG HVRPRVHSFC KTLTASDTST HGGFSVLRRH ADECLPPLDM  180
SRQPPTQELV AKDLHGVEWR FRHIFRGQPR RHLLQSGWSV FVSAKRLVAG DAFIFLRGEN  240
GELRVGVRRA MRQQTNVPSS VISSHSMHLG VLATAWHAVN TGTMFTVYYK PRTSPAEFVV  300
PYDRYMESLK QNYSIGMRFK MRFEGEEAPE QRFTGTIVGM GDSDPAGWPE SKWRSLKVRW  360
DEASSIPRPE RVSPWQIEPA VSPPPVNPLP VPRTKRLRPN ATALPADSSA IAKEAATKVV  420
VESEPNGTQR TFQTQENATP KSGFGNSSEL ESAQKSIMRP SGFDREKNNT PIQWKLGSDG  480
RMQMSKPESY SEMLSGFQPP KDVQIPQGFC SLPEQITAGH SNFWHTVNAQ YQDQQSNHNM  540
FPSSWSFMPP NTRLGLNKQN YSMIQEAGVL SQRPGNTKFG NGVYAALPGR GTEQYSGGWF  600
GHMMPNSHMD DTQPRLIKPK PLVVAHGDVQ KAKGASCKLF GIHLDSPAKS EPLKSPSSVV  660
YDGTPQTPGA TEWRRPDVTE VEKCSDPSKA MKPLDTPQPD SVPEKPSSQQ ASRNMSCKSQ  720
GVSTRSCKKV HKQGIALGRS VDLTKFNGYE ELIAELDDMF DFNGELKGPK KEWMVVYTDN  780
EGDMMLVGDD PWIEFCDMVH KIFIYTREEV QRMNPGTLNS RSEDSHANSM ERGSVGREMR  840
GCLSTSSLNS ENC                                                    853

SEQ ID NO: 127          moltype = AA  length = 719
FEATURE                 Location/Qualifiers
REGION                  1..719
                        note = misc_feature - Public GI ID no.50511471
REGION                  1..719
                        note = misc_feature - Bit score of 1618.2 for hmm based on
                         sequences of FIGURE 5.
REGION                  141..246
                        note = misc_feature - Pfam Name: B3 Pfam Description: B3
                         DNA binding domain
REGION                  268..349
                        note = misc_feature - Pfam Name: Auxin_resp Pfam
                         Description: Auxin response factor
REGION                  1..719
                        note = misc_feature - Is Acted Upon By Ceres SEEDLINE ID
                         no. ME00572 at SEQ ID NO. 111
source                  1..719
                        mol_type = protein
                        note = subspecies = japonica
                        organism = Oryza sativa
SEQUENCE: 127
MTGIDLNTVE EDEEEAAEEV AANGSSPAPA RAGAVCLELW HACAGPVAPL PRKGGVVVYL  60
PQGHLEHLGD APAAAAAAAA VPPHVFCRVV DVTLLADAAT DEVYAQLSLV PEKEEVARRA  120
DDGEGEDGDG MKQRFARMPH MFCKTLTASD TSTHGGFSVP RRAAEDCFPP LDYSQQRPSQ  180
ELVAKDLHST EWRFRHIYRG QPRRHLLTTG WSAFVNKKKL VSGDAVLFLR GDDGELRLGV  240
RRAAQLKNGS AFPALYNQCS NLGTLANVAH AVATESVFNI YYNPRLSQSE FIVPYWKFMK  300
SLSQPFSVGL RFKMRYESED ATERRYTGII TGSGDTDPMW HGSKWKCLLV RWDDDAEFRR  360
PNRVSPWEIE LTSSVSGSHL STPHSKRLKP CLPHVNPEYM VPRGGCPDF AESAQFHKVL  420
QGQELLGFKS HGGTAAATSQ PCEARHLQYI DERSCSSDAS NSILGVPRLG DRAPLGNPGF  480
SYHCSGFGES HRLQKVLQGQ ELFRPYRGTL VDASMGSNGF HQQDSPRAPG VVNKWQAQLH  540
GRAAFHGPPA LALPSQSSSP PSVLMFQQAN SKMPRLEFGH GQLDKHENDR RVRFGPSEGI  600
ERREQRIPLQ PYPTSGEVID GQVTVEKSHS PGRHGKDGPD NKAVGTNSCK IFGISLTEKV  660
PAREELDDGD ANYSLQSLKQ VPKSLGNSCA TMVAEYQGDG GTDDSDIFIL DVGVGALIM   719

SEQ ID NO: 128          moltype = AA  length = 608
FEATURE                 Location/Qualifiers
REGION                  1..608
                        note = misc_feature - Ceres LOCUS ID no. At2g33860
REGION                  1..608
                        note = misc_feature - Bit score of 1320.6 for hmm based on
                         sequences of FIGURE 5.
```

```
REGION                  158..263
                        note = misc_feature - Pfam Name: B3 Pfam Description: B3
                         DNA binding domain
REGION                  285..367
                        note = misc_feature - Pfam Name: Auxin_resp Pfam
                         Description: Auxin response factor
REGION                  1..608
                        note = misc_feature - Is Acted Upon By Ceres SEEDLINE ID
                         no. ME00572 at SEQ ID NO. 111
source                  1..608
                        mol_type = protein
                        organism = Arabidopsis thaliana
SEQUENCE: 128
MGGLIDLNVM ETEEDETQTQ TPSSASGSVS PTSSSSASVS VVSSNSAGGG VCLELWHACA  60
GPLISLPKRG SLVLYFPQGH LEQAPDFSAA IYGLPPHVFC RILDVKLHAE TTTDEVYAQV  120
SLLPESEDIE RKVREGIIDV DGGEEDYEVL KRSNTPHMFC KTLTASDTST HGGFSVPRRA  180
AEDCFPPLDY SQPRPSQELL ARDLHGLEWR FRHIYRGQPR RHLLTTGWSA FVNKKKLVSG  240
DAVLFLRGDD GKLRLGVRRA SQIEGTAALS AQYNQNMNHN NFSEVAHAIS THSVFSISYN  300
PKASWSNFII PAPKFLKVVD YPFCIGMRFK ARVESEDASE RRSPGIISGI SDLDPIRWPG  360
SKWRCLLVRW DDIVANGHQQ RVSPWEIEPS GSISNSGSFV TTGPKRSRIG FSSGKPDIPV  420
SEGIRATDFE ESLRFQRVLQ GQEIFPGFIN TCSDGGAGAR RGRFKGTEFG DSYGFHKVLQ  480
GQETVPAYSI TDHRQQHGLS QRNIWCGPFQ NFSTRILPPS VSSSPSSVLL TNSNSPNGRL  540
EDHHGGSGRC RLFGFPLTDE TTAVASATAV PCVEGNSMKG ASAVQSNHHH SQGRDIYAMR  600
DMLLDIAL                                                         608

SEQ ID NO: 129          moltype = DNA  length = 1995
FEATURE                 Location/Qualifiers
misc_feature            1..1995
                        note = Ceres ANNOT ID no.1536494
misc_feature            1..1995
                        note = Encodes the peptide sequence at SEQ ID NO. 130
source                  1..1995
                        mol_type = other DNA
                        organism = Populus balsamifera
                        sub_species = trichocarpa
SEQUENCE: 129
atggtgggta tgatagatct caacactatt gaagaagatg aaactacacc gtcttgtggg  60
tctttatctt ctccatcatc atcctctgct gcttctgctt tgagtgcttc tggctctggt  120
tctagtacct cttctgtttg tttggagctt tggcatgctt gtgctggccc actaatatct  180
ttgccaaaga gagggagtgt tgttgtgtat ttccctcaag gccacttgga acaactccct  240
gatttgcctc ttgcagttta tgatctccct tctcatgtct tctgtcgagt tgttgatgtc  300
aagctccatg tctccctggt tcctgagagt gaggaaattg agcagaagtt gagggagggg  360
atatttgagg gggatggtga ggaggaggat ggtgaagcca ctgtgaagat gacaacaccc  420
catatgttct gtaagaccct aactgcttct gacactagca ctcatggagg cttttcagtc  480
cctcgtcgag ctgctgagga ctgcttccct cctctggatt atactcaaca aaggccttca  540
caagagcttg tggcaaagga tcttcatggc tctgagtgga agtttcgaca tatctacagg  600
ggtcagccac ggaggcattt gctcactact ggatggagtg cgtttgtcaa taagaaaaaa  660
cttgtctctg ggatgccgt tctctttctc aggggtgagg atggggaatt gagactggga  720
gttcgaagag cagcacaagt taaatgtggc cctacatttc cagctcaatg gaatcatcag  780
ctgaatcaga tctctcctgg ggatgtagct aatgctattt ctactagaag ttttttccac  840
atttactaca atccaagggc cagctcatca gagttcataa taccttttaa taaattcttg  900
aagagccttg atcaatcctt ctcttctgga atgagattca aaatgcgttt tgaaacagaa  960
gatgcagcag agagaagata cactggaata ataactggag tcagtgagct agatcctgct  1020
agatggcctg gttcaaaatg gaaatgcctg ttggtaaggt gggatgatag ggaggctaac  1080
aggctcagca gggtttctcc ttgggaagtt gagccttctg gttctggttc tatttccagc  1140
tccaataact ttatggcacc tggtttgaag aggagcaggt ctggattgcc ttcatcaaag  1200
gcagaatttc caattcctga tgggatagga gcaccaggct ttagggaatc ttcaaggtcc  1260
caggaggtct tgcaaggaag tggtatcaga gactcgattg ccacttcaaa taactcctac  1320
aagggcatag gctttaacga atcttataga ttccataagg tcttccaagg tcaagaaatt  1380
tttccaagct caccatatgg aagaatccca aatgctaatg aggctcgtga aaattgtagt  1440
cttggattct ctgatggtgt ccaaaggtca agctcaagaa atggatggtc tacattgatg  1500
cagggctata atactcaaat tcgacctcct gcacaagtat catcaccatc ttcggtgtta  1560
atgtttcaac atgccagcaa tccagttcca aagcgatctt ccaattttaa tttcaatgat  1620
catgtgcagc agacagctac cacccgaagt tggttttgtg gtcctgaaat gcaggggggg  1680
aatttcaagt tgtctgcaca ttctgagccc agtgtaaaaa gagacggcca atggagcaat  1740
agtccttttg gtctgtccca tgagcatctt caacatggcg tttcacaacc tattgtagct  1800
caatcagcct ttaggggtag tcaagatttg gtgtcgtgca aaagcagctg cagactcttt  1860
ggtttctcat tgactgagga taaatgcctt gttaataagg aggacaatat gaccttaata  1920
acatctccat tgaatcctgg atcctccttt ctgcctcgcg ccggagagca cttccatcaa  1980
agcctccagc aataa                                                 1995

SEQ ID NO: 130          moltype = AA  length = 664
FEATURE                 Location/Qualifiers
REGION                  1..664
                        note = misc_feature - Ceres ANNOT ID no.1536494
REGION                  1..664
                        note = misc_feature - Bit score of 802.9 for hmm based on
                         sequences of FIGURE 5.
REGION                  142..247
```

-continued

```
                        note = misc_feature - Pfam Name: B3 Pfam Description: B3
                         DNA binding domain
REGION                  269..351
                        note = misc_feature - Pfam Name: Auxin_resp Pfam
                         Description: Auxin response factor
REGION                  1..664
                        note = misc_feature - Is Acted Upon By Ceres SEEDLINE ID
                         no. ME00572 at SEQ ID NO. 111
source                  1..664
                        mol_type = protein
                        note = subspecies = trichocarpa
                        organism = Populus balsamifera
SEQUENCE: 130
MVGMIDLNTI EEDETTPSCG SLSSPSSSSA ASALSASGSG SSTSSVCLEL WHACAGPLIS  60
LPKRGSVVVY FPQGHLEQLP DLPLAVYDLP SHVFCRVVDV KLHVSLVPES EEIEQKLREG  120
IFEGDGEEED GEATVKMTTP HMFCKTLTAS DTSTHGGFSV PRRAAEDCFP PLDYTQQRPS  180
QELVAKDLHG SEWKFRHIYR GQPRRHLLTT GWSAFVNKKK LVSGDAVLFL RGEDGELRLG  240
VRRAAQVKCG PTFPAQWNHQ LNQISPGDVA NAISTRSFFH IYYNPRASSS EFIIPFNKFL  300
KSLDQSFSSG MRFKMRFETE DAAERRYTGI ITGVSELDPA RWPGSKWKCL LVRWDDREAN  360
RLSRVSPWEV EPSGSGSISS SNNFMAPGLK RSRSGLPSSK AEFPIPDGIG APGFRESSRS  420
QEVLQGSGIR DSIATSNNSY KGIGFNESYR FHKVFQGQEI FPSSPYGRIP NANEARENCS  480
LGFSDGVQRS SSRNGWSTLM QGYNTQIRPP AQVSSPSSVL MFQHASNPVP KRSSNFNFND  540
HVQQTATTRS WFCGPEMQGG NFKLSAHSEP SVKRDGQWSN SPFGLSHEHL QHGVSQPIVA  600
QSAFRGSQDL VSCKSSCRLF GFSLTEDKCL VNKEDNMTLI TSPLNPGSSF LPRAGEHFHQ  660
SLQQ                                                              664

SEQ ID NO: 131          moltype = AA  length = 608
FEATURE                 Location/Qualifiers
REGION                  1..608
                        note = misc_feature - Public GI ID no.2245390
REGION                  1..608
                        note = misc_feature - Bit score of 1323.9 for hmm based on
                         sequences of FIGURE 5.
REGION                  158..263
                        note = misc_feature - Pfam Name: B3 Pfam Description: B3
                         DNA binding domain
REGION                  285..367
                        note = misc_feature - Pfam Name: Auxin_resp Pfam
                         Description: Auxin response factor
REGION                  1..608
                        note = misc_feature - Is Acted Upon By Ceres SEEDLINE ID
                         no. ME00572 at SEQ ID NO. 111
source                  1..608
                        mol_type = protein
                        organism = Arabidopsis thaliana
SEQUENCE: 131
MGGLIDLNVM ETEEDETQTQ TPSSASGSVS PTSSSSASVS VVSSNSAGGG VCLELWHACA  60
GPLISLPKRG SLVLYFPQGH LEQAPDFSAA IYGLPPHVFC RILDVKLHAE TTTDEVYAQV  120
SLLPESEDIE RKVREGIIDV DGGEEDYEVL KRSNTPHMFC KTLTASDTST HGGFSVPRRA  180
AEDCFPPLDY SQPRPSQELL ARDLHGLEWR FRHIYRGQPR RHLLTTGWSA FVNKKKLVSG  240
DAVLFLRGDD GKLRLGVRRA SQIEGTAALS AQYNQNMNHN NFSEVAHAIS THSVFSISYN  300
PKASWSNFII PAPKFLKVVD YPFCIGMRFK ARVESEDASE RRSPGIISGI SDLDPIRWPG  360
SKWRCLLVRW DDIVANGHQQ RVSPWEIEPS GSISNSGSFV TTGPKRSRIG FSSGKPDIPV  420
SEGIRATDFE ESLRFQRVLQ GQEIFPGFIN TCSDGGAGAR RGRFKGTEFG DSYGFHKVLQ  480
GQETVPAYSI TDHRQQHGLS QRNIWCGPFQ NFSTRILPPS VSSSPSSVLF TNSNSPNGRL  540
EDHHGGSGRC RLFGFPLTDE TTAVASATAV PCVEGNSMKG ASAVQSNHHH SQGRDIYAMR  600
DMLLDIAL                                                          608

SEQ ID NO: 132          moltype = AA  length = 608
FEATURE                 Location/Qualifiers
REGION                  1..608
                        note = misc_feature - Public GI ID no.3228517
REGION                  1..608
                        note = misc_feature - Bit score of 1320.4 for hmm based on
                         sequences of FIGURE 5.
REGION                  158..263
                        note = misc_feature - Pfam Name: B3 Pfam Description: B3
                         DNA binding domain
REGION                  285..367
                        note = misc_feature - Pfam Name: Auxin_resp Pfam
                         Description: Auxin response factor
REGION                  1..608
                        note = misc_feature - Is Acted Upon By Ceres SEEDLINE ID
                         no. ME00572 at SEQ ID NO. 111
source                  1..608
                        mol_type = protein
                        organism = Arabidopsis thaliana
SEQUENCE: 132
MGGLIDLNVM ETEEDETQTQ TPSSASGSVS PTSSSSASVS VVSSNSAGGG VCLELWHACA  60
```

-continued

```
GPLISLPKRG SLVLYFPQGH LEQAPDFSAA IYGLPPHVFC RILDVKLHAE TTTDEVYAQV  120
SLLPESEDIE RKVREGIIDV DGGEEDYEVL KRSNTPHMFC KTLTASDTST HGGFSVPRRA  180
AEDCFPPLDY SQPRPSQELL ARDLHGLEWR FRHIYRGQPR RHLLTTGWSA FVNKKKLVSG  240
DAVLFLRGDD GKLRLGVRRA SQIEGTAALS AQYNQNMNHN NFSEVAHAIS THSVFSISYN  300
PKASWSNFII PAPKFLKVVD YPFCIGMRFK ARVESEDASE RRSPGIISGI SDLDPIRWPG  360
SKWRCLLVRW DDIVANGHQQ RVSPWEIEPS GSISNSGSFV TTGPKRSRIG ISSGKPDIPV  420
SEGIRATDFE ESLRFQRVLQ QGEIFPGFIN TCSDGGAGAR RGRFKGTEFG DSYGFHKVLQ  480
GQETVPAYSI TDHRQQHGLS QRNIWCGPFQ NFSTRILPPS VSSSPSSVLL TNSNSPNGRL  540
EDHHGGSGRC RLFGFPLTDE TTAVASATAV PCVEGNSMKG ASAVQSNHHH SQGRDIYAMR  600
DMLLDIAL                                                          608

SEQ ID NO: 133          moltype = DNA  length = 2420
FEATURE                 Location/Qualifiers
misc_feature            1..2420
                        note = Ceres CLONE ID no.827306
misc_feature            1..2420
                        note = Encodes the peptide sequence at SEQ ID NO. 134
source                  1..2420
                        mol_type = other DNA
                        organism = Triticum aestivum
SEQUENCE: 133
acgcctcacg cctcacgccc gcgtcataaa atcgtgggcg actcgtgtcc cagtcccagc  60
aggctcagcc acagcccaca gcgacgcggc agcggcagca ggaacagcaa cagcgacctt  120
gcttcccgcg cgcggcagcc gagggagggg aggaggagat cgaggggggc aagcggggca  180
gggcggcatg gggacggggg gctagaacaa ggagatggct gcagagcgac gccctcgggg  240
gcattaatgg ggccctccct ctgctccaca tcctgctgct cccacatcct ccccgcggcc  300
gcggttgatt cctcgcccgc ctacttttaa ccgcgccccc ccttttccgg acgggacggc  360
tgggctgtgg gcgggcgcca tggcatcgga tctcaacgcg gcggacgagc ctggcaaggc  420
ggcggcggtg tcggtgtgcc gggacctgtg gcacgcctgc gcggggccgg tcgtggcgct  480
gccgcgccgg ggcagcgccg tcgtctacct gccgcaggcg cacctcgccg cggccggcgg  540
cggggggggac gtgccggtgg ccctgccgcc gcatgtggcg tgccgcgtgg tggacgtcga  600
gctatgcgcg gatccggcga ccgacgaggt ctacgcgcgg ctggctatgg tggcggaggg  660
cgagatcttt gagaagaaca tgggaggtgg tcggtttgaa ggggaagatg acatggaaga  720
tggcgatgga gaaaggaagt cccggatgct gcacatgttc tgcaagacac taacagcctc  780
tgacacaagc acacacgggg gattctctgt tccccgccgt gctgccgagg actgtttccc  840
cccactggac taccagcaga tcaggccttc ccaagagctt gttgcaaagg atttgcatgg  900
agcgaagtgg aggttccgcc atatctatag aggtcaacca cgtaggcatc ttttaacgac  960
tggatggagt tcatttgtca ataaaaagaa acttgtctct ggggatgcag tcttatttct  1020
ccgtggtgat gatggtgaac tacgacttgg tgtaaggaga gccattcagc ttaaaaatga  1080
ggcccttctg aaagctttca atagcaacag ctcaaagata cacacactgt ctgctgtggc  1140
taattccttg aaacatagaa gtgtttttca catctgttac aatccaaggg ctgctgcatc  1200
cgaatttatt gttccgtact ggaagttcct gaagagcctg aatcgtccat tttgtattgg  1260
aatgaggttt aagattcagt atgggagtga agatgttaat gagaggcgat ctggaatgat  1320
tacaggtatt aatgaagtag accccattag gtggactggt tcaaaatgga aaagcctgca  1380
ggtaagatgg gaggatggca ccgactgtaa tagccaaaat agactatcgc catgggatat  1440
cgagatagtt ggtggctcgg tctctattgc ccagtctctg tcagcatcca gttctaaacg  1500
aactaaactg tgccctcagg gcaatgtgga cgtcccaact ctgtatggga atgttcgtcc  1560
ggactccgtg ggagctgata aactccccag ggtcttgcaa ggtcaagaat tgatgggttc  1620
tggaactcat cgttttacat gtcctcctca gccaggtggc gccacagaat tccggcgttc  1680
tgatggtacg gggttcctta ctgatacacg aagctgcttg ctgagtggtc cagcaagcag  1740
gcttccacct caaagctcct atttcgccta ccaacctgta ggcttcggtg aatccgttgg  1800
gttcccggag gtcttgcaag gtcaagaagt ttgtcagacg gttcctctgt accaaggaat  1860
ggtgtctgat acatgttccg ctaaagcggg atacgggatg tacaattaca tgcgcacctc  1920
gtctgccatg aacggagggt tttcatctgc acctcagggt tatcctctct ccctgtctac  1980
tccgccccga gcagtggcgg cttcgccctc atccgcagcg gttccaccac agctttggct  2040
ggcaagcaag agcaatgaag aagctgcgaa tggcagccag cttaacccat ttggaattcg  2100
aaaggttcct ggtgatggtg ctgctaagct tggtgatggt gctgctaagc ttggatctga  2160
tggaaggaag gttgccagaa ccagttgcat gcttttcggg ttttccttga ccgagaagat  2220
gttgccaacg gaagaagact ctgccaagga agggaaccat gaagtcgact gtcagaatcc  2280
gcggatgcta gacttgtttg gatacaaccg cgccactccc ggcactcttc acgccctctg  2340
cgccgctccc ctgggaatat gatgccactc cagttccagt atgatccaag tactttgtag  2400
tgctctttct aagaaacttt                                              2420

SEQ ID NO: 134          moltype = AA  length = 660
FEATURE                 Location/Qualifiers
REGION                  1..660
                        note = misc_feature - Ceres CLONE ID no.827306
REGION                  1..660
                        note = misc_feature - Bit score of 1417.6 for hmm based on
                         sequences of FIGURE 5.
REGION                  126..231
                        note = misc_feature - Pfam Name: B3 Pfam Description: B3
                         DNA binding domain
REGION                  253..334
                        note = misc_feature - Pfam Name: Auxin_resp Pfam
                         Description: Auxin response factor
REGION                  1..660
                        note = misc_feature - Is Acted Upon By Ceres SEEDLINE ID
                         no. ME00572 at SEQ ID NO. 111
```

-continued

```
source                  1..660
                        mol_type = protein
                        organism = Triticum aestivum
SEQUENCE: 134
MGIDLNAADE PGKAAAVSVC RDLWHACAGP VVALPRRGSA VVYLPQAHLA AAGGGGDVPV  60
ALPPHVACRV VDVELCADPA TDEVYARLAM VAEGEIFEKN MGGGRFEGED DMEDGDGERK  120
SRMLHMFCKT LTASDTSTHG GFSVPRRAAE DCFPPLDYQQ IRPSQELVAK DLHGAKWRFR  180
HIYRGQPRRH LLTTGWSSFV NKKKLVSGDA VLFLRGDDGE LRLGVRRAIQ LKNEALLKAF  240
NSNSSKIHTL SAVANSLKHR SVFHICYNPR AAASEFIVPY WKFLKSLNRP FCIGMRFKIQ  300
YGSEDVNERR SGMITGINEV DPIRWTGSKW KSLQVRWEDG TDCNSQNRLS PWDIEIVGGS  360
VSIAQSLSAS SSKRTKLCPQ GNVDVPTLYG NVRPDSVGAD KLPRVLQGQE LMGSGTHRFT  420
CPPQPGGATE FRRSDGTGFL TDTRSCLLSG PASRLPPQSS YFAYQPVGFG ESVGFPEVLQ  480
GQEVCQTVPL YQGMVSDTCS AKAGYGMYNY MRTSSAMNGG FSSAPQGYPL SLSTPPRAVA  540
ASPSSAAVPP QLWLASKSNE EAANGSQLNP FGIRKVPGDG AAKLGDGAAK LGSDGRKVAR  600
TSCMLFGFSL TEKMLPTEED SAKEGNHEVD CQNPRMLDLF GYNRATPGTL HALCAAPLGI  660

SEQ ID NO: 135          moltype = DNA  length = 2339
FEATURE                 Location/Qualifiers
misc_feature            1..2339
                        note = Ceres CLONE ID no.1598488
misc_feature            1..2339
                        note = Encodes the peptide sequence at SEQ ID NO. 136
source                  1..2339
                        mol_type = other DNA
                        organism = Zea mays
SEQUENCE: 135
cctgtacgcc gtcccgcttc gcttcggaga ggtcgctgcc tgccatcaac gttccctcgc  60
tggtagagta gaggtagacc caccgacccc cagtactagt cgggagagag atggggattg  120
atctcaacgc cgtgggggag gacgacccgg cgggcgcggt gtgcgcggag ctgtggcacg  180
cgtgcgcggg ggctggagtg gcgctgccgc ggcggggcag cgccgtggtg tacctgcctc  240
aggcgcacct cgcggcgggc ggctgcgacg gtggtgggat gtcggcgccg gccccgccgc  300
gcgtgccgcc gcacgtggtg tgtcgcgtcg tcgacgtcga gctacgcgcg gatgcggcca  360
cggacgaggt gtacgcgcgg cttgcgctgg tggcgatgga tacgatgttt ggccgaaaca  420
tcaatgatgg tgaaactgaa gagaagaatg gcgaggaaga ggatggcgac ggagaaaaga  480
agcacgcatc acacatgttc tgcaagacac tcacagcttc tgataccagc acacatgggg  540
gattctctgt tccacggcga gctgcagagg actgctttcc acccttggac tatgagcagc  600
ttaggccttc ccaagagctt attgccaagg atttgcatgg catgaaatgg aggttccgtc  660
atatctatag aggtcaacct cgaaggcatc ttctgacaac tggatggagt tcatttatca  720
ataagaagaa actagtctca ggggatgcag tcttgtttct tagaggtaat gatggtgagc  780
taagattggg tgtgaggaga gcagttcaac tgaaaaatga agctctactt gaagctgtca  840
actgtactga ttcgaagcta cttatgctgt ctgctgtcgc caattctttg gacaacagaa  900
gtatatttca catctgtttc aacccaaggg ttggtgcatc agaatttatt gtgccgtatt  960
gcaagttctt gaagagtttg aactatccct tttcagttgg aaccagattt aaagttggct  1020
gcgagaatga agatgctaac gagaggtcct ttggattgat cataggtatt agtgaagttg  1080
atcccataca ctggcctgga tcaaaatgga aatctctcct gataaagtgg gatggtgcta  1140
ctaagtacag ccaccagaat agagtatctc catgggacat cgagggagtt ggcagctcag  1200
tttcagttac tcaccgtctt tcctcttctg tttcgaagcg aacaaaactg tgcttccctc  1260
caagcgattt ggacacgcca attctagatg gaaatggtcg tccagactcc gtggaaactg  1320
aacgtttcca cagggtcttg caaggtcaag aattggtgca ctctagtatt cacggtgctg  1380
catgctctca ttcatcagat agccccagat gtcaaggctc ttatggcagg agattctctg  1440
ctgatgcatg gaactgcaag atgaatgatg taatgagtgg gcctcgacac ctaaatgcca  1500
ctgggtttgc ttaccagccc ctaggcttca gtgaatctgt caaattctca gaggtcttgc  1560
aaggtcaaga aatgtctcag gcggttcctt ccttcatgag atctgctttc aactctggca  1620
cgcagaatgg cagggttcga ccatttgatt atgtgcagag atcagatgca actcaaggat  1680
acgctctcca gcagtttaat ctgccagcaa cagaagtgca ttcgccctct tctgttctta  1740
tgtttaacca aaccatggta ccacatgctg agctagatgg tgcgaccaac cgtgaagaag  1800
tacatggcag caggtacttg tcatccaatg caatagggag agaagctgaa ccatggccat  1860
ccatggagca gcaaagagcg agtgtaaatg gaagcgagcc tctcgacaca actgaagcct  1920
cagctcctgc aaggaacgct gaatctggat cggtcggcag gggcgtgggg cgaagcagct  1980
gtaagctttt tggtttctcc ctgactgaga agatccttgc aacggatggt ggtggtgtaa  2040
aagaaggaaa ctacgaagtg gaccgtcaaa ctcccgggt gctagacttg tttgggcacg  2100
gttctacgcc tggtgctctg catgctctct gtgctgctcc cttgggaata tgatgctgtt  2160
ctgcctagtt ttacagcagt tagatttatg taatccttca gccattttca tcgcgttgta  2220
cttgaccaat atgtccagcg tatgatttcc agttttaatt gtatgctgat gctacatatc  2280
ctctcttgag atccatgcat gagaattctg gcagaatgaa taaaggtaaa ttgatgtcc   2339

SEQ ID NO: 136          moltype = AA  length = 680
FEATURE                 Location/Qualifiers
REGION                  1..680
                        note = misc_feature - Ceres CLONE ID no.1598488
REGION                  1..680
                        note = misc_feature - Bit score of 1482.2 for hmm based on
                         sequences of FIGURE 5.
REGION                  129..234
                        note = misc_feature - Pfam Name: B3 Pfam Description: B3
                         DNA binding domain
REGION                  256..337
                        note = misc_feature - Pfam Name: Auxin_resp Pfam
                         Description: Auxin response factor
```

```
REGION                  1..680
                        note = misc_feature - Is Acted Upon By Ceres SEEDLINE ID
                         no. ME00572 at SEQ ID NO. 111
source                  1..680
                        mol_type = protein
                        organism = Zea mays
SEQUENCE: 136
MGIDLNAVGE DDPAGAVCAE LWHACAGAGV ALPRRGSAVV YLPQAHLAAG GCDGGGMSAP  60
APPRVPPHVV CRVVDVELRA DAATDEVYAR LALVAMDTMF GRNINDGETE EKNGEEEDGD  120
GEKKHASHMF CKTLTASDTS THGGFSVPRR AAEDCFPPLD YEQLRPSQEL IAKDLHGMKW  180
RFRHIYRGQP RRHLLTTGWS SFINKKKLVS GDAVLFLRGN DGELRLGVRR AVQLKNEALL  240
EAVNCTDSKL LMLSAVANSL DNRSIFHICF NPRVGASEFI VPYCKFLKSL NYPFSVGTRF  300
KVGCENEDAN ERSFGLIIGI SEVDPIHWPG SKWKSLLIKW DGATKYSHQN RVSPWDIEGV  360
GSSVSVTHRL SSSVSKRTKL CFPPSDLDTP ILDGNGRPDS VETERFHRVL QGQELVHSSI  420
HGAACSHSSD SPRCQGSYGR RFSADAWNCK MNDVMSGPRH LNATGFAYQP LGFSESVKFS  480
EVLQGQEMSQ AVPSFMRSAF NSGTQNGRVR PFDYVQRSDA TQGYALQQFN LPATEVHSPS  540
SVLMFNQTMV PHAELDGATN REEVHGSRYL SSNAIGREAE PWPSMEQQRA SVNGSEPLDT  600
TEASAPARNA ESGSVGRGVG RSSCKLFGFS LTEKILATDG GGVKEGNYEV DRQTPRVLDL  660
FGHGSTPGAL HALCAAPLGI                                            680

SEQ ID NO: 137          moltype = AA  length = 655
FEATURE                 Location/Qualifiers
REGION                  1..655
                        note = misc_feature - Public GI ID no.125527740
REGION                  1..655
                        note = misc_feature - Bit score of 1060.7 for hmm based on
                         sequences of FIGURE 5.
REGION                  114..219
                        note = misc_feature - Pfam Name: B3 Pfam Description: B3
                         DNA binding domain
REGION                  241..322
                        note = misc_feature - Pfam Name: Auxin_resp Pfam
                         Description: Auxin response factor
REGION                  1..655
                        note = misc_feature - Is Acted Upon By Ceres SEEDLINE ID
                         no. ME00572 at SEQ ID NO. 111
source                  1..655
                        mol_type = protein
                        note = subspecies = indica
                        organism = Oryza sativa
SEQUENCE: 137
MGIDLNYTAS GGEEDAPAPA PVCRDLWHAC AGPVVSLPRR GSAVVYLPQG HLSAAGAGGR  60
IRGEVAVALP PHVACRVVDV ELCVFERNLH GGGIEREDDM EDGDEERKSR MLHMFCKTLT  120
ASDTSTHGGF SVPRRAAEDC FPPLDHKQLR PSQELVAKDL HGAKWRFRHI YRGQPRRHLL  180
TTGWSSFVNK KKLVSGDAVL FLRGDDGELR LGVRRATQLK NEAIFKAFSS ESSKMRTLSA  240
VADSLKHGSV FHICYNPRAT ASEYVVPYWK FVKSFNHPVC IGMRFKFHYE SEDVNERRSG  300
MIAGVSEVDP IRWPGSKWRS LLVRWEDATD CNSQNRVSPW EIEIVGGSIS VAHSLSASSS  360
KRTKLCPQGN LDVPALYGNG RPDSVETEKF PRVLQGQELM GSRTHRVTCS PQSIDITKSK  420
SFDAWRFLTD TRSCMLGSST SRLPVQYSGY THQSVSFGES IGFPEVLQGQ EISQTVPPIQ  480
GMLPDACSAK SRYELKNYVC TPATMNGLSS ANEGYCLSLS TVPPSPPSSL MLYQTGVPQL  540
ELASKNNDKS GNDSQPALRQ HKLLSETSWD QFKIGKASTP GNATKPGNGG REVDRTSCRL  600
FGFSLTEKII PTDKDGEKEV SYETDCQNPR MLDLFGYNCS TPGALHALCA APLGI       655

SEQ ID NO: 138          moltype = AA  length = 719
FEATURE                 Location/Qualifiers
REGION                  1..719
                        note = misc_feature - Public GI ID no.125553314
REGION                  1..719
                        note = misc_feature - Bit score of 1618.5 for hmm based on
                         sequences of FIGURE 5.
REGION                  141..246
                        note = misc_feature - Pfam Name: B3 Pfam Description: B3
                         DNA binding domain
REGION                  268..349
                        note = misc_feature - Pfam Name: Auxin_resp Pfam
                         Description: Auxin response factor
REGION                  1..719
                        note = misc_feature - Is Acted Upon By Ceres SEEDLINE ID
                         no. ME00572 at SEQ ID NO. 111
source                  1..719
                        mol_type = protein
                        note = subspecies = indica
                        organism = Oryza sativa
SEQUENCE: 138
MTGIDLNTVE EDEEEAAEEV AANGSSPAPA RAGAVCLELW HACAGPVAPL PRKGGVVVYL  60
PQGHLEHLGD APAAAAAAAA VPPHVFCRVV DVTLLADAAT DEVYAQLSLV PEKEEVARRA  120
DDGEGEDGDG MKQRFARMPH MFCKTLTASD TSTHGGFSVP RRAAEDCFPP LDYSQQRPSQ  180
ELVAKDLHGT EWRFRHIYRG QPRRHLLTTG WSAFVNKKKL VSGDAVLFLR GDDGELRLGV  240
RRAAQLKNGS AFPALYNQCS NLGTLANVAH AVATESVFNI YYNPRLSQSE FIVPYWKFMK  300
```

-continued

```
SLSQPFSVGL RFKMRYESED ASERRYTGII TGSGDTDPMW HGSKWKCLLV RWDDDAEFRR  360
PNRVSPWEIE LTSSVSGSHL STPHSKRLKP CLPHVNPEYM VPRGGGCPDF AESAQFHKVL  420
QGQELLGFKS HGGTAAATSQ PCEARHLQYI DERSCSSDAS NSILGVPRLG DRAPLGNPGF  480
SYHCSGFGES QRLQKVLQGQ ELFRPYRGTL VDASMGSNGF HQQDSPRAPG VVNKWQAQLH  540
GRAAFHGPPA LALPSQSSSP PSVLMFQQAN SKMPRLEFGH GQLDKHENDR RVRFGPSEGI  600
ERREQRIPLQ PYPTSGEVID GQVTVEKSHS PGRHGKDGPD NKAVGTNSCK IFGISLTEKV  660
PAREELDDGD ANYSLQSLKQ VPKSLGNSCA TMVAEYQGDG GTDDSDIFIL DVGVGALIM   719

SEQ ID NO: 139          moltype = AA  length = 788
FEATURE                 Location/Qualifiers
REGION                  1..788
                        note = misc_feature - Ceres LOCUS ID no. At5g60450
REGION                  1..788
                        note = misc_feature - Bit score of 808.3 for hmm based on
                         sequences of FIGURE 5.
REGION                  176..281
                        note = misc_feature - Pfam Name: B3 Pfam Description: B3
                         DNA binding domain
REGION                  302..384
                        note = misc_feature - Pfam Name: Auxin_resp Pfam
                         Description: Auxin response factor
REGION                  1..788
                        note = misc_feature - Is Acted Upon By Ceres SEEDLINE ID
                         no. ME00572 at SEQ ID NO. 111
source                  1..788
                        mol_type = protein
                        organism = Arabidopsis thaliana
SEQUENCE: 139
MEFDLNTEIA EVEEEENDDV GVGVGGGTRI DKGRLGISPS SSSSCSSGSS SSSSSTGSAS  60
SIYSELWHAC AGPLTCLPKK GNVVVYFPQG HLEQDAMVSY SSPLEIPKFD LNPQIVCRVV  120
NVQLLANKDT DEVYTQVTLL PLQEFSMLNG EGKEVKELGG EEERNGSSSV KRTPHMFCKT  180
LTASDTSTHG GFSVPRRAAE DCFAPLDYKQ QRPSQELIAK DLHGVEWKFR HIYRGQPRRH  240
LLTTGWSIFV SQKNLVSGDA VLFLRDEGGE LRLGIRRAAR PRNGLPDSII EKNSCSNILS  300
LVANAVSTKS MFHVFYSPRA THAEFVIPYE KYITSIRSPV CIGTRFRMRF EMDDSPERRC  360
AGVVTGVCDL DPYRWPNSKW RCLLVRWDES FVSDHQERVS PWEIDPSVSL PHLSIQSSPR  420
PKRPWAGLLD TTPPGNPITK RGGFLDFEES VRPSKVLQGQ ENIGSASPSQ GFDVMNRRIL  480
DFAMQSHANP VLVSSRVKDR FGEFVDATGV NPACSGVMDL DRFPRVLQGQ EICSLKSFPQ  540
FAGFSPAAAP NPFAYQANKS SYYPLALHGI RSTHVPYQNP YNAGNQSSGP PSRAINFGEE  600
TRKFDAQNEG GLPNNVTADL PFKIDMMGKQ KGSELNMNAS SGCKLFGFSL PVETPASKPQ  660
SSSKRICTKV HKQGSQVGRA IDLSRLNGYD DLLMELERLF NMEGLLRDPE KGWRILYTDS  720
ENDMMVVGDD PWHDFCNVVW KIHLYTKEEV ENANDDNKSC LEQAALMMEA SKSSSVSQPD  780
SSPTITRV                                                           788

SEQ ID NO: 140          moltype = DNA  length = 2064
FEATURE                 Location/Qualifiers
misc_feature            1..2064
                        note = Ceres ANNOT ID no.1515383
misc_feature            1..2064
                        note = Encodes the peptide sequence at SEQ ID NO. 141
source                  1..2064
                        mol_type = other DNA
                        organism = Populus balsamifera
                        sub_species = trichocarpa
SEQUENCE: 140
atggaaattg atctgaatca tccagtgact gaggtggaga agaattcatt ttgtaccaat  60
ggggactctt catgttcttc taattcatct tcatctccag tttcctcttc aatttacttg  120
gagctttggc atgcttgtgc tggtcctctc acttctctcc ctaagaaagg gaatgtggtt  180
gtctacttcc ctcaaggcca cttggagcag cttgcctctt cctctccttt ctctcatagg  240
gacatgccca attttgatct ccacccacaa atattttgca aagttgtaaa tgtgcagcta  300
cttgccaata gggaaaatga tgaggtctac actcggctta ctttgcttcc tcaaccagag  360
gtggtaggac aggatttaga aggcaaagag cttcaagagt taggcgtgga tggagagggt  420
gacgacgcat caccaacaaa atcaacccca cacatgtttt gcaaaacact cacagcttct  480
gatactagca cccatggagg gttttccgtt cctcgaagag ctgccgaaga ctgtttccct  540
tcactggatt ataaacagca gagaccctct caagagcttt tggccaaaga cttgcatgga  600
gttgaatgga gatttcgtca tatttacaga ggtcaaccaa gaaggcatct tctaactacg  660
ggatggagta tttttgtgag tcaaaagaat cttgtttcag ggatgcagt gctatttctg  720
aggggcgaag gtggagagtt gagactgggg atcagacgag ctgctcgacc tagaaatggt  780
cttcctgatt ctgttactgg caagcagaat tcacttccca gtgctctctc cttggtgtct  840
aatgcaatat ccaccaagag cgtgttcact gtttcatata gtccaagggc cactcatgca  900
gtgtttgttg taccctacca aaagtatata aaaagcatca ccaatgcagt ttgcatcggg  960
acaagattca aaatgagatt tgaaatggat gattctcctg aaagaaggtg tagcggtgta  1020
gtaactggaa cagctgactt ggatccctat aagtggccca actcaaaatg gaggtgctta  1080
atggttagat gggatgaaga tgtcatcagt gatcatcaag aacgagtttc cccatgggaa  1140
attgacgctt ctgtttcact cccacccttg attattcaat cttcaccaag gttgaagaaa  1200
ctgcggactg ggctgcaagc agccccacct gataagccca tagctggagg gggtgggttt  1260
ttggatttca aggagtctgt aagatcctcc aaggtcttgc aaggtcaaga aatatgctcg  1320
ttgagttctg ttggtgcttt gggaaagccc aatactggac gcagttcttt ccagatgtat  1380
ccaggaccaa gacccgcttt ctatcctgta gcagcagaaa gccttagaag tatgtacttt  1440
ccctatggag atgtatacaa aaatggtcaa gatcccagaa cacaatctta tgctatcttc  1500
```

-continued

```
tctagagaaa atgcccattt caatacatct tctattcaga cttgtgtggt tagggaagaa  1560
gttagaaagc ctaatcaatc aagcgagtat aagacacaag aaagtatttc tgctgcaccg  1620
gctttatgtg caaatctaag aaaccaaaag gatgactttt ttaatgggaa tgctactggc  1680
tgcaaacttt ttgggttctc cttgaatgca gaaacatctc caaattcgca gaacactagt  1740
aagaggagtt gcacaaaggt tcacaagcaa ggtagcttgg tcggaagagc tattgatctt  1800
tcaaggctga atggctatag tgatctcttg aatgaactag agcgactatt tagcatggag  1860
ggtcttttac gaaatcctga ggaaggatgg cgaatcttgt atactgacag tgagaatgat  1920
gttatggttg tcggagatga cccatggctt gagttctgta atgtggcaac caagatccat  1980
atatataccc aagaagaagt ggagaagatg accgttggaa ttactgggga cgatactcaa  2040
agttgtttgg atcaagccct gtga                                         2064
```

```
SEQ ID NO: 141          moltype = AA  length = 687
FEATURE                 Location/Qualifiers
REGION                  1..687
                        note = misc_feature - Ceres ANNOT ID no.1515383
REGION                  1..687
                        note = misc_feature - Bit score of 794.3 for hmm based on
                         sequences of FIGURE 5.
REGION                  152..257
                        note = misc_feature - Pfam Name: B3 Pfam Description: B3
                         DNA binding domain
REGION                  279..361
                        note = misc_feature - Pfam Name: Auxin_resp Pfam
                         Description: Auxin response factor
REGION                  1..687
                        note = misc_feature - Is Acted Upon By Ceres SEEDLINE ID
                         no. ME00572 at SEQ ID NO. 111
source                  1..687
                        mol_type = protein
                        note = subspecies = trichocarpa
                        organism = Populus balsamifera
SEQUENCE: 141
MEIDLNHPVT EVEKNSFCTN GDSSCSSNSS SSPVSSSIYL ELWHACAGPL TSLPKKGNVV  60
VYFPQGHLEQ LASSSPFSHR DMPNFDLHPQ IFCKVVNVQL LANRENDEVY TRLTLLPQPE  120
VVGQDLEGKE LQELGVDGEG DDASPTKSTP HMFCKTLTAS DTSTHGGFSV PRRAAEDCFP  180
SLDYKQQRPS QELLAKDLHG VEWRFRHIYR GQPRRHLLTT GWSIFVSQKN LVSGDAVLFL  240
RGEGGELRLG IRRAARPRNG LPDSVTGKQN SLPSALSLVS NAISTKSVFT VSYSPRATHA  300
VFVVPYQKYI KSITNAVCIG TRFKMRFEMD DSPERRCSGV VTGTADLDPY KWPNSKWRCL  360
MVRWDEDVIS DHQERVSPWE IDASVSLPPL IIQSSPRLKK LRTGLQAAPP DKPIAGGGGF  420
LDFKESVRSS KVLQGQEICS LSSVGALGKP NTGRSSFQMY PGPRPAFYPV AAESLRSMYF  480
PYGDVYKNGQ DPRTQSYAIF SRENAHFNTS SIQTCVVREE VRKPNQSSEY KTQESISAAP  540
ALCANLRNQK DDFFNGNATG CKLFGFSLNA ETSPNSQNTS KRSCTKVHKQ GSLVGRAIDL  600
SRLNGYSDLL NELERLFSME GLLRNPEEGW RILYTDSEND VMVVGDDPWL EFCNVATKIH  660
IYTQEEVEKM TVGITGDDTQ SCLDQAL                                      687
```

```
SEQ ID NO: 142          moltype = DNA  length = 2722
FEATURE                 Location/Qualifiers
misc_feature            1..2722
                        note = Ceres CLONE ID no.462443
misc_feature            1..2722
                        note = Encodes the peptide sequence at SEQ ID NO. 143
source                  1..2722
                        mol_type = other DNA
                        organism = Zea mays
SEQUENCE: 142
agacaaccaa acgaaccctc ccggagcagc aaagcatagg cgctcgagcg ctccctcccg  60
agctcctccg cctcacggtc acgcctcgtg tccccccacc ccctcctcct cctcctcggc  120
cggccgcctc acgccgtcac ctccgctcgg cgagtctcgg ctccgaccgc tgccgccacg  180
tgcgacctcc cctactcctg agagatctgc ggggctcggc atggggtgac cagatcgggc  240
cgctgctcgg tgctttccag ctgaattttg cccgcagctc gtgtcggagg cagcgaagat  300
ggcggaggcc ggcgtggcac gcggctcagg gagcgctggc gatgctttgt tcagggaact  360
ctggcatgct tgtgctgggc cgttggtcac agtgcctcgc caaggcgagc tggtttatta  420
cttcccccag ggtcatatgg aacagcttga agcgtctaca gatcaacaac ttgatcagca  480
cttgcctttg tttaatctac cgcacaagat cctctgcaag gtggtcaatg tagaacttag  540
agctgaaact gattctgatg aagtttatgc tcaaattatg ctgcaaccac aaacagagca  600
aagtgagccc accagcccag atcctgaacc acctgagcct gaaagatgca acattcattc  660
cttctgcaag accttgactg cttcagatac aagtacccat ggtctctctg tcctcaggag  720
gcatgctgaa gaatgtttgc cccaactgga catgactcag aatccaccgt ggcaagaact  780
agtggctaaa gatctccatg gaaatgaatg gcatttccgt cacatctttc gagggcaacc  840
aaggaggcat ctacttacga caggctggag tgtttttgtt agctcaaaaa gattggttgc  900
gggtgacgcg tttatcttct tgagaggtga gaacggagag ctgcgagtcg gggtaaggag  960
gctcatgaga caactaaata acatgccgtc ttcggttatc tcaagccaca gcatgcatct  1020
tggagtccta gcaactgcat ctcatgccat ctccactgga actctatttt ctgttttcta  1080
caaacccaga acaagtagat ctgaatttgt cgttagtgta aacaagtacc tcgaagctaa  1140
gaatcacaag atgtctgttg gtatgaggtt taaaatgaga tttgagggtg atgaatcccc  1200
tgaaagaaga ttcagtggga taattattgg tatgggatgc atgccagcta actcaacatc  1260
tccatgggct aactctgaat ggagatcatt gaaggtccaa tgggacgagc cttctgctat  1320
tctgcgtcca gatagagttt caccatggga agtagaaccc cttaatcgaa caaatccaca  1380
gccacctcaa cctcctttac ggaataagcg agcacggcct cctgcttcac cttcgattgc  1440
```

-continued

```
tccagaactt gctccagttt ttggtttttg gaagtcccca gctgagcctg cccaagcttt  1500
ctcattctca ggactgcagc gaactcagga gctataccat tcaagcccca gttcaatgtt  1560
ctcatcgtcg ttgaatgtgg gattcaatcc aaagtacgag ggtcccactc caaacaccaa  1620
ccatttgtac tggacaatga gagagacaag aactgaatcc tactccgcta gcatcaacaa  1680
agctccaact gaaaagaagc aagaatccac tacttctggc tgcagattgt tcggtatcga  1740
gataggttct tctgcagtgt cacccgtggt tactgttgct agcgtcgggc atgatcctcc  1800
gccacctgct ctctcagtag acgctgaatc tgaccagctg tcacagccgt cccatgccaa  1860
caaagcaacg gatgccccag cggcaagcag cgatcgctct cctaacgaga cagagagccg  1920
gcaagccagg agctgcacca aggtaatcat gcaaggggtg gcggttggca gggcggtgga  1980
cttgacgagg ctagatgggt acgatgacct ccgccgcaag ttggaggaga tgttcgatat  2040
cccgggagag ctttccgcca gcctcaataa atggaaggtg atctacacag atgacgagga  2100
cgatatgatg ctggtcgggg acgatccatg gagtgaattt tgcaggatgg taaaaaggat  2160
atacatttat tcctacgagg aggccaagtc tttgactccc aaggcgaagc tgccggccat  2220
cggtggtgac accggcgtca agccggaccc aagtaaactg tcagcagaat ctgacgtgcc  2280
acagagcgac tccgacaaca gtgctcccgt ttctgctgat aaggactgat ggacgctagc  2340
tcggccgtac cttctcttta tgttggccat gggaggccag tgcagtgccc atgctccttg  2400
agactgctaa gaattgatca tctgttccat ctgcctcggc ttggaccagc gaggatggcc  2460
gggagggagt gcatgccgct ccgtgcgtgt ttcgtttgcc gtgtttggta ggagccatgg  2520
cttgttgccg gctacttggg ttctgtagac tgttacactg actgctgccg tctcacctgg  2580
ccgtcggcgc gggccgcccc ctctcacctc tctagtaata tactagggct tatgtacaca  2640
cagctgtttt ggtagtggca tatgtatatc gtcggtcatg ttgcttgcga catttagcat  2700
cctccgtagc tgctatttcc tc                                            2722

SEQ ID NO: 143         moltype = AA  length = 676
FEATURE                Location/Qualifiers
REGION                 1..676
                       note = misc_feature - Ceres CLONE ID no.462443
REGION                 1..676
                       note = misc_feature - Bit score of 1504.3 for hmm based on
                        sequences of FIGURE 5.
REGION                 121..225
                       note = misc_feature - Pfam Name: B3 Pfam Description: B3
                        DNA binding domain
REGION                 247..332
                       note = misc_feature - Pfam Name: Auxin_resp Pfam
                        Description: Auxin response factor
REGION                 1..676
                       note = misc_feature - Is Acted Upon By Ceres SEEDLINE ID
                        no. ME00572 at SEQ ID NO. 111
source                 1..676
                       mol_type = protein
                       organism = Zea mays
SEQUENCE: 143
MAEAGVARGS GSAGDALFRE LWHACAGPLV TVPRQGELVY YFPQGHMEQL EASTDQQLDQ  60
HLPLFNLPHK ILCKVVNVEL RAETDSDEVY AQIMLQPQTE QSEPTSPDPE PPEPERCNIH  120
SFCKTLTASD TSTHGLSVLR RHAEECLPQL DMTQNPPWQE LVAKDLHGNE WHFRHIFRGQ  180
PRRHLLTTGW SVFVSSKRLV AGDAFIFLRG ENGELRVGVR RLMRQLNNMP SSVISSHSMH  240
LGVLATASHA ISTGTLFSVF YKPRTSRSEF VVSVNKYLEA KNHKMSVGMR FKMRFEGDES  300
PERRFSGIII GMGCMPANST SPWANSEWRS LKVQWDEPSA ILRPDRVSPW EVEPLNRTNP  360
QPPQPPLRNK RARPPASPSI APELAPVFGF WKSPAEPAQA FSFSGLQRTQ ELYHSSPSSM  420
FSSSLNVGFN PKYEGPTPNT NHLYWTMRET RTESYSASIN KAPTEKKQES TTSGCRLFGI  480
EIGSSAVSPV VTVASVGHDP PPPALSVDAE SDQLSQPSHA NKATDAPAAS SDRSPNETES  540
RQARSCTKVI MQGVAVGRAV DLTRLDGYDD LRRKLEEMFD IPGELSASLN KWKVIYTDDE  600
DDMMLVGDDP WSEFCRMVKR IYIYSYEEAK SLTPKAKLPA IGGDTGVKPD PSKLSAESDV  660
PQSDSDNSAP VSADKD                                                   676

SEQ ID NO: 144         moltype = DNA  length = 329
FEATURE                Location/Qualifiers
misc_feature           1..329
                       note = Public GI No. 21403834
misc_feature           1..329
                       note = Homolog Of Ceres SEEDLINE ID no. ME00572 at SEQ ID
                        NO. 111
misc_feature           1..329
                       note = FRAGMENT
source                 1..329
                       mol_type = other DNA
                       organism = Arabidopsis thaliana
SEQUENCE: 144
tatctgagct tttagtcgga ttttttcttt tcaattattg tgttttatct agatgatgca  60
tttcattatt ctctttttct tgaccttgta aggccttttc ttgaccttgt aagaccccat  120
ctctttctaa acgttttatt atttctcgt tttacagatt ctattctatc tcttctcaat  180
atagaataga tatctatctc tacctctaat tcgttcgagt cattttctcc taccttgtct  240
atccctcctg agctaatctc cacatatatc ttttgtttgt tattgatgta tggttgacat  300
aaattcaata aagaagttga cgtttttcc                                     329

SEQ ID NO: 145         moltype = DNA  length = 350
FEATURE                Location/Qualifiers
misc_feature           1..350
```

```
                         note = Public GI No. 158087544
misc_feature             1..350
                         note = Homolog Of Ceres SEEDLINE ID no. ME00572 at SEQ ID
                          NO. 111
misc_feature             1..350
                         note = FRAGMENT
source                   1..350
                         mol_type = other DNA
                         organism = Solanum lycopersicum
SEQUENCE: 145
cctaacgatg agtgtcgcat cctcatctta atctcggtgc tatcctacct gagctttttc  60
tcaccgcttt tttttttctg ttgtgtattc tctttttga cttgttgcct ttcgttcctc  120
tacctacccc attcttcttg accttgtaag accttttctt gaccttgtaa gaccccgtgt  180
tatctcttac gtctttatgt tttgtttttt tgcaaatctt acgtcatgac ttcttcatgt  240
aagctttgtt tggtctcctt cttctttcct actcaactct cgttctcctt ccttgtctat  300
ccctcctgag ctgttgattt tattccatgt acaattgaac acaacaaaaa            350

SEQ ID NO: 146           moltype = DNA  length = 197
FEATURE                  Location/Qualifiers
misc_feature             1..197
                         note = Public GI No. 110797273
misc_feature             1..197
                         note = Homolog Of Ceres SEEDLINE ID no. ME00572 at SEQ ID
                          NO. 111
misc_feature             1..197
                         note = FRAGMENT
source                   1..197
                         mol_type = other DNA
                         organism = Brassica rapa
SEQUENCE: 146
aaaaaatttc tttctcccac tgaatgattt tttattttct tgaccttgta aggccttttc  60
ttgaccttgt aagaccccat ccctttctaa gtgtttcctt cttctatcat cttacagatt  120
ttcttttatc tctttttggt gtaagatatg tatgtatatc tacccctagt ttgtctgagt  180
catcttctcc taccttg                                                197

SEQ ID NO: 147           moltype = DNA  length = 207
FEATURE                  Location/Qualifiers
misc_feature             1..207
                         note = Public GI No. 118566241
misc_feature             1..207
                         note = FRAGMENT
misc_feature             1..207
                         note = Homolog Of Ceres SEEDLINE ID no. ME00572 at SEQ ID
                          NO. 111
source                   1..207
                         mol_type = other DNA
                         organism = Medicago truncatula
SEQUENCE: 147
gagcttttttt ttcacctttc tcttttctta acttttttttt tactctactt gtgtcttctt  60
gaccttgtaa gaccttttct tgaccttgta agacctcact ctgtgtcggt tttctttgtt  120
tttgcttttg tggaagacgc tatatcgaaa tttgttgata tagagtttcg tctccgtttt  180
tccttttac cacccaactc attctct                                      207

SEQ ID NO: 148           moltype = DNA  length = 188
FEATURE                  Location/Qualifiers
misc_feature             1..188
                         note = Public GI No. 147857869
misc_feature             1..188
                         note = FRAGMENT
misc_feature             1..188
                         note = Homolog Of Ceres SEEDLINE ID no. ME00572 at SEQ ID
                          NO. 111
source                   1..188
                         mol_type = other DNA
                         organism = Vitis vinifera
SEQUENCE: 148
cccggttgtg tttcctttttg ttcgggtcat tacttcttct tgaccttgta agaccttttc  60
ttgaccttgt aagaccccgg gcaaaatccg ctatccttat tatatcagtc gagaaggact  120
tcctattaga cactactgat aaagagttca ataatcaata cttgatgtcc ccaacctact  180
cgtcatct                                                          188

SEQ ID NO: 149           moltype = DNA  length = 182
FEATURE                  Location/Qualifiers
misc_feature             1..182
                         note = Public GI No. 58530789
misc_feature             1..182
                         note = FRAGMENT
misc_feature             1..182
                         note = Homolog Of Ceres SEEDLINE ID no. ME00572 at SEQ ID
```

```
                          NO. 111
source                   1..182
                         mol_type = other DNA
                         organism = Oryza sativa
SEQUENCE: 149
aaaacctcaa catcactttg tgtgggaatt aaaaggaatt ggtcttcttg accttgcaag  60
accttttctt gaccttgtaa gacccaacat cgttgtgttg tttttcttgt ttcttatttt  120
tcaatttcat ccacctcttc tttctacctc ccatctttct cctagttctt gccttctctc  180
tc                                                                 182

SEQ ID NO: 150           moltype = DNA  length = 232
FEATURE                  Location/Qualifiers
misc_feature             1..232
                         note = Public GI No. 21212701
misc_feature             1..232
                         note = FRAGMENT
misc_feature             1..232
                         note = Homolog Of Ceres SEEDLINE ID no. ME00572 at SEQ ID
                          NO. 111
source                   1..232
                         mol_type = other DNA
                         organism = Zea mays
SEQUENCE: 150
ccaagccagc tagcaactca aaggaggaag actagaagat atatagcctt ctccttgtgt  60
gacactcata aataaactgt tagcagcttg cgagcactgc aagatctttc tgctggcatc  120
tgaatagtca gctgctggca tctatccggg cacctctcga ccagccagag gcaggatacc  180
tggatcccaa actagctggc caacatggcg aacgatgacc ctgtggacga cg          232

SEQ ID NO: 151           moltype = DNA  length = 549
FEATURE                  Location/Qualifiers
misc_feature             1..549
                         note = Public GI No. 119010892
misc_feature             1..549
                         note = Homolog Of Ceres SEEDLINE ID no. ME00572 at SEQ ID
                          NO. 111
source                   1..549
                         mol_type = other DNA
                         note = Manhiot esculenta
                         organism = Manihot esculenta
SEQUENCE: 151
tttttttttt ctcttcttct ccttctcctt ctccttctca tctctctctc tctctctctc  60
tctctcagca tgaaagagag aggaaagcat tcagaggtga aactcaggca taagtttctt  120
caaggcattc atgaagttaa aatcatgaac aacgccacca tctgcaacgc ttccagtggt  180
gggtttttgg ctggcttctc gtttggggct aaaagtccct ttggaatggt ggttggttca  240
tgttgatggg gtgctatcct acctgagctt tttctattat tttccttttt attttttttc  300
ttacttttgt ttttaatctt cttgaccttg taagaccttt tcttgacctt gtaagacccc  360
tttttatgtt tatttatctt aatttttgta ttgtcataaa ttctatatca aaatttttttg  420
atatagaatt tcatgtttat ttttttctgt ttttgcccaa ctcatattct ccttccttgt  480
ctatccctcc tgagctattt gaataaaatt attatgctaa ttattcagaa aaaaaaaaaa  540
aaaaaatcg                                                          549

SEQ ID NO: 152           moltype = DNA  length = 168
FEATURE                  Location/Qualifiers
misc_feature             1..168
                         note = 000POPULUS
misc_feature             1..168
                         note = Homolog Of Ceres SEEDLINE ID no. ME00572 at SEQ ID
                          NO. 111
source                   1..168
                         mol_type = other DNA
                         organism = Populus balsamifera
                         sub_species = trichocarpa
SEQUENCE: 152
gttttttttt ttgttttttt ttcttgacct tgtaagacct tttcttgacc ttgtaagacc  60
ccattttttg ttctttgttt ctatagcatc cctcttgcca cccaactcat catctccttc  120
tctgtctatc cctcctgagc tatttcgatc acaccgcaag atcacatt               168

SEQ ID NO: 153           moltype = DNA  length = 167
FEATURE                  Location/Qualifiers
misc_feature             1..167
                         note = 000THEOBROMA
misc_feature             1..167
                         note = Homolog Of Ceres SEEDLINE ID no. ME00572 at SEQ ID
                          NO. 111
misc_feature             69
                         note = n is a, c, t, g, unknown, or other
misc_feature             71
                         note = n is a, c, t, g, unknown, or other
source                   1..167
```

-continued

```
                        mol_type = other DNA
                        organism = Theobroma cacao
SEQUENCE: 153
tttcttcttc ttttcttatc ttcttgacct tgtaagacct tttcttgacc ttgtaagacc  60
ccgttcggng ntccttggtt ttgcttctac cccattcccg ccaacttttc ttctcccttc  120
cttgctatcc ctcctgagct ggttgaatta gcctagccta gctatag                167

SEQ ID NO: 154          moltype = DNA  length = 168
FEATURE                 Location/Qualifiers
misc_feature            1..168
                        note = 000MALUS
misc_feature            1..168
                        note = Homolog Of Ceres SEEDLINE ID no. ME00572 at SEQ ID
                         NO. 111
source                  1..168
                        mol_type = other DNA
                        organism = Malus x domestica
SEQUENCE: 154
cgcatcgatc ccttcccttt ttcttgacct tgtaagacct tttcttgacc ttgtaagatg  60
tcatgccagg tctgttgtct ttggttcctc atcgttavvg vvvaattcat cttctccttc  120
cttgtctatc cctcctgagc tgttccacaa ttacctcaaa ctacaagc               168

SEQ ID NO: 155          moltype = DNA  length = 168
FEATURE                 Location/Qualifiers
misc_feature            1..168
                        note = 000GLYCINE
misc_feature            1..168
                        note = Homolog Of Ceres SEEDLINE ID no. ME00572 at SEQ ID
                         NO. 111
source                  1..168
                        mol_type = other DNA
                        organism = Glycine max
SEQUENCE: 155
gtttttccct tggagtcttc ttcttgacct tgtaagacct tttcttgacc ttgtaagacc  60
tcacacccta tctcttctct ttgttctttc cccgttacca cccaactcat actttccttc  120
cttgtctatc cctcctgagc tgttccaatt taattaattt ggcctacc               168

SEQ ID NO: 156          moltype = DNA  length = 168
FEATURE                 Location/Qualifiers
misc_feature            1..168
                        note = 000LOTUS
misc_feature            1..168
                        note = Homolog Of Ceres SEEDLINE ID no. ME00572 at SEQ ID
                         NO. 111
source                  1..168
                        mol_type = other DNA
                        organism = Lotus japonicus
SEQUENCE: 156
ccttgtttcc ccctccggtc ttcttgacct tgtaagacct tttcttgacc ttgtaagacc  60
tcacgccgtg tctgttttct tcagtctttc cccgttaccg tccaactcat cctctccttc  120
cttgtctatc cctcctgagc tatttcaatt ttggccaagc atgccaca               168

SEQ ID NO: 157          moltype = AA  length = 165
FEATURE                 Location/Qualifiers
REGION                  1..165
                        note = misc_feature - Ceres Annot ID no. 8670388
REGION                  1..165
                        note = misc_feature - Truncated
REGION                  1..165
                        note = misc_feature - Bit score of 420.2 for hmm based on
                         sequences of FIGURE 4.
REGION                  1..165
                        note = misc_feature - Functional Homolog Of SEQ ID NO. 93
source                  1..165
                        mol_type = protein
                        organism = Sorghum bicolor
SEQUENCE: 157
MIDTMIPLMK HSPYGARIVN VSSRLGRANG RRNRIGDASL RDRLLKDDCL SEQLVDEMIT  60
KFLEQVKQGT WSSNEWPQMY TDYSISKLAV NVYTRLMARR LSDRPEGQKI YINCFCPGWV  120
NTAMTGWEGN ISAEEGADTG VWLALLPQEP PTNGKFFAER CEISF                  165

SEQ ID NO: 158          moltype = AA  length = 165
FEATURE                 Location/Qualifiers
REGION                  1..165
                        note = misc_feature - Public GI ID no. 194696386
REGION                  1..165
                        note = misc_feature - Truncated
REGION                  1..165
                        note = misc_feature - Bit score of 411.4 for hmm based on
```

```
                         sequences of FIGURE 4.
REGION                  1..165
                        note = misc_feature - Functional Homolog Of SEQ ID NO. 93
source                  1..165
                        mol_type = protein
                        organism = Zea mays
SEQUENCE: 158
MIDAMIPLMK RSAYGARIVN VSSRLGRANG RRNRIGDVSL RDRLLKDDCL SEQLIDEMIT  60
KFLEQAKQGT WSLNEWPQMY TDYSISKLAV NAYTRLMARR LSDRPEGQKI YINCFCPGWV  120
KTAMTGWEGN VSAEEGADTG IWLALLPQET DTNGKFFAER CEISF                165

SEQ ID NO: 159          moltype = AA  length = 163
FEATURE                 Location/Qualifiers
REGION                  1..163
                        note = misc_feature - Ceres Clone ID no. 1906273
REGION                  1..163
                        note = misc_feature - Truncated
REGION                  1..163
                        note = misc_feature - Bit score of 400.6 for hmm based on
                         sequences of FIGURE 4.
REGION                  1..163
                        note = misc_feature - Functional Homolog Of SEQ ID NO. 93
source                  1..163
                        mol_type = protein
                        organism = Panicum virgatum
SEQUENCE: 159
MLTEALLPLF RQSPATSRIL NISSQLGLLN KVSDSSLKAL LLDEETLTEA AIDAMVSRFL  60
AQVKDGTWGA QGWPKVWTDY SVSKLALNAY SRLLARRLQA RGARVSVNCF CPGFTRTDMT  120
RGWGKRTAEE VADVGARLAL LPPGELPTGA FFKWCTPQLY SKL                  163

SEQ ID NO: 160          moltype = AA  length = 161
FEATURE                 Location/Qualifiers
REGION                  1..161
                        note = misc_feature - Ceres Clone ID no. 100894176
REGION                  1..161
                        note = misc_feature - Truncated
REGION                  1..161
                        note = misc_feature - Bit score of 364.2 for hmm based on
                         sequences of FIGURE 4.
REGION                  1..161
                        note = misc_feature - Functional Homolog Of SEQ ID NO. 93
source                  1..161
                        mol_type = protein
                        organism = Zea mays
SEQUENCE: 160
MLTEALLPLF RQSSATSRIL NISSQLGLLN KVGDPSLKAL LLDEERLTEA GIEAMVSRFL  60
AQVKDGTWGE QGWPKVWTDY SVSKLALNAY SRLLARRLEA RGVSVNCFCP GFTRTDMTRG  120
WGKRTAGEAA DVGARLALLP PTELPTGTFF KWRTPQLYSK L                    161

SEQ ID NO: 161          moltype = AA  length = 164
FEATURE                 Location/Qualifiers
REGION                  1..164
                        note = misc_feature - Ceres Annot ID no. 8459736
REGION                  1..164
                        note = misc_feature - Truncated
REGION                  1..164
                        note = misc_feature - Bit score of 361.8 for hmm based on
                         sequences of FIGURE 4.
REGION                  1..164
                        note = misc_feature - Functional Homolog Of SEQ ID NO. 93
source                  1..164
                        mol_type = protein
                        organism = Solanum lycopersicum
SEQUENCE: 161
MIKALTPLMR PSPAGSRIVS VTSRLGRLNS KRNGISNVAV REQLENVDTL SEEVIDKTMH  60
TFLEQVKDGT WESAGWPHVF TDYSLSKLAV NAYTRLMARI FEERPEGEKI YINCYCPGWV  120
KTAMTGWAGH VTIEEAADTA VWLALLPDQF VSGKFFAERR EINF                 164

SEQ ID NO: 162          moltype = DNA  length = 975
FEATURE                 Location/Qualifiers
misc_feature            1..975
                        note = Ceres Annot ID no. 8670388
misc_feature            1..975
                        note = Encodes the peptide sequence at SEQ ID NO. 163
source                  1..975
                        mol_type = other DNA
                        organism = Sorghum bicolor
SEQUENCE: 162
atggggaaga aagggaagga ggcggcgcgg gagcggcgcg agcagcgccg ccgcgaggtc  60
```

-continued

```
accctcctcc gggctctccc ctacgagccc caccagcgat ggtgggaccg cctggcgccg  120
cgggccgtgg cggtggtcac gggcgccaac cgcgggatag gcttcgaggc cgcccgccag  180
ctcgcgctcc acggcctgca cgtcgtgctc gcctcccgcg acgccgccaa gggccaggac  240
gccgcgggga ggatcctggc ggaggctccc gatggcgcgg tcgtcagcgt ggagtcccgg  300
cagcttgacg tggcggacgc cgcgtccgtg gaggccttcg cggcctgggc ggtggaaacc  360
cacggcggca tccatgtcct tgttaacaat gcaggtgtaa acttcaacaa aggagcagat  420
aattctgttg agtttgctga gcaagttatc aagacaaatt actatggcac aaagcggatg  480
attgatacta tgataccact aatgaaacac tccccgtatg gtgctcggat agtgaatgtc  540
agctcaaggc ttggtagagc caatggcaga cggaatagaa ttggtgatgc gagtctaaga  600
gatcgtctgt tgaaagatga ttgtttatca gagcagctag ttgatgagat gatcacgaaa  660
tttctcgaac aagtcaagca aggtacttgg tcctccaatg agtggccaca gatgtacacg  720
gactattcga tctcaaagct tgctgttaat gtttatacac gactgatggc aaggaggctc  780
tcggatcgac ctgaaggcca aaagatatac attaactgtt tctgccctgg ctgggtaaat  840
actgccatga ctggttggga agggaatatt tctgccgaag aaggtgctga cacaggtgta  900
tggctcgcct tattacctca ggaaccaccc acaaatggga agttcttcgc tgagagatgt  960
gagataagct tctaa                                                   975

SEQ ID NO: 163         moltype = AA  length = 324
FEATURE                Location/Qualifiers
REGION                 1..324
                       note = misc_feature - Ceres Annot ID no. 8670388
REGION                 1..324
                       note = misc_feature - Bit score of 760.0 for hmm based on
                        sequences of FIGURE 3.
REGION                 42..195
                       note = misc_feature - Pfam Name: adh_short Pfam Desc: short
                        chain dehydrogenase
REGION                 1..324
                       note = misc_feature - Functional Homolog Of SEQ ID NO. 74
source                 1..324
                       mol_type = protein
                       organism = Sorghum bicolor
SEQUENCE: 163
MGKKGKEAAR ERREQRRREV TLLRALPYEP HQRWWDRLAP RAVAVVTGAN RGIGFEAARQ  60
LALHGLHVVL ASRDAAKGQD AAGRILAEAP DGAVVSVESR QLDVADAASV EAFAAWAVET  120
HGGIHVLVNN AGVNFNKGAD NSVEFAEQVI KTNYYGTKRM IDTMIPLMKH SPYGARIVNV  180
SSRLGRANGR RNRIGDASLR DRLLKDDCLS EQLVDEMITK FLEQVKQGTW SSNEWPQMYT  240
DYSISKLAVN VYTRLMARRL SDRPEGQKIY INCFCPGWVN TAMTGWEGNI SAEEGADTGV  300
WLALLPQEPP TNGKFFAERC EISF                                         324

SEQ ID NO: 164         moltype = AA  length = 313
FEATURE                Location/Qualifiers
REGION                 1..313
                       note = misc_feature - Public GI ID no. 147853829
REGION                 1..313
                       note = misc_feature - Bit score of 757.9 for hmm based on
                        sequences of FIGURE 3.
REGION                 37..185
                       note = misc_feature - Pfam Name: adh_short Pfam Desc: short
                        chain dehydrogenase
REGION                 1..313
                       note = misc_feature - Functional Homolog Of SEQ ID NO. 74
source                 1..313
                       mol_type = protein
                       organism = Vitis vinifera
SEQUENCE: 164
MGRKERAEER RKQRQQEISL FRTIPYSDHQ RWWNSETIAV VTGANRGIGF EIARQLCGHG  60
LTVILTSRDS AIGREAASVL QEGGFNAVSH QLDVLDPSSI EQFAEWVQQN YGFVDILINN  120
AGVNYNMGSE NSVENAENVI ATNYFGTKNV IKAMVPLMKP SASGARIVNV SSRLGRINGR  180
RNKIEDSALR GQLEDVDSLS EEVIDQMVHT FVEQVKDGTW TSAGWPQTFT DYSVSKLAVN  240
CYTRIMAKVL SDRPEGEKIF INCYCPGWVK TAMTGWAGNV SVEEGADTGV WLALLPDQSV  300
TGKIFAERRE VHF                                                     313

SEQ ID NO: 165         moltype = AA  length = 324
FEATURE                Location/Qualifiers
REGION                 1..324
                       note = misc_feature - Public GI ID no. 194696386
REGION                 1..324
                       note = misc_feature - Bit score of 755.3 for hmm based on
                        sequences of FIGURE 3.
REGION                 42..195
                       note = misc_feature - Pfam Name: adh_short Pfam Desc: short
                        chain dehydrogenase
REGION                 1..324
                       note = misc_feature - Functional Homolog Of SEQ ID NO. 74
source                 1..324
                       mol_type = protein
                       organism = Zea mays
SEQUENCE: 165
```

```
MGKKGKEAAR ERREQRRREV ALLRSLPYEP HQRWWDRLAP RAVAVVTGAN RGIGFEAARQ  60
LALHGLHVVL ACRDAAKGQD AAERILAEAP DDTVVSVESR KLDVADAASV EAFAAWAVET  120
YGGIHVLVNN AGVNFNKGAD NSVEFAEQVI ETNYYGTKRM IDAMIPLMKR SAYGARIVNV  180
SSRLGRANGR RNRIGDVSLR DRLLKDDCLS EQLIDEMITK FLEQAKQGTW SLNEWPQMYT  240
DYSISKLAVN AYTRLMARRL SDRPEGQKIY INCFCPGWVK TAMTGWEGNV SAEEGADTGI  300
WLALLPQETD TNGKFFAERC EISF                                         324

SEQ ID NO: 166          moltype = DNA  length = 942
FEATURE                 Location/Qualifiers
misc_feature            1..942
                        note = Ceres Annot ID no. 8459736
misc_feature            1..942
                        note = Encodes the peptide sequence at SEQ ID NO. 167
source                  1..942
                        mol_type = other DNA
                        organism = Solanum lycopersicum
SEQUENCE: 166
atggataaaa aggaaagggc aaaggaaaaa aaggagaaaa gacgccagga gatctccctt  60
ctacgtacta ttccctattc tgatcaccaa agatggtggt catctgaaac aattgcggtt  120
gttacgggcg caaatagagg cattggattt gaaattgctc atcagcttgc atcacatggc  180
gttactgttg ttctcacgtc gcgagagaca gctgttggag aagaagcagt gaaagtcttt  240
caggaaggag gtctaaatgt ggcatttcat caattggata ttgtggatcc tgtatcaatt  300
caaacatttt gtgattggat taaagaaaca tatggtggcc tagatatact gatcaacaat  360
gcaggagtca atttcaattg cggaaaagat aattctgttg aattttctga aatggtaatc  420
caagttaact attttggcac caaaaacatg atcaaagcac ttactccgtt gatgaggcct  480
tcccctgctg gctctcgtat tgttagtgtc acctcgcgat tgggtagact taatagcaaa  540
cgaaatggaa tttcaaatgt agcagtgaga gaacaattag aaaacgtgga tacgctatct  600
gaggaagtta tcgataaaac tatgcacaca tttttggagc aagtaaaaga tggaacttgg  660
gaatcagcag gatggcctca tgtgttcaca gactactcat tgtcaaagct agcagttaat  720
gcctacacaa ggttaatggc aaggatattc gaggaacgac cagaaggtga aaaaatatac  780
ataaattgtt attgtccggg atgggtgaaa actgctatga ctggctgggc agggcatgtt  840
actattgaag aagctgctga tactgctgta tggcttgctt tgctccctga tcaatttgtg  900
agtggtaagt tcttcgctga gaggcgcgaa attaactttt aa                     942

SEQ ID NO: 167          moltype = AA  length = 313
FEATURE                 Location/Qualifiers
REGION                  1..313
                        note = misc_feature - Ceres Annot ID no. 8459736
REGION                  1..313
                        note = misc_feature - Bit score of 744.3 for hmm based on
                         sequences of FIGURE 3.
REGION                  37..193
                        note = misc_feature - Pfam Name: adh_short Pfam Desc: short
                         chain dehydrogenase
REGION                  1..313
                        note = misc_feature - Functional Homolog Of SEQ ID NO. 74
source                  1..313
                        mol_type = protein
                        organism = Solanum lycopersicum
SEQUENCE: 167
MDKKERAKEK KEKRRQEISL LRTIPYSDHQ RWWSSETIAV VTGANRGIGF EIAHQLASHG  60
VTVVLTSRET AVGEEAVKVF QEGGLNVAFH QLDIVDPVSI QTFCDWIKET YGGLDILINN  120
AGVNFNCGKD NSVEFSEMVI QVNYFGTKNM IKALTPLMRP SPAGSRIVSV TSRLGRLNSK  180
RNGISNVAVR EQLENVDTLS EEVIDKTMHT FLEQVKDGTW ESAGWPHVFT DYSLSKLAVN  240
AYTRLMARIF EERPEGEKIY INCYCPGWVK TAMTGWAGHV TIEEAADTAV WLALLPDQFV  300
SGKFFAERRE INF                                                     313

SEQ ID NO: 168          moltype = DNA  length = 1198
FEATURE                 Location/Qualifiers
misc_feature            1..1198
                        note = Ceres Clone ID no. 1906273
misc_feature            1..1198
                        note = Encodes the peptide sequence at SEQ ID NO. 169
source                  1..1198
                        mol_type = other DNA
                        organism = Panicum virgatum
SEQUENCE: 168
agtcagccac cccccgcgct ccccgctcgt ctccagctcg atggactatt cgagcaccaa  60
ggagttgcct ccggccgggg cctggtggtc gagggagacg gtggccgtgg tgacgggcgc  120
gaaccggggc atcgggcacg ccctcgccgc gcgcctggcc gagcacgggc tcaccgtggt  180
gctcaccgca cgggacggcg cgcgcgggga ggccgccgcg gccccgctcc gcgcgcgcgg  240
gctcgccgtc gccttccgca ggctcgacgt ctccgacgcc gcctccgtcg ccgagttcgc  300
cgcctggctc cgcgacgccg tcggcggcct cgacatcctg gtgaacaacg cggccgtgtc  360
cttcaacgag atcgacacca actcggtgga gcacgccgag acagtcctca ggaccaactt  420
ccacggcgcc aagatgctca cggaagcgct gctgccgctg ttccggcagt ccccggccac  480
cagcaggatc ctcaacatca gctcgcagct tggccttctc aacaaggtga gcgactcgtc  540
cctgaaggcg ctgctcctgg acgaggagac cctgacggag gcggcgatcg acgccatggt  600
gtcgcggttc ctggcgcagg tgaaggacgg gacgtggggc gctcagggct ggcccaaggt  660
gtggacggac tactcggtct ccaagctggc cctgaacgcc tactcccggc tgctggcgcg  720
```

```
gcggctgcag gcgcgcggcg cccgcgtgag cgtcaactgc ttctgccccg ggttcacgcg  780
caccgacatg accaggggct gggggaagcg caccgccgag gaggtggccg acgtcggcgc  840
gcggctcgcg ctgctgccgc ccggcgagct ccccacgggg gccttcttca agtggtgcac  900
gccgcagctc tactccaagc tgtgacctgc cgggagctag ccacgccgcc ggccggcgcg  960
ccccggccat ggcggcagtg ggagtatatg tatgtagcgt tggtttagct gctcctagtg  1020
acttgactcc ccatgcaaac aagaagtcga tcgagtagtt agtgcctctg gcagtctggc  1080
tttctgccaa ggtgctatgg ttgaagcaat gcaacctaac catgtcagca atcaatgtac  1140
tatgcctagt tagccgtgta agatttaaag ttaacttctg aacatgggaa gaatcatg    1198

SEQ ID NO: 169         moltype = AA  length = 294
FEATURE                Location/Qualifiers
REGION                 1..294
                       note = misc_feature - Ceres Clone ID no. 1906273
REGION                 1..294
                       note = misc_feature - Bit score of 656.4 for hmm based on
                        sequences of FIGURE 3.
REGION                 20..173
                       note = misc_feature - Pfam Name: adh_short Pfam Desc: short
                        chain dehydrogenase
REGION                 1..294
                       note = misc_feature - Functional Homolog Of SEQ ID NO. 74
source                 1..294
                       mol_type = protein
                       organism = Panicum virgatum
SEQUENCE: 169
MDYSSTKELP PAGAWWSRET VAVVTGANRG IGHALAARLA EHGLTVVLTA RDGARGEAAA  60
APLRARGLAV AFRRLDVSDA ASVAEFAAWL RDAVGGLDIL VNNAAVSFNE IDTNSVEHAE  120
TVLRTNFHGA KMLTEALLPL FRQSPATSRI LNISSQLGLL NKVSDSSLKA LLLDEETLTE  180
AAIDAMVSRF LAQVKDGTWG AQGWPKVWTD YSVSKLALNA YSRLLARRLQ ARGARVSVNC  240
FCPGFTRTDM TRGWGKRTAE EVADVGARLA LLPPGELPTG AFFKWCTPQL YSKL        294

SEQ ID NO: 170         moltype = AA  length = 319
FEATURE                Location/Qualifiers
REGION                 1..319
                       note = misc_feature - Public GI ID no. 198285679
REGION                 1..319
                       note = misc_feature - Bit score of 219.9 for hmm based on
                        sequences of FIGURE 2.
REGION                 252..296
                       note = misc_feature - Pfam Name: CCT Pfam Desc: CCT motif
REGION                 1..46
                       note = misc_feature - Pfam Name: zf-B_box Pfam Desc: B-box
                        zinc finger
REGION                 1..319
                       note = misc_feature - Functional Homolog Of SEQ ID NO. 20
source                 1..319
                       mol_type = protein
                       organism = Olea europaea
SEQUENCE: 170
MWVCEACERA PAAFLCKADA ASLCITCDSD IHSAQPLARR HQRVPILPIP GMLCGTPSAP  60
YPSGLVMGPT GVAAKIEFLT QDEDQTIHEE EDEDEAASWP LFNHVKNICN QSNNIGRFFG  120
GEVDEYLDLD EYNSYQDNQF SNQDNNQLQP YDVSQKSYGS DNVVPIQYGK SKDQIHNHGF  180
QLGREYEASK NVYDNPASIS HTVSFSSLDV GVVPESTTSE VSVPHPRPPK GTIDLFSSPP  240
IPMPTQLSPM DREARVLRYR EKKKARKFEK TIRYASRKAY AETRPRIKGR FAKRTDVRAN  300
QMFSSTLIEE GGYGIVPSF                                               319

SEQ ID NO: 171         moltype = DNA  length = 982
FEATURE                Location/Qualifiers
misc_feature           1..982
                       note = Ceres Clone ID no. 7088
misc_feature           1..982
                       note = Encodes the peptide sequence at SEQ ID NO. 172
source                 1..982
                       mol_type = other DNA
                       organism = Arabidopsis thaliana
SEQUENCE: 171
atagagagaa gaaaaagaag aggtttagag agagaaaaat ggcgtcaaag ctctgcgatt  60
cgtgcaaatc agcgacggcg gcgttatact gccgaccaga cgcagcgttt ctatgcttaa  120
gctgcgattc aaaagtccac gcggcgaaca aactcgcgtc acgacacgcg cgcgtgtgga  180
tgtgtgaagt gtgcgagcaa gcaccggcac acgtcacgtg caaagcagac gcggccgcgt  240
tatgcgtcac gtgcgaccgt gatatccact cggctaatcc gttagctcgc cgtcacgaac  300
gcgttcccgt tactccgttt tacgattccg tctctagtga cggttccgtt aaacacaccg  360
ccgttaattt ccttgacgac tgttacttct ccgatataga tggtaacgga agccgtgaag  420
aagaggagga agaagctgct tcgtggctgt tacttcccaa tccaaagact acaacgacgg  480
cgacggcggg gatcgttgct gttacttcag ctgaggaagt tccgggagat agtccggaga  540
tgaacactgg tcaacagtat ttgttctcgg atccggatcc gtatctggat ctggattatg  600
gaaatgttga tccgaaggtg gaatcgttag agcagaatag ctccggtact gatggtgttg  660
ttccggtgga gaatcggacg gttagaatcc cgacggtgaa cgagaattgc tttgaaatgg  720
attttaccgg aggatctaaa ggctttgctt atggaggtgg ttacaattgc atcagtcaca  780
```

```
gcgtgtcatc atcgtcgatg gaagtgggag tggtgccaga tggtggttcg gtggctgatg  840
tatcgtatcc ttacggtggt cctgcaacca gtggagctga tccggggaca cagcgggctg  900
ttccgctgac ttcagctgag agagaagcga gggtaatgag gtacagagag aagaggaaga  960
acaggaagtt tgagaagact at                                           982

SEQ ID NO: 172          moltype = AA  length = 314
FEATURE                 Location/Qualifiers
REGION                  1..314
                        note = misc_feature - Ceres Clone ID no. 7088
REGION                  1..314
                        note = misc_feature - Bit score of 334.7 for hmm based on
                         sequences of FIGURE 2.
REGION                  1..48
                        note = misc_feature - Pfam Name: zf-B_box Pfam Desc: B-box
                         zinc finger
REGION                  295..314
                        note = misc_feature - Pfam Name: CCT Pfam Desc: CCT motif
REGION                  1..314
                        note = misc_feature - Functional Homolog Of SEQ ID NO. 20
source                  1..314
                        mol_type = protein
                        organism = Arabidopsis thaliana
SEQUENCE: 172
MASKLCDSCK SATAALYCRP DAAFLCLSCD SKVHAANKLA SRHARVWMCE VCEQAPAHVT  60
CKADAAALCV TCDRDIHSAN PLARRHERVP VTPFYDSVSS DGSVKHTAVN FLDDCYFSDI  120
DGNGSREEEE EEAASWLLLP NPKTTTTATA GIVAVTSAEE VPGDSPEMNT GQQYLFSDPD  180
PYLDLDYGNV DPKVESLEQN SSGTDGVVPV ENRTVRIPTV NENCFEMDFT GGSKGFAYGG  240
GYNCISHSVS SSSMEVGVVP DGGSVADVSY PYGGPATSGA DPGTQRAVPL TSAEREARVM  300
RYREKRKNRK FEKT                                                    314

SEQ ID NO: 173          moltype = AA  length = 350
FEATURE                 Location/Qualifiers
REGION                  1..350
                        note = misc_feature - Public GI ID no. 118489345
REGION                  1..350
                        note = misc_feature - Bit score of 491.6 for hmm based on
                         sequences of FIGURE 2.
REGION                  1..48
                        note = misc_feature - Pfam Name: zf-B_box Pfam Desc: B-box
                         zinc finger
REGION                  287..331
                        note = misc_feature - Pfam Name: CCT Pfam Desc: CCT motif
REGION                  1..350
                        note = misc_feature - Functional Homolog Of SEQ ID NO. 20
source                  1..350
                        mol_type = protein
                        organism = Populus x generosa
SEQUENCE: 173
MASKLCDSCK SATATLFCRA DSAFLCISCD SKIHAANKLA SRHARVSVCE VCEQAPAHFT  60
CKADAAALCV TCDRDIHSAN PLASRHERVP ITPFFDSSST VHGGGAAVNL LEDRYFDEVD  120
GGRGDVSREE AEAESWLLPN PGGGTAKGVD SMDLNTGQYV FGSEMDPYLD LDPYVDPKVE  180
VQEQNSSGTT DGVVPVQSNK LGFQAPALVN DNCCYELDFS TGSKSFGGGY GYNSLSHSVS  240
SSSLDVGVVP DGSGSTLTDI SNPYCSRSVS NGMESANQTV QLSAVDREAR VLRYREKRKN  300
RKFEKTIRYA SRKAYAETRP RIKGRFAKRT DTEVEVDRSS LYGFGVVPSF             350

SEQ ID NO: 174          moltype = DNA  length = 1549
FEATURE                 Location/Qualifiers
misc_feature            1..1549
                        note = Ceres Clone ID no. 1769510
misc_feature            1..1549
                        note = Encodes the peptide sequence at SEQ ID NO. 175
source                  1..1549
                        mol_type = other DNA
                        organism = Panicum virgatum
SEQUENCE: 174
ctccctccac tacgccgcgc gcgctccctc ccacccctcc cctccaccac cacaagcacc  60
gcgtcgacac cacctgccat cgccgcgccg agctcagcct ctagctagct gcgccaggag  120
ggcgcccgcc tcgctccctc cctgccgacg ccagtgcgat ggagctgcat aagtactggg  180
gcgtgggggg ccggcggtgc ggcgactgcg aggcggcccc ggcggcggtg cactgccgct  240
cgtgccccgc caccgccggg ggcgcgttcc tctgcgctgc gtgcgacgcg cgcccggggc  300
acgcgcggct gggccacgag cgcgtgtgga tgtgcgaggt ctgcgagctg gcccccgccg  360
ccgtcacctg caaggccgac gccgccgtgc tctgcgccgc ctgcgacgcc gacatccacg  420
acgccaaccc gctggcgcgc cgccatgcgc gcgtccccgt cgcgcccatc gggtccgagg  480
ccgccgcctc cgccgtcgag gccatgctgt tcgggaccgg cgacggcgac ccggccgcgc  540
ccgaggccga ggagccgcag gacgcggcgg ccgggcacgg gcacgggcag ctccagcacc  600
accaccagca cgcgctgaac ctcaacgtgg aggccaagga catgaagctg gactacctct  660
tctccgacct ggacccctac ctcagcgtcg acatcccgcg cttccagcac gccgacagcg  720
tcgtccccag cggcgtcggc gccggagccg ccgccggcgc cgtcgagctg gacttcacgt  780
gcggcatcgg cgtcaagccc tcctcgtaca gctcctacac ggcaacatcc ttcgcccaca  840
```

-continued

```
gcggctcctc ctctgaggtc ggcgtggtgc cggaggcctt ctgcggcggc ggcgccggga  900
ccttcgagct cgacttcacc cggcccaagc ctcaagccta catgccgtac accgcgactc  960
ctcagagcca cagcgtgtcg tcggtggacg tggaggtggc ggcggcggag cggggggaca  1020
tggcggcggc gaggccggtg ccgctggtgg gggagagccg ggaggcgcgg ctgatgcgct  1080
accgggagaa gcggaagaac cggcggttcg agaagaccat ccggtacgcg tcccggaagg  1140
cctacgccga gacgcggccg cggatcaagg gccggttcgc caagcgcgcc gaccacgacg  1200
ccgacgacgc cgaggccgag gccgccgtgc cgtcgccggc gtcgtacgtg ctcgacttcg  1260
gctacggcgt cgtgcccagc ttctgatcga tcgacgacgg tccggcgggc ggcggcgcgc  1320
ctgacccggc actggcgcgc gcgccttgtg tacttgtatc gatgcatgat gtatagggga  1380
ggaatagtaa atcccatgta ctactctctt tttggagctg tgctagcctt gcgcacgcta  1440
gtgatgtata atttgtatac tacgcgctgc tacttactac tagcatgttc ttgctggaat  1500
tagccccggc tatttttgaa tcaaatctat gcaagaaatt tgtaacggt             1549

SEQ ID NO: 175         moltype = AA  length = 375
FEATURE                Location/Qualifiers
REGION                 1..375
                       note = misc_feature - Ceres Clone ID no. 1769510
REGION                 1..375
                       note = misc_feature - Bit score of 695.5 for hmm based on
                        sequences of FIGURE 2.
REGION                 301..345
                       note = misc_feature - Pfam Name: CCT Pfam Desc: CCT motif
REGION                 54..101
                       note = misc_feature - Pfam Name: zf-B_box Pfam Desc: B-box
                        zinc finger
REGION                 1..375
                       note = misc_feature - Functional Homolog Of SEQ ID NO. 20
source                 1..375
                       mol_type = protein
                       organism = Panicum virgatum
SEQUENCE: 175
MELHKYWGVG GRRCGDCEAA PAAVHCRSCP ATAGGAFLCA ACDARPGHAR LGHERVWMCE  60
VCELAPAAVT CKADAAVLCA ACDADIHDAN PLARRHARVP VAPIGSEAAA SAVEAMLFGT  120
GDGDPAAPEA EEPQDAAAGH GHGQLQHHHQ HALNLNVEAK DMKLDYLFSD LDPYLSVDIP  180
RFQHADSVVP SGVGAGAAAG AVELDFTCGI GVKPSSYSSY TATSFAHSGS SSEVGVVPEA  240
FCGGGAGTFE LDFTRPKPQA YMPYTATPQS HSVSSVDVEV AAAERGDMAA ARPVPLVGES  300
REARLMRYRE KRKNRRFEKT IRYASRKAYA ETRPRIKGRF AKRADHDADD AEAEAAVPSP  360
ASYVLDFGYG VVPSF                                                   375

SEQ ID NO: 176         moltype = AA  length = 336
FEATURE                Location/Qualifiers
REGION                 1..336
                       note = misc_feature - Public GI ID no. 170779038
REGION                 1..336
                       note = misc_feature - Bit score of 411.9 for hmm based on
                        sequences of FIGURE 2.
REGION                 13..60
                       note = misc_feature - Pfam Name: zf-B_box Pfam Desc: B-box
                        zinc finger
REGION                 267..311
                       note = misc_feature - Pfam Name: CCT Pfam Desc: CCT motif
REGION                 1..336
                       note = misc_feature - Functional Homolog Of SEQ ID NO. 20
source                 1..336
                       mol_type = protein
                       organism = Chenopodium rubrum
SEQUENCE: 176
MMKKEVPGGD NNSWARVCDT CRSAPCTVYC KEDSAFLCTS CDARIHAVNQ VASRHERVWV  60
CEACEREPAA FLCKADAASL CATCDADIHS ANPLARRHHR VPIMPVGCVY GPSDGRMSEE  120
GFLDLPDGDD QTTDHEGDED EAASWLLLNP GADNQFCEQY SQQQEFSVPE KNCGGDSVVP  180
VQCREVKDHQ IQYQKFLFGM ECETKSEYNY NTSISHSVSV SSLDVGVVPE STMSDMSVSH  240
SRPPKGTIDL FSSPPMQVPT QLSPLDREAR VMRYREKKKN RKFEKTIRYA SRKAYAETRP  300
RIKGRFAKRT DVEAEMDQMF TNSLMSDGGY GIVPSF                            336

SEQ ID NO: 177         moltype = DNA  length = 1357
FEATURE                Location/Qualifiers
misc_feature           1..1357
                       note = Ceres Clone ID no. 1996408
misc_feature           1..1357
                       note = Encodes the peptide sequence at SEQ ID NO. 178
source                 1..1357
                       mol_type = other DNA
                       organism = Panicum virgatum
SEQUENCE: 177
aaaaacaccc ccgaggccaa ccatttccga cgcaaaaccc cccggaatcc gtgacacccg  60
cccggaggag agcagagcag aggcaccagg catggacgcc gcggtggagc tggagctgga  120
gcagaagccg gcggtggggt actggggctt ggccggcgcg cggccctgcg acgcgtgcgc  180
cgcggaggcg gcgcggctgc actgccgcgc ggacggcgcc ttcctgtgcc ccgggtgcga  240
cgcccgcgcg cacggcgccg ggtcgcgcca cgcgcgcgtc tgtctctgcg aggtctgcga  300
```

```
gcacgccccc gccgccgtca cgtgccgcgc cgacgccgcc gcgctctgcg cggcctgcga  360
cgccgacatc cactcggcca acccgctcgc gcgccgccac gagcggctcc ccgtcgcgcc  420
cttcttcggc gcgctcgccg acgcgccgca gccgttcccg tcctcagcct tcgccgccgc  480
gggggtccag gcccaggggg acgcggctgc ggacgacgac gggagcaacg aggccgaggc  540
cgcctcgtgg ctcctccccg agcccgacaa ctgccacgag gacagcgccg ccgccaccga  600
cgccttcttc gctgactccg acgcgtacct cggcgtcgac ctcgacttcg cccggtccat  660
ggacggcatc aaggccatcg gcgtgccggt cgcgccgccc gagctggaca tggccaccgg  720
cggttactac taccccgaac actccatgaa ccacagcgtg tcgtcgtcgg aggtggcggt  780
tgtgccggac gcgctggcgg gcggcgcccc ggccgcgccg gcggtgccgg cggcgagccg  840
ggggaaggag cgggaggcgc ggctgatgcg gtaccgcgag aagcgcaaga accggcggtt  900
cgacaagacc atccggtacg cgtcccgcaa ggcgtacgcc gagacgcggc cgcgcatcaa  960
gggccgcttc gccaagcgct gctcctccgc ggaggccgag gccgaggacg aggcgctgct  1020
ggagcacgag gaagcggcgt gcttctcgcc cgcggcgtcg gcgcccgcgg cctcctcgga  1080
cggcgtcgtc ccgtcctgct gaggggacac gacgggcggc ggccgcgcct cctcctccca  1140
ggctccccgg cggcgacccc ttaattttgc cgactctgaa tcgatcccaa cgcatgcgaa  1200
catgcgatgc gatgcgcgct ccgtgcagca catgaataat tgtacagtag ttccacgaac  1260
tcgatcgtgg tcgcacggaa tcgcatgtaa tcctcctcac cgtccttgta atccagcctt  1320
gtacattacc gtctagaggt gtttgtgctt ctctcgc                          1357

SEQ ID NO: 178          moltype = AA  length = 336
FEATURE                 Location/Qualifiers
REGION                  1..336
                        note = misc_feature - Ceres Clone ID no. 1996408
REGION                  1..336
                        note = misc_feature - Bit score of 649.8 for hmm based on
                         sequences of FIGURE 2.
REGION                  254..298
                        note = misc_feature - Pfam Name: CCT Pfam Desc: CCT motif
REGION                  21..65
                        note = misc_feature - Pfam Name: zf-B_box Pfam Desc: B-box
                         zinc finger
REGION                  1..336
                        note = misc_feature - Functional Homolog Of SEQ ID NO. 20
source                  1..336
                        mol_type = protein
                        organism = Panicum virgatum
SEQUENCE: 178
MDAAVELELE QKPAVGYWGL AGARPCDACA AEAARLHCRA DGAFLCPGCD ARAHGAGSRH  60
ARVCLCEVCE HAPAAVTCRA DAAALCAACD ADIHSANPLA RRHERLPVAP FFGALADAPQ  120
PFPSSAFAAA GVQAQGDAAA DDDGSNEAEA ASWLLPEPDN CHEDSAAATD AFFADSDAYL  180
GVDLDFARSM DGIKAIGVPV APPELDMATG GYYYPEHSMN HSVSSSEVAV VPDALAGGAP  240
AAPAVPAASR GKEREARLMR YREKRKNRRF DKTIRYASRK AYAETRPRIK GRFAKRCSSA  300
EAEAEDEALL EHEEAACFSP AASAPAASSD GVVPSC                            336

SEQ ID NO: 179          moltype = DNA  length = 990
FEATURE                 Location/Qualifiers
misc_feature            1..990
                        note = Ceres Annot ID no. 8701721
misc_feature            1..990
                        note = Encodes the peptide sequence at SEQ ID NO. 180
source                  1..990
                        mol_type = other DNA
                        organism = Sorghum bicolor
SEQUENCE: 179
atggagggcg acgagaagtc ggcgggcggg gccccggcgt actggggcct gggcgcgcgg  60
ccctgcgacg cgtgcggcgc cgatgcggcg cgcctctact gccgcgcgga ctcggcgttc  120
ctgtgcgccg ggtgcgacgc gcgggcgcac ggggccgggt cgcccaacgc gcgggtctgg  180
ctctgcgagg tctgcgagca cgcgccggcg gcggtcacgt gccgcgccga cgccgccgcg  240
ctctgcgcct cctgcgacgc cgacatccac tcggccaacc cgctggcgcg acgccacgag  300
cgcctccccg tggcgccctt cttcggcgcg ctggccgacg cgcccaagcc cttcgcctcg  360
tcggcggcgg ccgtgccgcc caaagcgacg gccggggccg acgacgacgg gagcagcgag  420
gccgaggcgg cgtcgtggct cctccccgag cccgaccacg ggcacaaaga agaaggcgcc  480
accacggagg tgttcttcgc ggactccgac ccgtacctcg acctcgactt cgcgcgttcc  540
atggacgaca tcaagaccat cggcgtccag ggcgggccac cagagctcga cctcaacggc  600
gccaagctct tctactccga ccactccatg aaccacagtg tgtcatcgtc ggaggcagcg  660
gtggtgcccg acgcggcggc tggcgcggcg cccgtggtgg cagtggtcag caggggcctg  720
gagcgggagg cgcggctgat gcggtaccgg gagaagcgca agagcaggcg gttcgagaag  780
acgatccggt acgcgtcccg caaggcgtac gcggagacgc ggccgcgcat caagggccgg  840
ttcgccaagc gcacgccggg ggctggggag gacccgctgg aggagcacga ggagatgtac  900
tcctcggccg cggcggccgt ggctgcgctc atggccccccg gcggagccga cgcggactac  960
ggcgtcgacg gcgtcgtgcc cacatattga                                   990

SEQ ID NO: 180          moltype = AA  length = 329
FEATURE                 Location/Qualifiers
REGION                  1..329
                        note = misc_feature - Ceres Annot ID no. 8701721
REGION                  1..329
                        note = misc_feature - Bit score of 640.1 for hmm based on
                         sequences of FIGURE 2.
```

```
REGION                  242..286
                        note = misc_feature - Pfam Name: CCT Pfam Desc: CCT motif
REGION                  57..104
                        note = misc_feature - Pfam Name: zf-B_box Pfam Desc: B-box
                         zinc finger
REGION                  1..329
                        note = misc_feature - Functional Homolog Of SEQ ID NO. 20
source                  1..329
                        mol_type = protein
                        organism = Sorghum bicolor
SEQUENCE: 180
MEGDEKSAGG APAYWGLGAR PCDACGADAA RLYCRADSAF LCAGCDARAH GAGSPNARVW  60
LCEVCEHAPA AVTCRADAAA LCASCDADIH SANPLARRHE RLPVAPFFGA LADAPKPFAS  120
SAAAVPPKAT AGADDDGSSE AEAASWLLPE PDHGHKEEGA TTEVFFADSD PYLDLDFARS  180
MDDIKTIGVQ GGPPELDLNG AKLFYSDHSM NHSVSSSEAA VVPDAAAGAA PVVAVVSRGL  240
EREARLMRYR EKRKSRRFEK TIRYASRKAY AETRPRIKGR FAKRTPGAGE DPLEEHEEMY  300
SSAAAAVAAL MAPGGADADY GVDGVVPTY                                  329

SEQ ID NO: 181          moltype = AA  length = 343
FEATURE                 Location/Qualifiers
REGION                  1..343
                        note = misc_feature - Public GI ID no. 197726026
REGION                  1..343
                        note = misc_feature - Bit score of 521.0 for hmm based on
                         sequences of FIGURE 2.
REGION                  1..48
                        note = misc_feature - Pfam Name: zf-B_box Pfam Desc: B-box
                         zinc finger
REGION                  282..326
                        note = misc_feature - Pfam Name: CCT Pfam Desc: CCT motif
REGION                  1..343
                        note = misc_feature - Functional Homolog Of SEQ ID NO. 20
source                  1..343
                        mol_type = protein
                        organism = Prunus persica
SEQUENCE: 181
MASKLCDSCK SATATLFCRA DSAFLCVNCD SKIHAANKLA SRHARVWLCE VCEQAPAHVT  60
CKADDAALCV TCDRDIHSAN PLSRRHERVP VTPFYDSGNS AANSAPVVKS VVNFLDDRYF  120
SDVDGQDAET EVSREEAEAA SWLLPNPKAM ENPDLNSGEY FLPEMDPYLD LDYGHVDPKL  180
EDAQEQNSCG TDGVVPVQSK SVQPQLVNDH SFEIDFSAAS KPYVYGFHAQ CLSQSVSSSS  240
MDVSVVPDGN TTMTDVCDPY TKSMSAAVES THQAVQISSA DREARVLRYR EKRKNRKFEK  300
TIRYASRKAY AETRPRIKGR FAKRTEVEIE AERLCRYGVV PSF                  343

SEQ ID NO: 182          moltype = AA  length = 343
FEATURE                 Location/Qualifiers
REGION                  1..343
                        note = misc_feature - Public GI ID no. 194244824
REGION                  1..343
                        note = misc_feature - Bit score of 289.3 for hmm based on
                         sequences of FIGURE 2.
REGION                  7..54
                        note = misc_feature - Pfam Name: zf-B_box Pfam Desc: B-box
                         zinc finger
REGION                  281..325
                        note = misc_feature - Pfam Name: CCT Pfam Desc: CCT motif
REGION                  1..343
                        note = misc_feature - Functional Homolog Of SEQ ID NO. 20
source                  1..343
                        mol_type = protein
                        organism = Brassica nigra
SEQUENCE: 182
MLKQESNWAQ ACDTCRSAAC TVYCRADSAY LCTSCDAQIH AANRLASRHE RVRVCESCER  60
APAAFFCKAD AASLCTACDS QIHSANPLAR RHQRVPILPI SGCVATNHHS SETTEPENIV  120
VVGQEEEDEA EAASWLLPSS VKNCGDNNNN NSENNRFSVG EEYLDLVDYS SSMDKRFTGQ  180
ANQYQQDYNV PQRSYVADGV VPLQVGVSKG HMHHEQHNFQ FGFTNVSSEA HQISNGSPIH  240
MVSLVPESVT SDATVSHQRS PKSGTEELPE APVQMLSPME RKARVLRYRE KKKTRKFEKR  300
IRYASRKEYA EKRPRIKGRF AKRNEVDADQ AFPTVVMFDT GYG                  343

SEQ ID NO: 183          moltype = AA  length = 398
FEATURE                 Location/Qualifiers
REGION                  1..398
                        note = misc_feature - Public GI ID no. 158866355
REGION                  1..398
                        note = misc_feature - Bit score of 329.2 for hmm based on
                         sequences of FIGURE 2.
REGION                  327..371
                        note = misc_feature - Pfam Name: CCT Pfam Desc: CCT motif
REGION                  27..74
                        note = misc_feature - Pfam Name: zf-B_box Pfam Desc: B-box
```

```
                         zinc finger
REGION                  1..398
                        note = misc_feature - Functional Homolog Of SEQ ID NO. 20
source                  1..398
                        mol_type = protein
                        organism = Zea mays
SEQUENCE: 183
MDYNFDTSVL DEDVAGRGGR EGSCPPAWAR ACDGCRAAPS VVYCHADTAY LCASCDSRVH  60
AANRVASRHE RVRVCEACEC APAVLACRAD AAALCAACDA QVHSANPLAG RHQRVPVLPL  120
PAAAVPAASV LAEAAATAAA VAGDKDEEVD SWLLLTKDPD DDDKNHNCSS NNNNNNNISS  180
NTSTFYADVD EYFDLVGYSS YCDNHINSNT KQYGMQEQQL LLHKEFGDKE GSEYVVPSQV  240
GQQQSGYHRV IGTEQAASMT PGVSAYTDSI SNSISFSSSM EVGIVPDNMA TTDMPSSGIL  300
LTPAGAISLF SSGPPLQMPL HLASMDREAR VLRYREKKKS RKFEKTIRYA TRKTYAEARP  360
RIKGRFAKRS SDMDVEVDQM FSAAALSSDG SYGTVPWF                          398

SEQ ID NO: 184          moltype = DNA  length = 1320
FEATURE                 Location/Qualifiers
misc_feature            1..1320
                        note = Ceres Clone ID no. 472076
misc_feature            1..1320
                        note = Encodes the peptide sequence at SEQ ID NO. 185
source                  1..1320
                        mol_type = other DNA
                        organism = Glycine max
SEQUENCE: 184
tcttcactct cagaacacta actcccccaa tgttggaggg ccaagcaaca acgcccacgt  60
ggccgcgcat gtgcgacacg tgccgctccg tcccctccac cgtcttctgc cgctccccaca  120
ccgcctttct ctgcgccacg tgcgacactc gcctccacgt ctcgctcacg tggcacgagc  180
gcgtgtgggt gtgcgaggcg tgcgagcgcg ccccggcggc gttcctctgc aaggccgacg  240
ccgcctccct ctgcgcctcc tgcgacgccg acatccacgc cgccaacccc ctcgccagcc  300
gccaccaccg cgtccccatc ctccccatcg ccgccgccaa caacaacaac aacgacgacg  360
acgacgttgc tgacgttgac gacgaagacg aaaccgcttc atggctcttg ctcaacccta  420
tcaagagtgc tactgtccct aacaccaata acaataacaa taataacggg ttcttgtata  480
acggtgaggt tgatgagtat ttggaccttg ttgataattg taactcttgt ggtgataata  540
atcacttcgc ttcagctgct gctactactg atcattacgc tcagcaccaa catttcgctg  600
gtgtttctca gaagagttat gctggggaca gtgttgttcc ggttcagcaa caccagcatt  660
ttcagcttgg gttggacttt gacaactcca aacctgcctt cagttacaat ggttctgtta  720
gtcaaagtgt ttcagtttca tcaatggata ttggtgttgt acctgaatca ccaatgaggg  780
atgtctcaat tgcccataca agaccccccca aagggacaat tgacctattt tctggacctc  840
caattcaggt gccttcccat ttttctccaa tggacaggga ggccagagtc ctaaggtaca  900
gggagaaaaa gaagatgaga aaatttgaga agacaatcag gtatgcctca aggaaggcct  960
atgcagagac tagacctcgt ataaaaggtc gatttgccaa gagaacagat gtagaagctg  1020
aagtggatca gatgttctcg acaacactaa ttacagaagt tggatatgga attgttccct  1080
ctttctgaat atgctgtgta gaacaaatgg ccagaagaca ttgaagatgc tagaggatca  1140
tgattaatag aaatggaaac cacttgtgta ctaagttatt ctgctgataa tgtatttttt  1200
atgtaatcta attgcttgca gttgtactaa tcggatgctt tattattttg tttattgtct  1260
tttgaatgaa acttgtattt gtaaatacag tccttgtatt aaattattaa attacagtcg  1320

SEQ ID NO: 185          moltype = AA  length = 352
FEATURE                 Location/Qualifiers
REGION                  1..352
                        note = misc_feature - Ceres Clone ID no. 472076
REGION                  1..352
                        note = misc_feature - Bit score of 378.3 for hmm based on
                         sequences of FIGURE 2.
REGION                  283..327
                        note = misc_feature - Pfam Name: CCT Pfam Desc: CCT motif
REGION                  50..97
                        note = misc_feature - Pfam Name: zf-B_box Pfam Desc: B-box
                         zinc finger
REGION                  1..352
                        note = misc_feature - Functional Homolog Of SEQ ID NO. 20
source                  1..352
                        mol_type = protein
                        organism = Glycine max
SEQUENCE: 185
MLEGQATTPT WPRMCDTCRS VPSTVFCRSH TAFLCATCDT RLHVSLTWHE RVWVCEACER  60
APAAFLCKAD AASLCASCDA DIHAANPLAS RHHRVPILPI AAANNNNNDD DDVADVDDED  120
ETASWLLLNP IKSATVPNTN NNNNNNGFLY NGEVDEYLDL VDNCNSCGDN NHFASAAATT  180
DHYAQHQHFA GVSQKSYAGD SVVPVQQHQH FQLGLDFDNS KPAFSYNGSV SQSVSVSSMD  240
IGVVPESPMR DVSIAHTRPP KGTIDLFSGP PIQVPSHFSP MDREARVLRY REKKKMRKFE  300
KTIRYASRKA YAETRPRIKG RFAKRTDVEA EVDQMFSTTL ITEVGYGIVP SF          352

SEQ ID NO: 186          moltype = AA  length = 321
FEATURE                 Location/Qualifiers
REGION                  1..321
                        note = misc_feature - Public GI ID no. 33943521
REGION                  1..321
                        note = misc_feature - Bit score of 284.1 for hmm based on
```

```
                         sequences of FIGURE 2.
REGION                  252..296
                        note = misc_feature - Pfam Name: CCT Pfam Desc: CCT motif
REGION                  46..93
                        note = misc_feature - Pfam Name: zf-B_box Pfam Desc: B-box
                         zinc finger
REGION                  1..321
                        note = misc_feature - Functional Homolog Of SEQ ID NO. 20
source                  1..321
                        mol_type = protein
                        note = subspecies = campestris
                        organism = Brassica rapa
SEQUENCE: 186
MLKEESNESG GTRACDTCRS AACTIYREAD STYLCTTCDA RVHAAKRVRV CDSCESAPAA  60
FFCKADAASL CTACDAEIHS ANPLARRHQR VPITSNSCGS MATDGDNNVM MVSEEKEDAD  120
EVASWLMLNP GKNNQNNGFL FGVEYLDLVD YSSSIDNQFE DQYSKYHRSF GGGEDGVVPL  180
QLEESSTSHM QQSQHNFHLG VNYGYSTEPQ YSYVSVVPES LSDTTVQHAK ETIDQVCGPP  240
TQMVQQLTPA DREARVLRYR EKKKRRKFEK TIRYASRKAY AEVRPRIKGR FAKRIDMEAD  300
AEQLFSTSVM SNTSYGIVPS F                                            321

SEQ ID NO: 187          moltype = AA  length = 348
FEATURE                 Location/Qualifiers
REGION                  1..348
                        note = misc_feature - Public GI ID no. 186911830
REGION                  1..348
                        note = misc_feature - Bit score of 348.6 for hmm based on
                         sequences of FIGURE 2.
REGION                  6..53
                        note = misc_feature - Pfam Name: zf-B_box Pfam Desc: B-box
                         zinc finger
REGION                  313..348
                        note = misc_feature - Pfam Name: CCT Pfam Desc: CCT motif
REGION                  1..348
                        note = misc_feature - Functional Homolog Of SEQ ID NO. 20
source                  1..348
                        mol_type = protein
                        note = subspecies = vulgaris
                        organism = Beta vulgaris
SEQUENCE: 187
MGGGLMAAKL CDSCKSATAT IFCRADTAYL CISCDAKIHA ANKLASRHAR VWVCEVCEHA  60
PATVTCKADA AHLCATCDRD IHSANPLARR HERVPLTPFY DPLSPPNTTN NNNDDSDSSA  120
TAAAAKSAA INKLFGDEYY SDADEAEAAS WLLPNPNKTD EPKSIDYLFS SSGNDGDDID  180
PYLDLDFGAE AKPDPDLSSD GVVPDPDQKG VHHHHLTTLQ HPAASMFSLS SYHHHHHHHH  240
VSNNNGHFDG FENSSAACKP FALSSYHTQP SLSHSVSSSS LDFGVVPDAS NITDVASTGF  300
DKQQQMKIIG MDREARVLRY REKRKNRKFE KTIRYASRKA YAETRPRI               348

SEQ ID NO: 188          moltype = DNA  length = 1077
FEATURE                 Location/Qualifiers
misc_feature            1..1077
                        note = Ceres Annot ID no. 8457547
misc_feature            1..1077
                        note = Encodes the peptide sequence at SEQ ID NO. 189
source                  1..1077
                        mol_type = other DNA
                        organism = Solanum lycopersicum
SEQUENCE: 188
atgggaacgg agaattggag tttaacggcg aagttatgtg actcatgcaa aacgtcgccg  60
gcgacggtgt tctgccgggc agattcagca tttctctgct taggatgtga ctgcaaaatc  120
cacgcagcga acaagttagc gtcacgtcac gcgcgtgtct gggtttgtga agtgtgtgag  180
caagctccgg cgagtgtcac gtgtaaagcg gatgccgctg ctctctgcgt tacgtgtgac  240
cgtgatattc attcagcaaa tccgttagct cgtcgccatg agcgttttcc ggtagttccg  300
ttctatgatt tcgccgtcgc gaaatctcac ggcggtggtg ataccgatgc cgatgctgtt  360
gatgatgaga agtactttga tagtactaat gagaatcctt ctcaaccaga ggaagaagct  420
gaagcagcgt cgtggatact tccgacgccg aaagaaggaa ctgatcagta taaatctgct  480
gattacttgt ttaatgatat ggattcatat ttagatatag atctaatgtc atgtgagcaa  540
aaaccacata ttcttcatca tcaacagcat caacacaacc attacagctc cgacggagtt  600
gtaccagtac agaacaacaa cgaaactact catttacccg gtccagtcgt tgatggattc  660
cctacatacg aactcgattt cactggatct aaaccttata tgtacaattt cacctctcaa  720
tcgatcagcc aaagtgtttc atcatcatct cttgacgtcg gagttgtacc agaccacagc  780
acaatgacgg atgtatcaaa cacttttgtg atgaactcat cttccggtgc tattgccggc  840
gccggcgccg acgttgtacc gaatgcagtt tccggtttag acagagaagc aagggtaatg  900
aggtacagag agaagaggaa gaatagaaag ttcgagaaga cgattcgata tgcttctaga  960
aaagcttatg ctgagactcg gcccagaatc aaagggagat tcgctaaacg tactgaaact  1020
gaaatcgatt cactcatcac cgtcgatgca tcatacggtg tcgttccatc gttttaa     1077

SEQ ID NO: 189          moltype = AA  length = 358
FEATURE                 Location/Qualifiers
REGION                  1..358
                        note = misc_feature - Ceres Annot ID no. 8457547
```

-continued

```
REGION                  1..358
                        note = misc_feature - Bit score of 531.8 for hmm based on
                         sequences of FIGURE 2.
REGION                  8..55
                        note = misc_feature - Pfam Name: zf-B_box Pfam Desc: B-box
                         zinc finger
REGION                  295..339
                        note = misc_feature - Pfam Name: CCT Pfam Desc: CCT motif
REGION                  1..358
                        note = misc_feature - Functional Homolog Of SEQ ID NO. 20
source                  1..358
                        mol_type = protein
                        organism = Solanum lycopersicum
SEQUENCE: 189
MGTENWSLTA KLCDSCKTSP ATVFCRADSA FLCLGCDCKI HAANKLASRH ARVWVCEVCE  60
QAPASVTCKA DAAALCVTCD RDIHSANPLA RRHERFPVVP FYDFAVAKSH GGGDTDADAV  120
DDEKYFDSTN ENPSQPEEEA EAASWILPTP KEGTDQYKSA DYLFNDMDSY LDIDLMSCEQ  180
KPHILHHQQH QHNHYSSDGV VPVQNNNETT HLPGPVVDGF PTYELDFTGS KPYMYNFTSQ  240
SISQSVSSSS LDVGVVPDHS TMTDVSNTFV MNSSSGAIAG AGADVVPNAV SGLDREARVM  300
RYREKRKNRK FEKTIRYASR KAYAETRPRI KGRFAKRTET EIDSLITVDA SYGVVPSF    358

SEQ ID NO: 190          moltype = AA  length = 369
FEATURE                 Location/Qualifiers
REGION                  1..369
                        note = misc_feature - Public GI ID no. 188484477
REGION                  1..369
                        note = misc_feature - Bit score of 209.9 for hmm based on
                         sequences of FIGURE 2.
REGION                  300..344
                        note = misc_feature - Pfam Name: CCT Pfam Desc: CCT motif
REGION                  22..69
                        note = misc_feature - Pfam Name: zf-B_box Pfam Desc: B-box
                         zinc finger
REGION                  1..369
                        note = misc_feature - Functional Homolog Of SEQ ID NO. 20
source                  1..369
                        mol_type = protein
                        organism = Lolium perenne
SEQUENCE: 190
MLMNCDFNCD LFEQEAKRRS YPWARPCDGC HAAPSAVYCH ADAAYLCASC DTQVHSANRL  60
ASSHERVRVC VSCESAAAVL ECHADSAALC TTCDAQVHSA NPIAQRHQRV PVLPLPALAI  120
PAASVFAEAE AATTVYGDKE EGEEVDSWLL LERDSDDNNC TNNIDQYFNL FGYDMYYDKF  180
SCNPGPGEEY RLQEQDVQNM YRENEVCEFA VPSQVGMASE QPESSYGMIG AEQDASMTAG  240
TSTYTASISN GIPFSSMEVG IIPDNTRPDV SNTNIQRTSE AMELAGHSLQ MPVHFSSMDR  300
DARVLRYKEK KQARTFQKTI RYATRKAYAE ARPRIKGRFA KRSDIEHELD QMLTIPALPD  360
SGHATVLWF                                                          369

SEQ ID NO: 191          moltype = DNA  length = 1131
FEATURE                 Location/Qualifiers
misc_feature            1..1131
                        note = Ceres Annot ID no. 8743875
misc_feature            1..1131
                        note = Encodes the peptide sequence at SEQ ID NO. 192
source                  1..1131
                        mol_type = other DNA
                        organism = Sorghum bicolor
SEQUENCE: 191
atggagctgc acaagtactg gggcgtgggt ggccggcggt gcggcagctg cgaggcggcg  60
ccggcggcgg tgcactgccg cacgtgcgtc ggcgggtcgt cgtcgttcct ctgcacgacg  120
tgcgacgcgc gccccgcgca cgcgcgcctg gcccacgagc gcgtgtgggt gtgcgaggtc  180
tgcgagctgg cccccgccgc cgtcacgtgc aaggccgacg ccgccgtgct ctgcgccgcc  240
tgcgacgccg acatccacga cgccaacccg ctggcgcgcc gccacgcgcg ggtccccgtc  300
gcgcccatcg gctccgaggc cgccgccgcg gccgtcgagg ccatgctgtt cgggaccggc  360
gacgcggccg aggccgacga ccagcacaac aacgcggcgg cggcggccga gcagcatcag  420
catcagcacc acgctcacca cgcgcacgcg ctgaacctca acgtggaggc gaaggacatg  480
aagctggact acctcttctc tgagctggat ccctacctca gcgtcgagat cccgcgcttc  540
caccacgccg acagcgtcgt ccccaacggc gccggcgctg ccggcgccgt cgagctcgac  600
ttcacgtgcg gcatcggcgt caagcactcc tcctacagct cctacaccgc cacctccctc  660
gatctcgcgc atagcggctc ctcgtcggag gtcggcgtgg tgccagaggc cttcggcggc  720
ggcggcggcg gcggcggcgg gagctttgag ctcgacttca caaggccaaa gcctcaggcc  780
tacatgccat acacggcgac tccccagagc cacagcgtgt cgtccgtgga cgtggaggtg  840
gtgccggagc ggggagactt gccggcggtg aggccggtgc cgctgatggg ggagagccgg  900
gaggcgcggc tgatgcggta ccgtgagaag aggaagaacc ggcggttcga gaagaccatc  960
cggtacgcgt cccggaaggc ctacgccgag acgcggccgc ggatcaaggg gaggtttgcc  1020
aagcgcgccg accacgacgg cgacggcgac gccgacgacg ccgaggccga ggccgccgtg  1080
ccgtcgtcgt acgtgctcga cttcggctac ggcgtcgtgc cgagcttctg a           1131

SEQ ID NO: 192          moltype = AA  length = 376
FEATURE                 Location/Qualifiers
```

```
REGION              1..376
                    note = misc_feature - Ceres Annot ID no. 8743875
REGION              1..376
                    note = misc_feature - Bit score of 743.4 for hmm based on
                     sequences of FIGURE 2.
REGION              300..344
                    note = misc_feature - Pfam Name: CCT Pfam Desc: CCT motif
REGION              53..100
                    note = misc_feature - Pfam Name: zf-B_box Pfam Desc: B-box
                     zinc finger
REGION              1..376
                    note = misc_feature - Functional Homolog Of SEQ ID NO. 20
source              1..376
                    mol_type = protein
                    organism = Sorghum bicolor
SEQUENCE: 192
MELHKYWGVG GRRCGSCEAA PAAVHCRTCV GGSSSFLCTT CDARPAHARL AHERVWVCEV  60
CELAPAAVTC KADAAVLCAA CDADIHDANP LARRHARVPV APIGSEAAAA AVEAMLFGTG  120
DAAEADDQHN NAAAAAEQHQ HQHHAHHAHA LNLNVEAKDM KLDYLFSELD PYLSVEIPRF  180
HHADSVVPNG AGAAGAVELD FTCGIGVKHS SYSSYTATSL DLAHSGSSSE VGVVPEAFGG  240
GGGGGGGSFE LDFTRPKPQA YMPYTATPQS HSVSSVDVEV VPERGDLPAV RPVPLMGESR  300
EARLMRYREK RKNRRFEKTI RYASRKAYAE TRPRIKGRFA KRADHDGDGD ADDAEAEAAV  360
PSSYVLDFGY GVVPSF                                                  376

SEQ ID NO: 193      moltype = AA  length = 444
FEATURE             Location/Qualifiers
REGION              1..444
                    note = misc_feature - Public GI ID no. 193735598
REGION              1..444
                    note = misc_feature - Bit score of 405.5 for hmm based on
                     sequences of FIGURE 2.
REGION              377..421
                    note = misc_feature - Pfam Name: CCT Pfam Desc: CCT motif
REGION              79..126
                    note = misc_feature - Pfam Name: zf-B_box Pfam Desc: B-box
                     zinc finger
REGION              1..444
                    note = misc_feature - Functional Homolog Of SEQ ID NO. 20
source              1..444
                    mol_type = protein
                    organism = Picea abies
SEQUENCE: 193
MVKEEDKDWH TVEDLHRGSH VDHKEFLRGI GGWRMSMPKL CDVCQVSNSV LYCRAHTAQL  60
CLVCDVKIHG GSKASLCHER VWVCEVCEQA PAVVTCKADA AALCVSCDTD IHSANPLASR  120
HERAPVIPFY ECPNMPNNNT ATNANNDNLD CNVLLNEDGG GDDPLKHDYV DDDYDDYDDD  180
ENDHNNLLNH QEDDNDAEIC CAEEAATASW LIPEANRNNL TNINGGNSEG EDKMVKDKLK  240
FKAYMQSIDF LQDVENYVDL EYLGTTTTIT TPTTTPTAHMG ADSMVPVHTP EVIEHSSTKV  300
SVETARSLDV DAASKCNYVY RTTSLNHCVS SSSIDVGIVP DSNTTTDIST PYHDPRGVFE  360
IPPRVVHPGG HVEVMGREAR VLRYREKRKN RRFEKTIRYA SRKAYAETRP RIKGRFAKRT  420
EVEVEQIYSS SLLPDQGYGV VPSY                                         444

SEQ ID NO: 194      moltype = AA  length = 384
FEATURE             Location/Qualifiers
REGION              1..384
                    note = misc_feature - Public GI ID no. 116787635
REGION              1..384
                    note = misc_feature - Bit score of 467.1 for hmm based on
                     sequences of FIGURE 2.
REGION              23..70
                    note = misc_feature - Pfam Name: zf-B_box Pfam Desc: B-box
                     zinc finger
REGION              320..364
                    note = misc_feature - Pfam Name: CCT Pfam Desc: CCT motif
REGION              1..384
                    note = misc_feature - Functional Homolog Of SEQ ID NO. 20
source              1..384
                    mol_type = protein
                    organism = Picea sitchensis
SEQUENCE: 194
MVKEEDCKVP KEAGIVKEFQ AWTMPKPCNV CRIASASLYC RADSAYLCSG CDVKVHGANK  60
LASRHERVWL CEVCEQAPAA VTCKADAASL CVSCDADIHS ANPLARRHDR VPIVPFYECA  120
SVAKTFLPPP PPPPTSSLQD SDVVGTLDYE DHDDDDEIYA AEAASWLLPN PKSSAEGTKN  180
CDDGGSCFGV DAGPPVNKAA GGYFSVVDLF PDVDPYLDLD YASPLEATGG TDSVVPVQSN  240
VSSQDGAVST PSDCFDTEKV TYSYTTTTSL SHSVSSSSLD VGVVPDATLS DMPRPLNRGV  300
FELANPGVVN VGIQYVQLDR EARVLRYKEK RKNRKFEKTI RYASRKAYAE TRPRIKGRFA  360
KRVDADVAQM YTSAELSYGL VPSF                                         384

SEQ ID NO: 195      moltype = AA  length = 383
FEATURE             Location/Qualifiers
```

```
REGION                  1..383
                        note = misc_feature - Public GI ID no. 169807976
REGION                  1..383
                        note = misc_feature - Bit score of 230.7 for hmm based on
                         sequences of FIGURE 2.
REGION                  314..358
                        note = misc_feature - Pfam Name: CCT Pfam Desc: CCT motif
REGION                  19..66
                        note = misc_feature - Pfam Name: zf-B_box Pfam Desc: B-box
                         zinc finger
REGION                  1..383
                        note = misc_feature - Functional Homolog Of SEQ ID NO. 20
source                  1..383
                        mol_type = protein
                        organism = Triticum aestivum
SEQUENCE: 195
MNCVSNGTVY EEAVGREGSW ARLCDGCCTV PSVVYCRADS AYLCASCDAQ IHAANRVASR  60
HERVLLSEAY KHAPVVLECH ADAAALCAAY EAQVHYANLL ATMHQRVPVV SHPVAAIPAA  120
SLFAEAAATA PVLGSKEEDA SWLLLSKDSD NHNHSGNHSS SSSSSRYFGE VDQYFDLVGY  180
NSYYDSHMNN QEQYVMQEQQ HLQQMQKEYA EQQMQKEYVE KEGSECIVPS QSAIVSRPHQ  240
SGYAPLVRAE QAASVTAGVS AYTDSVNNSI SFSMEAGIVP DNTVQSSILR PAGAIGHFSS  300
PSLQTPLHFS SKEREARVLR YKEKKKSRKF EKTTRYATRK AYAEARPRIK GRFAKRSDAD  360
MEVDQTFSTA ALSDSSYSTV PWF                                          383

SEQ ID NO: 196          moltype = AA  length = 397
FEATURE                 Location/Qualifiers
REGION                  1..397
                        note = misc_feature - Public GI ID no. 157422228
REGION                  1..397
                        note = misc_feature - Bit score of 334.9 for hmm based on
                         sequences of FIGURE 2.
REGION                  326..370
                        note = misc_feature - Pfam Name: CCT Pfam Desc: CCT motif
REGION                  27..74
                        note = misc_feature - Pfam Name: zf-B_box Pfam Desc: B-box
                         zinc finger
REGION                  1..397
                        note = misc_feature - Functional Homolog Of SEQ ID NO. 20
source                  1..397
                        mol_type = protein
                        organism = Zea mays
SEQUENCE: 196
MDYNFDTSVL DEDVAGRGGR EGSCPPAWAR ACDGCRAAPS VVYCHADTAY LCASCDSRVH  60
AANRVASRHE RVRVCEACEC APAVLACRAD AAALCAACDA QVHSANPLAG RHQRVPVLPL  120
PAAAVPAASV LAEATATAAS VAGDKDEEVD SWLLLTKDPD DDDKNHNCSS NNNNNNISSN  180
TSTFYADVDE YFDLVGYSSY CDNHINSNTK QYGMQEQQLL LHKEFGDKEG SEYVVPSQVG  240
QQQSGYHRVI GTEQAASMTP GVSAYTDSIS NSISYSSSME VGIVPDNMAT TDMPSSGILL  300
TPAGAISLFS SGPPLQMPLH LASMDREARV LRYREKKKSR KFEKTIRYAT RKTYAEARPR  360
IKGRFAKRSS DMDDEVDQMF SAAALSSDGS YGTVPWF                            397

SEQ ID NO: 197          moltype = DNA  length = 1423
FEATURE                 Location/Qualifiers
misc_feature            1..1423
                        note = Ceres Clone ID no. 1755159
misc_feature            1..1423
                        note = Encodes the peptide sequence at SEQ ID NO. 198
source                  1..1423
                        mol_type = other DNA
                        organism = Panicum virgatum
SEQUENCE: 197
gcgcgctccc tcccctcccc tcctcccacc agcccaccac caccacaagc accgcgtcgt  60
ccacaccacc tgccattgcc gcgccgagct cagcctctag ctgcgccagg agggcgcccg  120
cctccctccc tgccgacgcc ggtgtgatgg agctgcacaa gtactggggc gtggggggcc  180
gccggtgcgg cggctgcgag gcggccccgg cggcggtgca ctgccgctcg tgccccgccg  240
ggggcgcgtt cctctgcacg gcgtgcgacg cgcgcccggg gcacgcgcat ctgggccacg  300
agcgcgtgtg gatgtgcgag gtctgcgagc tggcgcccgc cgccgtcacg tgcaaggccg  360
acgccgccgt gctctgcgcc gcctgcgacg ccgacatcca cgacgccaac ccgctggcgc  420
gccgccacgc acgcgtcccc gtcgcgccca tcggctcgga ggccgcggcc gccgccgtgg  480
aggccatgct gttcgggacc ggcgagccgg ccgcgtccga ggccgaggag ccgcagaacg  540
cggcggccag gcacaaccac cagcacgcgc tgaacctcaa cgtggaggcc aaggacatga  600
agctggacta cctcttttcc gacctggacc cctacctcag cgtcgatatc ccgcgcttcc  660
agcacgccga cagcgtcgtc cccagcggcg tcggcgccgg agcagccggc gccgtcgagc  720
tggacttcac gtgcggcatc ggcgtcgagc cctcctcata cagctcctac acggcaacat  780
ccctcgccca cagcggctcc tcttctgagg tcggcgtggt gccagaggcc ttctgcggcg  840
gcggcgggag cttcgagctc gacttcacaa ggcccaagcc tcaagcctac atgccgtaca  900
ccgcgactcc tcaaagtcac agcgtgtcgt cggtggacgt ggaggtggtg ccggagcggg  960
gggacatgat ggcggcggcg aggccggtgc cgctggtggg ggagagccgg gaggcgcggc  1020
tgatgcgcta ccgggagaag cggaagaacc ggcggttcga gaagaccatc cggtacgcgt  1080
cccggaaggc ctacgccgag atgcggccgc ggatcaaggg ccggttcgcc aagcgcgccg  1140
```

```
accacgacgc cgacgccgac gacaccgagg ccgaggccga ggccgccgtg ccgtcgccgg  1200
cgtcgtacgt gctcgacttc ggctacggcg tcgtgcccag cttctgatcg acgacgatcg  1260
tctcgctcgt tccacgcgcg gcgcgcttga cccggcccgg cgcgcgcgcc ttgtacttgt  1320
atcgatgcat gtataggga ggaatagtaa tcccatgtac tctcgtcttg gagctgcgct  1380
agccctgcgt acgtacgcta gtgatgtata atttgtacaa ccc                   1423

SEQ ID NO: 198         moltype = AA  length = 366
FEATURE                Location/Qualifiers
REGION                 1..366
                       note = misc_feature - Ceres Clone ID no. 1755159
REGION                 1..366
                       note = misc_feature - Bit score of 709.8 for hmm based on
                        sequences of FIGURE 2.
REGION                 288..332
                       note = misc_feature - Pfam Name: CCT Pfam Desc: CCT motif
REGION                 52..99
                       note = misc_feature - Pfam Name: zf-B_box Pfam Desc: B-box
                        zinc finger
REGION                 1..366
                       note = misc_feature - Functional Homolog Of SEQ ID NO. 20
source                 1..366
                       mol_type = protein
                       organism = Panicum virgatum
SEQUENCE: 198
MELHKYWGVG GRRCGGCEAA PAAVHCRSCP AGGAFLCTAC DARPGHAHLG HERVWMCEVC  60
ELAPAAVTCK ADAAVLCAAC DADIHDANPL ARRHARVPVA PIGSEAAAAA VEAMLFGTGE  120
PAASEAEEPQ NAAARHNHQH ALNLNVEAKD MKLDYLFSDL DPYLSVDIPR FQHADSVVPS  180
GVGAGAAGAV ELDFTCGIGV EPSSYSSYTA TSLAHSGSSS EVGVVPEAFC GGGGSFELDF  240
TRPKPQAYMP YTATPQSHSV SSVDVEVVPE RGDMMAAARP VPLVGESREA RLMRYREKRK  300
NRRFEKTIRY ASRKAYAEMR PRIKGRFAKR ADHDADADDT EAEAEAAVPS PASYVLDFGY  360
GVVPSF                                                            366

SEQ ID NO: 199         moltype = AA  length = 362
FEATURE                Location/Qualifiers
REGION                 1..362
                       note = misc_feature - Public GI ID no. 170779036
REGION                 1..362
                       note = misc_feature - Bit score of 423.2 for hmm based on
                        sequences of FIGURE 2.
REGION                 13..60
                       note = misc_feature - Pfam Name: zf-B_box Pfam Desc: B-box
                        zinc finger
REGION                 297..341
                       note = misc_feature - Pfam Name: CCT Pfam Desc: CCT motif
REGION                 1..362
                       note = misc_feature - Functional Homolog Of SEQ ID NO. 20
source                 1..362
                       mol_type = protein
                       organism = Chenopodium rubrum
SEQUENCE: 199
MMKKEVPGGD NNSWARVCDT CRSAPCTVYC KEDSAFLCTS CDARIHAVNQ MASRHERVWV  60
CEACEREPAA FLCKADAASL CATCDADIHS ANPLARRHHR VPIMPVGCVY GPSDGRMSED  120
GFLDLPDRDD QTTDHEGDED EAASWLLLNP GKNSNNQTTN GFLTGGGEVD EYLDLFEYNS  180
GADNQFCEQY NQQQEFSVPE KNCGGDSVVP VQCREVKDHQ IQYQNFLFGM ECETKSEYTY  240
NTSISHSVSV SSLDVGVVPE STMSDMSVSH SRPPKGTIDL FSSTPMQVPT QLSPLDREAR  300
VMRYREKKKN RKFEKTIRYA SRKAYAETRP RIKGRFAKRT DVEAERTNSL MSDGGYGIVP  360
SF                                                                362

SEQ ID NO: 200         moltype = DNA  length = 1116
FEATURE                Location/Qualifiers
misc_feature           1..1116
                       note = Ceres Annot ID no. 1731456
misc_feature           1..1116
                       note = Encodes the peptide sequence at SEQ ID NO. 201
source                 1..1116
                       mol_type = other DNA
                       organism = Oryza sativa
SEQUENCE: 200
atgatggagt tgcgcaagta ctggggcgtc ggcgggcggc ggtgcggtgc gtgcgaggcg  60
tcgccggcgg ccgtgcactg ccgcggctgc ggcggggtgt acctgtgcac ggcgtgcgac  120
gcgcgcccgg gccacgcgcg ggcggcgcac gagcgggtgt gggtgtgcga ggtctgcgag  180
gtggcgcccg ccgccgtcac ctgcaaggcc gacgccgcgg tgctctgcgc cgcctgcgac  240
gccgacatcc acgacgccaa cccgctggcc cgccgccacg cgcgcgtccc cgtcgcgccc  300
atcggctccg ccgccgccgc cgccgtggcc gccgaggcca tgctgttcgg cgtcgccgcc  360
gccggggccg aggccgaggc ggtggaggat aaggccgcgg ccgagcacca ccaccaccag  420
cagcggcagc agcacggcgc gctcaacctc aacgtggagg cgaaggacat gaagctcgac  480
tacctcttct ccgacctcga cccttacctc aacgtcgagt tcgcccgctt cccccacgcc  540
gacagcgtcg tccccaacgg cgccggcgcc ggcgccgcca tagagctcga cttcacctgc  600
ggcctaggcg tcggcgtcgg cggcgccaag cagtcctaca gctcctacac cgccaccgac  660
```

-continued

```
ctcgctcaca gcggctcgtc gtcggaggtg ggcgtggtgc cggaggccat gtgcggcggc  720
ggcggcgcca tcgatctcga cttcacgagg ccgaagcctc aaccctacat gccgtacacg  780
gcgactcctc ctccgagcca cagcgtagta agcgcgcaga tgtcgtcgtc ggtggtcgac  840
gtgggcgtgg tgccggagcg ggcggcggcg atgggggaag ggagggaggc gaggctgatg  900
aggtacaggg agaagcggaa gaaccggcgg ttcgagaaga cgatccggta cgcgtcgcgc  960
aaggcctacg ccgagacgcg cccccggatc aagggccgct tcgccaagcg cgccgaccac  1020
gacgccgacg acgccgacgc cgacgccgac gaccccgccg ccgtcccatc ctcctacatg  1080
ctcgacttcg gctacggcgt cgtcccgtcc ttctga                            1116

SEQ ID NO: 201         moltype = AA  length = 371
FEATURE                Location/Qualifiers
REGION                 1..371
                       note = misc_feature - Ceres Annot ID no. 1731456
REGION                 1..371
                       note = misc_feature - Bit score of 611.8 for hmm based on
                        sequences of FIGURE 2.
REGION                 295..339
                       note = misc_feature - Pfam Name: CCT Pfam Desc: CCT motif
REGION                 51..98
                       note = misc_feature - Pfam Name: zf-B_box Pfam Desc: B-box
                        zinc finger
REGION                 1..371
                       note = misc_feature - Functional Homolog Of SEQ ID NO. 20
source                 1..371
                       mol_type = protein
                       organism = Oryza sativa
SEQUENCE: 201
MMELRKYWGV GGRRCGACEA SPAAVHCRGC GGVYLCTACD ARPGHARAAH ERVWVCEVCE  60
VAPAAVTCKA DAAVLCAACD ADIHDANPLA RRHARVPVAP IGSAAAAAVA AEAMLFGVAA  120
AGAEAEAVED KAAAEHHHHQ QRQQHGALNL NVEAKDMKLD YLFSDLDPYL NVEFARFPHA  180
DSVVPNGAGA GAAIELDFTC GLGVGVGGAK QSYSSYTATD LAHSGSSSEV GVVPEAMCGG  240
GGAIDLDFTR PKPQPYMPYT ATPPPSHSVV SAQMSSSVVD VGVVPERAAA MGEGREARLM  300
RYREKRKNRR FEKTIRYASR KAYAETRPRI KGRFAKRADH DADDADADAD DPAAVPSSYM  360
LDFGYGVVPS F                                                       371

SEQ ID NO: 202         moltype = DNA  length = 1251
FEATURE                Location/Qualifiers
misc_feature           1..1251
                       note = Ceres Clone ID no. 1770031
misc_feature           1..1251
                       note = Encodes the peptide sequence at SEQ ID NO. 203
source                 1..1251
                       mol_type = other DNA
                       organism = Panicum virgatum
SEQUENCE: 202
agcgagctcc cggcgcgcga taatggaggg tgacgagaag tcggcaggcg gggccccggc  60
cccggcctac tggggcctgg gcgcgcggcc ctgcgacgcg tgcggcgacg aggcggcgag  120
gctctactgc cgcgcggacg cggcgttcct ctgcgccggg tgcgacgcgc gcgcgcacgg  180
cgccgggtcg cgccacgccc gcgtctggct ctgcgaggtc tgcgagcacg cgccggccgc  240
ggtcacgtgc cgcgcggacg ccgccgcgct ctgcgcctcg tgcgacgccg acatccactc  300
cgccaacccg ctcgcgcgcc gccacgagcg ccaggccgtg gcgcccttct acggcgcgct  360
ggccgacgcg cccaagccct tcgcctcgtc ggcggccgtg cccaaagcgg ccgacgacga  420
cgggagcaac gaggccgagg cggcgtcgtg gctcctcccc gagcccgacc acgggctcaa  480
ggaaggcgcc acgacggagg tgttcttcgc ggactccgac ccgtacctcg acctcgactt  540
cgcgcgcacc atggacgaca tcaaggccat cggcgtccag aacggccccg ccgagctcga  600
cctcaccggc gccaagctct tctactccga ccactccatg aaccacagcg tgtcgtcatc  660
ggaggcagca gtggtgcccg acgcggcggc gggcgcggcg cccgtggttc cagtggtgag  720
caggggtctg gagcgggagg cccggctgat gcggtaccgg gagaagcgca agagccggcg  780
gttcgagaag acgatccggt acgcgtcccg caaggcgtac gcggagacgc ggccgcgcat  840
caagggccgg ttcgccaagc gcacccccgg gcccggcggc gcggacgggg aggacccgct  900
ggaggagcac gaggaggaga tgtactcctc cgccgcggca gccgtggccg cgctcatggt  960
ccccggcggc gccgacgccg actacggcgt cgtgcccacg tattgatcgg cgccggcctg  1020
ttgtaacact agccagcctc gacctcgccg ccggggctgt aatttttgct gcatgccctg  1080
catgcaaagc tgccgtgtag cattaattac ctgtaatatg attccacgga agccatcagg  1140
ccggacttcc aagctattct tcctccctaa tcattccgcc atgtatgtat attattatga  1200
gtaaattgca ctcatcatac aataaattga cagatagata caaattgatc c           1251

SEQ ID NO: 203         moltype = AA  length = 327
FEATURE                Location/Qualifiers
REGION                 1..327
                       note = misc_feature - Ceres Clone ID no. 1770031
REGION                 1..327
                       note = misc_feature - Bit score of 643.2 for hmm based on
                        sequences of FIGURE 2.
REGION                 238..282
                       note = misc_feature - Pfam Name: CCT Pfam Desc: CCT motif
REGION                 19..63
                       note = misc_feature - Pfam Name: zf-B_box Pfam Desc: B-box
                        zinc finger
```

```
REGION               1..327
                     note = misc_feature - Functional Homolog Of SEQ ID NO. 20
source               1..327
                     mol_type = protein
                     organism = Panicum virgatum
SEQUENCE: 203
MEGDEKSAGG APAPAYWGLG ARPCDACGDE AARLYCRADA AFLCAGCDAR AHGAGSRHAR  60
VWLCEVCEHA PAAVTCRADA AALCASCDAD IHSANPLARR HERQAVAPFY GALADAPKPF  120
ASSAAVPKAA DDDGSNEAEA ASWLLPEPDH GLKEGATTEV FFADSDPYLD LDFARTMDDI  180
KAIGVQNGPA ELDLTGAKLF YSDHSMNHSV SSSEAAVVPD AAAGAAPVVP VVSRGLEREA  240
RLMRYREKRK SRRFEKTIRY ASRKAYAETR PRIKGRFAKR TPGPGGADGE DPLEEHEEEM  300
YSSAAAAVAA LMVPGGADAD YGVVPTY                                    327

SEQ ID NO: 204       moltype = AA  length = 345
FEATURE              Location/Qualifiers
REGION               1..345
                     note = misc_feature - Public GI ID no. 194244874
REGION               1..345
                     note = misc_feature - Bit score of 278.5 for hmm based on
                      sequences of FIGURE 2.
REGION               7..54
                     note = misc_feature - Pfam Name: zf-B_box Pfam Desc: B-box
                      zinc finger
REGION               283..327
                     note = misc_feature - Pfam Name: CCT Pfam Desc: CCT motif
REGION               1..345
                     note = misc_feature - Functional Homolog Of SEQ ID NO. 20
source               1..345
                     mol_type = protein
                     organism = Brassica nigra
SEQUENCE: 204
MLKQESNWAQ ACDTCRSAAC TVYCRADSAY LCTSCDAQIH AANRLASRHE RVRVCESCER  60
APAAFFCKAD AASLCTACDS QIHSANPLAR RHQRVPILPI SGCVATNHSS KTTEPENIVV  120
VGQEEEDEAE AASWLLPSSV KNCGDNNNNN NNNSENNRFS VGEEYLDLVD YSSSIDKRFT  180
GQSNQYQQDY NVPQRSYVAD GVVPLQVGVA NGHMHHEQHN FQFGFTNVSS EAHQISNGSP  240
IHMVSLVPES VTSDATVSHP RSPKAGTEEL PEAPVQMLSP MERKARVLRY REKKKTRKFE  300
KRIRYASRKE YAEKRPRIKG RFAKRNEVDA DHALSTMVVF DTGYG                345

SEQ ID NO: 205       moltype = AA  length = 384
FEATURE              Location/Qualifiers
REGION               1..384
                     note = misc_feature - Public GI ID no. 150014754
REGION               1..384
                     note = misc_feature - Bit score of 466.3 for hmm based on
                      sequences of FIGURE 2.
REGION               23..70
                     note = misc_feature - Pfam Name: zf-B_box Pfam Desc: B-box
                      zinc finger
REGION               320..364
                     note = misc_feature - Pfam Name: CCT Pfam Desc: CCT motif
REGION               1..384
                     note = misc_feature - Functional Homolog Of SEQ ID NO. 20
source               1..384
                     mol_type = protein
                     organism = Picea abies
SEQUENCE: 205
MVKEEDCKVP KEAGIVKEFQ AWTMPKPCNV CRIASASLYC RADSAYLCSG CDVKVHGANK  60
LASRHERVWL CEVCEQAPAA VTCKADAASL CVSCDADIHS ANPLARRHDR VPIVPFYECA  120
SVAKTFLPPP PPPPTSSLQD SDVVGTLDYE DDDEDDEIYA AEAASWLLPN PKSSAEGAKN  180
CDDGGSCFGV DAGPPVNKAA GGYFSVVDLF PDVDPYLDLD YASPLEATGG TDSVVPVQSN  240
VSSQDGAVST PSDCFDTEKA TYSYTTTTSL SHSVSSSSLD VGVVPDATLS DMSRPLNRGV  300
FELANPGVVN VGIQYVQLDR EARVLRYKEK RKNRKFEKTI RYASRKAYAE TRPRIKGRFA  360
KRVDADVAQM YTSAELSYGL VPSF                                       384

SEQ ID NO: 206       moltype = AA  length = 340
FEATURE              Location/Qualifiers
REGION               1..340
                     note = misc_feature - Public GI ID no. 194244844
REGION               1..340
                     note = misc_feature - Bit score of 276.3 for hmm based on
                      sequences of FIGURE 2.
REGION               7..54
                     note = misc_feature - Pfam Name: zf-B_box Pfam Desc: B-box
                      zinc finger
REGION               280..324
                     note = misc_feature - Pfam Name: CCT Pfam Desc: CCT motif
REGION               1..340
                     note = misc_feature - Functional Homolog Of SEQ ID NO. 20
source               1..340
```

```
                         mol_type = protein
                         organism = Brassica nigra
SEQUENCE: 206
MLKQESNWAQ ACDTCRSAAC TVYCRADSAY LCTSCDAQIH AANRLASRHE RVRVCESCER  60
APAAFFCKAD AASLCTACDS QIHSANPLAR RHQRVPILPI SGCVATNHHS SETTEPENIV  120
VVGQEEEDEA EAASWLLPSS VKNCGDNNNN TENNRFSVGE EYLDLVDYSS SIDKRFTGQT  180
NQYQQDYNVP QRSYVADGVV PLQVGVSKGH MHHEQHNFQF GFTNVSSEAH QISNGSPIHM  240
VSLVPESVTS DATVSHQRSP KAGTEELPEA PVQMLSPMER KARVLRYREK KKTRKFEKRI  300
RYASRKEYAE KRPRIKGRFA KRNEVDADQA FPTVVMFDTG                        340

SEQ ID NO: 207           moltype = AA  length = 340
FEATURE                  Location/Qualifiers
REGION                   1..340
                         note = misc_feature - Public GI ID no. 189014382
REGION                   1..340
                         note = misc_feature - Bit score of 510.4 for hmm based on
                          sequences of FIGURE 2.
REGION                   1..48
                         note = misc_feature - Pfam Name: zf-B_box Pfam Desc: B-box
                          zinc finger
REGION                   279..323
                         note = misc_feature - Pfam Name: CCT Pfam Desc: CCT motif
REGION                   1..340
                         note = misc_feature - Functional Homolog Of SEQ ID NO. 20
source                   1..340
                         mol_type = protein
                         organism = Malus x domestica
SEQUENCE: 207
MALKLCDSCK SATGTLFCRA DSAFLCVNCD SKIHAANKLA SRHARVWLCE VCEQAPAHVT  60
CKADDAALCV TCDRDIHSAN PLSRRHERVP VTPFYDSVNS ATDSVPAVKS AVNFLNDRYF  120
SDVDGEIEAR REEAEAASWL LPNPKAMENP DLNSGQYLFP EMDPYMDLDY GHVDPKLEDA  180
QEQNSCITDG VVPEQSKNMQ PQLVNDHSFE IDFSAASKPF VYGYHHAQCL RQSVSSSSMD  240
VSIVPDDNAM TDDSNPYNKS MTSAVESSHP AVQLSSADRE ARVLRYREKR KNRKFEKTIR  300
YASRKAYAET RPRIKGRFAK RTEVEIEAEP MCRYGIVPSF                        340

SEQ ID NO: 208           moltype = AA  length = 386
FEATURE                  Location/Qualifiers
REGION                   1..386
                         note = misc_feature - Public GI ID no. 186915025
REGION                   1..386
                         note = misc_feature - Bit score of 486.0 for hmm based on
                          sequences of FIGURE 2.
REGION                   307..351
                         note = misc_feature - Pfam Name: CCT Pfam Desc: CCT motif
REGION                   22..63
                         note = misc_feature - Pfam Name: zf-B_box Pfam Desc: B-box
                          zinc finger
REGION                   1..386
                         note = misc_feature - Functional Homolog Of SEQ ID NO. 20
source                   1..386
                         mol_type = protein
                         organism = Solanum lycopersicum
SEQUENCE: 208
MGIFREAPNC FPGGWNIGAA ARMAKSCEYC HLAAALVFCR TDNTFVCLSC DTRLHARHER  60
VWVCEVCEQA AASVTCRADA AALCVACDRD IHSANPLARR HERVPVVPFY DPVESVVKST  120
AATLLVSING TTTTATTTAT ITPELGKVDT CIGHHENNND PWIPPNTITS KLPLNTEMKG  180
MDFIFTDSEN FLDFDYPACV DTQSQPHYNS SNDSVVPVQA NTPIKSLPFH HQEKHFEIDF  240
TQSHIKSYNT PSLSVSSSSL DVGIVPDGSS ISEISYPYIR TMNNSNSSID LSNSANHQGE  300
KLLGLDREAR VLRYREKKKN RKFEKTIRYA SRKAYAETRP RIKGRFAKRT DGSAGAGEFD  360
DVDGIFSGTD FIAAESRYGV VPSFLT                                       386

SEQ ID NO: 209           moltype = DNA  length = 772
FEATURE                  Location/Qualifiers
misc_feature             1..772
                         note = Ceres Clone ID no. 100941305
misc_feature             1..772
                         note = Encodes the peptide sequence at SEQ ID NO. 210
source                   1..772
                         mol_type = other DNA
                         organism = Zea mays
SEQUENCE: 209
gatggagggt gacgagaagt cggcgggcgg ggcccctgct tactggggcc tgggcgcgcg  60
gccctgcgac gcgtgcggcg ccgaggcggc gcgcctctac tgccgcgcgg acgcggcgtt  120
cctgtgcgcc gggtgcgacg cgcgggcgca cggcgccggg tcgcgccacg cgcgggtctg  180
gctctgcgag gtctgcgagc acgcgccggc ggcggtcacg tgccgcgcgg acgctgccgc  240
gctctgcgcc tcctgcgacg ccgacatcca ctcggcgaac ccgctcgcgc gccgccacga  300
gcgcctccac gtggcgccct tcttcggcgc gctggccgac gcgcccaagc ccttcgcctc  360
ggcggcgccg cccaaagcaa ccgacgacga cgggagcaac gaggacgagg cggcgtcgtg  420
gctcctcccc gagcccgacc acgggcagaa agaaggcgcc acgacggagg tgttcttcgc  480
```

-continued

```
ggactctgac ccgtacctcg acctcgactt cgcgcgttcc atggacgaaa tcaagaccat  540
cggcgtccag cagagcgggt caccagagct cgacctcgcc ggcaccaagc tcttctactc  600
cgatcactcc gtgaaccaca gtgtgtcatc gtcggaggca gcggttgtgc ccgacgcggc  660
gtctggcatg gcgcccatgg tggcagtggt cagcaggggc ctggagcgag aggcgcggct  720
gatgcggtac cgggagaagc gcaagagcag gcggttcgag aagacgatcc gg          772

SEQ ID NO: 210          moltype = AA  length = 257
FEATURE                 Location/Qualifiers
REGION                  1..257
                        note = misc_feature - Ceres Clone ID no. 100941305
REGION                  1..257
                        note = misc_feature - Bit score of 429.2 for hmm based on
                         sequences of FIGURE 2.
REGION                  17..61
                        note = misc_feature - Pfam Name: zf-B_box Pfam Desc: B-box
                         zinc finger
REGION                  236..257
                        note = misc_feature - Pfam Name: CCT Pfam Desc: CCT motif
REGION                  1..257
                        note = misc_feature - Functional Homolog Of SEQ ID NO. 20
source                  1..257
                        mol_type = protein
                        organism = Zea mays
SEQUENCE: 210
MEGDEKSAGG APAYWGLGAR PCDACGAEAA RLYCRADAAF LCAGCDARAH GAGSRHARVW  60
LCEVCEHAPA AVTCRADAAA LCASCDADIH SANPLARRHE RLHVAPFFGA LADAPKPFAS  120
AAPPKATDDD GSNEDEAASW LLPEPDHGQK EGATTEVFFA DSDPYLDLDF ARSMDEIKTI  180
GVQQSGSPEL DLAGTKLFYS DHSVNHSVSS SEAAVVPDAA SGMAPMVAVV SRGLEREARL  240
MRYREKRKSR RFEKTIR                                                257

SEQ ID NO: 211          moltype = AA  length = 358
FEATURE                 Location/Qualifiers
REGION                  1..358
                        note = misc_feature - Public GI ID no. 157341339
REGION                  1..358
                        note = misc_feature - Bit score of 452.0 for hmm based on
                         sequences of FIGURE 2.
REGION                  289..333
                        note = misc_feature - Pfam Name: CCT Pfam Desc: CCT motif
REGION                  18..65
                        note = misc_feature - Pfam Name: zf-B_box Pfam Desc: B-box
                         zinc finger
REGION                  1..358
                        note = misc_feature - Functional Homolog Of SEQ ID NO. 20
source                  1..358
                        mol_type = protein
                        organism = Vitis vinifera
SEQUENCE: 211
MLKDEGCNAD AAAGGGGGWA RVCDTCRSAA CTIYCRADSA YLCAGCDARI HAANRVASQH  60
ERVWVCESCE RAPAAFVCKA DAASLCATCD ADIHSANPLA RRHHRVPVLP IAGCLYGPPA  120
TDPGGTVTID EEDEDEAASW LLLNPVKNNN GSSNNQNNGL LFGGEVDEYL DLVEYNSCPE  180
NQFSDQYNQQ QPPPHYSVPH KNYGGDRVVP VQCGEAKGQL HQQHQQQGFH LGMDHSVSVS  240
SMDVGVVPEA TTMSDISISI SHPRPPKGTI DLFSGPPIQM PTQLTPMDRE ARVLRYREKK  300
KTRKFEKTIR YASRKAYAET RPRIKGRFAK RTDVEVEVDQ MFSTTLMAES GYGIVPSF    358

SEQ ID NO: 212          moltype = AA  length = 338
FEATURE                 Location/Qualifiers
REGION                  1..338
                        note = misc_feature - Public GI ID no. 157327254
REGION                  1..338
                        note = misc_feature - Bit score of 612.5 for hmm based on
                         sequences of FIGURE 2.
REGION                  1..48
                        note = misc_feature - Pfam Name: zf-B_box Pfam Desc: B-box
                         zinc finger
REGION                  271..315
                        note = misc_feature - Pfam Name: CCT Pfam Desc: CCT motif
REGION                  1..338
                        note = misc_feature - Functional Homolog Of SEQ ID NO. 20
source                  1..338
                        mol_type = protein
                        organism = Vitis vinifera
SEQUENCE: 212
MASKLCDSCK SAPPTLFCRA DSAFLCVACD SKVHAANKLA SRHARVWMCE VCEQAPAHVT  60
CKADAAALCV TCDRDIHSAN PLARRHERVP VVPFYDSAAA AAKSNAVNLL VDDRYYSDPD  120
GDASREEAEA ASWLLPNPNP KLAESSDLNS SHYMFSDIDP YLDLDYPSMD PKLQSQQQQQ  180
SSGTDGVVPV QNKSVQAPLV NDNCFDMDFS GSKSFYNGQS LSQSVSSSSL EVGVVPDGNA  240
MVDVTNPFGR SMNTGSESAN QTAQISSGID REARVLRYRE KRKNRKFEKT IRYASRKAYA  300
ETRPRIKGRF AKRSEIEVDY SSSGALTADS GYGVVPSF                          338
```

```
SEQ ID NO: 213          moltype = AA  length = 395
FEATURE                 Location/Qualifiers
REGION                  1..395
                        note = misc_feature - Public GI ID no. 187830112
REGION                  1..395
                        note = misc_feature - Bit score of 326.8 for hmm based on
                         sequences of FIGURE 2.
REGION                  324..368
                        note = misc_feature - Pfam Name: CCT Pfam Desc: CCT motif
REGION                  27..74
                        note = misc_feature - Pfam Name: zf-B_box Pfam Desc: B-box
                         zinc finger
REGION                  1..395
                        note = misc_feature - Functional Homolog Of SEQ ID NO. 20
source                  1..395
                        mol_type = protein
                        organism = Zea mays
SEQUENCE: 213
MDYNFDTSVL DEDVAGRGGR EGSCPPAWAR ACDGCRAAPS VVYCHADTAY LCASCNSRVH  60
AANRVASRHE RVRVCEACEC APAVLACRAD AAALCAACDA QVHSANPLAG RHQRVPVLPL  120
PAAAVPAASV LAEAAATAAA VAGDKDEEVD SWLLLTKDPD DDDKNHNCSS NNNNISSNTS  180
TFYADVDEYF DLVGYSSYCD NHINSNTKQY GMQEQQLLLH KEFGDKEGSE YVVPSQVGQQ  240
QSGYHRVIGT EQAASMTPGV SAYTDSISNS ISFSSSMEVG IVPDNMATTD MPSSGILLTP  300
AGAISLFSSG PPLQMPLHLA SMDREARVLR YREKKKSRKF EKTIRYATRK TYAEARPRIK  360
GRFAKRSSDM DVEVDQMFSA AALSSDGSYG TVPWF                           395

SEQ ID NO: 214          moltype = AA  length = 317
FEATURE                 Location/Qualifiers
REGION                  1..317
                        note = misc_feature - Public GI ID no. 110277457
REGION                  1..317
                        note = misc_feature - Bit score of 385.4 for hmm based on
                         sequences of FIGURE 2.
REGION                  1..48
                        note = misc_feature - Pfam Name: zf-B_box Pfam Desc: B-box
                         zinc finger
REGION                  256..300
                        note = misc_feature - Pfam Name: CCT Pfam Desc: CCT motif
REGION                  1..317
                        note = misc_feature - Functional Homolog Of SEQ ID NO. 20
source                  1..317
                        mol_type = protein
                        organism = Medicago sativa
SEQUENCE: 214
MATKLCDSCK SSKATLFCRS DSAFLCLTCD SNIHAANKLA SRHHRVTLCQ VCEQAPAHVT  60
CKADAAALCI SCDHDIHSAN PLARRHERVP LTTFHHHNNN SQQQSFFSEN DHDATNEEAG  120
AASWLLQTPS NPKFPDLNYS HYSYPEIDDF VTVNAKTDTP EQNSPGTTAD GVVPVQSQSK  180
TTTEHQHEHY SDINIDFSNS KPFTYNFNHT VSSPSMEVGV VPDGNVMTEI SYCGYQTTAT  240
ETAPMTVAVP MTAVEREARV SRYREKRKNR KFEKTIRYAS RKAYAETRPR IKGRFAKRSD  300
LNMNLIAEDE YGVVPSC                                               317

SEQ ID NO: 215          moltype = DNA  length = 1290
FEATURE                 Location/Qualifiers
misc_feature            1..1290
                        note = Ceres Annot ID no. 8736698
misc_feature            1..1290
                        note = Encodes the peptide sequence at SEQ ID NO. 216
source                  1..1290
                        mol_type = other DNA
                        organism = Sorghum bicolor
SEQUENCE: 215
atggcaaagg atctgccgat gatgcaaagg aggagtctgg aagctgccgg tcgttatgtg  60
gaggagtttc gctccaacgc tctcgacgag gaggaggtcg ctggaagagg cggggaagga  120
gggagctgcg ccgcagcacc agcatgggcc aggccctgcg acgggtgccg ggcggcgccc  180
agcgtggtgt actgccacgc cgacgcggcg tacctgtgcg cgtcgtgcga cgtgcgggtg  240
cacgccgcca accgcgttgc gtcgcgccac gagcgcgtgc gcgtgtgcga ggcctgcgag  300
cgcgcgccag cagtgctggc gtgccgcgcc gacgccgccg cgctctgcgt cgtctgcgac  360
gcgcaggtcc actccgcgaa cccgctggcc gggaggcacc agcgcgtgcc cgtgctgccg  420
ctcccccgtcg cggccatccc ggctgcttcc gtgctcgccg aggctgcggc caccgccgtg  480
gccgtgggtg acaagcagga agaggaggtg gactcgtggc tgctgctcac caacaccaag  540
gatccagttt cagacaacaa caactgcaac tgcagcagca gcagcaacaa caacatcagc  600
agcagcaaca ccagcacctt ctacgcggat gttgatgagt actttgatct cgtgggctac  660
aattcctact gtgacaacca catcaacagc aacccaaagc agtacgggat gcaagaacga  720
cagcaacagc agcagctgct gctgcaaaag gaatttggag acaaggaggg aagcgagcac  780
gttgtgcctg cttcacaggt cgcgatggca aatgagcagc agcagagtgg ttatggagtt  840
attggggtag agcaggctgc ctccatgact gccgcggtca gtgcttacac agattccatc  900
actaacagca tatctttctc atcatcaatg gaggtgggta tagtcccaga caacatggca  960
acgacgacag acatgccaaa ctccggcatc ctgctgacac ctgctgaggc catcagcctc  1020
```

```
ttctcgtcag gttcttcgct tcagatgcca ctccacttga cctccatgga cagagaggcc  1080
agggtcctca ggtacaagga gaagaagaag agcagaaagt tcgcgaagac catacgatat  1140
gcgacgagga agacatatgc agaagcaagg ccgaggatca agggccgctt cgccaagaga  1200
tcttctgata tggaaatcga agtggaccag atgttctcat ctgcagctct gtcgtctgat  1260
ggtagctacg gtacggttct atggttctga                                   1290

SEQ ID NO: 216          moltype = AA  length = 429
FEATURE                 Location/Qualifiers
REGION                  1..429
                        note = misc_feature - Ceres Annot ID no. 8736698
REGION                  1..429
                        note = misc_feature - Bit score of 297.5 for hmm based on
                         sequences of FIGURE 2.
REGION                  358..402
                        note = misc_feature - Pfam Name: CCT Pfam Desc: CCT motif
REGION                  48..95
                        note = misc_feature - Pfam Name: zf-B_box Pfam Desc: B-box
                         zinc finger
REGION                  1..429
                        note = misc_feature - Functional Homolog Of SEQ ID NO. 20
source                  1..429
                        mol_type = protein
                        organism = Sorghum bicolor
SEQUENCE: 216
MAKDLPMMQR RSLEAAGRYV EEFRSNALDE EEVAGRGGEG GSCAAAPAWA RPCDGCRAAP  60
SVVYCHADAA YLCASCDVRV HAANRVASRH ERVRVCEACE RAPAVLACRA DAAALCVVCD  120
AQVHSANPLA GRHQRVPVLP LPVAAIPAAS VLAEAAATAV AVGDKQEEEV DSWLLLTNTK  180
DPVSDNNNCN CSSSSNNNIS SSNTSTFYAD VDEYFDLVGY NSYCDNHINS NPKQYGMQER  240
QQQQQLLLQK EFGDKEGSEH VVPASQVAMA NEQQQSGYGV IGVEQAASMT AAVSAYTDSI  300
TNSISFSSSM EVGIVPDNMA TTTDMPNSGI LLTPAEAISL FSSGSSLQMP LHLTSMDREA  360
RVLRYKEKKK SRKFAKTIRY ATRKTYAEAR PRIKGRFAKR SSDMEIEVDQ MFSSAALSSD  420
GSYGTVLWF                                                          429

SEQ ID NO: 217          moltype = DNA  length = 1125
FEATURE                 Location/Qualifiers
misc_feature            1..1125
                        note = Ceres Annot ID no. 8671780
misc_feature            1..1125
                        note = Encodes the peptide sequence at SEQ ID NO. 218
source                  1..1125
                        mol_type = other DNA
                        organism = Sorghum bicolor
SEQUENCE: 217
atggaggccc tggtggcggg gaggtactgg ggtgtcgggg gacggcggtg cgaggcgtgc  60
gggggctcgc cggcggcggt gcactgccgg acgtgcccgg gcggcggggc gtacctgtgc  120
gcggggtgcg acgcgggcca cgcgcgggcc gggcacgaga gggtgtgggt gtgcgaggtg  180
tgcgagcgcg cgccggccgc cgtcacgtgc cgcgccgacg cggccgcgct ctgcgccgcg  240
tgcgacgccg acatccacga cgcgaacccg ctggcgcgcc gccacgagcg cgtgcccgtg  300
cagcccatcg gcgcggccgc ggccgcgccc gccgcggaga cgctgctgtt cggcgccgcc  360
gcggaagaga atcaggacga cgacgacggc gccgccgcgg cggctaaggt cgtcggcgtc  420
gacgccggta agctggcgga cttcctgttc gcggacgtca tggacccgtt cttcggccaa  480
gacttcactg gtggcaccag gttcccgcac gccgacagcg ttgtgcctaa ccagggatcc  540
tgcggcgccg tcgctgccaa gccgtcctac agctcctaca ccgcggcgtc gctcggccac  600
agcggctcgt cgtcggaggt cggcctggtc ccagacgcga tgtgcggccg cggcgggagc  660
gtgaccggcg gcgtcatcga gctcgacttc gcgcagtcca aggccgccta cctgccttac  720
gctgcaactc cgacccacag tatgtcatct ttggacgtgg gtgcggtgcc ggaacgcggt  780
gacggggtca tggcgggcag ggtcgcgacg ccgccggcgg cggcggccgc ggagagcagg  840
gaggcgcggc tgatgcggta ccgcgagaag cggaagaacc ggcggttcga gaagacgatc  900
cgctacgcgt cccggaaggc ctacgcggag tcgcggccgc gcatcaaggg ccgcttcgcg  960
aagcgcgcgg acgacaacga cgccgacgcc gacgccgact tcgacttcga cgcgggtgcc  1020
gcggcggcga cggcgccggc gcggtcgcgg tcgcagcagc agcagccatc gtacccctat  1080
gtgctcgact tcgccgccgg ctacggcgtc gtgcccacat tctga                  1125

SEQ ID NO: 218          moltype = AA  length = 374
FEATURE                 Location/Qualifiers
REGION                  1..374
                        note = misc_feature - Ceres Annot ID no. 8671780
REGION                  1..374
                        note = misc_feature - Bit score of 474.1 for hmm based on
                         sequences of FIGURE 2.
REGION                  280..324
                        note = misc_feature - Pfam Name: CCT Pfam Desc: CCT motif
REGION                  53..100
                        note = misc_feature - Pfam Name: zf-B_box Pfam Desc: B-box
                         zinc finger
REGION                  1..374
                        note = misc_feature - Functional Homolog Of SEQ ID NO. 20
source                  1..374
                        mol_type = protein
```

```
                        organism = Sorghum bicolor
SEQUENCE: 218
MEALVAGRYW GVGGRRCEAC GGSPAAVHCR TCPGGGAYLC AGCDAGHARA GHERVWVCEV  60
CERAPAAVTC RADAAALCAA CDADIHDANP LARRHERVPV QPIGAAAAAP AAETLLFGAA  120
AEENQDDDDG AAAAAKVVGV DAGKLADFLF ADVMDPFFGQ DFTGGTRFPH ADSVVPNQGS  180
CGAVAAKPSY SSYTAASLGH SGSSSEVGLV PDAMCGRGGS VTGGVIELDF AQSKAAYLPY  240
AATPTHSMSS LDVGAVPERG DGVMAGRVAT PPAAAAAESR EARLMRYREK RKNRRFEKTI  300
RYASRKAYAE SRPRIKGRFA KRADDNDADA DADFDFDAGA AAATAPARSR SQQQQPSYPY  360
VLDFAAGYGV VPTF                                                   374

SEQ ID NO: 219          moltype = AA  length = 367
FEATURE                 Location/Qualifiers
REGION                  1..367
                        note = misc_feature - Public GI ID no. 186911828
REGION                  1..367
                        note = misc_feature - Bit score of 434.9 for hmm based on
                         sequences of FIGURE 2.
REGION                  13..60
                        note = misc_feature - Pfam Name: zf-B_box Pfam Desc: B-box
                         zinc finger
REGION                  298..342
                        note = misc_feature - Pfam Name: CCT Pfam Desc: CCT motif
REGION                  1..367
                        note = misc_feature - Functional Homolog Of SEQ ID NO. 20
source                  1..367
                        mol_type = protein
                        note = subspecies = vulgaris
                        organism = Beta vulgaris
SEQUENCE: 219
MMKEEVSGSD TNSWARVCDT CRAAPCTVYC RADSAFLCTS CDARIHAANQ VASRHERVWV  60
CEACERAPAA FLCKADAASL CATCDAEIHS ANPLARRHQR VPIMPVAGCV YGPQGGRMSE  120
DRFLTLPEGD DHTTDHEGDE DEAASWLLLN PVKNSNNQNT NGFLTGGGEV DEYLDLLEYN  180
SGADNQLCEQ YNQQQEFKVP EKNCGGDSVV PVQCREAKDH QIQYQNFLFG MECETKSGYT  240
YNTSISQSVS VSSMDVGVVP ESAMSDISMS HPRPPKGTID LFSSPPMQVP TQLSPLDREA  300
RVMRYREKKK NRKFEKTIRY ASRKAYAETR PRIKGRFAKR TDVEAEMDQM FTNSLMADSG  360
YGIVPSY                                                           367

SEQ ID NO: 220          moltype = AA  length = 368
FEATURE                 Location/Qualifiers
REGION                  1..368
                        note = misc_feature - Public GI ID no. 168062896
REGION                  1..368
                        note = misc_feature - Bit score of 368.4 for hmm based on
                         sequences of FIGURE 2.
REGION                  301..345
                        note = misc_feature - Pfam Name: CCT Pfam Desc: CCT motif
REGION                  1..47
                        note = misc_feature - Pfam Name: zf-B_box Pfam Desc: B-box
                         zinc finger
REGION                  1..368
                        note = misc_feature - Functional Homolog Of SEQ ID NO. 20
source                  1..368
                        mol_type = protein
                        note = subspecies = patens
                        organism = Physcomitrella patens
SEQUENCE: 220
MPKSCDACQA SSAVVYCRAD AAYLCLGCDG KVHGANKLAS RHERLWMCEV CEVAAAVVTC  60
KADAASLCVS CDTDIHSANP LAQRHERVPV QPLFDCVSQF RGTHFSVLAP KNECNNNLLK  120
GDEDPAVAEA VSWLLPHPKT LSSAILRGIA AADEAPAFPF RERPFSPKLK KLKVEQAADI  180
YSDVDPFLVL DGGNGTGFQP DSMVPVHIPE GPDDSPSLAN STAPSSAINF RASQKSGCSY  240
GTSTLTHSMS CSSVDAAVVP DSSLSDISTP YSKALDSQDS QDLSGALVPH QASKPIDTVD  300
REARVMRYKE KRQKRKFEKT IRYASRKAYA ESRPRIKGRF TKRTDSDVEQ MFSSCTADSG  360
FGVVPSSC                                                          368

SEQ ID NO: 221          moltype = AA  length = 342
FEATURE                 Location/Qualifiers
REGION                  1..342
                        note = misc_feature - Public GI ID no. 194244852
REGION                  1..342
                        note = misc_feature - Bit score of 286.3 for hmm based on
                         sequences of FIGURE 2.
REGION                  7..54
                        note = misc_feature - Pfam Name: zf-B_box Pfam Desc: B-box
                         zinc finger
REGION                  280..324
                        note = misc_feature - Pfam Name: CCT Pfam Desc: CCT motif
REGION                  1..342
                        note = misc_feature - Functional Homolog Of SEQ ID NO. 20
source                  1..342
```

```
                        mol_type = protein
                        organism = Brassica nigra
SEQUENCE: 221
MLKQESNWAQ ACDTCRSAAC TVYCRADSAY LCTSCDAQIH AANRLASRHE RVRVCESCER  60
APAAFFCKAD AASLCTACDS QIHSANPLAR RHQRVPILPI SGCVATNHHS SETTEPENIV  120
VVGQEEEDEA EAASWLLPSS VKNCGDNNNN TENNRFSVGE EYLDLVDYSS SIDKRFTGQT  180
NQYQQDYNVP QRSYVADGVV PLQVGVSKGH MHHEQHNFQF GFTNVSSEAH QISNGSPIHM  240
VSLVPESVTS DATVSHQRSP KAGTEELPEA PVQMLSPMER KARVLRYREK KKTRKFEKRI  300
RYASRKEYAE KRPRIKGRFA KRNEVDADQA FPTVVMFDTG YG                    342

SEQ ID NO: 222          moltype = DNA  length = 1011
FEATURE                 Location/Qualifiers
misc_feature            1..1011
                        note = Ceres Annot ID no. 8680182
misc_feature            1..1011
                        note = Encodes the peptide sequence at SEQ ID NO. 223
source                  1..1011
                        mol_type = other DNA
                        organism = Sorghum bicolor
SEQUENCE: 222
atggacaccg cggtggagct ggagctggag cagaagccgg cggtgggtta ctggagcgtg  60
gtgggcgccc ggccctgcga cgcgtgcgcc gcggagccgg cgcggctgca ctgccgcgag  120
gacggcgcgt tcctgtgccc cggctgcgac gcccgggcgc acggcgccgg gtcccgccac  180
gcgcgcgtct ggctgtgcga ggtctgcgag cacgcccccg ccgccgtcac ctgccgcgcc  240
gacgccgccg cgctctgcgc cgcctgcgac gccgacatcc actcggccaa cccgctcgcg  300
cgccgccacg agcgcctccc cgtcgcgccc ttcttcggcg cgctcgctga cgcgccccag  360
cccttcccgt ccccggcctt cgccgccgct gccgcagcgg ggggccaggc tcaggggggaa  420
gccgcggcgg cggacaacga cgacgacgac gggagcaacg aggccgaggc ggcgtcgtgg  480
ctgctcgccg agcccgacaa cagccacgag gacagcgccg ccgccaccgc cgccgacacg  540
ttgttcgcgg aatcggacgc gtacctcggc gtcgacctgg acttcgcccg gtgcatggac  600
ggcgtcaagg ccatcggcgt gccggtcgcg ccgcccgagc tggacatcgc tgccggcagc  660
tttttctacc ccgaacactc catgaaccac agtttgtcgt cgtcggaggt ggcggtggtg  720
ccggacgcgc aggcggccgg cgtgccggcg gtggtgagca gggggaagga gcgggaggcg  780
cggctgatgc ggtaccgtga gaagcgcaag aaccgccggt tcgacaagac catccgctac  840
gcgtcccgca aggcgtacgc cgagacgcgg ccgcgcatca agggccgctt cgccaagcgc  900
tgctccgcgg aggccgacga cgacgcgctg gagcacgacg aaggcgcgtg cttctcgccc  960
gcggggtcgg cgcacgcggc gtcggacggc gtcgtcccgt ccttctgttg a          1011

SEQ ID NO: 223          moltype = AA  length = 336
FEATURE                 Location/Qualifiers
REGION                  1..336
                        note = misc_feature - Ceres Annot ID no. 8680182
REGION                  1..336
                        note = misc_feature - Bit score of 634.7 for hmm based on
                         sequences of FIGURE 2.
REGION                  258..302
                        note = misc_feature - Pfam Name: CCT Pfam Desc: CCT motif
REGION                  21..65
                        note = misc_feature - Pfam Name: zf-B_box Pfam Desc: B-box
                         zinc finger
REGION                  1..336
                        note = misc_feature - Functional Homolog Of SEQ ID NO. 20
source                  1..336
                        mol_type = protein
                        organism = Sorghum bicolor
SEQUENCE: 223
MDTAVELELE QKPAVGYWSV VGARPCDACA AEPARLHCRE DGAFLCPGCD ARAHGAGSRH  60
ARVWLCEVCE HAPAAVTCRA DAAALCAACD ADIHSANPLA RRHERLPVAP FFGALADAPQ  120
PFPSPAFAAA AAAGGQAQGE AAAADNDDDD GSNEAEAASW LLAEPDNSHE DSAAATAADT  180
LFAESDAYLG VDLDFARCMD GVKAIGVPVA PPELDIAAGS FFYPEHSMNH SLSSSEVAVV  240
PDAQAAGVPA VVSRGKEREA RLMRYREKRK NRRFDKTIRY ASRKAYAETR PRIKGRFAKR  300
CSAEADDDAL EHDEGACFSP AGSAHAASDG VVPSFC                            336

SEQ ID NO: 224          moltype = DNA  length = 2463
FEATURE                 Location/Qualifiers
misc_feature            1..2463
                        note = Ceres Annot ID no. 8457344
misc_feature            1..2463
                        note = Encodes the peptide sequence at SEQ ID NO. 225
source                  1..2463
                        mol_type = other DNA
                        organism = Solanum lycopersicum
SEQUENCE: 224
atggctactt ctgagaattg ccggaacgct gccggcgccg gaaaagttga tgctgagaaa  60
gcgttgtaca cggagctatg gcgagcatgt gcaggtccgc ttgtgacagt gccatgtgaa  120
ggcgagctgg tgttctattt cccacaaggt catattgaac aggttgaagc atcaacaaac  180
caagcttcag accagcagat gccagtatat aatcttcctt ctaagatcct ctgtcgtgtg  240
attaacgtcc tgctgaaggc tgaacccgat acagatgagg tgtatgcaca agtgactttg  300
ttgccagaac caaatcaaga tgagaatgtg gtatcaaagg aaccgatgcc ctctccgcca  360
```

```
ccacgattcc atgtgcactc tttttgtaag acattaacag cctctgatac cagcactcat  420
ggaggatttt ctgtcttgag acggcatgct gatgaatgcc tcccgcctct ggatatgtct  480
cggcagcctc caacacagga gttggtggcc aaagatttgc atgcaaatga gtggcgcttc  540
aggcacatat tccggggcca gcctaggagg caccttcttc agagtggttg gagtgtcttt  600
gttagttcga aaaggcttgt tgcaggggat gcattcatat ttcttagagg tgagaatggg  660
gagcttcgtg ttggagtccg acgtgccatg agacagcagg gtaatgctcc atcatcagtg  720
atatccagtc atagcatgca tcttggtgtc cttgctacag cttggcatgc tattcagacg  780
aaaacactga cgagccctgc tgactttata gttccatatg atcagtatat ggagtctctg  840
aaaaacaatt actccatcgg gatgaggttt aaaatgaggt ttgaaggtga agaagctcca  900
gaacagaggt ttactggaac tatagttggc attgaaaatg ctgacctcaa aggtggcct  960
gagtcaaaat ggagatgcct gaaggttcga tgggatgaaa cttctgctat tcctaggcca  1020
gaccgagttt caccctggaa agtagagcca gctcttagcc ctcctgcact taatccactt  1080
ccaataccaa ggcagaaaag gccgcgatca aatgttctgc cctcgtctcc tgattcttct  1140
gtacttacta gggaaggttc atccaaagta gttgtagaca cttcacaagc cagtgggttt  1200
tcaagagttt tgcaaggtca agaaatatca accttgagag gcaattttgt agaaaataac  1260
gagtcggact cttctgagaa gccacctata tggcaaccat tactggatga cgagaaggct  1320
gatgttcatt ctgcgtcaag gaaatgtata tcagataaac ggcttccttt agggaggcct  1380
gaatcatctt ttacagatct tttatcaggt tttgggggc aatctagttc atctcatgga  1440
ttccattcac ccactggggg ccaaacagca cctgctagct gggttaagcg acaagctctg  1500
gataaggaaa ctgatttcag cttactggca aaacaatggt ctctagtgtc ttctggtctc  1560
tcacttaatc tgatggaatc aggattgaag ggtgcagata ctctgtatca aatgcgggga  1620
acatctcgac tcaattgttt taacgagtat ccaaccttcc ctggtcatag acctgacaat  1680
cagcagggaa attggttaat gcccccgtcc gtgctgcctt atattcagat gtccgctcat  1740
tctggagaaa ttatgcctaa acccatggct tcaccacagc ccgaagccat gaaacccaaa  1800
gaagggaact gcaaactatt tggcattccc cttgtaagta aatgtgccac catagatcct  1860
gtcatgttgc ggaaaaattc cccgattcac tcaacaagta acatgcactt tggtatacat  1920
ccacatcaat tccctataat tgaatctgat caaaggtctg agcaatcaaa gggatcaaag  1980
ctaccagatg atggcttcat agttcatgat caggaagaac aattccaaac ctctcatcct  2040
ggtactcgag atagagaggg caaaggcctt gttcattcaa caaggagttg caccaaggtt  2100
cataaacagg gtacagccct tggaaggtct gttgatcttg caaagttcaa caactatgaa  2160
gaattgatag ctgaactgga tcacattttt gattttaatg gtgagctcaa ggctcgtaac  2220
aagaactggc tggttgtata tactgatgat gagggtgaca tgatgcttgt tggagatgat  2280
ccatgggaat tttgtggtat ggttcggaag atttttatct acacgaaaga tgaggtgcag  2340
cggatgaacc ctgggactct caattcaaaa ggcgaggaca attcttctgt tgcagaaggc  2400
tctgatgcta aagaagtgaa gaatctacag cttcacattg attccagtcc ggaagattct  2460
tag                                                                2463

SEQ ID NO: 225         moltype = AA  length = 820
FEATURE                Location/Qualifiers
REGION                 1..820
                       note = misc_feature - Ceres Annot ID no. 8457344
REGION                 1..820
                       note = misc_feature - Bit score of 1560.8 for hmm based on
                        sequences of FIGURE 5.
REGION                 254..328
                       note = misc_feature - Pfam Name: Auxin_resp Pfam Desc:
                        Auxin response factor
REGION                 127..232
                       note = misc_feature - Pfam Name: B3 Pfam Desc: B3 DNA
                        binding domain
REGION                 1..820
                       note = misc_feature - Is Acted Upon By Ceres SEEDLINE ID
                        no. ME00572 at SEQ ID NO. 111
source                 1..820
                       mol_type = protein
                       organism = Solanum lycopersicum
SEQUENCE: 225
MATSENCRNA AGAGKVDAEK ALYTELWRAC AGPLVTVPCE GELVFYFPQG HIEQVEASTN  60
QASDQQMPVY NLPSKILCRV INVLLKAEPD TDEVYAQVTL LPEPNQDENV VSKEPMPSPP  120
PRFHVHSFCK TLTASDTSTH GGFSVLRRHA DECLPPLDMS RQPPTQELVA KDLHANEWRF  180
RHIFRGQPRR HLLQSGWSVF VSSKRLVAGD AFIFLRGENG ELRVGVRRAM RQQGNAPSSV  240
ISSHSMHLGV LATAWHAIQT KTLTSPADFI VPYDQYMESL KNNYSIGMRF KMRFEGEEAP  300
EQRFTGTIVG IENADLKRWP ESKWRCLKVR WDETSAIPRP DRVSPWKVEP ALSPPALNPL  360
PIPRQKRPRS NVLPSSPDSS VLTREGSSKV VVDTSQASGF SRVLQGQEIS TLRGNFVENN  420
ESDSSEKPPI WQPLLDDEKA DVHSASRKCI SDKRLPLGRP ESSFTDLLSG FGGQSSSSHG  480
FHSPTGGQTA PASWVKRQAL DKETDFSLLA KQWSLVSSGL SLNLMESGLK GADTLYQMRG  540
TSRLNCFNEY PTFPGHRPDN QQGNWLMPPS VLPYIQMSAH SGEIMPKPMA SPQPEAMKPK  600
EGNCKLFGIP LVSKCATIDP VMLRKNSPIH STSNMHFGIH PHQFPIIESD QRSEQSKGSK  660
LPDDGFIVHD QEEQFQTSHP GTRDREGKGL VHSTRSCTKV HKQGTALGRS VDLAKFNNYE  720
ELIAELDHIF DFNGELKARN KNWLVVYTDD EGDMMLVGDD PWEFCGMVRK IFIYTKDEVQ  780
RMNPGTLNSK GEDNSSVAEG SDAKEVKNLQ LHIDSSPEDS                        820

SEQ ID NO: 226         moltype = AA  length = 563
FEATURE                Location/Qualifiers
REGION                 1..563
                       note = misc_feature - Public GI ID no. 157327120
REGION                 1..563
                       note = misc_feature - Bit score of 794.2 for hmm based on
                        sequences of FIGURE 5.
```

```
REGION                 202..281
                       note = misc_feature - Pfam Name: Auxin_resp Pfam Desc:
                        Auxin response factor
REGION                 75..180
                       note = misc_feature - Pfam Name: B3 Pfam Desc: B3 DNA
                        binding domain
REGION                 1..563
                       note = misc_feature - Is Acted Upon By Ceres SEEDLINE ID
                        no. ME00572 at SEQ ID NO. 111
source                 1..563
                       mol_type = protein
                       organism = Vitis vinifera
SEQUENCE: 226
MEQLQASTNQ GVDQRIPLFN LPSKILCRVV HTRLLAEQET DEVYAQITLQ PEADQTEPKS  60
PDSCPDEAPK QTVHSFCKIL TASDTSTHGG FSVLRKHANE CLPPLDMSQA TPTQELVARD  120
LHGYEWRFKH IFRGQPRRHL LTTGWSTFVT SKRLVAGDAF VFLRGDNGEL RVGVRRLARQ  180
QSPMPSSVIS SQSMHLGVLA TASHAVTTQT LFVVYYKPRT SQFIISLNKY LEAVNYGFAV  240
GMRFKMRFEG EDSPERRFTG TIVGIGDISP QWSNSKWRSL KIQWDEPATI QRPERVSSWD  300
IEPFVASASL NLTQPPVKIK RPRPLDLPVA VPSPFWYAGS SPSHELTQLD SKTVSTRSIL  360
SGYNTSLSSR PNNGLISDQV EKGKRIEASI GCRLFGIDLT NNSKATALLE MIQNLDVSKS  420
SNEQKQVVPE ASQKETQGRQ SCTPSSRTRT KKVQMQGVAV GRAVDLTALE GYDELISELE  480
KMFEIKGELC PRNKWEVVFT DDEGDMMLVG DDPWQEFCKM VRKIFIYSSE EVKKMSPRCK  540
LSTSSLDGEG TVISLDSELR TEP                                         563

SEQ ID NO: 227         moltype = AA  length = 737
FEATURE                Location/Qualifiers
REGION                 1..737
                       note = misc_feature - Public GI ID no. 157358702
REGION                 1..737
                       note = misc_feature - Bit score of 957.5 for hmm based on
                        sequences of FIGURE 5.
REGION                 278..360
                       note = misc_feature - Pfam Name: Auxin_resp Pfam Desc:
                        Auxin response factor
REGION                 151..256
                       note = misc_feature - Pfam Name: B3 Pfam Desc: B3 DNA
                        binding domain
REGION                 1..737
                       note = misc_feature - Is Acted Upon By Ceres SEEDLINE ID
                        no. ME00572 at SEQ ID NO. 111
source                 1..737
                       mol_type = protein
                       organism = Vitis vinifera
SEQUENCE: 227
MIDLNTVDDD ETPSSGSSSS SSSSASASAS TVCGSLLSAA SSVCLELWHA CAGPLISLPK  60
KGSLVVYFPQ GHLEQLSDYP AVAYDLPPHV FCRVVDVKLH AEVVTDEVYA QVSLVPETKQ  120
IKQKLQEGEI EADGGEEEDI EGSIKSMTPH MFCKTLTASD TSTHGGFSVP RRAAEDCFPP  180
LDYKQQRPSQ ELVAKDLHGF EWRFRHIYRG QPRRHLLTTG WSAFVNKKKL VSGDAVLFLR  240
GGDGELRLGI RRAAQIKGSS PFPALCSQQL NLNTLTAVVN AISTRSVFNI CYNPRASSSE  300
FIIPLRKFSK SIDHSFSAGM RFKMRVETED AAERRYTGLI TGISDMDPVR WPGSKWRCLL  360
VRWDDIEANR HNRVSPWEIE LSGSLSGSGS LTVPGSKRTR IGLPGTRPDF SVPNGMGVSD  420
FGESSRFQKV LQGQEIFGFN TPYDGVDTQD HHPSEIRCFP GSSCSGIAAI GNGVRNPLGN  480
SDISYKGIGF GESFRFHKVL QGQETFPSPP CGRALSANQA HENGSFGIFD GVQVPTSRNG  540
WPALVQGYNA HTHLSTPSVQ VSSPSSVLMF QQASTAAPNI YSMHSANNQE KEQEISNRSS  600
FDIPEVYGEK LTPSRCELSV RGGGQGGMNF FGLLNEHNQL AVPHPLVTQS AFRGSQDLVP  660
TCKSSCRLFG FSLTEERSIG NKVDNPTPVT SSLIPGTSFL PQQLHSEPPV MTKAIGSNCT  720
KVSDFYAVRD MLFDIAL                                                737

SEQ ID NO: 228         moltype = DNA  length = 2922
FEATURE                Location/Qualifiers
misc_feature           1..2922
                       note = Ceres Clone ID no. 1892720
misc_feature           1..2922
                       note = Encodes the peptide sequence at SEQ ID NO. 229
source                 1..2922
                       mol_type = other DNA
                       organism = Panicum virgatum
SEQUENCE: 228
aaaaaaaaaa cccaacgcct cggctccaag ccagccagcc aaccaacccg ccccgggcag  60
caaagcacag gcgcacgagc tcccacagct ccccagctcc acgcctcctc cctcgcgctc  120
ccgccatcct ctcctccgcc gcgcgccttc ccgcccgccg agcctttggg gtggttccgg  180
agtcgcggcc gcgcgcgcga gagcgagacc ctcccctgct gccgagcgta aatctgccga  240
gctcggcatg gggtgaccag atcggggcgc ggctcggtgc tctacggctg aattccgctc  300
gaggaggggg gtttgccttg cctagaagag gccgcgggga tggcgaacgc cggcgtggcc  360
gtcggctcag ggggtgttag ccatgctttg ttcagggaac tctggcatgc ttgtgctggg  420
ctgttggtca cggtgcctcg ccaaggcgag ctggtttact acttcccgca aggtcatatg  480
gaacagcttg aagcatctac agatcagcaa cttgaccagc acttaccttt gtttaatcta  540
ccatccaaga tcctgtgcaa ggtggtaaat gtagaactca gagctgaaac tgattccgat  600
gaagtttatg ctcaaattat gctgcaacca gaagcagatc aaagtgagcc caccagccca  660
```

-continued

```
gctcctgagc taccagagcc agaaaggtgc aatgtccatt ccttctgcaa gactttgact  720
gcttcagaca cgagcaccca tggtggtttc tctgtcctca ggagacatgc tgaagaatgt  780
ttgccccaat tggatatgac tcagaaccca ccgtggcaag aactggtggc taaagatctc  840
catggaaatg aatggcattt ccgtcacatc tttcgaggtc aaccaaggag gcatctactt  900
acaacaggtt ggagtgtttt tgttagctca aaaagattgg ttgccggtga tgcatttatc  960
tttttgagag gtgagaatgg agagctacga gtcggggtaa gaaggctcat gaggcaagta  1020
aataacatgc catcatcagt tatctcaagc cacagcatgc atcttggagt cctcgcaact  1080
gcatctcatg ccatctccac tggaactctc ttttctgttt tctacaaacc cagaacaagt  1140
cgatcggagt ttgttgtgag cgtaaacaag taccttgaag ctaagaatca caagatgtct  1200
gtcggtatga ggtttaaaat gagatttgag ggtgatgaat ctcctgaaag aagatttagt  1260
ggaacaatta ttggtctggg aagcatgcca gctaactcaa catctccgtg ggctgactct  1320
gattggagat ctttgaaggt ccaatgggat gagccttctg ctgttgtccg tccagataga  1380
gtttcaccat gggaactaga accccttgat gcaactaaca cacaaccgcc tcagcctcct  1440
ttacggagta agcgtgcacg gcctcctgct tcaccttcta ttgctccaga acttcctcca  1500
gcttttggtt tttggaaatc ccccacctgag cctacccatg ctttctcatt ttcgggactg  1560
cagcgaaccc aggaactata ccattcaaat cccaattcga tcttttcatc atcgttgaat  1620
gtgggattta attcaaagaa cgagcattct actccaacca acaatcattt gtattggcca  1680
attcgagaca ctagaacgga atcctactct gctagcatta acaaacttcc acctgaaagg  1740
aagcaagaat tcactattgc tggctgcaga ttgtttggta ttgagttaag taatgcagta  1800
tcaccagtgg ttgctgttgc tagtgctggt caagaccaac cacctgttgt gtcagtagat  1860
gttgagcctg atcagctgtc acagccatcc caagccaaca aaacggatgc cccagcagca  1920
agcagtgagc gctctcctca tgagactgag agccggcaag tcaggagctg caccaaggta  1980
atcatgcaag gaatggcggt tggcagggca gtggacttga cgaggctaga agggtatgat  2040
gatcttctcc acaagttgga ggagatgttt gatatccagg gggagctttc tgctagcctc  2100
aagaaatgga aggttattta cacggatgat gaggatgata tgatgctggt tggggatgat  2160
ccgtggcctg aattttgcgg catggtgaaa aggatataca tttactccta tgaggaggcc  2220
aagtctttga ctcccaaggt gaagctgccg gtcattggtg acaccactaa actgaaccta  2280
gacaaattgt caccagaatc tgacatgccg cagagtgact caaacaacat cgctctggtt  2340
gccgccgata aggactgatg gatgctaact tggtgcttta ccttttcttc ccttttttgga  2400
tgtttgggag gcaatgccca tgctccttga gactgctaag agttatctgt ttgttgcgct  2460
gtgggcctca aggacgttgc cccacaatct gcctgactgc cttggtttgc aatggctgat  2520
gtaggaccag tggtggtcct ctgccagcaa ggacgactgg aacgtaatgg caagcaggct  2580
gcgtgcgcgc cgttccctgt ggcaccaacc tgtgttttgt ttgccgtgtt tggtaggagg  2640
catggcgaat tgccggctgc ttggttttgg agactgccac tgactgctgc cgtctcgttg  2700
gtcgacgtcg gccggcaggc cgcgcccctc acctccagta aataggactt catgtacaac  2760
tagtttggta gtagcagtag tggtttatgt atatcagcgt catgttcctt gctacctata  2820
taagcatcat catctgtagc tgctgctccc accttgcatt gtattctacc cccggcttgg  2880
taccgaatga tctggtgcaa aaaagtctca gcttgctgtt cc                     2922
```

```
SEQ ID NO: 229         moltype = AA  length = 672
FEATURE                Location/Qualifiers
REGION                 1..672
                       note = misc_feature - Ceres Clone ID no. 1892720
REGION                 1..672
                       note = misc_feature - Bit score of 1319.2 for hmm based on
                        sequences of FIGURE 5.
REGION                 248..333
                       note = misc_feature - Pfam Name: Auxin_resp Pfam Desc:
                        Auxin response factor
REGION                 121..226
                       note = misc_feature - Pfam Name: B3 Pfam Desc: B3 DNA
                        binding domain
REGION                 1..672
                       note = misc_feature - Is Acted Upon By Ceres SEEDLINE ID
                        no. ME00572 at SEQ ID NO. 111
source                 1..672
                       mol_type = protein
                       organism = Panicum virgatum
SEQUENCE: 229
MANAGVAVGS GGVSHALFRE LWHACAGLLV TVPRQGELVY YFPQGHMEQL EASTDQQLDQ  60
HLPLFNLPSK ILCKVVNVEL RAETDSDEVY AQIMLQPEAD QSEPTSPAPE LPEPERCNVH  120
SFCKTLTASD TSTHGGFSVL RRHAEECLPQ LDMTQNPPWQ ELVAKDLHGN EWHFRHIFRG  180
QPRRHLLTTG WSVFVSSKRL VAGDAFIFLR GENGELRVGV RRLMRQVNNM PSSVISSHSM  240
HLGVLATASH AISTGTLFSV FYKPRTSRSE FVVSVNKYLE AKNHKMSVGM RFKMRFEGDE  300
SPERRFSGTI IGLGSMPANS TSPWADSDWR SLKVQWDEPS AVVRPDRVSP WELEPLDATN  360
TQPPQPPLRS KRARPPASPS IAPELPPAFG FWKSPPEPTH AFSFSGLQRT QELYHSNPNS  420
IFSSSLNVGF NSKNEHSTPT NNHLYWPIRD TRTESYSASI NKLPPERKQE FTIAGCRLFG  480
IELSNAVSPV VAVASAGQDQ PPVVSVDVEP DQLSQPSQAN KTDAPAASSE RSPHETESRQ  540
VRSCTKVIMQ GMAVGRAVDL TRLEGYDDLL HKLEEMFDIQ GELSASLKKW KVIYTDDEDD  600
MMLVGDDPWP EFCGMVKRIY IYSYEEAKSL TPKVKLPVIG DTTKLNLDKL SPESDMPQSD  660
SNNIALVAAD KD                                                     672
```

```
SEQ ID NO: 230         moltype = DNA  length = 2076
FEATURE                Location/Qualifiers
misc_feature           1..2076
                       note = Ceres Annot ID no. 8667998
misc_feature           1..2076
                       note = Encodes the peptide sequence at SEQ ID NO. 231
source                 1..2076
```

```
                        mol_type = other DNA
                        organism = Sorghum bicolor
SEQUENCE: 230
atggcgggca ttgacctcaa caccgtggag gaggaggacg aggaggaggc ggaggcggag  60
gcgccgcctg tggccgccag ggccggtggt ggcgccgtgt gtctggagct gtggcacgcg  120
tgcgcgggcc ccgtcgcgcc gctgccgcgc aagggcagcg ccgtcgtgta cctgccgcag  180
ggccacctcg agcacatcgg cggcgacgct gacgcggcgg gagcagcggt gccgccacac  240
gtgctctgcc gcgtcgtcga cgtcaccctc cacgcggacg gcgccaccga cgaggtgtac  300
gcgcgggtgt cgctgctgcc cgaggacgag gaggcggaga ggcgggcgcg ggcgcgggtt  360
cgggaggacg aggacgcgga tcgcgacggc gaggacgggg ccgccatgaa gccgctcgca  420
cggacgccgc acatgttctg caagacgctc acggcctctg acaccagcac gcacggcggc  480
ttctccgtgc cgcgccgcgc cgccgaggac tgcttcccgc cgctggacta cagccagcag  540
aggccgtctc aggagctcgt ggccaaggat ctacacggca cggagtggaa gttccgacat  600
atctaccgag gccagccacg aaggcatctc ttaaccactg gatggagtgc atttgttaat  660
aagaagaagc ttgtttctgg cgatgcagtt ctgttccttc gaggtgaaga tggagtgctt  720
cgactgggag tgcgccgagc agcccagcta aaaattgtaa ctcctattcc tgcactgcat  780
aaccagtgct caagccagac cactctggga aatgttgcac aagctgtggc cacgaggact  840
gttttccaca tttactacaa tcccaggtta agtcaatctg aattcattgt accctattgg  900
aagttcacca gaagcttgaa tcaaccaatt tctgttggaa tgagatgcag aatgcgatat  960
gaaagtgacg atgcttctga aagaaggtgc actgggataa taattggaag cagagaagct  1020
gagcctattt ggtatggttc aaaatggaaa tgcttggtgg ttagatggga tgatggtata  1080
gagtgccatt ggcccaatag ggtatctcct tgggagattg aggtcacagg atcagtttca  1140
ggatctcata tgtgcgctcc caattcaaaa cgtctgaaac catgcctccc tcaagttaat  1200
ccggagattg tgcttccaaa tggaagcgtt tcttcagatt ttgcgggatc tgtcagattc  1260
cacaaggtct tgcaaggtca agaattgttg ggtttgaaaa cccatgacgg tactgctatt  1320
tctgcttttc aggcaactga agcaagtaat ttgcagtaca gtgatgaacg tagtaacatg  1380
agtaacaata tcttagggat cccaaggctc ggtgttagat ctccaaatgg aatccctgga  1440
tttccctacc attgctcagg ctttggggaa tctcaaagat tccaaaaggt cttgcaaggt  1500
caagaagtgt ttcgtccttt ccgaggagga tgtttggctg atggccatat aagaactgct  1560
ggcatgtatc aacctaaatg gcctgcacca caagggtgtg attttccaca gccagcaaaa  1620
ccggtacttg tgttgcaagc atcctcccca tcatctgtgc tgatgtttcc acaaactggt  1680
tctaagataa ctccattgga atatgagtac agctgcctgg ataaggatga ggatggtaga  1740
tttgatagga ctgtccctac tcaagatatg ggaagaaaca atcaaacatt atctctttgg  1800
cctcatcttg tttccggcga agcaatagaa gaatgtactg gaactgagaa tatgcactct  1860
tctgtcagtg gtgcagagca tgaatcaaac aatgagagta cagttgaaaa tggctgcaaa  1920
atctttggta tctcattggc tgaaaagatc cgatcatgtg atgaagcaga ctcttgtagt  1980
gcaaaacgta attctgggct ccagccttcg aggtcacaaa tactaggcag ctgttgggcc  2040
acttttgcct gtaattttca agaccgaatc ttttga                            2076

SEQ ID NO: 231          moltype = AA  length = 691
FEATURE                 Location/Qualifiers
REGION                  1..691
                        note = misc_feature - Ceres Annot ID no. 8667998
REGION                  1..691
                        note = misc_feature - Bit score of 955.7 for hmm based on
                         sequences of FIGURE 5.
REGION                  272..353
                        note = misc_feature - Pfam Name: Auxin_resp Pfam Desc:
                         Auxin response factor
REGION                  145..250
                        note = misc_feature - Pfam Name: B3 Pfam Desc: B3 DNA
                         binding domain
REGION                  1..691
                        note = misc_feature - Is Acted Upon By Ceres SEEDLINE ID
                         no. ME00572 at SEQ ID NO. 111
source                  1..691
                        mol_type = protein
                        organism = Sorghum bicolor
SEQUENCE: 231
MAGIDLNTVE EEDEEEAEAE APPVAARAGG GAVCLELWHA CAGPVAPLPR KGSAVVYLPQ  60
GHLEHIGGDA DAAGAAVPPH VLCRVVDVTL HADGATDEVY ARVSLLPEDE EAERRARARV  120
REDEDADRDG EDGAAMKPLA RTPHMFCKTL TASDTSTHGG FSVPRRAAED CFPPLDYSQQ  180
RPSQELVAKD LHGTEWKFRH IYRGQPRRHL LTTGWSAFVN KKKLVSGDAV LFLRGEDGVL  240
RLGVRRAAQL KIVTPIPALH NQCSSQTTLG NVAQAVATRT VFHIYYNPRL SQSEFIVPYW  300
KFTRSLNQPI SVGMRCRMRY ESDDASERRC TGIIIGSREA EPIWYGSKWK CLVVRWDDGI  360
ECHWPNRVSP WEIEVTGSVS GSHMCAPNSK RLKPCLPQVN PEIVLPNGSV SSDFAGSVRF  420
HKVLQGQELL GLKTHDGTAI SAFQATEASN LQYSDERSNM SNNILGIPRL GVRSPNGIPG  480
FPYHCSGFGE SQRFQKVLQG QEVFRPFRGG CLADGHIRTA GMYQPKWPAP QGCDFPQPAK  540
PVLVLQASSP SSVLMFPQTG SKITPLEYEY SCLDKDEDGR FDRTVPTQDM GRNNQTLSLW  600
PHLVSGEAIE ECTGTENMHS SVSGAEHESN NESTVENGCK IFGISLAEKI RSCDEADSCS  660
AKRNSGLQPS RSQILGSCWA TFACNFQDRI F                                691

SEQ ID NO: 232          moltype = DNA  length = 2439
FEATURE                 Location/Qualifiers
misc_feature            1..2439
                        note = Ceres Annot ID no. 8721170
misc_feature            1..2439
                        note = Encodes the peptide sequence at SEQ ID NO. 233
source                  1..2439
```

```
                        mol_type = other DNA
                        organism = Sorghum bicolor
SEQUENCE: 232
atggcggcgg ctgcaccggc ggccggcggc ggcggtggtg cggaagcggg atgcggagga  60
ggcggaggga aggacccgct gttcgtcgag ctgtggaagg cctgcgcggg gccgctgtct  120
agcgtgccgc cgctcgggga gaaggtctac tacttcccgc agggccacat cgagcaggtg  180
gaggcatcga cgaaccagat tgctgagcag cagggcacgc ccctctacaa cctgccatgg  240
aagattccat gcaagctcat gaacatcgag ctgaaggctg agccggatac tgatgaggtg  300
tacgcccagc tcaccctgct ccctgataag aagcaagatg agaatacatc tacaacagtg  360
gagaatgagg aggcagagga ggaggtggtg cctcatgcgc caccaacaaa tgagggacct  420
cggatccatt ccttttgcaa gacattgact gcctcagaca caagcacgca tggtggtttc  480
tcagtgttgc gccggcatgc agatgagtgc ctcccaccat tggatatgag tcaacacccc  540
ccaaatcaag aattggtggc caaggacctg catgggattg agtggcggtt ccgtcacatc  600
tttcgaggtc agccacggag acacctcctt cagagtggtt ggagtgtttt tgttagcgcc  660
aagcgtcttg ttgcagggga tgccttcata tttctcagag gtgagaatgg ggagttacgt  720
gttggggttc ggcgtgcact gaggcaccaa accactatcc catcttcagt catatcaagc  780
cacagtatgc atcttggtgt tcttgcgaca gcatggcatg cagtcaacac tgggagtatg  840
ttcactgtct actacaagcc aaggactagt ccagctgaat ttgtggtctc gcgagatagg  900
tactatgaat cactgaaacg aaattattca atagggatga gatttaagat gagatttgaa  960
ggtgaagaag cagcagagca aagattcact ggcacaatag ttggaatagg tgcttctgat  1020
ccatctggtt gggctgactc aaaatggcgt tcccttaagg tgagatggga tgaagcttct  1080
tctgttcctc gtcctgaaag agtttctcct tggcaaatag aacctgctat tagcccatct  1140
cctgtgaacc ctcttccagt cagattcaag aggtctcgtt caagtgttaa tgcttcacca  1200
tctgacgtgc ctactgtatc cagagaaggt cgataccatg atagcagtga tgtgaagact  1260
gctcaggatc ttaccatgtg gtcttcagga actgagcagc agagaaacaa tattgctgcc  1320
cagacaaagc gaagtctgga gggatggacg caatctagaa ctcctgaagg ttacaatcag  1380
ctgttctcgg catttcaacc actgaaagat acacataatc cactttgtac tttccctagt  1440
caaatatctg ggactcgctc aaatacctgg gacacagccg atgctcgtta tccagcccaa  1500
caagccaatc acaacatgtt acatggcaca tggccttttta tgcctcatag cagtggtttt  1560
aggacgaatc aacagaatta tctagtgatg cctgaagctg caaagtttac tgggaaatca  1620
gctttcactt cacttcaggg ccatggcact gatcagtgct ccacaggctg gtttggacat  1680
attgagtcaa gttcccgcac agaccatgca tcgtcaagtt cgatcaggcc ccagcctttg  1740
gttattggta atgatgttca gaaaaccaaa ggcacttcat tcaaactatt tgggattcct  1800
cttggcagcc cggaaaaatc tgaacctctg gtatccccac caagtgtcgc atatgacggg  1860
aaacttcaaa cttctccatc agaaaaaggg aatcagctag acatagttgg agtggataat  1920
tgttctgatc cttcgaagac tgtgaagcca tttgatggtc ctcaatcaga ttcgattaca  1980
gagaataatc agccttgtcc agaagctacc cagaatattc agaacaaagt gcaaagtagt  2040
tccaccagaa gctgcaagaa ggtccataag caaggcagtg ccctcggcag atcgattgat  2100
ctaacaaagt tcacttgcta cgatgagctg attgctgaac tggatcagat gtttgacttt  2160
gatggtgagc tgaagaatcc atgcaaaaat tggctggttg tctacactga caatgaaggc  2220
gatataatgc tggttggcga tgacccctgg aatgaattct gcgacatggt ccacaagatc  2280
ttcatctaca caagggagga agtggaaagg atgaacccag gtgccctaaa ctcaaggtcc  2340
gaggatagtc tgtctgactc gcagggaaga gggttggctt ccaaagagcc gccccgaggt  2400
ggcccgtcta cttcgactcc caattccgag agctgctaa                        2439

SEQ ID NO: 233          moltype = AA  length = 812
FEATURE                 Location/Qualifiers
REGION                  1..812
                        note = misc_feature - Ceres Annot ID no. 8721170
REGION                  1..812
                        note = misc_feature - Bit score of 1310.2 for hmm based on
                         sequences of FIGURE 5.
REGION                  271..353
                        note = misc_feature - Pfam Name: Auxin_resp Pfam Desc:
                         Auxin response factor
REGION                  144..249
                        note = misc_feature - Pfam Name: B3 Pfam Desc: B3 DNA
                         binding domain
REGION                  1..812
                        note = misc_feature - Is Acted Upon By Ceres SEEDLINE ID
                         no. ME00572 at SEQ ID NO. 111
source                  1..812
                        mol_type = protein
                        organism = Sorghum bicolor
SEQUENCE: 233
MAAAAPAAGG GGGAEAGCGG GGGKDPLFVE LWKACAGPLS SVPPLGEKVY YFPQGHIEQV  60
EASTNQIAEQ QGTPLYNLPW KIPCKLMNIE LKAEPDTDEV YAQLTLLPDK KQDENTSTTV  120
ENEEAEEEVV PHAPPTNEGP RIHSFCKTLT ASDTSTHGGF SVLRRHADEC LPPLDMSQHP  180
PNQELVAKDL HGIEWRFRHI FRGQPRRHLL QSGWSVFVSA KRLVAGDAFI FLRGENGELR  240
VGVRRALRHQ TTIPSSVISS HSMHLGVLAT AWHAVNTGSM FTVYYKPRTS PAEFVVSRDR  300
YYESLKRNYS IGMRFKMRFE GEEAAEQRFT GTIVGIGASD PSGWADSKWR SLKVRWDEAS  360
SVPRPERVSP WQIEPAISPS PVNPLPVRFK RSRSSVNASP SDVPTVSREG RYHDSSDVKT  420
AQDLTMWSSG TEQQRNNIAA QTKRSLEGWT QSRTPEGYNQ LFSAFQPLKD THNPLCTFPS  480
QISGTRSNTW DTADARYPAQ QANHNMLHGT WPFMPHSSGF RTNQQNYLVM PEAAKFTGKS  540
AFTSLQGHGT DQCSTGWFGH IESSSRTDHA SSSSIRPQPL VIGNDVQKTK GTSFKLFGIP  600
LGSPEKSEPL VSPPSVAYDG KLQTSPSEKG NQLDIVGVDN CSDPSKTVKP FDGPQSDSIT  660
ENNQPCPEAT QNIQNKVQSS STRSCKKVHK QGSALGRSID LTKFTCYDEL IAELDQMFDF  720
DGELKNPCKN WLVVYTDNEG DIMLVGDDPW NEFCDMVHKI FIYTREEVER MNPGALNSRS  780
EDSLSDSQGR GLASKEPPRG GPSTSTPNSE SC                               812
```

```
SEQ ID NO: 234          moltype = DNA  length = 2007
FEATURE                 Location/Qualifiers
misc_feature            1..2007
                        note = Ceres Annot ID no. 8679636
misc_feature            1..2007
                        note = Encodes the peptide sequence at SEQ ID NO. 235
source                  1..2007
                        mol_type = other DNA
                        organism = Sorghum bicolor
SEQUENCE: 234
atggcggacg ccggcgtggc gcgcggccca gggagtgctg gcgatgctct gttcagggaa  60
ctctggcatg cttgtgctgg gccgttggtc acagtgcctc gccaaggcga gctggtttac  120
tacttcccgc agggtcatat ggaacagctt gaagcatcta cagatcaaca acttgatcag  180
cacttacctc tgtttaatct accacccaag atcctctgca aggtggtcaa tgtagaactt  240
agagctgaaa ctgattccga tgaagtttat gctcagatta tgctacaacc cgaagcagag  300
caaaatgagc ccaccagccc agatgctgag ccacccgagc ctgaaagatg caacgtccat  360
tccttctgca agaccttgac tgcttcagat acaagtaccc atggtggatt ctctgtcctc  420
aggaggcatg ctgaagaatg tctgccccaa ctggacatga ctcagaatcc accatggcaa  480
gaactggtgg ctaaagatct ccatggaaat gaatggcatt tccgtcacat ctttcgaggg  540
caaccaagga ggcatctact tacgacaggc tggagtgttt ttgttagctc gaaaagattg  600
gttgctggtg acgcgtttat ctttttgaga ggtgagaatg gagagctgcg agtcggggtg  660
aggaggctca tgaggcaact aaacaacatg ccatcttcgg ttatctcaag ccacagcatg  720
catcttggag tccttgcaac tgcatctcat gccatctcca ctggaactct cttttctgtt  780
ttctacaaac ccagaacaag tcgatcagaa tttgtcgtta gtgtaaacaa gtaccttgaa  840
gctaagaatc acaagatgtc tgttggtatg aggtttaaaa tgagatttga gggtgacgaa  900
tctcctgaaa gaagattcag tgggacaatt attggtctgg gaagcatgcc agctaactca  960
acatctccgt gggctaactc tgagtggaga tctttgaagg tccaatggga cgagccttct  1020
gctattctgc gtccagatag agtttcacca tgggaactag aaccccttga tgcaactaat  1080
ccacaaccac ctcaacctcc tttacggaat aagcgtgcgc ggcctcctgc ttcaccttcc  1140
attgctccag aacttcctcc agtttttggt ttttggaaat ccccagctga gcctgcccaa  1200
gctttctcat tttcaggact gcagcgaact caggaattat accattcaaa ccccaattca  1260
atcttctcgt catcgttgaa tgtaggattc aattcaaaga atgagcgttc tactccaaac  1320
aacaatcatt tgtactggac aatgagagag acaagaactg aatcctactc tgctagcatt  1380
aacaaagctc ctactgaaaa gaagcaagaa tctgctactt ctggctgcag attgtttggt  1440
attgagatag gttctgcagt atcaccagtg gttactgttg ctagtgttgg tcaggatcca  1500
ccacctgctc tctcagtaga tgttgaatct gatcagctgt cacaaccatc ccatgccaac  1560
aaaacggatg ccccagcggc aagcagtgag cgctctccta atgaaacaga gagccgacaa  1620
gtcaggagct gcaccaaggt aatcatgcaa ggaatggcgg ttggcagggc agtggacttg  1680
acgaggttag atgggtatga tgatcttcac cgcaagttgg aggagatgtt tgatatccat  1740
ggagagcttt ctgccaacct caggaaatgg aaggttgttt acacagatga tgaggatgac  1800
atgatgctgg tcggggacga tccatggaag atggtaaaaa ggatatatat ttactcttac  1860
gaggaggcca aatctttgac tcccaaagcg aagctgccag tcattggtga caccatcaag  1920
ccagacccaa acaaattgtc accggaatct gacatgccac agagtgacac aaacagcaat  1980
gctcccgttg ctgctgataa ggattga                                    2007

SEQ ID NO: 235          moltype = AA  length = 668
FEATURE                 Location/Qualifiers
REGION                  1..668
                        note = misc_feature - Ceres Annot ID no. 8679636
REGION                  1..668
                        note = misc_feature - Bit score of 1385.0 for hmm based on
                         sequences of FIGURE 5.
REGION                  248..333
                        note = misc_feature - Pfam Name: Auxin_resp Pfam Desc:
                         Auxin response factor
REGION                  121..226
                        note = misc_feature - Pfam Name: B3 Pfam Desc: B3 DNA
                         binding domain
REGION                  1..668
                        note = misc_feature - Is Acted Upon By Ceres SEEDLINE ID
                         no. ME00572 at SEQ ID NO. 111
source                  1..668
                        mol_type = protein
                        organism = Sorghum bicolor
SEQUENCE: 235
MADAGVARGP GSAGDALFRE LWHACAGPLV TVPRQGELVY YFPQGHMEQL EASTDQQLDQ  60
HLPLFNLPPK ILCKVVNVEL RAETDSDEVY AQIMLQPEAE QNEPTSPDAE PPEPERCNVH  120
SFCKTLTASD TSTHGGFSVL RRHAEECLPQ LDMTQNPPWQ ELVAKDLHGN EWHFRHIFRG  180
QPRRHLLTTG WSVFVSSKRL VAGDAFIFLR GENGELRVGV RRLMRQLNNM PSSVISSHSM  240
HLGVLATASH AISTGTLFSV FYKPRTSRSE FVVSVNKYLE AKNHKMSVGM RFKMRFEGDE  300
SPERRFSGTI IGLGSMPANS TSPWANSEWR SLKVQWDEPS AILRPDRVSP WELEPLDATN  360
PQPPQPPLRN KRARPPASPS IAPELPPVFG FWKSPAEPAQ AFSFSGLQRT QELYHSNPNS  420
IFSSSLNVGF NSKNERSTPN NNHLYWTMRE TRTESYSASI NKAPTEKKQE SATSGCRLFG  480
IEIGSAVSPV VTVASVGQDP PPALSVDVES DQLSQPSHAN KTDAPAASSE RSPNETESRQ  540
VRSCTKVIMQ GMAVGRAVDL TRLDGYDDLH RKLEEMFDIH GELSANLRKW KVVYTDDEDD  600
MMLVGDDPWK MVKRIYIYSY EEAKSLTPKA KLPVIGDTIK PDPNKLSPES DMPQSDTNSN  660
APVAADKD                                                         668
```

```
SEQ ID NO: 236          moltype = DNA  length = 2415
FEATURE                 Location/Qualifiers
misc_feature            1..2415
                        note = Ceres Annot ID no. 8670373
misc_feature            1..2415
                        note = Encodes the peptide sequence at SEQ ID NO. 237
source                  1..2415
                        mol_type = other DNA
                        organism = Sorghum bicolor
SEQUENCE: 236
atggcgctgc cgtcccaggc cccgtctaac tcaggggatc cgctgtaccc ggagctctgg  60
cgcgcctgcg ccggcccgct cgtcaccgtc cctcgcgtcg gcgacctcgt cttctacttt  120
ccccagggac acatcgagca ggtggaggcg tccatgaacc aggtcgccgg gaaccagatg  180
cgcctctacg atctgccctc caagctgctc tgccgcgtgc tcaacgtcga gcttaaggcg  240
gagacggaca ccgacgaggt ctacgcgcag atcatgctca tgccagagcc cgagcaaacc  300
gatgtggcgg ctgagaaggc gagttctgcg tccgctgcgt cgccgaggcc agcagtgagg  360
tccttctgca agacgctcac cgcctccgac accagcacac acggaggctt ctctgtgctg  420
cgccgccacg cagacgagtg cctcccacca ctggatatga cgcagtcgcc tcccacacag  480
gagctggtgg cgaaggatct gcatggcatg gagtggcgct tccgccacat ctttcgcggg  540
caacccagga ggcatctcct tcagagtggt tggagtgttt ttgttagttc caaaaggctt  600
gttgctggag acgccttcat tttcctcaga ggagaaaatg gtgaacttcg ggttggtgtt  660
aggcgggcta tgaggcagtt gtctaatgta ccttcttcag tcatatctag ccaaagcatg  720
cacctcggag tccttgcgac tgcatggcac gccatcaaca ccaaatccat gttcactgtc  780
tactacaagc ctaggacgag cccttcagag ttcatcatac catatgatca atatatggag  840
tcagtgaaaa ataactattc aattgggatg agattcagaa tgaggtttga aggggaagag  900
gcaccagagc agaggtttac tggtacaatc gttggctgtg aaaatcttga cccactatgg  960
cctgattcca gttggagata cttgaaggtg cgctgggatg agccttctac tatcccacga  1020
ccagataggg tctctccttg gaagatagag cctgcttcat cacctccagt taatccactc  1080
ccgctttctt ctagagtaaa aagacctaga caaaatgctc ctccaccttc acctgaagca  1140
tctgttctca caaaagaaag tgcagccaag atcgatattg actctgctca aacacaacat  1200
caaaattcgg tcttgcaagg tcaagagcaa atgaccttga ggaacaacct gactgaaagc  1260
aacgactctg attccactgt tcaaaagccg atgatgtggt ccccatcacc caatgggaaa  1320
gcccacacta actttcagca gagacctgct atggatagtt ggatgccaat gggaaggcgt  1380
gaaacggact tcaaggactc acgttccgcc ttcaaggatg cccgcactgc ctctcaatca  1440
tttagagata cacaggggtt cttcatgcaa gcttatgatg acaatcatca ccgtctttct  1500
ttcaacaacc agtttcagga tcagggttca gctcatcgct ttgcggatcc atacttctat  1560
atggcccaac aaccttctct gactgttgaa tcaagcacaa ggacacaaac agcaaacaac  1620
gacttgcgtt tctggggcga ccagaattcg atctatggta atccaggtga tcaacagcag  1680
cagggtttca gctttggaca aaacccatca agttggttga accagccatt tccccaggtt  1740
gaacagccac gagtggttag gcctcatgca acagttgctc catttgattt ggaaaagacc  1800
agagaaggca gcgggttcaa gatctttggg ttccaagttg atacaaccag tccatctcct  1860
gcccagttga gctctccatt atgtgctatc cgggagcatg tggtacaaac ccgaccatcg  1920
gcaccagtga atgaattgca acctgtgcaa aatgagtgct tgcctgaggg atctgtaagc  1980
actgctggaa ctgcaactga gaacgagaaa aacattcagc aagcccagcc aagttcaaaa  2040
gatattcaaa gcaagtccca gggtgcttcg acaaggagct gcacaaaggt tcataagcaa  2100
ggggttgcgc ttggcagatc tgtggacctc tcaaaattca ctgactacga tgaactcaaa  2160
gcagaattag acaagatgtt tgaattcaat ggcgaattag tatctgccaa cagaagctgg  2220
cagatcgttt atactgacaa tgagggtgac atgatgcttg tgggggatga cccgtgggaa  2280
gagttctgta gcatagtgcg caagatctac atctatacga aggaggaggt ccagaagatg  2340
aactcaaaat catctgcgcc aaggaaggag gagcctctaa cagtgggtga aggatgcgcc  2400
gccacaaatg agtag                                                   2415

SEQ ID NO: 237          moltype = AA  length = 804
FEATURE                 Location/Qualifiers
REGION                  1..804
                        note = misc_feature - Ceres Annot ID no. 8670373
REGION                  1..804
                        note = misc_feature - Bit score of 1526.4 for hmm based on
                         sequences of FIGURE 5.
REGION                  248..329
                        note = misc_feature - Pfam Name: Auxin_resp Pfam Desc:
                         Auxin response factor
REGION                  121..226
                        note = misc_feature - Pfam Name: B3 Pfam Desc: B3 DNA
                         binding domain
REGION                  1..804
                        note = misc_feature - Is Acted Upon By Ceres SEEDLINE ID
                         no. ME00572 at SEQ ID NO. 111
source                  1..804
                        mol_type = protein
                        organism = Sorghum bicolor
SEQUENCE: 237
MALPSQAPSN SGDPLYPELW RACAGPLVTV PRVGDLVFYF PQGHIEQVEA SMNQVAGNQM  60
RLYDLPSKLL CRVLNVELKA ETDTDEVYAQ IMLMPEPEQT DVAAEKASSA SAASPRPAVR  120
SFCKTLTASD TSTHGGFSVL RRHADECLPP LDMTQSPPTQ ELVAKDLHGM EWRFRHIFRG  180
QPRRHLLQSG WSVFVSSKRL VAGDAFIFLR GENGELRVGV RRAMRQLSNV PSSVISSQSM  240
HLGVLATAWH AINTKSMFTV YYKPRTSPSE FIIPYDQYME SVKNNYSIGM RFRMRFEGEE  300
APEQRFTGTI VGCENLDPLW PDSSWRYLKV RWDEPSTIPR PDRVSPWKIE PASSPPVNPL  360
PLSSRVKRPR QNAPPPSPEA SVLTKESAAK IDIDSAQTQH QNSVLQGQEQ MTLRNNLTES  420
```

-continued

```
NDSDSTVQKP MMWSPSPNGK AHTNFQQRPA MDSWMPMGRR ETDFKDSRSA FKDARTASQS  480
FRDTQGFFMQ AYDDNHHRLS FNNQFQDQGS AHRFADPYFY MAQQPSLTVE SSTRTQTANN  540
DLRFWGDQNS IYGNPGDQQQ QGFSFGQNPS SWLNQPFPQV EQPRVVRPHA TVAPFDLEKT  600
REGSGFKIFG FQVDTTSPSP AQLSSPLCAI REHVVQTRPS APVNELQPVQ NECLPEGSVS  660
TAGTATENEK NIQQAQPSSK DIQSKSQGAS TRSCTKVHKQ GVALGRSVDL SKFTDYDELK  720
AELDKMFEFN GELVSANRSW QIVYTDNEGD MMLVGDDPWE EFCSIVRKIY IYTKEEVQKM  780
NSKSSAPRKE EPLTVGEGCA ATNE                                         804

SEQ ID NO: 238          moltype = DNA  length = 2565
FEATURE                 Location/Qualifiers
misc_feature            1..2565
                        note = Ceres Annot ID no. 8690553
misc_feature            1..2565
                        note = Encodes the peptide sequence at SEQ ID NO. 239
source                  1..2565
                        mol_type = other DNA
                        organism = Sorghum bicolor
SEQUENCE: 238
atgacttcgg cggcggccgc ggcccaggcg gcgggagggg gtggaggagg aggaggagtc  60
tgcgaggggg atgccgctgc cgcggcgcga ggcggaggcg gaggcggaac ggaggacggc  120
atgtacacgg agctctggag cctctgcgcc ggcccgctgg tcacggtgcc cagggtcggg  180
gacaaggtct actacttccc acagggccat atcgagcagg tggaggcatc gaccaaccag  240
gtggctgagc agcacatgca actttacaat ctcccatgga agatcctgtg tgaggtcatg  300
aatgttgaat tgaaggctga gccggacaat gatgaggttt atgcccagct cactctgcta  360
cctgaatcga agccagagga gaatggctct agtcaggagg agatgcctgc tgcacctcct  420
gctgcacttg caaggccacg tgtgcactcc ttctgcaaga cattgacagc ctctgacacc  480
agcacacatg gtggtttctc ggtgctgcgt cgccatgcag atgaatgcct tccaccgctg  540
gatatgagtc gtcaacctcc aacacaagag cttgtggcca aggatctgca tggtgtggaa  600
tggcgctttc gtcacatatt cagaggtcaa cccggaaggc tttttttgca gagtggctgg  660
agtgtttttg ttagtgcaaa gcgtcttgtt gctggggatg ccttcatctt tctgagaggt  720
gataatgggg agctgcgtgt gggagtcagg cgtgccatga ggcagcaagc aaatgttccg  780
tcttcagtaa tatcaagcca cagcatgcat cttggtgttc ttgctactgc atggcatgct  840
gttaacactg ggaccatgtt cactgtctac tacaaaccta ggacaagtcc agctgagttt  900
gttgtcccct gtgatcgcta tacggagtca ctgaaacgaa attaccctat agggatgaga  960
tttaaaatga ggtttgaagg tgaagaggct ccagagcaaa ggttcactgg gacgattgtt  1020
ggaaatgtgg atcctgaaca agctggatgg gctgaatcta aatggcgtta cctcaaggtg  1080
aggtgggatg aagcttcctc cattccacgt cctgaaaggg tttctccttg gcaaatagaa  1140
cctgcagtca gccctccccc tgtcaatcca cttccagtac acaggcccaa gaggcctcgc  1200
tctaatgctg tagcttctct ggctgagtct tcagctccaa caaaagaagc tgctccgaag  1260
gtcacattag agactcaaca acatgccctg caaaggccct tgcagaccca ggataatgcg  1320
gccccaaaaa gtggttttgg tgataacagt gagttggacg ctgctcataa gtcagccctg  1380
cgaccatcag ggtttgatct agagaagaac accattggca tgcagaggaa gctgggttca  1440
gatagttgga tgcatatgaa cagacctgaa ggatacaatg aaatgttatc tggatatcaa  1500
caacctaata aagatgtaca gaatccacag ggtttctgtt ctttacctga tcagattgct  1560
gccggtcgtc ctaatttctg gcacaccgta aatgctcatt atcaagacca gcaaggcaat  1620
cacaatctat tccctggttc atggtccatg atgccttcaa gtactggctt tgggttgaac  1680
agacagagct atccaatgat gcaggaagtt ggtgggttgt ctcagagtgc tacgaacacc  1740
aagtttggga atggagctta tgctgcacta cctggtcatg gcattgatca atactcttct  1800
ggatggtttg ggcacatgat acctggtgct cgcatggacg atgtccagcc acgcgtgatt  1860
aagcctcaac ctttggtcct tgctcatggt gaagctcaga aaatgaaagg caattcatgc  1920
aagctttttg gaattcacct tgatagccca gccaaatctg aacctttgaa atctccacca  1980
agtgttgcct atgatgggat gccacaaact ccagcagcag ctgaatggcg gatggttgat  2040
tcaattgaag cagacagatg ttctgatcca cttaagatgc caaagcaact cgatgctaca  2100
caggtagatc ctgttccaga gaaatgttca caagtttcaa gaggcacaca gtgcaaatca  2160
caaggtggat caactaggag ctgcaagaag gtccacaagc aaggaatcgc acttggcagg  2220
tctgtggatc ttacaaagtt caatggctac acggaattga ttgctgagct ggatgagatg  2280
tttgacttca atggggagct gaaaggttct aacaaggaat ggatggttgt gtacaccgac  2340
aatgaaggtg atatgatgct ggttggggat gatccctgga atgagttctg caacatggtc  2400
cacaagatct tcatctacac aagggaggag gtccagagga tgaatccggg caccctgaat  2460
tcaaggtccg aggacagcct tgctaattca atggaaaggg gctctactgc tagggagaca  2520
cctggcagcc tatccgcctc ttcccttgac tctgagaact gctaa                  2565

SEQ ID NO: 239          moltype = AA  length = 854
FEATURE                 Location/Qualifiers
REGION                  1..854
                        note = misc_feature - Ceres Annot ID no. 8690553
REGION                  1..854
                        note = misc_feature - Bit score of 1661.5 for hmm based on
                         sequences of FIGURE 5.
REGION                  277..359
                        note = misc_feature - Pfam Name: Auxin_resp Pfam Desc:
                         Auxin response factor
REGION                  150..255
                        note = misc_feature - Pfam Name: B3 Pfam Desc: B3 DNA
                         binding domain
REGION                  1..854
                        note = misc_feature - Is Acted Upon By Ceres SEEDLINE ID
                         no. ME00572 at SEQ ID NO. 111
source                  1..854
```

```
                         mol_type = protein
                         organism = Sorghum bicolor
SEQUENCE: 239
MTSAAAAAQA AGGGGGGGGV CEGDAAAAAR GGGGGGTEDG MYTELWSLCA GPLVTVPRVG  60
DKVYYFPQGH IEQVEASTNQ VAEQHMQLYN LPWKILCEVM NVELKAEPDN DEVYAQLTLL  120
PESKPEENGS SQEEMPAAPP AALARPRVHS FCKTLTASDT STHGGFSVLR RHADECLPPL  180
DMSRQPPTQE LVAKDLHGVE WRFRHIFRGQ PGRLFLQSGW SVFVSAKRLV AGDAFIFLRG  240
DNGELRVGVR RAMRQQANVP SSVISSHSMH LGVLATAWHA VNTGTMFTVY YKPRTSPAEF  300
VVPCDRYTES LKRNYPIGMR FKMRFEGEEA PEQRFTGTIV GNVDPEQAGW AESKWRYLKV  360
RWDEASSIPR PERVSPWQIE PAVSPPPVNP LPVHRPKRPR SNAVASLAES SAPTKEAAPK  420
VTLETQQHAL QRPLQTQDNA APKSGFGDNS ELDAAHKSAL RPSGFDLEKN TIGMQRKLGS  480
DSWMHMNRPE GYNEMLSGYQ QPNKDVQNPQ GFCSLPDQIA AGRPNFWHTV NAHYQDQQGN  540
HNLFPGSWSM MPSSTGFGLN RQSYPMMQEV GGLSQSATNT KFGNGAYAAL PGHGIDQYSS  600
GWFGHMIPGA RMDDVQPRVI KPQPLVLAHG EAQKMKGNSC KLFGIHLDSP AKSEPLKSPP  660
SVAYDGMPQT PAAAEWRMVD SIEADRCSDP LKMPKQLDAT QVDPVPEKCS QVSRGTQCKS  720
QGGSTRSCKK VHKQGIALGR SVDLTKFNGY TELIAELDEM FDFNGELKGS NKEWMVVYTD  780
NEGDMMLVGD DPWNEFCNMV HKIFIYTREE VQRMNPGTLN SRSEDSLANS MERGSTARET  840
PGSLSASSLD SENC                                                    854

SEQ ID NO: 240           moltype = DNA  length = 2924
FEATURE                  Location/Qualifiers
misc_feature             1..2924
                         note = Ceres Clone ID no. 1744705
misc_feature             1..2924
                         note = Encodes the peptide sequence at SEQ ID NO. 241
source                   1..2924
                         mol_type = other DNA
                         organism = Panicum virgatum
SEQUENCE: 240
agccagccaa cctacccgcc ccggacagca aagcacaggc gcacgagccc ccccagctcc  60
acgcctcctc ctcctccctc cccctctccc gccatcctcc tccgccgcgc gccttcccgc  120
ccgccgagcc tttaggaggg ggtttccgga gtcgcggacg cgcgtgcgag acccccttccc  180
ctgccgccga gcgcaagtaa gatctccggc ctcccgcccc gcgcgctccg ggcgcctcct  240
ctctcccctg aattgcccgg gctcggggc tctaacggct gccccggtgg cgctgcgcgc  300
gcagatctgc cgagctcggc atggggtgac cagatcgggg cgcggctcgg ggctctacgg  360
ctgaattccg ctcggtgagg agggagctgg tctcggagag gccgggggga tggcgaacgc  420
cggcgcggcc gtcggtccag gggtgctag cgatgctttg ttcagggaac tctggcatgc  480
ttgtgctggg ccgttggtca cggtgcctcg ccaaggcgag ctggtttact acttcccgca  540
aggtcatatg gaacagcttg aagcatctac agatcagcaa cttgaccagc acttaccttt  600
gtttaatcta ccatccaaga tcctgtgcaa agtggtaaat gtagaactca gagctgaaac  660
tgattccgat gaagtttatg ctcaaattat gctgcaacca gaagcagatc aaaatgagcc  720
cactggccca gatcctgagc caccagagcc agaaaggtgc aatgtccatt ccttctgcaa  780
gactttgact gcttcagaca cgagcaccca tggtggtttc tctgtcctca ggagacatgc  840
tgaagaatgt ttgccccaat tggatatgac tcagaatcca ccatggcaag aactggtggc  900
taaagatctc catggaaatg aatggcattt ccgtcacatc tttcgaggtc aaccaaggag  960
gcatctactt acaacaggct ggagtgtttt tgttagctca aaaagattgg ttgctggtga  1020
tgcatttatc tttttgagag gtgataatgg agagctacga gtcggggtaa gaaggctcat  1080
gaggcaacta aataacatgc catcatcagt tatctcaagc catagcatgc atcttggagt  1140
cctcgcaaca gcatctcatg ccatctccac tggaactctc ttttctgttt tctacaaacc  1200
cagaacaagt cgatcggagt ttgttgtgag cgtaaacaag taccttgaag ctaagaatca  1260
caagatgtct gtcggtatga ggtttaaaat gagatttgag ggtaatgaat ctcctgaaag  1320
aagatttagt gggacaatta ttggtctggg aagcatgcca gctaactcaa catctccgtg  1380
ggctgactct gattggagat ctttgaaggt ccaatgggat gagccttctg ctgttgtccg  1440
tccagataga gtttcaccat gggaactaga accccttaat gcaactaaca cacaaccgcc  1500
tcagcctcct ttacggaata agcgtgcacg gcctcctgct tcaccttcta ttgctccaga  1560
acttcctcca gcttttggtt tttggaaatc cccagctgag cctacccatc ctttctcatt  1620
ttcgggactg cagcgaactc aggaattata ccattcaaac cccaattcaa tcttttcatc  1680
atcgttgaat gtgggattta attcaaagaa tgaacattct actccaacca acaatcattt  1740
gtactggcca attcgagaca ctagaacgga atcctactct gctagcatta acaaacttct  1800
acctgaaagg aagcaagaat ccgctactgc tggctgcaga ttgtttggta ttgagataag  1860
taatgcagta tcaccagtgg ttactgttgc tagtgttggt caagaccagc cacctgttga  1920
gtcagtagat gttgagtctg atcagctgtc acagccatcc caagccaaca aaacagatgc  1980
tccagcagca agcagtgagc gctctcctca tgagactgag agccggcaag tcaggagctg  2040
caccaaggta atcatgcaag gaatggcggt tggcagggca gtggacttga cgaggctaga  2100
aggatatgat gatcttctcc acaagttgga ggagatgttt gatatccagg gggagctttc  2160
tgctagcctc aagaaatgga aggttattta cacggatgat gaggatgata tgatgctggt  2220
cggggatgat ccgtggcctg aattttgcag catggtgaaa aggatataca tttactccta  2280
tgaggaggcc aagtctttga ctcccaaggc gaagctgccg gtcattggtg ataccactaa  2340
accgaaccca gacaagttgt caccggaatc tgacatgccg cagagtgact caaacaacag  2400
cgctctggtt gctgccgata aggactgatg gatgctaact tggcgctcta cctttaattc  2460
ccgttttgga tgtttgggag gcaatgccca tactccttga gactgctgag agttatctgt  2520
ttgttgcgct gtgggcccga aggacgttgc cccacaatct gcctgactgc cttggtttgg  2580
aatggctgat gtaggaccag tggtggtcct ctgccagcaa ggtcgactgg aatgtaatgg  2640
caagcaggcc gcattgcgcg ccgttccctg tgccaccaac ctgtgttttg tttgccgtgt  2700
ttggtaggag gcatggcgta tcgctggcct cacctccaga gtaaatagga ctttatgtac  2760
aactattttg gtagtagcag tagcggttta tgtatatcag cgtcatgttc cttgctacct  2820
atataagcat tatcatctgt agctgctgtt cccacctgca ttgtattcta cccccggctt  2880
ggtaccggat gctctggtgc aaaaatgtct ctgcttgctg ttcc                   2924
```

```
SEQ ID NO: 241          moltype = AA  length = 672
FEATURE                 Location/Qualifiers
REGION                  1..672
                        note = misc_feature - Ceres Clone ID no. 1744705
REGION                  1..672
                        note = misc_feature - Bit score of 1346.5 for hmm based on
                         sequences of FIGURE 5.
REGION                  248..333
                        note = misc_feature - Pfam Name: Auxin_resp Pfam Desc:
                         Auxin response factor
REGION                  121..226
                        note = misc_feature - Pfam Name: B3 Pfam Desc: B3 DNA
                         binding domain
REGION                  1..672
                        note = misc_feature - Is Acted Upon By Ceres SEEDLINE ID
                         no. ME00572 at SEQ ID NO. 111
source                  1..672
                        mol_type = protein
                        organism = Panicum virgatum
SEQUENCE: 241
MANAGAAVGP GGASDALFRE LWHACAGPLV TVPRQGELVY YFPQGHMEQL EASTDQQLDQ  60
HLPLFNLPSK ILCKVVNVEL RAETDSDEVY AQIMLQPEAD QNEPTGPDPE PPEPERCNVH  120
SFCKTLTASD TSTHGGFSVL RRHAEECLPQ LDMTQNPPWQ ELVAKDLHGN EWHFRHIFRG  180
QPRRHLLTTG WSVFVSSKRL VAGDAFIFLR GDNGELRVGV RRLMRQLNNM PSSVISSHSM  240
HLGVLATASH AISTGTLFSV FYKPRTSRSE FVVSVNKYLE AKNHKMSVGM RFKMRFEGNE  300
SPERRFSGTI IGLGSMPANS TSPWADSDWR SLKVQWDEPS AVVRPDRVSP WELEPLNATN  360
TQPPQPPLRN KRARPPASPS IAPELPPAFG FWKSPAEPTH PFSFSGLQRT QELYHSNPNS  420
IFSSSLNVGF NSKNEHSTPT NNHLYWPIRD TRTESYSASI NKLLPERKQE SATAGCRLFG  480
IEISNAVSPV VTVASVGQDQ PPVESVDVES DQLSQPSQAN KTDAPAASSE RSPHETESRQ  540
VRSCTKVIMQ GMAVGRAVDL TRLEGYDDLL HKLEEMFDIQ GELSASLKKW KVIYTDDEDD  600
MMLVGDDPWP EFCSMVKRIY IYSYEEAKSL TPKAKLPVIG DTTKPNPDKL SPESDMPQSD  660
SNNSALVAAD KD                                                      672

SEQ ID NO: 242          moltype = AA  length = 670
FEATURE                 Location/Qualifiers
REGION                  1..670
                        note = misc_feature - Public GI ID no. 140053546
REGION                  1..670
                        note = misc_feature - Bit score of 1133.4 for hmm based on
                         sequences of FIGURE 5.
REGION                  250..332
                        note = misc_feature - Pfam Name: Auxin_resp Pfam Desc:
                         Auxin response factor
REGION                  119..228
                        note = misc_feature - Pfam Name: B3 Pfam Desc: B3 DNA
                         binding domain
REGION                  1..670
                        note = misc_feature - Is Acted Upon By Ceres SEEDLINE ID
                         no. ME00572 at SEQ ID NO. 111
source                  1..670
                        mol_type = protein
                        organism = Medicago truncatula
SEQUENCE: 242
MCFSITFTGS TNDALYKELW HACAGPLVTL PREGERVYYF PQGHMEQLEA SMNQGLEQQM  60
PSFNLPSKIL CKVVNIHLRA EPETDEVYAQ ITLLPETDQS EVTSPDDPLP EPPRCTVHSF  120
CKTLTASDTS THGGFSVLRR HADDCLPPLD MTQQPPWQEL VATDLHGNEW HFRHIFRGQP  180
RRHLLTTGWS VFVSSKKLVA GDAFIFLRQV VLGENGELRV GVRRLMRQQS NMPSSVISSH  240
SMHLGVLATA SHAISTGTLF SVFYKPRTSR SEFIVSINKY LEARNHKLSV GMRFKMRFEG  300
DEVPERRFSG TIVGVEDNKS SVWADSEWRS LKVQWDEPSS ILRPDRVSPW ELEPLVSTPP  360
ANSQPTQRNK RSRPPILPST MTDSSLQGIW KSPADSPPFP YRDPQHGRDL YPSPRFSSTA  420
TSFLGFGGNS PASNKSMYWS SRLENSTEPF SPVALEESGE KRQGTGNGCR LFGIQLLENS  480
NAEESLQTAP LSGRVGDDRS VPSLDVESDQ HSEPSNVNRS DIPSVSCDAD KSCLRSPQES  540
QSRQIRSCTK VHMQGMAVGR AVDLTRFDGY EDLLRKLEEM FDIEGELCGA TKKWLVVYTD  600
NEDDMMMVGD DPWLEFCSVV RKMFIYTPEE VKKLSPKIGL PSNEEGKPSK LDSEAVVNPE  660
DRSSIVGPGC                                                         670

SEQ ID NO: 243          moltype = DNA  length = 2031
FEATURE                 Location/Qualifiers
misc_feature            1..2031
                        note = Ceres Annot ID no. 8733583
misc_feature            1..2031
                        note = Encodes the peptide sequence at SEQ ID NO. 244
source                  1..2031
                        mol_type = other DNA
                        organism = Sorghum bicolor
SEQUENCE: 243
atggggattg atctcaacag cgtggaggag gacgagcagg cgccggcggg cgcggtgtgc  60
tgcggggagc tgtggcacgc gtgcgcgggg gctggggtgg cgctgccgcg gcggggcagc  120
gccgtggtgt acctgcctca ggcgcacctc gcggccggcg gcgacggtgg ggagctgccg  180
```

```
gcccttgcgg cggcgccgcg cgtgccgccg cacgtggtgt gtcgcgtcgt cgacgtcgag  240
ctacgcgcgg atgcggcgac ggacgaggtc tatgcgcggc ttgcgctggt ggcggaggat  300
aagatgtttg gccgaaacat ccatgatggt gaaactgaag agaaggatgg tgagaaagag  360
gatggtgatg gagaaaagct cacatcgcac atgttctgca agacactcac agcttctgat  420
acaagcactc atggggatt ctctgttcct cggcgggctg cagaggactg ctttccacca  480
ttggactatg agcagcttag gccttcccaa gagcttattg ccaaggattt gcatggcatg  540
aaatggaggt tccgtcatat ctatagaggt caacctcgta ggcatcttct gacaactgga  600
tggagttcat ttattaataa gaagaaacta gtctcagggg atgcagtctt gtttctgaga  660
ggtagtgatg gcgagctaag attgggtgtg aggagagcag ttcaactgaa aaatgaagct  720
ctacttgaag ctgtcaactg tactgattcg aagctactta tgctgtctgc tgtggccagt  780
tctttggaca atagaagtat atttcacatc tgtttcaacc caaggattgg tgcatcagaa  840
tttattgtgc catattgcaa gtttttgaag ggcttgaact atccttttc aattggaacc  900
agatttaaag ttggctgcaa gaatgaagat gctaacgaga ggtcctttgg attgatctca  960
ggtattagtg aagttgatcc catacgctgg cctggatcaa aatggaaatc tctcttggta  1020
aagtgggatg gtgataccaa gtacagccac cagaatagag tatctccatg ggacatcgag  1080
agagttggca gctcagtttc agttactcac tgtctttcat cttgtgtttc gaagcgaatg  1140
aagttgtgct tcccccaagg caatttggac gctccaattc tagatggaaa tggtcgtcca  1200
gactctgtgg gaactgaagg tttccaccag gtcttgcaag gtcaagaatt ggtgagggtt  1260
catggtgctg catgctctca ttcatcagat acccccagat gtcaaggctc ttatggaagg  1320
agattctctg ccgatgtgtg gaactgcaag atgaatgatg gacacctaaa taccactggg  1380
tttgcttacc agcccctagg cttcagtgaa tctgtcaaat tctcagaggt cttgcaaggt  1440
caagaaatgt ctcaggtggc agccccttcc ttcatgagag atgctttcag tgctggcaca  1500
cagaatggca gggttcgatc atttgattat gtgcagagat cagctgcaac tcaaggatat  1560
gctctccagc aatttaatct gccagcaaca gaagtgcatt caccgtcttc tgttcttatg  1620
tttaaccaaa ccatggtacc acagcctgag ttagatggtc tgaccaaccg tgaagaagca  1680
tatggcagcg ggtactcatc cattgcaata cagagagaag ctgaaccatg gccatccacg  1740
cagcagcaaa gagtgcgcga aaatggaagc gagcctctcg acacaactga agcctcagct  1800
cctgcaagga tcgcaaaatc tggatcggtg gacaggggcg tcgggggaag cagctgtaag  1860
ctttttggtt tctccttgac tgagaagatc cttggaacag agggagttgg tgggaaagaa  1920
gggaactacg aagcggatcg gcagactccc cgggttctag acttgcttgg gcacggccat  1980
tctacgcccg gtgctctgca tgctctttgc gctgctccct tgggaatatg a           2031

SEQ ID NO: 244         moltype = AA  length = 676
FEATURE                Location/Qualifiers
REGION                 1..676
                       note = misc_feature - Ceres Annot ID no. 8733583
REGION                 1..676
                       note = misc_feature - Bit score of 1288.5 for hmm based on
                        sequences of FIGURE 5.
REGION                 258..339
                       note = misc_feature - Pfam Name: Auxin_resp Pfam Desc:
                        Auxin response factor
REGION                 131..236
                       note = misc_feature - Pfam Name: B3 Pfam Desc: B3 DNA
                        binding domain
REGION                 1..676
                       note = misc_feature - Is Acted Upon By Ceres SEEDLINE ID
                        no. ME00572 at SEQ ID NO. 111
source                 1..676
                       mol_type = protein
                       organism = Sorghum bicolor
SEQUENCE: 244
MGIDLNSVEE DEQAPAGAVC CGELWHACAG AGVALPRRGS AVVYLPQAHL AAGGDGGELP  60
ALAAAPRVPP HVVCRVVDVE LRADAATDEV YARLALVAED KMFGRNIHDG ETEEKDGEKE  120
DGDGEKLTSH MFCKTLTASD TSTHGGFSVP RRAAEDCFPP LDYEQLRPSQ ELIAKDLHGM  180
KWRFRHIYRG QPRRHLLTTG WSSFINKKKL VSGDAVLFLR GSDGELRLGV RRAVQLKNEA  240
LLEAVNCTDS KLLMLSAVAS SLDNRSIFHI CFNPRIGASE FIVPYCKFLK GLNYPFSIGT  300
RFKVGCKNED ANERSFGLIS GISEVDPIRW PGSKWKSLLV KWDGDTKYSH QNRVSPWDIE  360
RVGSSVSVTH CLSSCVSKRM KLCFPQGNLD APILDGNGRP DSVGTEGFHQ VLQGQELVRV  420
HGAACSHSSD TPRCQGSYGR RFSADVWNCK MNDGHLNTTG FAYQPLGFSE SVKFSEVLQG  480
QEMSQVAAPS FMRDAFSAGT QNGRVRSFDY VQRSAATQGY ALQQFNLPAT EVHSPSSVLM  540
FNQTMVPQPE LDGLTNREEA YGSGYSSIAI QREAEPWPST QQQRVRENGS EPLDTTEASA  600
PARIAKSGSV DRGVGGSSCK LFGFSLTEKI LGTEGVGGKE GNYEADRQTP RVLDLLGHGH  660
STPGALHALC AAPLGI                                                 676

SEQ ID NO: 245         moltype = DNA  length = 1974
FEATURE                Location/Qualifiers
misc_feature           1..1974
                       note = Ceres Annot ID no. 8700968
misc_feature           1..1974
                       note = Encodes the peptide sequence at SEQ ID NO. 246
source                 1..1974
                       mol_type = other DNA
                       organism = Sorghum bicolor
SEQUENCE: 245
atggacgcgc ccaaccctgc agcggctgct ggctcaggag gaatgcctag tgacgccctg  60
taccgagagc tgtggcatgc gtgtgccggc ccgttggtca cagtacctag acaaggcgag  120
cgcgtctatt acttccccca gggccatatg gagcagcttg aggcgtctac acaccagcag  180
cttgatcagt acttaccgat gttcaatcta ccacccaaga tcctatgcag tgtagtcaac  240
```

-continued

```
gtggaactac gggccgaagc tgattcagat gaagtttatg ctcaaattat gttgcaacca  300
gaagctgatc aaaacgaact caccagcctg gaccctgaac cacaagaacc tgaaaaatgc  360
actgcccatt ccttctgcaa gacactgaca gcttcagata cgagcactca cggcggtttt  420
tctgttcttc ggaggcatgc tgaagaatgt cttcctcagc tggacatgtc tctaaatcca  480
ccttgccaag aactggttgc caaagatctc catggcactg aatggcattt tcgacacatt  540
tttcgagggc aacccaagag gcatctcctt acaactggct ggagtgtctt tgttagctca  600
aagagattgg ttgcgggga tgcatttatc ttcatgagag gtgaaaatgg tgagctacgg  660
gttggtgtaa ggaggctcat gagacaagta aatagcatgc cgtcatctgt catatcaagc  720
cacagcatgc atcttggagt cttggccaca gcctcccatg ccatctccac tggaaccctc  780
ttttccgttt tctacaaacc aagaactagc cgatctgatt ttattgtgag tgttaacaag  840
taccttgaag ctaagaagca gaaaatatct gttggaatga ggtttaagat gagatttgaa  900
ggtgatgagg ctcctgaaag aaggttcagt ggaacaatta ttggcattgg cagtttgccg  960
gcaatgtcaa aatctctgtg ggcagattct gactggagat ctctaaaggt tcaatgggac  1020
gaaccttcat ccattcttcg tccagataga atctcaccat gggaagtgga gcccctggat  1080
gctgctaatc cacaatcccc tcaacctcca ccaaggccta agcgtccacg acccccagct  1140
tcaccttgta tggtttcaga actgccttca ggttttggac tctggaaatc cccaacagaa  1200
tcatcccgta cactctcatt ttcggaacct caacgggctc gagagttatt tccttcaatt  1260
cccacatcaa ccttctcatc ttcatcaaac gtcagtttca attcaaagaa tgagccatcc  1320
atgctaacca cacagttcta ctggtcagca agggatacaa gagctgactc ctgcgctgct  1380
agcaccaaca cagtcatagt tgaaaagaag caagagccaa gttctggtgg ttgcagattg  1440
tttggaattg atatatgctc agctgaggaa gaagtattac ctgtggttac tgctccaggt  1500
gttggttatg agcagactgc tgcctctgta gagttgaact cggataagct ctcacaggga  1560
tctgatgtca acaattctga tgccccagca gctagcagtg agcgttcacc tcttgaatcc  1620
caaagccggc aagtgaggag ctgcaccaag gtaattatgc aaggaatggc agttggaagg  1680
gctgtagacc tgacaaagct tagtggctac agtgatcttt gccagaagtt ggaggagatg  1740
tttgacatcc acggggagct aggttgcaca ctcaagaaat ggcgggtcat tttcactgat  1800
gatgaggatg acatgatgct tgttggggat gatccttggg atgagttttg cagaatggtg  1860
aaaaggattt acatttacac atatgaggag gcgaagaaac tgacatccaa gtcaaagtta  1920
cctgttagca gtgacagcag caagctgagt gctgtaaact cactgtctga atga        1974

SEQ ID NO: 246          moltype = AA  length = 657
FEATURE                 Location/Qualifiers
REGION                  1..657
                        note = misc_feature - Ceres Annot ID no. 8700968
REGION                  1..657
                        note = misc_feature - Bit score of 1132.7 for hmm based on
                         sequences of FIGURE 5.
REGION                  251..336
                        note = misc_feature - Pfam Name: Auxin_resp Pfam Desc:
                         Auxin response factor
REGION                  124..229
                        note = misc_feature - Pfam Name: B3 Pfam Desc: B3 DNA
                         binding domain
REGION                  1..657
                        note = misc_feature - Is Acted Upon By Ceres SEEDLINE ID
                         no. ME00572 at SEQ ID NO. 111
source                  1..657
                        mol_type = protein
                        organism = Sorghum bicolor
SEQUENCE: 246
MDAPNPAAAA GSGGMPSDAL YRELWHACAG PLVTVPRQGE RVYYFPQGHM EQLEASTHQQ  60
LDQYLPMFNL PPKILCSVVN VELRAEADSD EVYAQIMLQP EADQNELTSL DPEPQEPEKC  120
TAHSFCKTLT ASDTSTHGGF SVLRRHAEEC LPQLDMSLNP PCQELVAKDL HGTEWHFRHI  180
FRGQPKRHLL TTGWSVFVSS KRLVAGDAFI FMRGENGELR VGVRRLMRQV NSMPSSVISS  240
HSMHLGVLAT ASHAISTGTL FSVFYKPRTS RSDFIVSVNK YLEAKKQKIS VGMRFKMRFE  300
GDEAPERRFS GTIIGIGSLP AMSKSLWADS DWRSLKVQWD EPSSILRPDR ISPWEVEPLD  360
AANPQSPQPP PRPKRPRPPA SPCMVSELPS GFGLWKSPTE SSRTLSFSEP QRARELFPSI  420
PTSTFSSSSN VSFNSKNEPS MLTTQFYWSA RDTRADSCAA STNTVIVEKK QEPSSGGCRL  480
FGIDICSAEE EVLPVVTAPG VGYEQTAASV ELNSDKLSQG SDVNNSDAPA ASSERSPLES  540
QSRQVRSCTK VIMQGMAVGR AVDLTKLSGY SDLCQKLEEM FDIHGELGCT LKKWRVIFTD  600
DEDDMMLVGD DPWDEFCRMV KRIYIYTYEE AKKLTSKSKL PVSSDSSKLS AVNSLSE     657

SEQ ID NO: 247          moltype = AA  length = 831
FEATURE                 Location/Qualifiers
REGION                  1..831
                        note = misc_feature - Public GI ID no. 147770011
REGION                  1..831
                        note = misc_feature - Bit score of 909.6 for hmm based on
                         sequences of FIGURE 5.
REGION                  280..362
                        note = misc_feature - Pfam Name: Auxin_resp Pfam Desc:
                         Auxin response factor
REGION                  153..258
                        note = misc_feature - Pfam Name: B3 Pfam Desc: B3 DNA
                         binding domain
REGION                  1..831
                        note = misc_feature - Is Acted Upon By Ceres SEEDLINE ID
                         no. ME00572 at SEQ ID NO. 111
SITE                    606
```

```
                        note = misc_feature - Xaa is any aa, unknown, or other
source                  1..831
                        mol_type = protein
                        organism = Vitis vinifera
SEQUENCE: 247
MVAMIDLNTV DDDETPSSGS SSSSSSSASA SASTVCGSLL SAASSVCLEL WHACAGPLIS  60
LPKKGSLVVY FPQGHLEQLS DYPAVAYDLP PHVFCRVVDV KLHAEVVTDE VYAQVSLVPE  120
TKIKQKLQEG EIEADGGEEE DIEGSIKSMT PHMFCKTLTA SDTSTHGGFS VPRRAAEDCF  180
PPLDYKQQRP SQELVAKDLH GFEWRFRHIY RGQPRRHLLT TGWSAFVNKK KLVSGDAVLF  240
LRGGDGELRL GIRRAAQIKG SSPFPALCSQ QLNLNTLTAV VNAISTRSVF NICYNPRASS  300
SEFIIPLRKF SKSIDHSFSA GMRFKMRVET EDAAERRYTG LITGISDMDP VRWPGSKWRC  360
LLLHHSHGSE CVLLPCLPYY SDSATFFDLS LQVRWDDIEA NRHNRVSPWE IELSGSLSGS  420
GSLTVPGSKR TRIGLPGTRP DFSVPNGMGV SDFGESSRFQ KVLQGQEIFG FNTPYDGVDT  480
QDHHPSEIRC FPGSSCSRIA AIGNGVRNPL GNSDISYKGI GFGESFRFHK VLQGQETFPS  540
PPCGRALSAN QAHENGSFGI FDGVQVPTSR NGWPALVQGY NAHTHLSTPS VQVSSPSSVL  600
MRRSKXLSNR SSFDIPEVYG EKLTPSRCEL SVRGGGQGGM NFFGLLNEHN QLAVPHPLVT  660
QSAFRGSQDL VPTCKSSCRL FGFSLTEERS IGNKVDNPTP VTSSLIPGTS FLPQQLHSEP  720
PVMTKAIGSN CTKRTAVVRS KLQFHKLGSV VDQAINRWKL DRHDDLICAL KHLFDMEGGL  780
LHGEGNDMHL SLTPAFYSPK SGLAEIQNGY PFANSYVRPV FPENRILDII I           831

SEQ ID NO: 248          moltype = DNA  length = 2049
FEATURE                 Location/Qualifiers
misc_feature            1..2049
                        note = Ceres Annot ID no. 8668727
misc_feature            1..2049
                        note = Encodes the peptide sequence at SEQ ID NO. 249
source                  1..2049
                        mol_type = other DNA
                        organism = Sorghum bicolor
SEQUENCE: 248
atgggaatcg atctcaacat ggtgggcggc gagggccacg atcgccgccc gccgccgccg  60
gtgagccggg agctgtggca cgcgtgcgcg gggcccgtgg tcgcgctacc gcggcggggg  120
agcctggtcg tgtacctgcc gcagggccac ctagccgcgg cgggcggcgg ggacgtcgct  180
gcggacctgc cgccgcacgt ggtgtgccgc gtcgcggatg tcgagctatg cgcggatgcg  240
gcgacggacg aggtgtacgc gcggctggcg ctggttgcgg aaggcgaggc atttgggaga  300
aatctgcacg gcggcggagc tgaaggggac gatgacatgg aggatttgga tgctgaaagg  360
aagtcccgga tgttgcacat gttctgcaaa acgcttacag cctctgacac aagcacgcat  420
ggagggttct ctgttcctcg ccgtgctgct gaggactgtt tcccgcctct ggattataat  480
cagctcaggc cttctcaaga gctggttgcc aaggatttgc atggaactaa atggaagttt  540
cgtcatatat ataggggtca gcctcgtagg catctcttga ctactggatg gagttcattt  600
gtcaataaaa agaaactggt ttcaggggat gctgtgttat ttctccgagg tgatgatggt  660
gaactaaggc ttggtgtacg gagagccatt cagcttaaaa atgaggccct ttttgaagat  720
ttcagtagtg acagtacaaa gcggcataca ttgtcggctg tagctgattc cttgaagcac  780
agaagtgttt ttcacatttc ttacaatcca agagctactg cttcagaata tattattcca  840
taccataagt tcctgaagag cctcaatcat ccagtctgtg ttggagcaag gatcaacttt  900
cagtgccata atgaagatgt tagtgaaagg cgatctggaa tggttgttcg cattagtgaa  960
atagatccca tgaaatggcc tggctcgaag tggagaagcc tgctggtaag atgggaggat  1020
ggtgctgaat gtaacggcca agatagagta tctccatggg agatcgaggt agctggtggt  1080
tctgtctctg ttgctcattc tctgtccgca tctagttcta aaagaaccaa gttgtgtgct  1140
cagggaaatt tggacgttcc aacaatgtgg aatggttgta ctgactccgt ggaaactgga  1200
aagttaccca gggtcttgca aggtcaagaa ttgatgggtt ttaggactcg tcatgttccg  1260
tgtgctcctc aaactgctga ggctgcaaaa cttcaatctt ctgatgctag taggtttctt  1320
agtaatgcac gtgactgcgc attgagtgct ccaacaagca gactcgcagt gcataactct  1380
ggttttacct accaatctgt aggcttcaat gaatctattg gattctcaga ggtcttgcaa  1440
ggtcaagaaa tttctcgggc agttcctatg ttccaaggaa tgatgtctga ggcttgttca  1500
ctgaaaggcg gatatgggct acatagttat atgcataccc cagttgctgt taatggatta  1560
tcagccccag ctcaagaatg ttgtctgaca ctatctactc cgccaggagc acaagtgccc  1620
tctctctacc ctgataatat ttttaaccga actgtggttc cgcagcttgg actggcaagc  1680
aagtttggtg gtggaggtac aaatggccag cagtctggcc catttgatag gcggagggaa  1740
atttggacca agccacagca tgaaacacct gatcaaatga acttggatca gtttgagact  1800
agaagagctt cagcacctgg agatgctggt aagcttgggt ctggtggagg ggaggttcgc  1860
aaaactagct gcagactttt tggtttctcc ttgactgaga agatcttgcc agcagatgat  1920
gatggcgtca aggaagtgag ctatgagcct gagtgccaga acccacggat gctggatctg  1980
tttgggtaca actgctcaac cccgagtgct gctcttccgg ctctgtgtgc tgcccccatt  2040
ggaatgtga                                                          2049

SEQ ID NO: 249          moltype = AA  length = 682
FEATURE                 Location/Qualifiers
REGION                  1..682
                        note = misc_feature - Ceres Annot ID no. 8668727
REGION                  1..682
                        note = misc_feature - Bit score of 1041.4 for hmm based on
                         sequences of FIGURE 5.
REGION                  127..232
                        note = misc_feature - Pfam Name: B3 Pfam Desc: B3 DNA
                         binding domain
REGION                  254..335
                        note = misc_feature - Pfam Name: Auxin_resp Pfam Desc:
                         Auxin response factor
```

```
REGION                  1..682
                        note = misc_feature - Is Acted Upon By Ceres SEEDLINE ID
                         no. ME00572 at SEQ ID NO. 111
source                  1..682
                        mol_type = protein
                        organism = Sorghum bicolor
SEQUENCE: 249
MGIDLNMVGG EGHDRRPPPP VSRELWHACA GPVVALPRRG SLVVYLPQGH LAAAGGGDVA  60
ADLPPHVVCR VADVELCADA ATDEVYARLA LVAEGEAFGR NLHGGGAEGD DDMEDLDAER  120
KSRMLHMFCK TLTASDTSTH GGFSVPRRAA EDCFPPLDYN QLRPSQELVA KDLHGTKWKF  180
RHIYRGQPRR HLLTTGWSSF VNKKKLVSGD AVLFLRGDDG ELRLGVRRAI QLKNEALFED  240
FSSDSTKRHT LSAVADSLKH RSVFHISYNP RATASEYIIP YHKFLKSLNH PVCVGARINF  300
QCHNEDVSER RSGMVVRISE IDPMKWPGSK WRSLLVRWED GAECNGQDRV SPWEIEVAGG  360
SVSVAHSLSA SSSKRTKLCA QGNLDVPTMW NGCTDSVETG KLPRVLQGQE LMGFRTRHVP  420
CAPQTAEAAK LQSSDASRFL SNARDCALSA PTSRLAVHNS GFTYQSVGFN ESIGFSEVLQ  480
GQEISRAVPM FQGMMSEACS LKGGYGLHSY MHTPVAVNGL SAPAQECCLT LSTPPGAQVP  540
SLYPDNIFNR TVVPQLGLAS KFGGGGTNGQ QSGPFDRRRE IWTKPQHETP DQMNLDQFET  600
RRASAPGDAG KLGSGGGEVR KTSCRLFGFS LTEKILPADD DGVKEVSYEP ECQNPRMLDL  660
FGYNCSTPSA ALPALCAAPI GM                                           682

SEQ ID NO: 250          moltype = AA  length = 670
FEATURE                 Location/Qualifiers
REGION                  1..670
                        note = misc_feature - Public GI ID no. 157354310
REGION                  1..670
                        note = misc_feature - Bit score of 1095.7 for hmm based on
                         sequences of FIGURE 5.
REGION                  246..329
                        note = misc_feature - Pfam Name: Auxin_resp Pfam Desc:
                         Auxin response factor
REGION                  119..224
                        note = misc_feature - Pfam Name: B3 Pfam Desc: B3 DNA
                         binding domain
REGION                  1..670
                        note = misc_feature - Is Acted Upon By Ceres SEEDLINE ID
                         no. ME00572 at SEQ ID NO. 111
source                  1..670
                        mol_type = protein
                        organism = Vitis vinifera
SEQUENCE: 250
MTCCCLLGAP CDALYKELWH ACAGPLVTVP REGERVYYFP QGHMEQLEAS TTHQGLDQQM  60
PSFNLPSKIL CKVVHVQLRA EPETDEVYAQ VTLLPEPDQS EITSPDPPLP EPQRCTVHSF  120
CKTLTASDTS THGGFSVLRR HADDCLPPLD MSQQPPWQEL VAADLHGNEW HFRHIFRGQP  180
RRHLLTTGWS VFVSSKKLVA GDAFIFLRGE NGELRVGVRR LMRQLSNMPS SVISSHSMHL  240
GVLATASHAI STGTLFSVFY KPRTSRSEFI VSLNKYLEAR NHKLSVGMRF KMRFEGEEVP  300
ERRFSGTIVG VGDKNTSSGW ADSEWRSLKV QWDEPASIFR PERVSAWELE PLVAAAAPTN  360
LQPAQRNKRA RPPVLPSATP DLSVLGMWKS SVESPSGFPY CDPHRGRDLY PSPKFSSITK  420
TNSFSFSGNS SPAAVSSNSM YWSNRMETAT ESFAPAVNKE SGEKRRDTGS GCRLFGFQLL  480
DNSTLEETLP VLTVGEDQPV PSLDVESDQH SEPSNINRSD IPSVSCEPDK LSLRSPQESQ  540
SRQIRSCTKV HMQGIAVGRA VDLTRFDRYE DLLKKLEEMF DIQGELCGLT SIWQVVYTDD  600
EDDMMMVGDD PWLEFCSMVR KIFIYTAEEV KRLSPKIKLP AMEEIKPGKL DSDVAVAGTD  660
DQSSVVGPGC                                                         670

SEQ ID NO: 251          moltype = DNA  length = 2721
FEATURE                 Location/Qualifiers
misc_feature            1..2721
                        note = Ceres Clone ID no. 1769972
misc_feature            1..2721
                        note = Encodes the peptide sequence at SEQ ID NO. 252
source                  1..2721
                        mol_type = other DNA
                        organism = Panicum virgatum
SEQUENCE: 251
attaatgggg tgctcatcct cctgacctcc tcgtcctccc cctcctctcc tcctccccgc  60
cgggtcgcgg tcggctccgc cttttaaccg ccttgccctg gagggggccg agcggcggac  120
cgcacgggcg cacgaccgcg gggggaccgg agcaggaccc ggaaccctag tggcggccgc  180
gcgcgccatg ggcatcgatc tcaacatggt ggacggcgag ggcgaggagc ggcgcccccc  240
gccggcggtg tgccgggacc tgtggcacgc gtgcgcgggg cccgtagtcg cgctgccgcg  300
gcggggcagc ctcgtcgtgt acctgccgca gggccacctc gctgcggctg gcggcgggga  360
cgtcgcggcg gacctgccgc cgcacgtggt gtgccgcgtc gcggacatcg agctatgcgc  420
ggatgcggcg acggacgagg tgtacgcacg gctggcgctg gtggcggagg gtgaggcatt  480
tgggagaaat gtgcgtgttg gtggagttga aggggacgag gacatggagg attttgatgc  540
tgaaaggaag tcccggatgc tgcacatgtt ctgcaaaacg ctcactgcct ctgacacaag  600
cacgcatgga gggttctctg ttcctcgtcg agctgctgag gactgtttcc caccgctgga  660
ctataatcaa ctcaggcctt ctcaagagct tgttgccaag gatttgcatg gagccaagtg  720
gaagtttcgt catatttata ggggtcagcc tcgtaggcat ctcttaacaa ctggatggag  780
ttcatttgtc aataaaaaga aactggtttc aggggatgca gtcttatttc tccgaggtga  840
tgatggtgaa ctaagactgg gtgtaaggag agctgttcag cttaaaaatg aggccctttt  900
tgaagaattc agtagcgaca gtgcaaagcg acatacgttg tctgctgtat ataattcctt  960
```

-continued

```
gaaacataaa agtgtctttc acatttctta caatccaaga gttgctgctt cagaatatat  1020
aattccttac cggaagttcc ttaagagcct caaccatcca gtctgtattg gagcgaggat  1080
caacttccaa tgccagaatg aagatgttag tgaaaggcga tctggaatgg ttgttggcaa  1140
tagtgaagta gatcccatga aatggcctgg ctcaaagtgg agaagcctgc tggtaagatg  1200
ggaggatggt tctgaatgca atggccaaga tagagtatct ccatgggaga tcgatatagt  1260
tggtggctca gtctctgctg cccattctct gtccgcatct agttctaaaa gaaccaagtt  1320
atgccctccg ggaaatttgg acgttccaac aatgtggaat ggttgtactg actccgtgga  1380
aactggaaag ttacccaggg tcttgcaagg tcaagaattg atgggtttta ggactcatcg  1440
tgttacgtgt gctcctcaaa cagctgaggt tgcaaaattt caatcttctg atgctagtag  1500
gttccttact aatgcacgaa gctgcatgtt gagtggtcca acaggcagac ttgcagtaca  1560
gaactctggc tttacctacc aatctctggg cttcagtgaa tctattggat tctcagaggt  1620
cttgcaaggt caagaaattt ctcaggcagt tcctatgttc caaggaatga tatctgcggc  1680
atgttcactg aagggcggat atgggctgcg tggttatgtg catacccccag ctgctgttaa  1740
tggattatca gccacagctc aagaatgttc tctcacacta tgtactccac ctgcagcaca  1800
agtgccccct cctcatccca atcatatgtt taaccaaact gtgtcgtccc agcttggatt  1860
gggaaacaag tctgctggcg aagttgcaaa tggcagtcag cctcgcccat ttgatatgtc  1920
gtgggaagct cagaccaggc cacagcatga aatacctgct caaattagct tggatcaatt  1980
tgaggctagg agagcttcag cacctggaga tgctgctaaa attgggtctg gtggaaggga  2040
ggtgcgcaaa actagctgca ggctttttgg tttctcattg actgagaaga tcttgccagc  2100
tgatgatgat ggcgtgaagg aagtgagtta tgaggctgag tgccagaatc cacggatgct  2160
ggacttgttc gggtacaact gctccacccc aagtgctgct cttccagctc tctgtgccgc  2220
ccccttcgga atgtgatgct actttagtaa tctttccaag tattttcaag cactcagatt  2280
agacgtactt tcccagtacc ccagtgtgtg cataagctgt cttttgacct cattccctcc  2340
attggcctgc tcatgttaat cagtcatctg cacgagtcaa ggaaggatga ttggtgaacc  2400
attcctctgc atggctcacc tggccaccca aagtattatg gttgtgtatc gtgatatgca  2460
ccattgtaac ttttgtggct atccttcaga cccattgtgc gatgaagcta acgatgtgcc  2520
ctaaaagtac ttcgctcaca gatttggatt catgggaagg tctgtcagct ttgatgtacc  2580
ggttatgtgt ctttaactga gctcctgtat gacttttgta gctcagtcat gagccgtgtt  2640
tgcactggtg cctaggtcgt gtgattgtat cagtatgtaa gactattgct tcgtttcaag  2700
atatgttgct tatggacctt t                                            2721
```

```
SEQ ID NO: 252          moltype = AA  length = 682
FEATURE                 Location/Qualifiers
REGION                  1..682
                        note = misc_feature - Ceres Clone ID no. 1769972
REGION                  1..682
                        note = misc_feature - Bit score of 1072.6 for hmm based on
                         sequences of FIGURE 5.
REGION                  127..232
                        note = misc_feature - Pfam Name: B3 Pfam Desc: B3 DNA
                         binding domain
REGION                  254..335
                        note = misc_feature - Pfam Name: Auxin_resp Pfam Desc:
                         Auxin response factor
REGION                  1..682
                        note = misc_feature - Is Acted Upon By Ceres SEEDLINE ID
                         no. ME00572 at SEQ ID NO. 111
source                  1..682
                        mol_type = protein
                        organism = Panicum virgatum
SEQUENCE: 252
MGIDLNMVDG EGEERRPPPA VCRDLWHACA GPVVALPRRG SLVVYLPQGH LAAAGGGDVA  60
ADLPPHVVCR VADIELCADA ATDEVYARLA LVAEGEAFGR NVRVGGVEGD EDMEDFDAER  120
KSRMLHMFCK TLTASDTSTH GGFSVPRRAA EDCFPPLDYN QLRPSQELVA KDLHGAKWKF  180
RHIYRGQPRR HLLTTGWSSF VNKKKLVSGD AVLFLRGDDG ELRLGVRRAV QLKNEALFEE  240
FSSDSAKRHT LSAVYNSLKH KSVFHISYNP RVAASEYIIP YRKFLKSLNH PVCIGARINF  300
QCQNEDVSER RSGMVVGNSE VDPMKWPGSK WRSLLVRWED GSECNGQDRV SPWEIDIVGG  360
SVSAAHSLSA SSSKRTKLCP PGNLDVPTMW NGCTDSVETG KLPRVLQGQE LMGFRTHRVT  420
CAPQTAEVAK FQSSDASRFL TNARSCMLSG PTGRLAVQNS GFTYQSLGFS ESIGFSEVLQ  480
GQEISQAVPM FQGMISAACS LKGGYGLRGY VHTPAAVNGL SATAQECSLT LCTPPAAQVP  540
PPHPNHMFNQ TVSSQLGLGN KSAGEVANGS QPRPFDMSWE AQTRPQHEIP AQISLDQFEA  600
RRASAPGDAA KIGSGGREVR KTSCRLFGFS LTEKILPADD DGVKEVSYEA ECQNPRMLDL  660
FGYNCSTPSA ALPALCAAPF GM                                           682
```

```
SEQ ID NO: 253          moltype = DNA  length = 2421
FEATURE                 Location/Qualifiers
misc_feature            1..2421
                        note = Ceres Annot ID no. 8460878
misc_feature            1..2421
                        note = Encodes the peptide sequence at SEQ ID NO. 254
source                  1..2421
                        mol_type = other DNA
                        organism = Solanum lycopersicum
SEQUENCE: 253
atggctactt ctgagaattg ccggaacgct gccggcgccg gaaaagttga tgctgagaaa  60
gcgttgtaca cggagctatg gcgagcatgt gcaggtccgc ttgtgacagt gccatgtgaa  120
ggcgagctgg tgttctattt ccccacaaggt catattgaac aggttgaagc atcaacaaac  180
caagcttcag accagcagat gccagtatat aatcttcctt ctaagatcct ctgtcgtgtg  240
attaacgtcc tgctgaaggc tgaacccgat acagatgagg tgtatgcaca agtgactttg  300
```

-continued

```
ttgccagaac caaatcaaga tgagaatgtg gtatcaaagg aaccgatgcc ctctccgcca  360
ccacgattcc atgtgcactc tttttgtaag acattaacag cctctgatac cagcactcat  420
ggaggatttt ctgtcttgag acggcatgct gatgaatgcc tcccgcctct ggttagaaag  480
aattctttct caatacagtt atggtgcctg tattttgata atcctccaac acaggagttg  540
gtggccaaag atttgcatgc aaatgagtgg cgcttcaggc acatattccg gggccagcct  600
aggaggcacc ttcttcagag tggttggagt gtctttgtta gttcgaaaag gcttgttgca  660
ggggatgcat tcatatttct tagaggtgag aatggggagc ttcgtgttgg agtccgacgt  720
gccatgagac agcagggtaa tgctccatca tcagtgatat ccagtcatag catgcatctt  780
ggtgtccttg ctacagcttg gcatgctatt cagacgaaaa cactgacgag ccctgctgac  840
tttatagttc catatgatca gtatatggag tctctgaaaa acaattactc catcgggatg  900
aggtttaaaa tgaggtttga aggtgaagaa gctccagaac agaggtttac tggaactata  960
gttggcattg aaaatgctga cctcaaaagg tggcctgagt caaaatggag atgcctgaag  1020
gttcgatggg atgaaacttc tgctattcct aggccagacc gagtttcacc ctggaaagta  1080
gagccagctc ttagccctcc tgcacttaat ccacttccaa taccaaggca gaaaaggccg  1140
cgatcaaatg ttctgccctc gtctcctgat tcttctgtac ttactaggga aggttcatcc  1200
aaagtagttg tagacacttc acaagccagt gggttttcaa gagttttgca aggtcaagaa  1260
atatcaacct tgagaggcaa ttttgtagaa aataacgagt cggactcttc tgagaagcca  1320
cctatatggc aaccattact ggatgacgag aaggctgatg ttcattctgc gtcaaggaaa  1380
tgtatatcag ataaacggct tcctttaggg aggcctgaat catcttttac agatctttta  1440
tcaggttttg gggggcaatc tagttcatct catggattcc attcacccac tgggggccaa  1500
acagcacctg ctagctgggt taagcgacaa gctctggata aggaaactga tttcagctta  1560
ctggcaaaac aatggtctct agtgtcttct ggtctctcac ttaatctgat ggaatcagga  1620
ttgaagggtg cagatactct gtatcaaatg cggggaacat ctcgactcaa ttgttttaac  1680
gagtatccaa ccttccctgg tcatagacct gacaatcagc agggaaattg gttaatgccc  1740
ccgtccgtgc tgccttatat tcagatgtcc gctcattctg gagaaattat gcctaaaccc  1800
atggcttcac cacagcccga agccatgaaa cccaaagaag ggaactgcaa actatttggc  1860
attccccttg taagtaaatg tgccaccata gatcctgtca tgttgcggaa aaattccccg  1920
attcactcaa caagtaacat gcactttggt atacatccac atcaattccc tataattgaa  1980
tctgatcaaa ggtctgagca atcaaaggga tcaaagctac cagatgatgg cttcatagtt  2040
catgatcagg aagaacaatt ccaaacctct catcctggta ctcgagatag agagggcaaa  2100
ggccttgttc attcaacaag gagttgcacc aaggttcata aacagggtac agcccttgga  2160
aggtctgttg atcttgcaaa gttcaacaac tatgaagaat tgatagctga actggatcac  2220
atttttgatt ttaatggtga gctcaaggct cgtaacaaga actggctgat ttttatctac  2280
acgaaagatg aggtgcagcg gatgaaccct gggactctca attcaaaagg cgaggacaat  2340
tcttctgttg cagaaggctc tgatgctaaa gaagtgaaga atctacagct tcacattgat  2400
tccagtccgg aagattctta g                                          2421
```

```
SEQ ID NO: 254          moltype = AA  length = 806
FEATURE                 Location/Qualifiers
REGION                  1..806
                        note = misc_feature - Ceres Annot ID no. 8460878
REGION                  1..806
                        note = misc_feature - Bit score of 1407.8 for hmm based on
                         sequences of FIGURE 5.
REGION                  266..340
                        note = misc_feature - Pfam Name: Auxin_resp Pfam Desc:
                         Auxin response factor
REGION                  127..244
                        note = misc_feature - Pfam Name: B3 Pfam Desc: B3 DNA
                         binding domain
REGION                  1..806
                        note = misc_feature - Is Acted Upon By Ceres SEEDLINE ID
                         no. ME00572 at SEQ ID NO. 111
source                  1..806
                        mol_type = protein
                        organism = Solanum lycopersicum
SEQUENCE: 254
MATSENCRNA AGAGKVDAEK ALYTELWRAC AGPLVTVPCE GELVFYFPQG HIEQVEASTN  60
QASDQQMPVY NLPSKILCRV INVLLKAEPD TDEVYAQVTL LPEPNQDENV VSKEPMPSPP  120
PRFHVHSFCK TLTASDTSTH GGFSVLRRHA DECLPPLVRK NSFSIQLWCL YFDNPPTQEL  180
VAKDLHANEW RFRHIFRGQP RRHLLQSGWS VFVSSKRLVA GDAFIFLRGE NGELRVGVRR  240
AMRQQGNAPS SVISSHSMHL GVLATAWHAI QTKTLTSPAD FIVPYDQYME SLKNNYSIGM  300
RFKMRFEGEE APEQRFTGTI VGIENADLKR WPESKWRCLK VRWDETSAIP RPDRVSPWKV  360
EPALSPPALN PLPIPRQKRP RSNVLPSSPD SSVLTREGSS KVVVDTSQAS GFSRVLQGQE  420
ISTLRGNFVE NNESDSSEKP PIWQPLLDDE KADVHSASRK CISDKRLPLG RPESSFTDLL  480
SGFGGQSSSS HGFHSPTGGQ TAPASWVKRQ ALDKETDFSL LAKQWSLVSS GLSLNLMESG  540
LKGADTLYQM RGTSRLNCFN EYPTFPGHRP DNQQGNWLMP PSVLPYIQMS AHSGEIMPKP  600
MASPQPEAMK PKEGNCKLFG IPLVSKCATI DPVMLRKNSP IHSTSNMHFG IHPHQFPIIE  660
SDQRSEQSKG SKLPDDGFIV HDQEEQFQTS HPGTRDREGK GLVHSTRSCT KVHKQGTALG  720
RSVDLAKFNN YEELIAELDH IFDFNGELKA RNKNWLIFIY TKDEVQRMNP GTLNSKGEDN  780
SSVAEGSDAK EVKNLQLHID SSPEDS                                     806
```

```
SEQ ID NO: 255          moltype = AA  length = 862
FEATURE                 Location/Qualifiers
REGION                  1..862
                        note = misc_feature - Public GI ID no. 157343873
REGION                  1..862
                        note = misc_feature - Bit score of 1864.9 for hmm based on
                         sequences of FIGURE 5.
```

-continued

```
REGION                  289..371
                        note = misc_feature - Pfam Name: Auxin_resp Pfam Desc:
                         Auxin response factor
REGION                  162..267
                        note = misc_feature - Pfam Name: B3 Pfam Desc: B3 DNA
                         binding domain
REGION                  1..862
                        note = misc_feature - Is Acted Upon By Ceres SEEDLINE ID
                         no. ME00572 at SEQ ID NO. 111
source                  1..862
                        mol_type = protein
                        organism = Vitis vinifera
SEQUENCE: 255
MASSEVSIKG NCGHGRGESF TSGYSEPNDG GVSRSVAEGQ KGHSSVSGAG KDFETALYTE  60
LWHACAGPLV TVPRERERVF YFPQGHIEQV EASTNQVSDQ QMPVYDLPSK ILCRVINVQL  120
KAEPDTDEVF AQVTLLPEPN QDETAQEKEP LPPPPPRFHV HSFCKTLTAS DTSTHGGFSV  180
LRRHADECLP QLDMSRQPPT QELVAKDLHG NEWRFRHIFR GQPRRHLLQS GWSVFVSSKR  240
LVAGDAFIFL RGENGELRVG VRRAMRQQGN VPSSVISSHS MHLGVLATAW HAKSTGTMFT  300
VYYKPRTSPA EFIVPFDQYM ESVKNNYSIG MRFKMRFEGE EAPEQRFTGT IVGIEDADPK  360
RWRDSKWRCL KVRWDETSTI PRPDRVSPWK IEPAVTPPAL NPLPVPRPKR PRSNMVPSSP  420
DSSVLTREGS SKVTVDPSPA SGFSRVLQGQ EFSTLRGTFA ESNESDTAEK SVVWPPLLDD  480
EKIDVVSTSR RFGSDNWMHL VRHEPTCTDL LSGFGARTDS SHGFSSFVDQ NDVAANTMKK  540
HLEHESKFNL LAGPWSMMPS GLSLNLLESS IKVPVQGSDM PYQTRGDARF GGFSEYPTLH  600
GHRVELQQGN WLMPPPAQSH FENFAHSREL MPKPILVQKQ EAVKPKDGNC KLFGIPLIGN  660
PVISEPAMSY RSMTNEPAGH LHLAPSAFDS DQKSEQSKGA KSTDNPLAVS EQEKPCQTSL  720
PLSRDVQGKV QSVSTRSCTK VHKQGIALGR SVDLTKFNNY DELIAELDQL FEFGGELMAP  780
KKNWLIVYTD DEGDMMLVGD DPWQEFCGMV RKIYIYTREE VQRMNPGTLN SKNDDNPSVA  840
EGMDAKEVKR QPVPLTSNLE NC                                         862

SEQ ID NO: 256          moltype = AA  length = 946
FEATURE                 Location/Qualifiers
REGION                  1..946
                        note = misc_feature - Public GI ID no. 147791931
REGION                  1..946
                        note = misc_feature - Bit score of 1795.4 for hmm based on
                         sequences of FIGURE 5.
REGION                  289..371
                        note = misc_feature - Pfam Name: Auxin_resp Pfam Desc:
                         Auxin response factor
REGION                  162..267
                        note = misc_feature - Pfam Name: B3 Pfam Desc: B3 DNA
                         binding domain
REGION                  1..946
                        note = misc_feature - Is Acted Upon By Ceres SEEDLINE ID
                         no. ME00572 at SEQ ID NO. 111
source                  1..946
                        mol_type = protein
                        organism = Vitis vinifera
SEQUENCE: 256
MASSEVSIKG NCGHGRGESF TSGYSEPNDG GVSRSVAEGQ KGHSSVSGAG KDFETALYTE  60
LWHACAGPLV TVPRERERVF YFPQGHIEQV EASTNQVSDQ QMPVYDLPSK ILCRVINVQL  120
KAEPDTDEVF AQVTLLPEPN QDETAQEKEP LPPPPPRFHV HSFCKTLTAS DTSTHGGFSV  180
LRRHADECLP QLDMSRQPPT QELVAKDLHG NEWRFRHIFR GQPRRHLLQS GWSVFVSSKR  240
LVAGDAFIFL RGENGELRVG VRRAMRQQGN VPSSVISSHS MHLGVLATAW HAKSTGTMFT  300
VYYKPRTSPA EFIVPFDQYM ESVKNNYSIG MRFKMRFEGE EAPEQRFTGT IVGIEDADPK  360
RWRDSKWRCL KVRWDETSTI PRPDRVSPWK IEPAVTPPAL NPLPVPRPKR PRSNMVPSSP  420
DSSVLTREGS SKVTVDPSPA SGFSRVLQGQ EFSTLRGTFA ESNESDTAEK SVVWPPLLDD  480
EKIDVVSTSR RFGSDNWMHL VRHEPTCTDL LSGFGARTDS SHGFSSFVDQ NDVAANTMKK  540
HLEHESKFNL LAGPWSMMPS GLSLNLLESS IKVPVQGSDM PYQTRGDARF GGFSEYPTLH  600
GHRVELQQGN WLMPPPAQSH FENFAHSREL MPKPILVQKQ EAVKPKDGNC KLFGIPLIGN  660
PVISEPAMSY RSMTNEPAGH LHLAPSAFDS DQKSEQSKGA KSTDNPLAVS EQEKPCQTSL  720
PLSRDVQGKV QSVSTRSCTK VCIHSLDGCW FLNNEYEIWK MLAGYKIVPQ ICFIAVSCLM  780
SIGNLVHKQG IALGRSVDLT KFNNYDELIA ELDQLFEFGG ELMAPKKNWL IVYTDDEGDM  840
MLVGDDPWQE FCGMVRKIYI YTREEVQRMN PGTLNSKNDD NPSVAEGMDA KEVKQKLAMV  900
VLVGRAIELI EMHKSLLPLL DRFLNGCTFG WFLFSGLWEA PVDDGF                946

SEQ ID NO: 257          moltype = DNA  length = 2124
FEATURE                 Location/Qualifiers
misc_feature            1..2124
                        note = Ceres Annot ID no. 8734042
misc_feature            1..2124
                        note = Encodes the peptide sequence at SEQ ID NO. 258
source                  1..2124
                        mol_type = other DNA
                        organism = Sorghum bicolor
SEQUENCE: 257
atggcgggga tcgacctcaa cgacaccgtg gaggaggacg aggaggaggc ggagcccggc  60
aaccccgcct gctcccagca aagccggacc agctccgcgg ccacgccccc acccccgccg  120
ctgaccccgc tgctccagcc gaggccgggc gccgcggtgt gcctcgagct ctggcacgcc  180
```

-continued

```
tgcgccggcc ccgtcgcgcc gctgccgcgg aaagggaccg tcgtcgtcta cctcccgcag  240
ggacacctgg agcacctcgg tgacgccgcc gcggccgcag ccggaggcgc gccggcgccc  300
gccgccctgc cgccccacgt cttctgccgc gtcgtcgacg tcactctcca tgcggacgcg  360
tccacggacg aggtgtacgc ccagctcgcc ctcgtcgccg agaacgagga tgtcgcgagg  420
cggctgcgcg gagggtccga ggacgggagc gctggggacg gcgacgacgg ggaggccgtg  480
aagcagcggt tctcgcggat gccgcacatg ttctgcaaga cgctcacggc ctccgacacc  540
agcacgcacg gcggcttctc cgtgccgcgc cgcgccgccg aggactgctt cccgcctctg  600
gactacagcc agcagcggcc gtcgcaggag cttgtcgcca aggatttgca cggaaccgag  660
tggaggttcc gccacattta tcgaggccag ccccgcaggc accttttaac cactggatgg  720
agtgcatttg tcaacaagaa gaagcttgtc tcaggggacg ctgtactatt tttgagaggt  780
gatgatgggg agctaagact tggagtgcgc cgtgcagctc agcttaaaaa tggatctgct  840
tttccagctc tttataatca gtgttctaat cttggttcac tagctaacgt agcacatgct  900
gtggccacaa aaagcgtgtt ccacatctac tacaacccca gattaagcca atctgaattc  960
attataccgt attcaaagtt tatgaagagc ttcagtcaac aattttctgc tggtttgagg  1020
ttcaaaatga gatatgagag tgatgatgct tctgaaagaa gatgcactgg ggtaatagca  1080
ggaattggtg atgctgaccc catgtggcgt ggttcgaagt ggaaatgttt gatggtccga  1140
tgggatgatg atgtagattt tcgtcgaccg aacaggattt ctccttggga gattgagctg  1200
actagttcag tttcaggatc ccatctgtct gcaccaaatg caaagagact caaaccatgt  1260
cttccccccgg actacctagt tccaaatgga agtggttgtc ctgattttgc ggaatctgcc  1320
caattccaca aggtcttgca aggtcaagaa ttattgggtt atagaactcg tgacaatgct  1380
gctgttgcaa cttctcaaac accactagga aaccctaggt tttcctacca ttgctcaggc  1440
tttggggagt ctccaagatt ccaaaaggtc ttgcaaggtc aagaagtatt tcaaccctac  1500
cgaggaactc tagtcgatcc aagtttgaga aatagtggct ttcatcagca agatggttct  1560
catgtgccta ctcaagcgaa taagtggcat ccacagcttc atgggtgtgc ttttcgtggg  1620
acacaagcac cagctattcc atctcaatcc tcatcgccac catctgtcct aatgtttcaa  1680
cgagataatc caaagatgtc cccttttgaa tttgggcatt gtcacatgga taagaatgag  1740
gatatgcgtg caatgtttgg ccatgctgga ggtattggaa gaactgagca aacaatgatg  1800
ctccaggctc ataatgtttc tggaggaatg ggaaatagag atgtgaccgt tgagaaattt  1860
cagcccactg ttgctgttgg aagggatgga tcagacaaca gggaagttac caaaaatagt  1920
tgcaaaatat ttggcatatc tttgactgag aaggttccag caatcaaaga aaaggactgt  1980
ggtgatacca actatccatc ccccttcctg tctttgaagc aacacgtgcc aaaatcgctg  2040
ggcaacagtt gtgccactat tcatgagcag aggcctgttg ttggtagggt gattgatgtt  2100
tcaacagtgg atatgatgat ctga                                        2124

SEQ ID NO: 258          moltype = AA  length = 707
FEATURE                 Location/Qualifiers
REGION                  1..707
                        note = misc_feature - Ceres Annot ID no. 8734042
REGION                  1..707
                        note = misc_feature - Bit score of 1084.7 for hmm based on
                         sequences of FIGURE 5.
REGION                  297..378
                        note = misc_feature - Pfam Name: Auxin_resp Pfam Desc:
                         Auxin response factor
REGION                  170..275
                        note = misc_feature - Pfam Name: B3 Pfam Desc: B3 DNA
                         binding domain
REGION                  1..707
                        note = misc_feature - Is Acted Upon By Ceres SEEDLINE ID
                         no. ME00572 at SEQ ID NO. 111
source                  1..707
                        mol_type = protein
                        organism = Sorghum bicolor
SEQUENCE: 258
MAGIDLNDTV EEDEEEAEPG NPACSQQSRT SSAATPPPPP LTPLLQPRPG AAVCLELWHA  60
CAGPVAPLPR KGTVVVYLPQ GHLEHLGDAA AAAAGGAPAP AALPPHVFCR VVDVTLHADA  120
STDEVYAQLA LVAENEDVAR RLRGGSEDGS AGDGDDGEAV KQRFSRMPHM FCKTLTASDT  180
STHGGFSVPR RAAEDCFPPL DYSQQRPSQE LVAKDLHGTE WRFRHIYRGQ PRRHLLTTGW  240
SAFVNKKKLV SGDAVLFLRG DDGELRLGVR RAAQLKNGSA FPALYNQCSN LGSLANVAHA  300
VATKSVFHIY YNPRLSQSEF IIPYSKFMKS FSQQFSAGLR FKMRYESDDA SERRCTGVIA  360
GIGDADPMWR GSKWKCLMVR WDDDVDFRRP NRISPWEIEL TSSVSGSHLS APNAKRLKPC  420
LPPDYLVPNG SGCPDFAESA QFHKVLQGQE LLGYRTRDNA AVATSQTPLG NPRFSYHCSG  480
FGESPRFQKV LQGQEVFQPY RGTLVDPSLR NSGFHQQDGS HVPTQANKWH PQLHGCAFRG  540
TQAPAIPSQS SSPPSVLMFQ RDNPKMSPFE FGHCHMDKNE DMRAMFGHAG GIGRTEQTMM  600
LQAHNVSGGM GNRDVTVEKF QPTVAVGRDG SDNREVTKNS CKIFGISLTE KVPAIKEKDC  660
GDTNYPSPFL SLKQHVPKSL GNSCATIHEQ RPVVGRVIDV STVDMMI                707

SEQ ID NO: 259          moltype = AA  length = 687
FEATURE                 Location/Qualifiers
REGION                  1..687
                        note = misc_feature - Public GI ID no. 158564103
REGION                  1..687
                        note = misc_feature - Bit score of 984.1 for hmm based on
                         sequences of FIGURE 5.
REGION                  259..340
                        note = misc_feature - Pfam Name: Auxin_resp Pfam Desc:
                         Auxin response factor
REGION                  132..237
                        note = misc_feature - Pfam Name: B3 Pfam Desc: B3 DNA
```

-continued

```
                         binding domain
REGION                  1..687
                        note = misc_feature - Is Acted Upon By Ceres SEEDLINE ID
                         no. ME00572 at SEQ ID NO. 111
source                  1..687
                        mol_type = protein
                        note = subspecies = japonica
                        organism = Oryza sativa
SEQUENCE: 259
MGIDLNTVEE EAEEGAAAAV CGELWHACAG PGVALPRRGS ALVYLPQAHL AADGGGGEVP  60
PAGAAAVPPH VACRVVGVEL RADAATDEVY ARLALVAEGE MLQRNFREGG GEDGAGEMEG  120
CDAEKKPRMP HMFCKTLTAS DTSTHGGFSV PRRAAEDCFP PLDYKTVRPS QELIAVDLHG  180
TQWKFRHIYR GQPRRHLLTI GWSSFVNRKK LVSGDAVLFL RGDDGQLRLG VRRAVQLRNE  240
ALFEPVNSSD SKLRILSSVA SSLENKSVFH ICFNPRSGAS EFIVPYWRLL KSLNHPFSIG  300
MRFRVCYESE DANERSAGLI SGISEVDPIR WPGSRWKCLL VRWDDSTDSS HQNRVSPWEI  360
ERVGGSVSVT HSLSSGSKRT KLHFPQGSLD TPFLNGNGHP DSMGTENFHR VLQGQEFRGS  420
RSHGVVCSES PGVPNFQSPD NRRFSADMRG YMMPASGPPQ RNTEFTYQPI GFSESLGFPE  480
VLQGQEMSQV VPLFRGATFG ARTQNDRVVS ANSVHRSAAQ SGLLASTLGH PISQFTLSSS  540
KVSSPSSVLM FNQATAPNHE TVSGTNNKGM HVSQFASQEM LSETVTWPGT QRQTPSEITS  600
NQFALARIPA PPSGAESGLP KRDAGRSSCR LFGFSLTGNM LGEDGEGLDD GAIEAGCENP  660
PVLELFGHSH STPGALHALC AAAPLGM                                     687

SEQ ID NO: 260          moltype = AA  length = 653
FEATURE                 Location/Qualifiers
REGION                  1..653
                        note = misc_feature - Public GI ID no. 157360302
REGION                  1..653
                        note = misc_feature - Bit score of 952.6 for hmm based on
                         sequences of FIGURE 5.
REGION                  243..322
                        note = misc_feature - Pfam Name: Auxin_resp Pfam Desc:
                         Auxin response factor
REGION                  116..221
                        note = misc_feature - Pfam Name: B3 Pfam Desc: B3 DNA
                         binding domain
REGION                  1..653
                        note = misc_feature - Is Acted Upon By Ceres SEEDLINE ID
                         no. ME00572 at SEQ ID NO. 111
source                  1..653
                        mol_type = protein
                        organism = Vitis vinifera
SEQUENCE: 260
MMVGFGGEGD DLYAELWKAC AGPLVDVPRR GERVFYFPQG HVEQLEASTN QELSQRIPLF  60
NLPSKILCRV IHIQLRAEQE TDEVYAQITL LPEPDQAEPR SPDPCTPEPP RPTVHSFCKV  120
LTASDTSTHG GFSVLRKHAN ECLPQLDMNQ ATPTQELVAK DLHGYEWRFK HIFRGQPRRH  180
LLTTGWSTFV TSKRLVAGDS FVFLRGDNGE LRVGVRRLAR QQSTMPTSVI SSQSMHLGVL  240
ATASHAVATQ TLFIVYYKPR TSQFIIGLNK YLEAVSNGFA VGMRFKMRFE GEDSPERRFS  300
GTIVGGEDFS PEWKDSEWRS LKVQWDEPAS IPRPEKVSPW EIEHYVSSVP QGLAPPGVLK  360
NKRPRSNESP VPGSAAASAV WHLGLTQSHD LTQMSSTAEG KRSENHQADI GAIPPTEGSW  420
LSSSHVSASQ HQFQDATEDS KSVSAWPALS GYSTLHSSKL TSDTIIDPNG NGKKAVAEMA  480
TSCRLFGFEL MNHSSSPPVG KAHGHSISSD LSKASKEQKQ GQSHVSPKEI QSKQNCYSNT  540
RSRTKVQMQG IAVGRAVDLT ALEGYDELID ELEEMFEIKG ELRPRYKWEI VFTDDEGDMM  600
LVGDDPWPEF CNMVRRIFIC SSQDVKKMSP GSKLPISSME GEGTTISLDS TEN         653
```

NUCLEOTIDE SEQUENCES AND POLYPEPTIDES ENCODED THEREBY USEFUL FOR MODIFYING PLANT CHARACTERISTICS IN RESPONSE TO COLD

CROSS REFERENCE TO RELATED APPLICATIONS

This application is a divisional of U.S. patent application Ser. No. 18/049,501, filed on Oct. 25, 2022, (now U.S. Pat. No. 12,024,713), which is a divisional of U.S. patent application Ser. No. 16/829,740, filed on Mar. 25, 2020, (now U.S. Pat. No. 11,542,521), which is a divisional of U.S. patent application Ser. No. 14/273,492, filed on May 8, 2014 (now U.S. Pat. No. 10,689,661), which is a continuation of U.S. patent application Ser. No. 12/863,773, filed on Nov. 23, 2010 (now abandoned) which is the U.S. National Stage Entry of International No. PCT/US2009/031609, filed on Jan. 21, 2009, which claims priority under 35 U.S.C. 119 (c) to U.S. Provisional Application No. 61/022,786, filed on Jan. 22, 2008. The entire contents of all applications listed above are hereby incorporated by reference.

INCORPORATION-BY-REFERENCE OF SEQUENCE LISTING OR TABLE

The material in the accompanying sequence listing is hereby incorporated by reference into this application. The accompanying file, named CRES006USD4_ST26.xml was created on May 13, 2024 and is 815 KB. The file can be accessed using Microsoft Word on a computer that uses Windows OS.

TECHNICAL FIELD

This document relates to methods and materials involved in modulating cold tolerance in plants, including growth levels in plants grown under low or chilling temperature stress conditions (a.k.a. "cold stress"). For example, this document provides plants having increased growth rate, vegetative growth, seedling vigor and/or biomass under cold stress conditions as compared to wild-type plants grown under similar conditions, as well as materials and methods for making plants and plant products having increased growth levels under cold stress conditions.

BACKGROUND

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., TT Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry, efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a method for increasing growth potential, decreasing chilling damage, and/or increasing levels of cold acclimation in plants under low temperature, chilling or cold conditions, characterized by expression of recombinant DNA molecules stably integrated into the plant genome.

SUMMARY

This document provides methods and materials related to plants having modulated levels of cold tolerance. For example, this document provides transgenic plants and plant cells having increased levels of cold tolerance, nucleic acids (i.e. isolated polynucleotides), polypeptides encoded thereby used to generate transgenic plants and plant cells having increased levels of cold tolerance, and methods for making plants and plant cells having increased levels of cold tolerance. Such plants and plant cells having increased biomass levels may be useful in producing biomass for conversion to a liquid fuel or other chemicals, or may be useful as a thermochemical fuel.

Methods of producing a plant and/or plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 130, 180, 650, or 315, using an HMM generated from the amino acid sequences depicted in one of FIG. 1, 2, 3, or 4, respectively. The plant and/or plant tissue has a difference in the level of cold tolerance as compared to the corresponding level of cold tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NOs: 2, 20, 74, or 93. A plant and/or plant tissue produced from the plant cell has a difference in the level of cold tolerance as compared to the corresponding level of cold tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence or at a fragment thereof set forth in SEQ ID NO: 1, 19, 92, 97, or 111. A plant and/or plant tissue produced from the plant cell has a difference in the level of cold tolerance as compared to the corresponding level of cold tolerance of a control plant that does not comprise the exogenous nucleic acid.

Methods of modulating the level of cold tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 130, 180, 650, 315 or 790 using an HMM generated from the amino acid sequences depicted in any one of FIG. 1, 2, 3, 4 or 5, respectively. A plant and/or plant tissue produced from the plant cell has a difference in the level of cold tolerance as compared to the corresponding level of cold tolerance of a control plant that does not comprise the exogenous nucleic acid.

In certain embodiments, the amino acid sequence of the polypeptide has an HMM score greater than about 180, using an HMM generated from the amino acid sequences depicted in FIG. 2, wherein the polypeptide comprises an CCT motif domain having 80 percent or greater sequence identity to amino acid residues 285 to 329 of SEQ ID NO: 20, residues 291 to 335 of SEQ ID NO: 22, residues 235 to 279 of SEQ ID NO: 24, residues 217 to 261 of SEQ ID NO: 26, residues 311 to 355 of SEQ ID NO: 28, residues 285 to 329 of SEQ ID NO: 29, residues 281 to 325 of SEQ ID NO: 30, residues 302 to 346 of SEQ ID NO: 32, residues 289 to 333 of SEQ ID NO: 34, residues 295 to 339 of SEQ ID NO: 36, residues 261 to 305 of SEQ ID NO: 38, residues 284 to 328 of SEQ ID NO: 40, residues 288 to 332 of SEQ ID NO: 42, residues 261 to 305 of SEQ ID NO: 43, residues 239 to 283 of SEQ ID NO: 44, residues 294 to 338 of SEQ ID NO: 45, residues 279 to 323 of SEQ ID NO: 46, residues 261 to 305 of SEQ ID NO: 47, residues 239 to 283 of SEQ ID NO: 48, residues 294 to 338 of SEQ ID NO: 49, residues 261 to 305 of SEQ ID NO: 50, residues 298 to 342 of SEQ ID NO: 51, residues 241 to 285 of SEQ ID NO: 52, residues 268 to 312 of SEQ ID NO: 53, residues 245 to 289 of SEQ ID NO: 54, residues 238 to 282 of SEQ ID NO: 56, residues 245 to 289 of SEQ ID NO: 58, residues 279 to 323 of SEQ ID NO: 59, residues 236 to 280 of SEQ ID NO: 60, residues 250 to 294 of SEQ ID NO: 61, residues 322 to 366 of SEQ ID NO: 62, residues 297 to 341 of SEQ ID NO: 63, residues 348 to 392 of SEQ ID NO: 64, residues 312 to 356 of SEQ ID NO: 65, residues 340 to 384 of SEQ ID NO: 68, residues 307 to 351 of SEQ ID NO: 69, or residues 253 to 297 of SEQ ID NO: 71.

In certain embodiments, the amino acid sequence of the polypeptide has an HMM score greater than about 180, using an HMM generated from the amino acid sequences depicted in FIG. 2, wherein the polypeptide comprises a B-box zinc finger domain having 80 percent or greater sequence identity to amino acid residues 56 to 103 of SEQ ID NO: 20, residues 62 to 109 of SEQ ID NO: 22, residues 64 to 106 of SEQ ID NO: 24, residues 34 to 81 of SEQ ID NO: 26, residues 63 to 110 of SEQ ID NO: 28, residues 56 to 103 of SEQ ID NO: 29, residues 56 to 103 of SEQ ID NO: 30, residues 60 to 107 of SEQ ID NO: 32, residues 56 to 103 of SEQ ID NO: 34, residues 51 to 98 of SEQ ID NO: 36, residues 70 to 112 of SEQ ID NO: 38, residues 51 to 98 of SEQ ID NO: 40, residues 52 to 99 of SEQ ID NO: 42, residues 72 to 114 of SEQ ID NO: 43, residues 62 to 104 of SEQ ID NO: 44, residues 50 to 97 of SEQ ID NO: 45, residues 55 to 102 of SEQ ID NO: 46, residues 72 to 114 of SEQ ID NO: 47, residues 62 to 104 of SEQ ID NO: 48, residues 50 to 97 of SEQ ID NO: 49, residues 27 to 71 of SEQ ID NO: 50, residues 60 to 107 of SEQ ID NO: 51, residues 1 to 48 of SEQ ID NO: 52, residues 1 to 48 of SEQ ID NO: 53, residues 1 to 48 of SEQ ID NO: 54, residues 62 to 104 of SEQ ID NO: 56, residues 64 to 106 of SEQ ID NO: 58, residues 1 to 48 of SEQ ID NO: 59, residues 61 to 103 of SEQ ID NO: 60, residues 70 to 112 of SEQ ID NO: 61, residues 52 to 99 of SEQ ID NO: 62, residues 51 to 98 of SEQ ID NO: 63, residues 77 to 119 of SEQ ID NO: 64, residues 59 to 106 of SEQ ID NO: 65, residues 59 to 106 of SEQ ID NO: 68, residues 34 to 66 of SEQ ID NO: 69, or residues 64 to 106 of SEQ ID NO: 71.

In certain embodiments, the amino acid sequence of the polypeptide has an HMM score greater than about 650, using an HMM generated from the amino acid sequences depicted in FIG. 3, wherein the polypeptide comprises an short-chain dehydrogenase domain having 80 percent or greater sequence identity to amino acid residues 38 to 173 of SEQ ID NO: 74, residues 37 to 174 of SEQ ID NO: 76, residues 23 to 160 of SEQ ID NO: 77, residues 7 to 168 of SEQ ID NO: 79, residues 43 to 179 of SEQ ID NO: 81, residues 49 to 188 of SEQ ID NO: 82, residues 48 to 187 of SEQ ID NO: 83, residues 37 to 172 of SEQ ID NO: 85, residues 35 to 170 of SEQ ID NO: 86, residues 20 to 160 of SEQ ID NO: 88, or residues 37 to 174 of SEQ ID NO: 90.

In certain embodiments, the amino acid sequence of the polypeptide has an HMM score greater than about 790, using an HMM generated from the amino acid sequences depicted in FIG. 5, wherein the polypeptide comprises a B3 DNA binding domain and an auxin response factor.

In another aspect, a method comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NO: 2, 20, 74, 93 or 112. A plant and/or plant tissue produced from the plant cell has a difference in the level of cold tolerance as compared to the corresponding level of cold tolerance of a control plant that does not comprise the exogenous nucleic acid.

In another aspect, a method comprises introducing into a plant cell an exogenous nucleic acid, that comprises a regulatory region operably linked to a nucleotide sequence having 80 percent or greater sequence identity to a nucleotide sequence set forth in SEQ ID NO: 1, 19, 92, 97, or 111, or a fragment thereof. A plant and/or plant tissue produced from the plant cell has a difference in the level of cold tolerance as compared to the corresponding level of cold tolerance of a control plant that does not comprise the exogenous nucleic acid.

Methods of modulating the level of cold tolerance in a plant are provided herein. In one aspect, a method comprises introducing into a plant cell an exogenous nucleic acid, that comprises a regulatory region operably linked to a nucleotide sequence encoding a trans-activating small-interfering RNA (tasiRNA) that acts upon, e.g. suppresses expression of, an auxin responsive factor (ARF) polypeptide. The HMM bit score of the amino acid sequence of the ARF polypeptide is greater than about 790, using an HMM generated from the amino acid sequences depicted in FIG. 5. A plant and/or plant tissue produced from the plant cell has a difference in the level of cold tolerance as compared to the corresponding level of cold tolerance of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a tasiRNA. In some embodiments, the nucleotide sequence comprises a tasiRNA coding region having 80 percent or greater sequence identity to a nucleic acid sequence selected from the group consisting of residues 305 to about 346 of SEQ ID NO: 111, residues 21 to about 62 of SEQ ID NO: 66, residues 20 to about 61 of SEQ ID NO: 67, residues 21 to about 62 of SEQ ID NO: 72, residues 21 to about 62 of SEQ ID NO: 73, residues 77 to about 118 of SEQ ID NO: 144, residues 292 to about 313 of SEQ ID NO: 145, residues 37 to about 78 of SEQ ID NO: 146, residues 56 to about 97 of SEQ ID NO: 147, residues 37 to about 78 of SEQ ID NO: 148, residues 45 to about 86 of SEQ ID NO: 149, residues 46 to about 98 of SEQ ID NO: 150, residues 476 to about 497 of SEQ ID NO: 151, residues 21 to about 62 of SEQ ID NO: 152, residues 21 to about 62 of SEQ ID NO: 153, residues 21 to about 62 of SEQ ID NO: 154, residues 21 to about 62 of SEQ ID NO: 155, and residues 21 to about 62 of SEQ ID NO: 156, wherein a plant produced from said plant cell has a difference in the level of cold tolerance as compared to the corresponding level of cold tolerance of a control plant that does not comprise said nucleic acid. Transgenic plants comprising such plant cells are provided herein. In some embodiments, the transgenic plant comprises an exogenous nucleic acid having a sequence selected from the group consisting of SEQ ID NO: 66, 67, 72, 73, 111, 144, 145, 146, 147, 148, 149, 150, 151, 152, 153, 154, 155, and 156.

Methods of producing a plant and/or plant tissue are provided herein. In one aspect, a method comprises introducing into a plant cell an exogenous nucleic acid, said exogenous nucleic acid comprising a regulatory region operably linked to a nucleotide sequence encoding a gene suppressing tasiRNA, said nucleotide sequence comprising a tasiRNA coding region having 80 percent or greater sequence identity to a nucleic acid sequence selected from the group consisting of residues 305 to about 346 of SEQ ID NO: 111, residues 21 to about 62 of SEQ ID NO: 66, residues 20 to about 61 of SEQ ID NO: 67, residues 21 to about 62 of SEQ ID NO: 72, residues 21 to about 62 of SEQ ID NO: 73, residues 77 to about 118 of SEQ ID NO: 144, residues 292 to about 313 of SEQ ID NO: 145, residues 37 to about 78 of SEQ ID NO: 146, residues 56 to about 97 of SEQ ID NO: 147, residues 37 to about 78 of SEQ ID NO: 148, residues 45 to about 86 of SEQ ID NO: 149, residues 46 to about 98 of SEQ ID NO: 150, residues 476 to about 497 of SEQ ID NO: 151, residues 21 to about 62 of SEQ ID NO: 152, residues 21 to about 62 of SEQ ID NO: 153, residues 21 to about 62 of SEQ ID NO: 154, residues 21 to about 62 of SEQ ID NO: 155, and residues 21 to about 62 of SEQ ID NO: 156, wherein a plant produced from said plant cell has a difference in the level of cold tolerance as compared to the corresponding level of cold tolerance of a control plant that does not comprise said nucleic acid. In certain embodiments, the expression of a target ARF gene is suppressed in a plant. In some embodiments, the ARF gene encodes a polypeptide having 80 percent or greater sequence identity to an amino acid sequence selected from the group consisting of SEQ ID NO: 112, 114, 116, 117, 118, 119, 120, 121, 122, 123, 124, 125, 126, 127, 128, 130, 131, 132, 134, 136, 137, 138, 139, 141, and 143. In other embodiments, the ARF gene encodes a polypeptide and the HMM bit score of the amino acid sequence of said polypeptide is greater than about 790, said HMM based on the amino acid sequences depicted in FIG. 5. In other embodiments, the gene suppressing tasiRNA or its complement is complementary to RNA transcribed from said target ARF gene. In other embodiments, the nucleotide sequence encoding a gene suppressing tasiRNA comprises a microRNA recognition site having 80 percent or greater sequence identity to a nucleic acid sequence selected from the group consisting of residues 109 to about 129 of SEQ ID NO: 66, residues 114 to about 135 of SEQ ID NO: 67, residues 119 to about 139 of SEQ ID NO: 72, residues 108 to about 128 of SEQ ID NO: 73, residues 234 to about 254 of SEQ ID NO: 144, residues 135 to about 176 of SEQ ID NO: 145, residues 173 to about 189 of SEQ ID NO: 147, residues 154 to about 170 of SEQ ID NO: 148, residues 134 to about 157 of SEQ ID NO: 149, residues 154 to about 198 of SEQ ID NO: 150, residues 319 to about 360 of SEQ ID NO: 151, residues 121 to about 141 of SEQ ID NO: 152, residues 120 to about 140 of SEQ ID NO: 153, residues 121 to about 141 of SEQ ID NO: 154, residues 121 to about 141 of SEQ ID NO: 155, residues 121 to about 141 of SEQ ID NO: 156, and residues 462 to about 483 of SEQ ID NO: 111.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 130, using an HMM based on the amino acid sequences depicted in one of FIG. 1, 2, 3, or 4. The plant and/or plant cells has a difference in the level of cold tolerance as compared to the corresponding level of cold tolerance of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO: 2, 20, 93, or 74. A plant and/or plant tissue produced from the plant cell has a difference in the level of cold tolerance as compared to the corresponding level of cold tolerance of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO: 1, 19, 92, 97, or 111. A plant and/or plant tissue produced from the plant cell has a difference in the level of cold tolerance as compared to the corresponding level of cold tolerance of a control plant that does not comprise the exogenous nucleic acid. A transgenic plant comprising such a plant cell is also provided. Also provided is a seed product. The product comprises embryonic tissue from a transgenic plant.

Isolated nucleic acids are also provided. In one aspect, an isolated nucleic acid comprises a nucleotide sequence having 80% or greater sequence identity to the nucleotide sequence set forth in SEQ ID NO: 3, 5, 7, 9, 11, 14, 16, 21, 23, 25, 27, 33, 35, 37, 39, 41, 55, 57, 70, 75, 80, 84, 87, 91, 92, 97, 105, 113, 115, 129, 133, 140, or 142.

In another aspect, an isolated nucleic acid comprises a nucleotide sequence encoding a polypeptide having 80% or greater sequence identity to the amino acid sequence set forth in SEQ ID NO: 4, 6, 8, 10, 12, 22, 24, 26, 28, 36, 38, 40, 42, 71, 74, 85, 88, 93, 105, 114, 116, 130, 134, 136, 141, or 143.

In another aspect, methods of identifying a genetic polymorphism associated with variation in the level of cold tolerance are provided. The methods include providing a population of plants, and determining whether one or more genetic polymorphisms in the population are genetically linked to the locus for a polypeptide selected from the group consisting of the polypeptides depicted in FIGS. 1, 2, 3, and 4 and functional homologs thereof, such as, but not limited to, those identified in the Sequence Listing. The correlation between variation in the level of cold tolerance in a tissue in plants of the population and the presence of the one or more genetic polymorphisms in plants of the population is measured, thereby permitting identification of whether or not the one or more genetic polymorphisms are associated with such variation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 and the other alignment figures provided herein were generated using the program MUSCLE version 3.52.

FIG. 3 is an alignment of full length homologous and/or orthologous amino acid sequences of Ceres SEEDLINE ID no.ME 17294 (SEQ ID NO: 93), including Ceres CLONE ID no.473040 (SEQ ID NO: 79), Ceres CLONE ID no.922223 (SEQ ID NO: 81), GI ID no.125528967 (SEQ ID NO: 82), GI ID no.125573200 (SEQ ID NO: 83), Ceres ANNOT ID no.1527409 (SEQ ID NO: 85), GI ID no.92871098 (SEQ ID NO: 86), Ceres CLONE ID no.1831117 (SEQ ID NO: 88), and Ceres ANNOT ID no.857222 (SEQ ID NO: 90).

DETAILED DESCRIPTION

Figure 1:
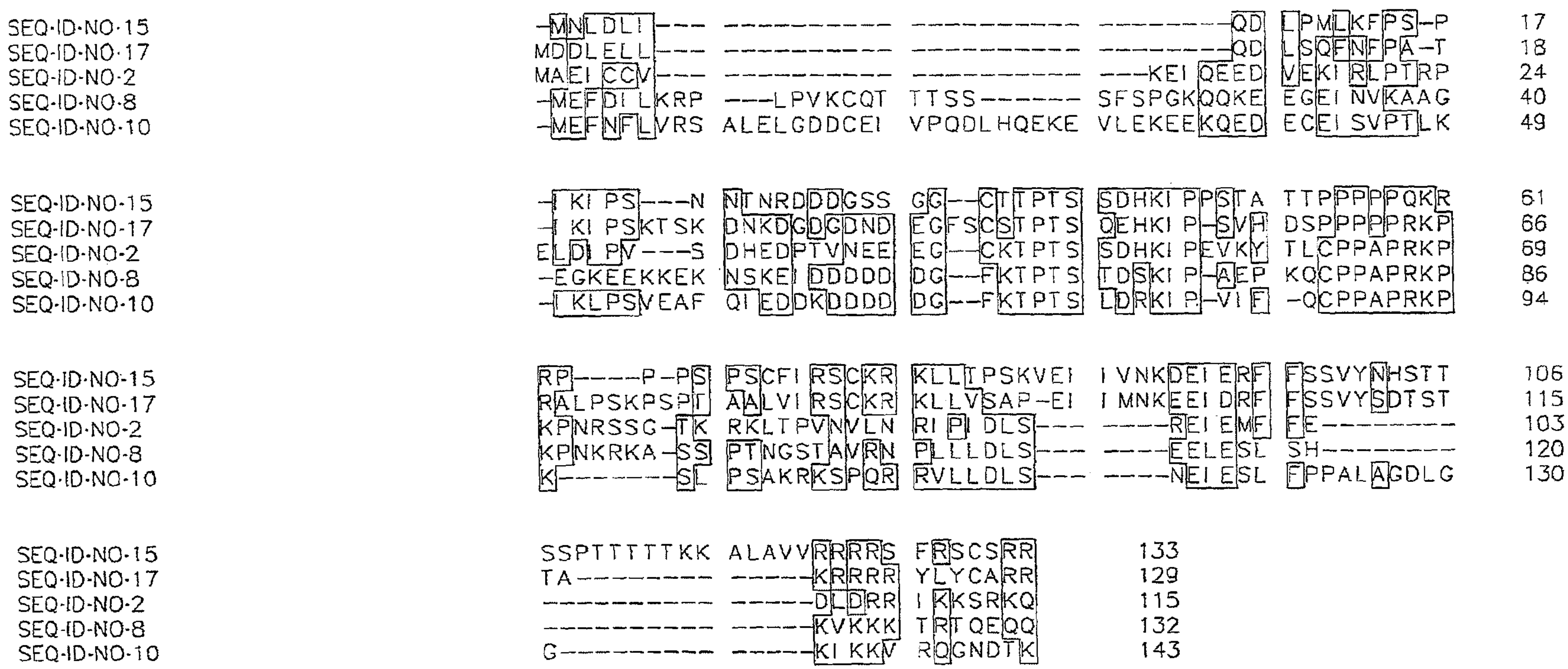
FIG. 1 is an alignment of Ceres SEEDLINE ID no.ME00327 with homologous and/or orthologous amino acid sequences Ceres SEEDLINE ID no.ME00327 (SEQ ID NO: 2), Ceres CLONE ID no.1915941 (SEQ ID NO: 8), Ceres ANNOT ID no.1461830 (SEQ ID NO: 10), Ceres CLONE ID no.1080942 (SEQ ID NO: 15), and Ceres CLONE ID no.1073190 (SEQ ID NO: 17). In all the alignment figures shown herein, a dash in an aligned sequence represents a gap, i.e., a lack of an amino acid at that position. Identical amino acids or conserved amino acid substitutions among aligned sequences are identified by boxes.

The invention features methods and materials related to modulating cold tolerance levels in plants. In some embodiments, the cold tolerance plants of the invention, under cold stress and/or cold flux conditions, have modulated levels of growth, cold acclimation, and/or cold damage. The methods can include transforming a plant cell with a nucleic acid encoding a cold tolerance modulating polypeptide, wherein expression of the polypeptide results in a modulated level of cold tolerance. Plant cells produced using such methods can be grown to produce plants having an increased cold tolerance. Such plants, and the seeds of such plants, may be used to produce, for example, plants and/or plant tissues having increased biomass.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Cold." Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress cannot be generalized. However, cold tolerant plants are characterized by their ability to retain their normal appearance, recover quickly from low temperature conditions, exhibit normal or increased growth under low temperature conditions, and/or have improved cold acclimation. Such cold tolerant plants produce higher biomass and/or yield than plants that are not cold tolerant. Differences in physical appearance, recovery and yield can be quantified and statistically analyzed using well known measurement and analysis methods.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of a cold tolerance refers to the change in the level of the indicated compound or constituent that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell,* 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. POLYPEPTIDES

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 130, as described in more detail herein. In some embodiments, cold tolerance-modulating polypeptides have greater than 80% identity to SEQ ID NOs: 2, 20, 74, 93 or 112, as described in more detail herein.

A. Domains Indicative of Cold Tolerance-Modulating Polypeptides

A cold tolerance-modulating polypeptide can contain a B-box zinc finger domain. The B-box zinc finger domain is often found associated with CCT motif. SEQ ID NO: 20 sets forth the amino acid sequence of an *Arabidopsis* clone, identified herein as Ceres SEEDLINE ID no.ME04315 (SEQ ID NO: 20), that is predicted to encode a polypeptide containing a CCT motif and a B-box zinc finger domain. A B-box zinc finger domain is typically around 40 amino acids in length. This motif is generally associated with a finger. It is found, for example, in transcription factors, ribonucleoproteins and protooncoproteins. It has been shown to be essential but not sufficient to localize the PML protein in a punctate pattern in interphase nuclei. Among the 7 possible ligands for the zinc atom contained in a B-box, only 4 are used and bind one zinc atom in a Cys2-His2 tetrahedral arrangement. The NMR analysis reveals that the B-box structure comprises two beta-strands, two helical turns and three extended loop regions different from any other zinc binding motif. A CCT motif can be found in a number of plant proteins. It is rich in basic amino acids and has been called a CCT motif after Co, Col and Toc 1. The CCT motif is about 45 amino acids long and contains a putative nuclear localization signal within the second half of the CCT motif. Toc1 mutants have been identified in this region. The CCT (CONSTANS, CO-like, and TOC1) domain is a highly conserved basic module of −43 amino acids, which is found near the C-terminus of plant proteins. The CCT domain is often found in association with other domains, such as the B-box zinc finger, the GATA-type zinc finger, the ZIM motif or the response regulatory domain. The CCT domain contains a putative nuclear localization signal within the second half of the CCT motif and has been shown to be involved in nuclear localization and probably also has a role in protein-protein interaction.

In embodiments of the invention, a cold tolerance-modulating polypeptide can comprise a CCT motif having 80% or greater sequence identity to amino acid residues 285 to 329 of SEQ ID NO: 20, residues 291 to 335 of SEQ ID NO: 22, residues 235 to 279 of SEQ ID NO: 24, residues 217 to 261 of SEQ ID NO: 26, residues 311 to 355 of SEQ ID NO: 28, residues 285 to 329 of SEQ ID NO: 29, residues 281 to 325 of SEQ ID NO: 30, residues 302 to 346 of SEQ ID NO: 32, residues 289 to 333 of SEQ ID NO: 34, residues 295 to 339 of SEQ ID NO: 36, residues 261 to 305 of SEQ ID NO: 38, residues 284 to 328 of SEQ ID NO: 40, residues 288 to 332 of SEQ ID NO: 42, residues 261 to 305 of SEQ ID NO: 43, residues 239 to 283 of SEQ ID NO: 44, residues 294 to 338 of SEQ ID NO: 45, residues 279 to 323 of SEQ ID NO: 46, residues 261 to 305 of SEQ ID NO: 47, residues 239 to 283 of SEQ ID NO: 48, residues 294 to 338 of SEQ ID NO: 49, residues 261 to 305 of SEQ ID NO: 50, residues 298 to 342 of SEQ ID NO: 51, residues 241 to 285 of SEQ ID NO: 52, residues 268 to 312 of SEQ ID NO: 53, residues 245 to 289 of SEQ ID NO: 54, residues 238 to 282 of SEQ ID NO: 56, residues 245 to 289 of SEQ ID NO: 58, residues 279 to 323 of SEQ ID NO: 59, residues 236 to 280 of SEQ ID NO: 60, residues 250 to 294 of SEQ ID NO: 61, residues 322 to 366 of SEQ ID NO: 62, residues 297 to 341 of SEQ ID NO: 63, residues 348 to 392 of SEQ ID NO: 64, residues 312 to 356 of SEQ ID NO: 65, residues 340 to 384 of SEQ ID NO: 68, residues 307 to 351 of SEQ ID NO: 69, or residues 253 to 297 of SEQ ID NO: 71.

In embodiments of the invention, a cold tolerance-modulating polypeptide can comprise a B-box zinc finger domain having 80% or greater sequence identity to amino acid residues 56 to 103 of SEQ ID NO: 20, residues 62 to 109 of SEQ ID NO: 22, residues 64 to 106 of SEQ ID NO: 24, residues 34 to 81 of SEQ ID NO: 26, residues 63 to 110 of SEQ ID NO: 28, residues 56 to 103 of SEQ ID NO: 29, residues 56 to 103 of SEQ ID NO: 30, residues 60 to 107 of SEQ ID NO: 32, residues 56 to 103 of SEQ ID NO: 34, residues 51 to 98 of SEQ ID NO: 36, residues 70 to 112 of SEQ ID NO: 38, residues 51 to 98 of SEQ ID NO: 40, residues 52 to 99 of SEQ ID NO: 42, residues 72 to 114 of SEQ ID NO: 43, residues 62 to 104 of SEQ ID NO: 44, residues 50 to 97 of SEQ ID NO: 45, residues 55 to 102 of SEQ ID NO: 46, residues 72 to 114 of SEQ ID NO: 47, residues 62 to 104 of SEQ ID NO: 48, residues 50 to 97 of SEQ ID NO: 49, residues 27 to 71 of SEQ ID NO: 50, residues 60 to 107 of SEQ ID NO: 51, residues 1 to 48 of SEQ ID NO: 52, residues 1 to 48 of SEQ ID NO: 53, residues 1 to 48 of SEQ ID NO: 54, residues 62 to 104 of SEQ ID NO: 56, residues 64 to 106 of SEQ ID NO: 58, residues 1 to 48 of SEQ ID NO: 59, residues 61 to 103 of SEQ ID NO: 60, residues 70 to 112 of SEQ ID NO: 61, residues 52 to 99 of SEQ ID NO: 62, residues 51 to 98 of SEQ ID NO: 63, residues 77 to 119 of SEQ ID NO: 64, residues 59 to 106 of SEQ ID NO: 65, residues 59 to 106 of SEQ ID NO: 68, residues 34 to 66 of SEQ ID NO: 69, or residues 64 to 106 of SEQ ID NO: 71.

A cold tolerance-modulating polypeptide can contain a short-chain dehydrogenase domain. The motif is present in SEQ ID NO: 93, which sets forth the amino acid sequence of an *Arabidopsis* clone, identified herein as Ceres SEEDLINE ID no.ME 17294 (SEQ ID NO: 93), that is predicted to encode a polypeptide containing a short-chain dehydrogenase domain. The short-chain dehydrogenases/reductases family (SDR) is a very large family of enzymes, most of which are known to be NAD- or NADP-dependent oxidoreductases. As the first member of this family to be characterized was Drosophila alcohol dehydrogenase, this family used to be called 'insect-type', or 'short-chain' alcohol dehydrogenases. Most members of this family are proteins of about 250 to 300 amino acid residues.

In embodiments of the invention, a cold tolerance-modulating polypeptide can comprise a short-chain dehydrogenase domain having 80% or greater identity to amino acid residues 38 to 173 of SEQ ID NO: 74, residues 37 to 174 of SEQ ID NO: 76, residues 23 to 160 of SEQ ID NO: 77, residues 7 to 168 of SEQ ID NO: 79, residues 43 to 179 of SEQ ID NO: 81, residues 49 to 188 of SEQ ID NO: 82, residues 48 to 187 of SEQ ID NO: 83, residues 37 to 172 of SEQ ID NO: 85, residues 35 to 170 of SEQ ID NO: 86, residues 20 to 160 of SEQ ID NO: 88, or residues 37 to 174 of SEQ ID NO: 90.

In some embodiments, a cold tolerance-modulating polypeptide is truncated at the amino-or carboxy-terminal end of a naturally occurring polypeptide. A truncated polypeptide may retain certain domains of the naturally occurring polypeptide while lacking others. Thus, length variants that are up to 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, or 170 amino acids shorter or longer typically exhibit the cold tolerance-modulating activity of a truncated polypeptide. In some embodiments, a truncated polypeptide is a dominant negative polypeptide. SEQ ID NO: 93 sets forth the amino sequence of a cold tolerance-modulating polypeptide that is truncated at the amino-terminal end relative to a naturally occurring polypeptide. Expression in a plant and/or plant tissue of such a truncated polypeptide confers a difference in the level of cold tolerance in a plant and/or tissue of the plant as compared to the corresponding level in tissue of a control plant.

B. Functional Homologs Identified by Reciprocal BLAST

In some embodiments, one or more functional homologs of a reference cold tolerance-modulating polypeptide defined by one or more of the Pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Examples of amino acid sequences of functional homologs of the polypeptide set forth in SEQ ID NO: 2 are provided in FIG. 1 and in the Sequence Listing. Such exemplary functional homologs include Ceres CLONE ID no.1897908 (SEQ ID NO:4), Ceres CLONE ID no.1938030 (SEQ ID NO: 6), Ceres CLONE ID no.1915941 (SEQ ID NO: 8), Ceres ANNOT ID no.1461830 (SEQ ID NO: 10), Ceres ANNOT ID no.1439985 (SEQ ID NO: 12), GI ID no.15241794 (SEQ ID NO: 13), Ceres CLONE ID no.1080942 (SEQ ID NO:15), and Ceres CLONE ID no.1073 190 (SEQ ID NO:17). In some cases, a functional homolog of SEQ ID NO: 2 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2.

Figure 2:
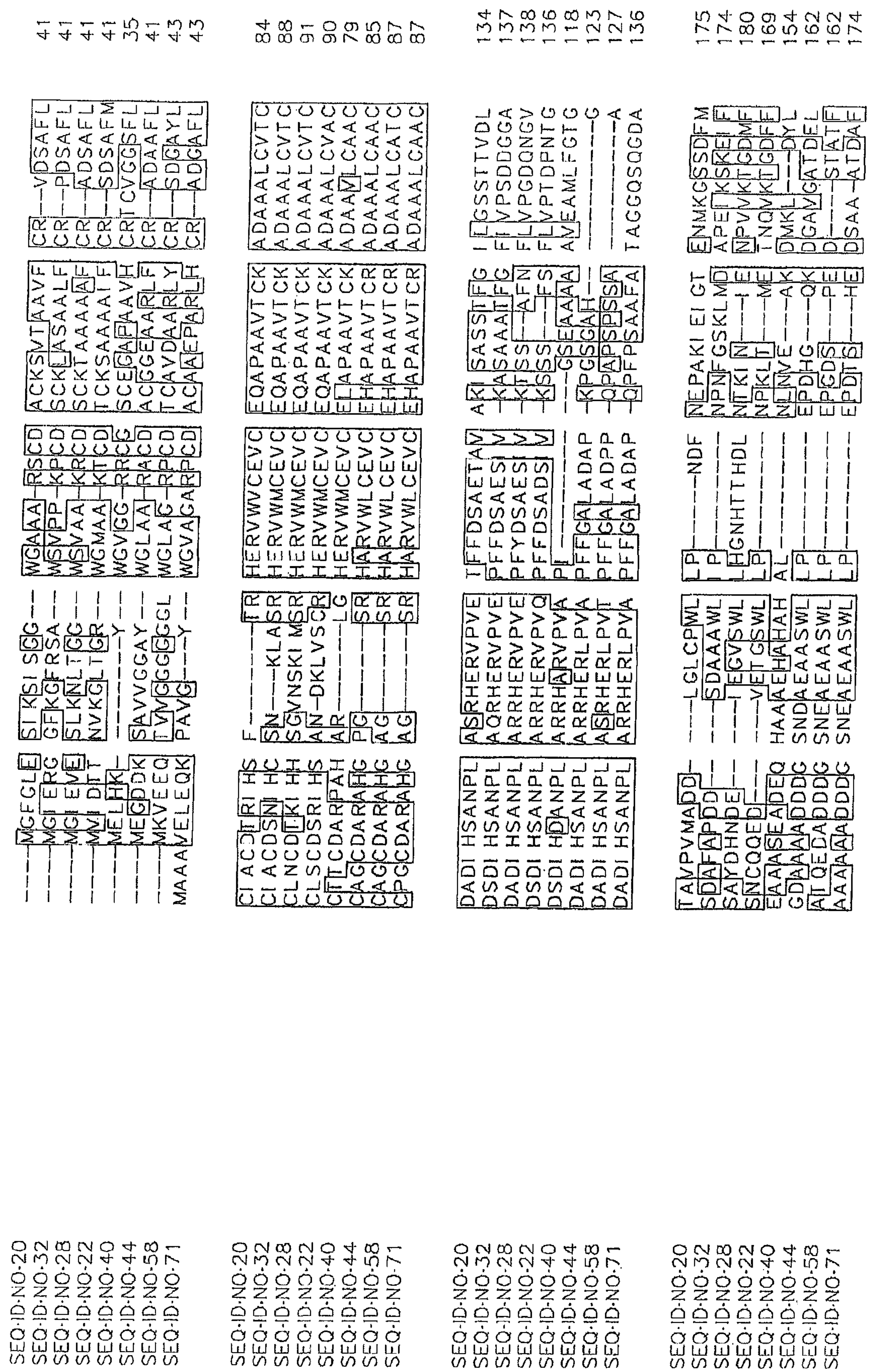
FIG. 2 is an alignment of Ceres SEEDLINE ID no.ME04315 (SEQ ID NO: 20) with homologous and/or orthologous amino acid sequences Ceres CLONE ID no.1842825 (SEQ ID NO: 22), Ceres ANNOT ID no.1482536 (SEQ ID NO: 28), Ceres CLONE ID no.463157 (SEQ ID NO: 32), Ceres CLONE ID no.1674443 (SEQ ID NO:40), GI ID no.1163 10719 (SEQ ID NO: 44), Ceres CLONE ID no.907473 (SEQ ID NO: 58), and Ceres CLONE ID no.1755065 (SEQ ID NO: 71).
Figure 2:
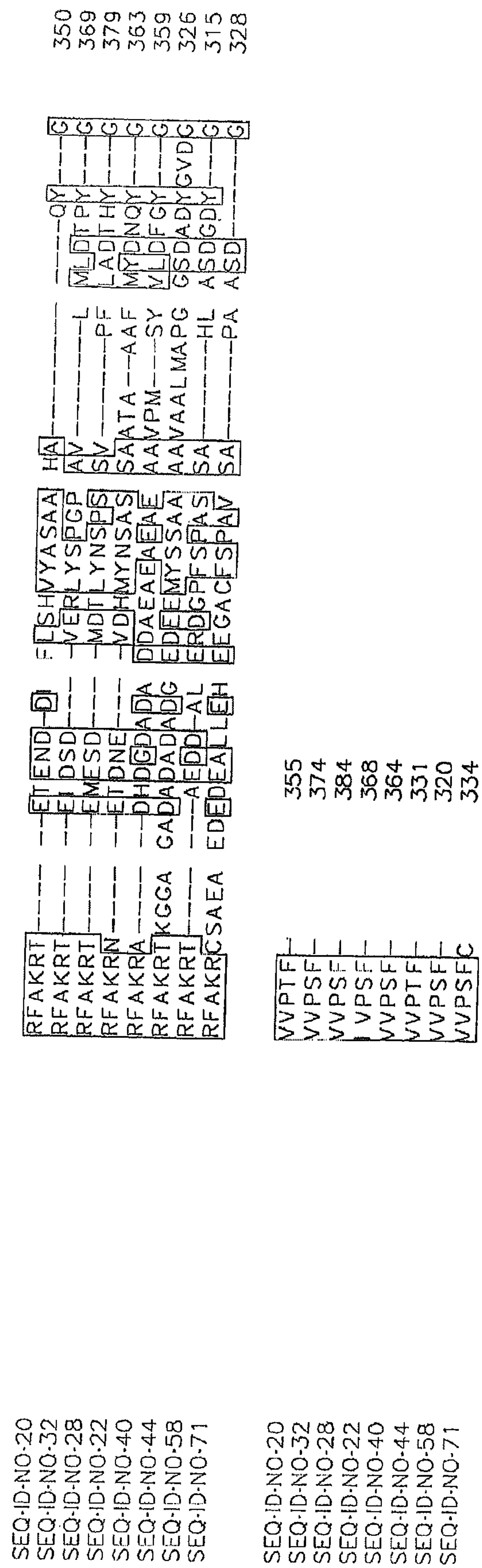

Examples of amino acid sequences of functional homologs of the polypeptide set forth in SEQ ID NO: 20 are provided in FIG. 2 and in the Sequence Listing. Such exemplary functional homologs include Ceres CLONE ID no.1842825 (SEQ ID NO: 22), Ceres CLONE ID no.1834027 (SEQ ID NO: 24), Ceres CLONE ID no.1837064 (SEQ ID NO: 26), Ceres ANNOT ID no.1482536 (SEQ ID NO: 28), GI ID no.18424009 (SEQ ID NO: 29), GI ID no.9759262 (SEQ ID NO: 30), Ceres CLONE ID no.463157 (SEQ ID NO: 32), Ceres CLONE ID no.685991 (SEQ ID NO: 34), Ceres CLONE ID no.702632 (SEQ ID NO: 36), Ceres CLONE ID no.1559496 (SEQ ID NO: 38), Ceres CLONE ID no.1674443 (SEQ ID NO: 40), Ceres CLONE ID no.1828897 (SEQ ID NO: 42), GI ID no.125540249 (SEQ ID NO: 43), GI ID no.116310719 (SEQ ID NO: 44), GI ID no.125556324 (SEQ ID NO: 45), GI ID no.125538317 (SEQ ID NO: 46), GI ID no.115447239 (SEQ ID NO: 47), GI ID no.115459216 (SEQ ID NO: 48), GI ID no.115469296 (SEQ ID NO: 49), GI ID no.125582846 (SEQ ID NO: 50), GI ID no.92875402 (SEQ ID NO: 51), GI ID no.3341723 (SEQ ID NO: 52), GI ID no.4091806 (SEQ ID NO: 53), GI ID no.60459257 (SEQ ID NO: 54), Ceres CLONE ID no.1756710 (SEQ ID NO: 56), Ceres CLONE ID no.907473 (SEQ ID NO: 58), GI ID no.4091804 (SEQ ID NO: 59), GI ID no.21667487 (SEQ ID NO: 60), GI ID no.21655154 (SEQ ID NO: 61), GI ID no.45544883 (SEQ ID NO: 62), GI ID no.21655166 (SEQ ID NO: 63), GI ID no.10946337 (SEQ ID NO: 64), GI ID no.90657642 (SEQ ID NO: 65), GI ID no.45544887 (SEQ ID NO: 68), GI ID no.47606678 (SEQ ID NO: 69), or Ceres CLONE ID no.1755065 (SEQ ID NO: 71). In some cases, a functional homolog of SEQ ID NO: 20 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 20.

Examples of amino acid sequences of full length functional homologs of the truncated polypeptide set forth in SEQ ID NO: 93 are provided in FIG. 3 and in the Sequence Listing. Such exemplary functional homologs include Ceres CLONE ID no.1844076 (SEQ ID NO: 74), Ceres CLONE ID no.35974 (SEQ ID NO: 76), GI ID no.10176876 (SEQ ID NO: 77), Ceres CLONE ID no.473040 (SEQ ID NO: 79), Ceres CLONE ID no.922223 (SEQ ID NO: 81), GI ID no.125528967 (SEQ ID NO: 82), GI ID no.125573200 (SEQ ID NO: 83), Ceres ANNOT ID no.1527409 (SEQ ID NO: 85), GI ID no.92871098 (SEQ ID NO: 86), Ceres CLONE ID no.1831117 (SEQ ID NO: 88), and Ceres ANNOT ID no.857222 (SEQ ID NO: 90). In some cases, a full length functional homolog of SEQ ID NO: 93 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 74, 76, 77, 79, 81, 82, 83, 85, 86, 88, 90, or 93.

Figure 4:
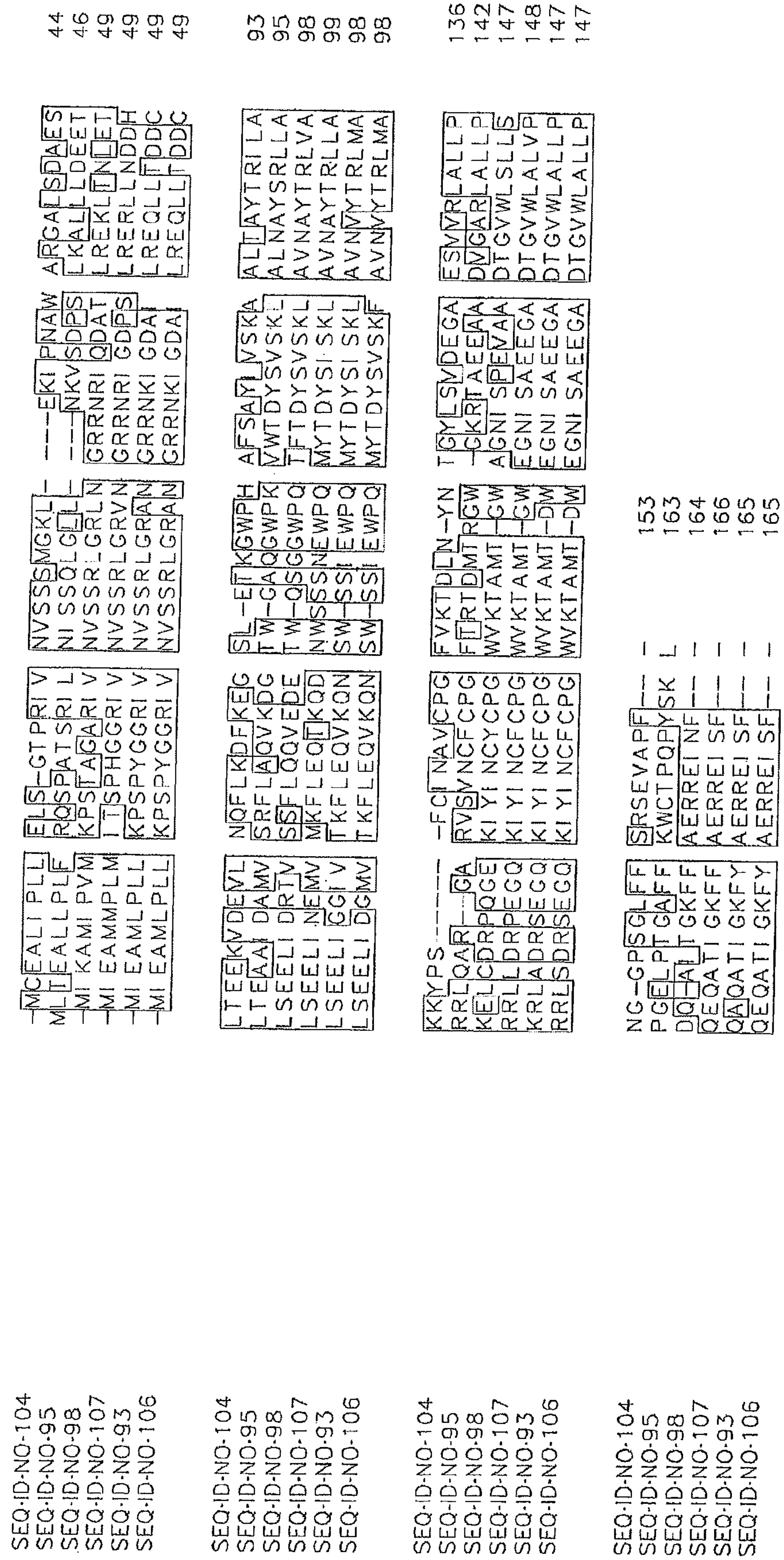
FIG. 4 is an alignment of a truncated version of Ceres SEEDLINE ID no.ME17294 (SEQ ID NO: 93) with homologous and/or orthologous amino acid truncated sequences, Ceres CLONE ID no.1831117 (SEQ ID NO: 95), Ceres CLONE ID no.1844076 (SEQ ID NO: 98), Ceres CLONE ID no.473040 (SEQ ID NO:104), Ceres CLONE ID no.922223 (SEQ ID NO: 106), and GI ID no.125528967 (SEQ ID NO:107).

Examples of amino acid sequences of functional homologs of the polypeptide set forth in SEQ ID NO: 93 are provided in FIG. 4 and in the Sequence Listing. Such exemplary functional homologs include Ceres ANNOT ID no.857222 (SEQ ID NO: 110), Ceres CLONE ID no.1831117 (SEQ ID NO: 95), GI ID no.92871098 (SEQ ID NO: 96), Ceres CLONE ID no.1844076 (SEQ ID NO: 98), Ceres CLONE ID no.35974 (SEQ ID NO: 100), GI ID no.110737329 (SEQ ID NO: 101), GI ID no.10176876 (SEQ ID NO: 102), Ceres CLONE ID no.473040 (SEQ ID NO: 104), Ceres CLONE ID no.922223 (SEQ ID NO: 106), GI ID no.125528967 (SEQ ID NO: 107), and GI ID no.115442007 (SEQ ID NO: 108). In some cases, a functional homolog of SEQ ID NO: 93 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 93.

Figure 5:
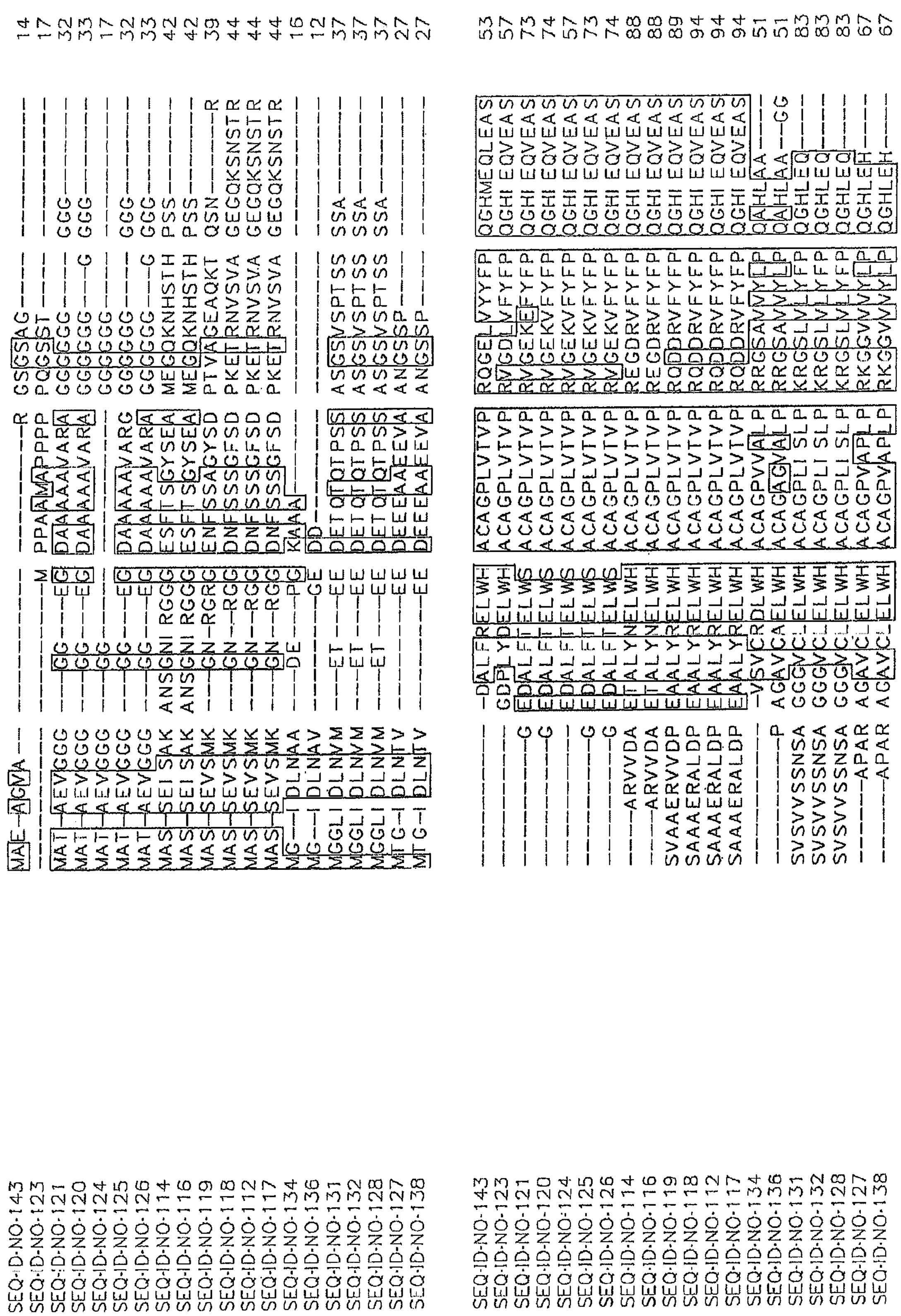
FIG. 5 is an alignment of functional homologs of the ARF (Auxin Response Factor) genes ARF2, ARF3, and ARF4, including LOCUS ID no.AT5G62000 (SEQ ID NO: 112), Ceres ANNOT ID no.1527370 (SEQ ID NO: 114), Ceres ANNOT ID no.1473961 (SEQ ID NO: 116), GI ID no.62319853 (SEQ ID NO: 117), GI ID no.62319903 (SEQ ID NO:118), GI ID no.47716275 (SEQ ID NO: 119), GI ID no.125534572 (SEQ ID NO:120), GI ID no.26251300 (SEQ ID NO:121), GI ID no.115441981 (SEQ ID NO:123), GI ID no.23893346 (SEQ ID NO:124), GI ID no.115485689 (SEQ ID NO:125), GI ID no.108864435 (SEQ ID NO:126), GI ID no.50511471 (SEQ ID NO:127), LOCUS ID no.At2g33860 (SEQ ID NO:128), GI ID no.2245390 (SEQ ID NO:131), GI ID no.3228517 (SEQ ID NO:132), Ceres CLONE ID no.827306 (SEQ ID NO: 134), Ceres CLONE ID no.1598488 (SEQ ID NO: 136), GI ID no.125553314 (SEQ ID NO:138), and Ceres CLONE ID no.462443 (SEQ ID NO:143).
Figure 5:
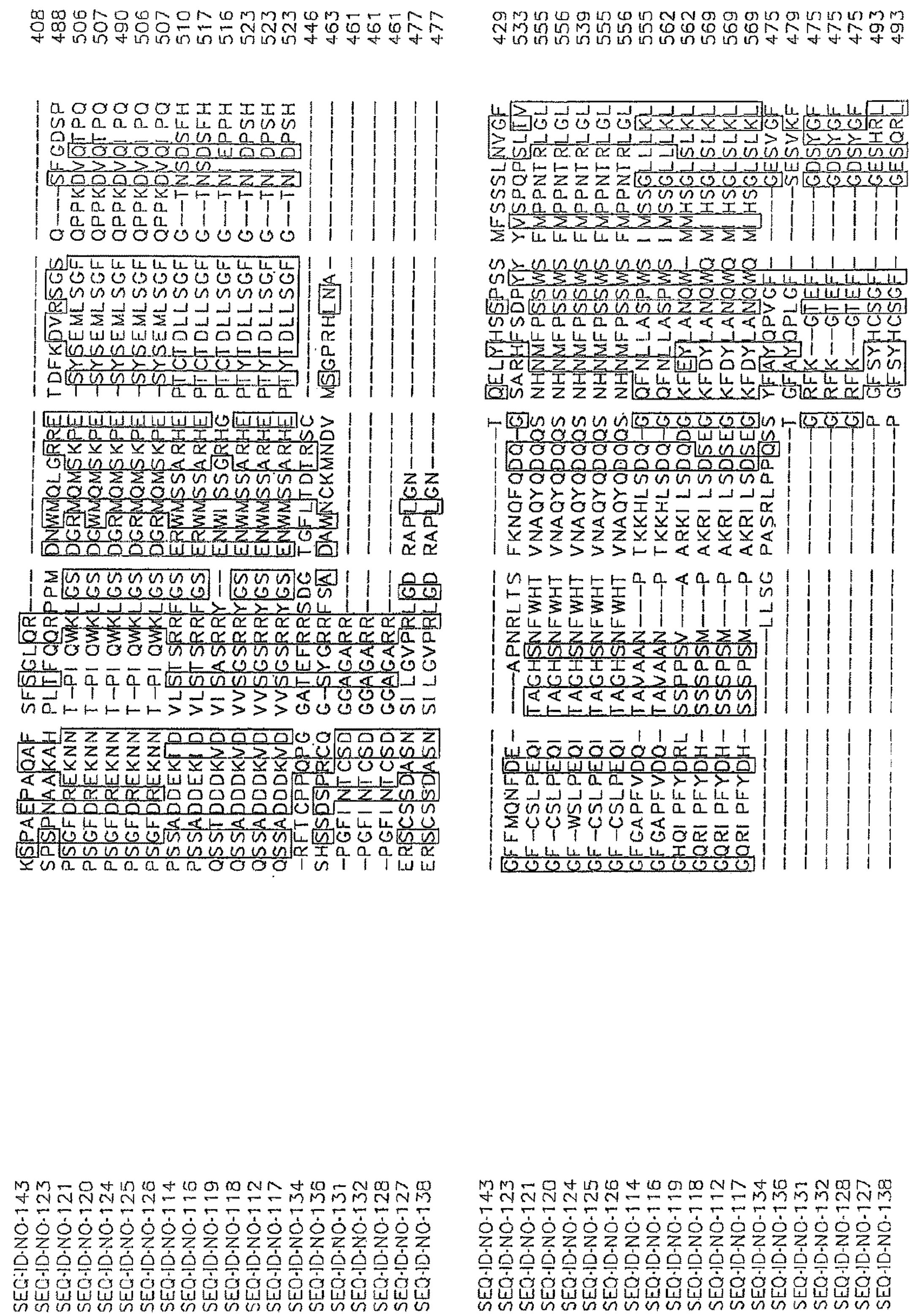
Figure 5:
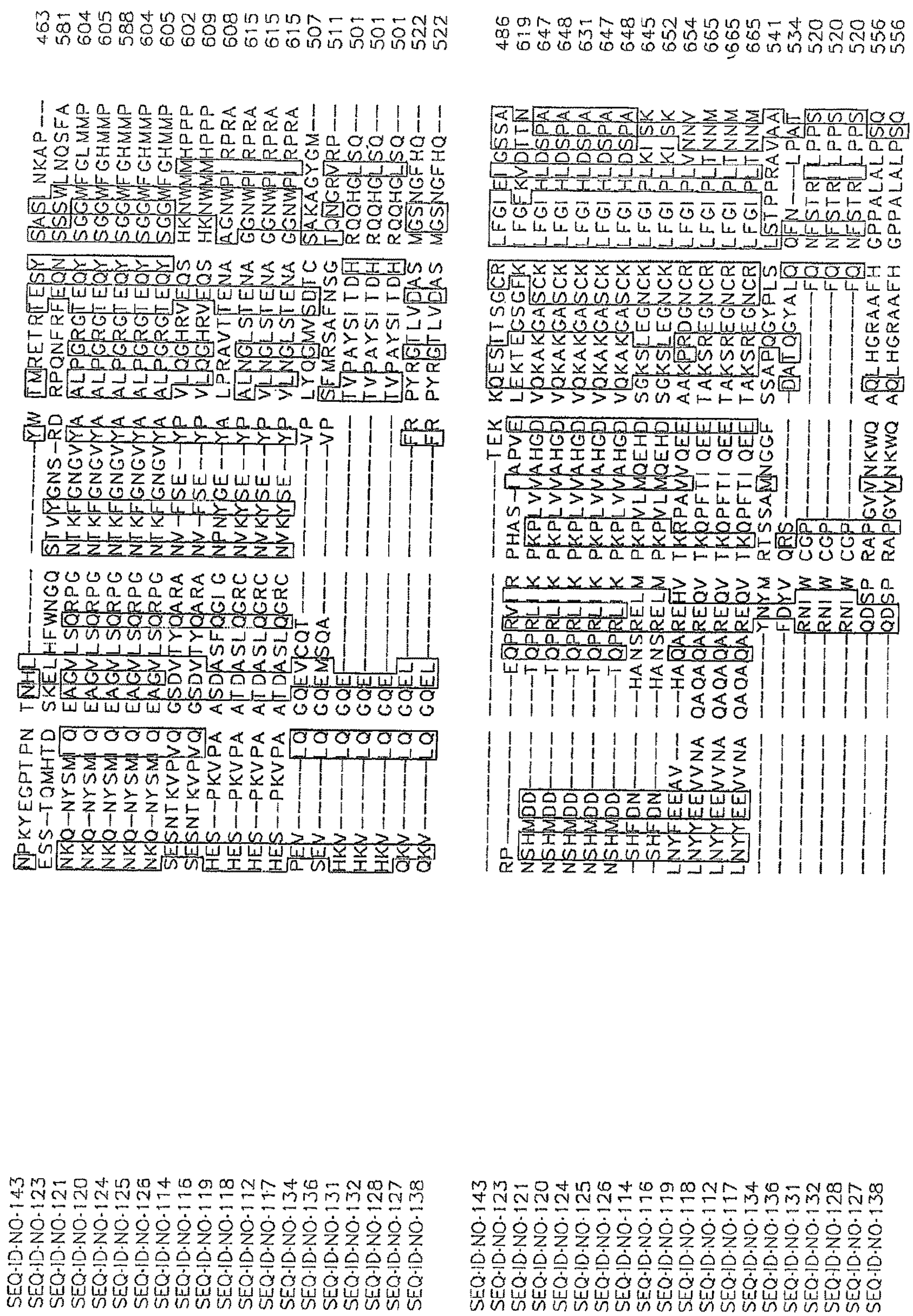
Figure 5:
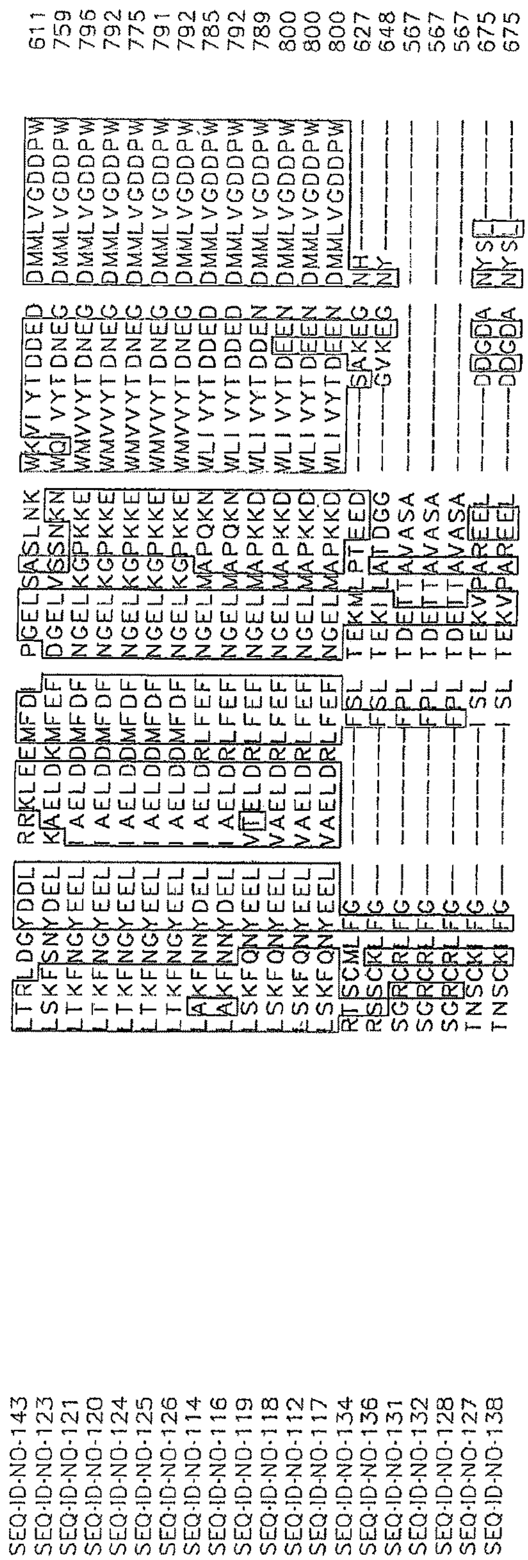
Figure 5:
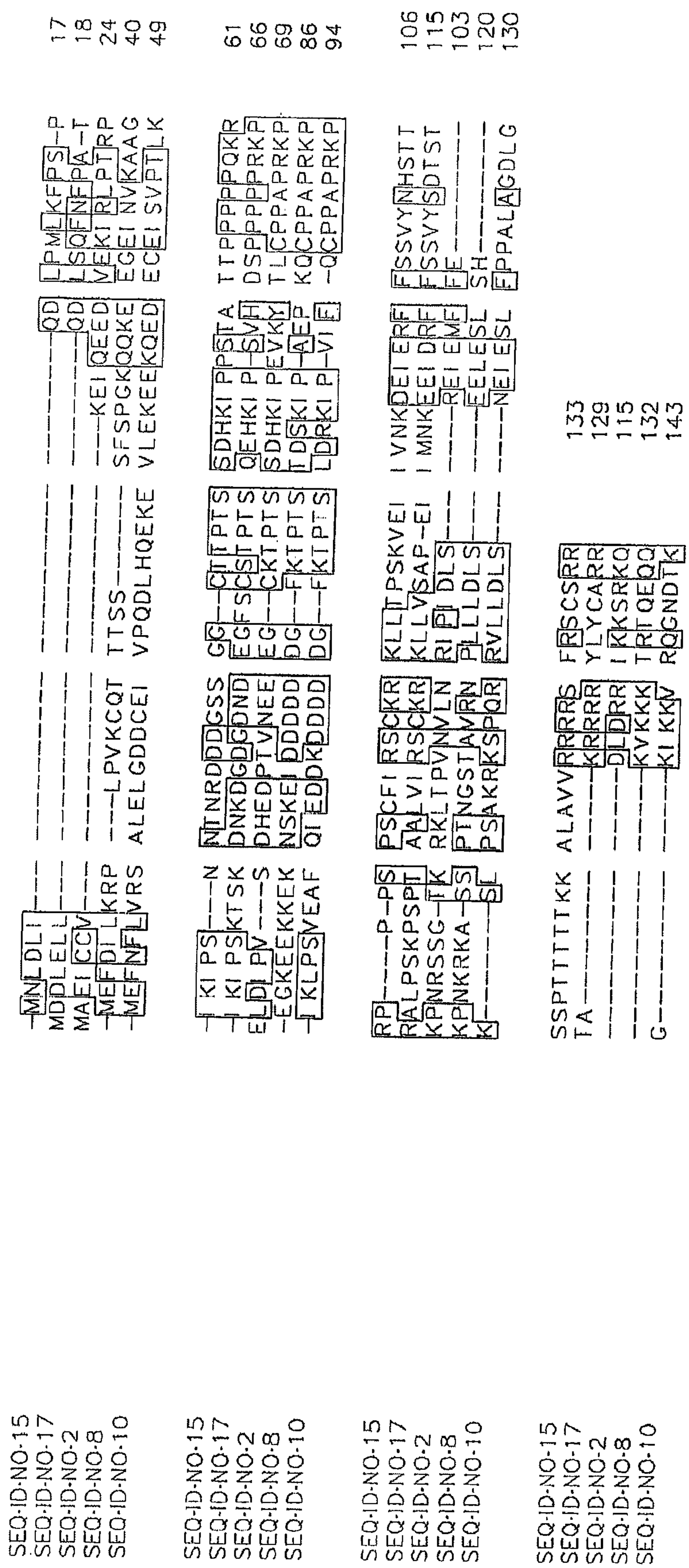

Examples of amino acid sequences of functional homologs of the polypeptide set forth in SEQ ID NO: 116 are provided in FIG. 5 and in the Sequence Listing. Such exemplary functional homologs include LOCUS ID no.AT5G62000 (SEQ ID NO: 112), Ceres ANNOT ID no.1527370 (SEQ ID NO: 114), GI ID no.623 19853 (SEQ ID NO: 117), GI ID no.62319903 (SEQ ID NO: 118), GI ID no.47716275 (SEQ ID NO: 119), GI ID no.125534572 (SEQ ID NO: 120), GI ID no.26251300 (SEQ ID NO: 121), GI ID no.125528952 (SEQ ID NO: 122), GI ID no.115441981 (SEQ ID NO: 123), GI ID no.23893346 (SEQ ID NO: 124), GI ID no.115485689 (SEQ ID NO: 125), GI ID no.108864435 (SEQ ID NO: 126), GI ID no.50511471 (SEQ ID NO: 127), LOCUS ID no.At2g33860 (SEQ ID NO: 128), Ceres ANNOT ID no.1536494 (SEQ ID NO: 130), GI ID no.2245390 (SEQ ID NO: 131), GI ID no.3228517 (SEQ ID NO: 132), Ceres CLONE ID no.827306 (SEQ ID NO: 134), Ceres CLONE ID no.1598488 (SEQ ID NO: 136), GI ID no.125527740 (SEQ ID NO: 137), GI ID no.125553314 (SEQ ID NO: 138), LOCUS ID no. At5g60450 (SEQ ID NO: 139), Ceres ANNOT ID no.15 15383 (SEQ ID NO: 141), and Ceres CLONE ID no.462443 (SEQ ID NO: 143). In some cases, a functional homolog of SEQ ID NO: 116 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 116.

Examples of nucleic acid sequences of functional homologs of the tasiRNA encoding nucleic acid sequence set forth in SEQ ID NO: 111 are found in the Sequence Listing. Such exemplary functional homologs include 66, 67, 72, 73, 144, 145, 146, 147, 148, 149, 150, 151, 152, 153, 154, 155, and 156. In some cases, a functional homolog of SEQ ID NO: 111 has an nucleic acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the nucleic acid sequence set forth in SEQ ID NO: 111.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, or FIG. 4 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful cold tolerance-modulating polypeptides include those that fit a Hidden Markov Model based on the polypeptides set forth in any one of FIGS. 1-4 or ARFs that are acted upon by tasiRNA (FIG. 5). A Hidden Markov Model (HMM) is a statistical model of a consensus sequence for a group of functional homologs. See, Durbin et al., *Biological Sequence Analysis: Probabilistic Models of Proteins and Nucleic Acids,* Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in the Sequence Listing of this application. In some embodiments, a cold tolerance-modulating polypeptide discussed below fits the indicated HMM with an HMM bit score greater than 20, and has a domain indicative of a cold tolerance-modulating polypeptide. In some embodiments, a cold tolerance-modulating polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-5.

Examples of polypeptides are shown in the Sequence Listing that have HMM bit scores greater than 130 when fitted to an HMM generated from the amino acid sequences set forth in FIG. 1 are identified in the Sequence Listing of this application. Such polypeptides include Ceres CLONE ID no.1915941 (SEQ ID NO: 8), Ceres ANNOT ID no.1461830 (SEQ ID NO: 10), Ceres CLONE ID no.1080942 (SEQ ID NO: 15), and Ceres CLONE ID no.1073190 (SEQ ID NO: 17).

Examples of polypeptides are shown in the Sequence Listing that have HMM bit scores greater than 185 when fitted to an HMM generated from the amino acid sequences set forth in FIG. 2 are identified in the Sequence Listing of this application. Such polypeptides include Ceres CLONE ID no.1842825 (SEQ ID NO:22), Ceres ANNOT ID no.1482536 (SEQ ID NO: 28), Ceres CLONE ID no.463157 (SEQ ID NO: 32), Ceres CLONE ID no.1674443 (SEQ ID NO: 40), GI ID no.1163 10719 (SEQ ID NO: 44), Ceres CLONE ID no.907473 (SEQ ID NO: 58), and Ceres CLONE ID no.1755065 (SEQ ID NO:71).

Examples of polypeptides are shown in the Sequence Listing that have HMM bit scores greater than 655 when fitted to an HMM generated from the amino acid sequences set forth in FIG. 3 are identified in the Sequence Listing of this application. Such polypeptides include Ceres CLONE ID no.473040 (SEQ ID NO: 79), Ceres CLONE ID no.922223 (SEQ ID NO: 81), GI ID no.125528967 (SEQ ID NO: 82), GI ID no.125573200 (SEQ ID NO: 83), Ceres ANNOT ID no.1527409 (SEQ ID NO: 85), GI ID no.92871098 (SEQ ID NO: 86), Ceres CLONE ID no.1831117 (SEQ ID NO: 88), and Ceres ANNOT ID no.857222 (SEQ ID NO: 90).

Examples of polypeptides are shown in the Sequence Listing that have HMM bit scores greater than 315 when fitted to an HMM generated from the amino acid sequences set forth in FIG. 4 are identified in the Sequence Listing of this application. Such polypeptides include Ceres SEEDLINE ID no.ME17294 (SEQ ID NO: 93), Ceres CLONE ID no.1831117 (SEQ ID NO: 95), Ceres CLONE ID no.1844076 (SEQ ID NO: 98), Ceres CLONE ID no.473040

(SEQ ID NO: 104), Ceres CLONE ID no.922223 (SEQ ID NO: 106), and GI ID no.125528967 (SEQ ID NO: 107).

Examples of polypeptides are shown in the Sequence Listing that have HMM bit scores greater than 790 when fitted to an HMM generated from the amino acid sequences set forth in FIG. 5 are identified in the Sequence Listing of this application. Such polypeptides include LOCUS ID no.AT5G62000 (SEQ ID NO: 112), Ceres ANNOT ID no.1527370 (SEQ ID NO: 114), Ceres ANNOT ID no.1473961 (SEQ ID NO: 116), GI ID no.623 19853 (SEQ ID NO: 117), GI ID no.62319903 (SEQ ID NO:118), GI ID no.47716275 (SEQ ID NO: 119), GI ID no.125534572 (SEQ ID NO:120), GI ID no.26251300 (SEQ ID NO:121), GI ID no.115441981 (SEQ ID NO:123), GI ID no.23893346 (SEQ ID NO:124), GI ID no.115485689 (SEQ ID NO:125), GI ID no.108864435 (SEQ ID NO:126), GI ID no.50511471 (SEQ ID NO:127), LOCUS ID no.At2g33860 (SEQ ID NO:128), GI ID no.2245390 (SEQ ID NO:131), GI ID no.3228517 (SEQ ID NO:132), Ceres CLONE ID no.827306 (SEQ ID NO: 134), Ceres CLONE ID no.1598488 (SEQ ID NO: 136), GI ID no.125553314 (SEQ ID NO: 138), and Ceres CLONE ID no.462443 (SEQ ID NO:143).

D. Percent Identity

In some embodiments, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 20, 93, and 74.

Polypeptides having such a percent sequence identity often have a domain indicative of a cold tolerance-modulating polypeptide and/or have an HMM bit score that is greater than 130, as discussed above. Amino acid sequences of cold tolerance-modulating polypeptides having at least 80% sequence identity to one of the amino acid sequences set forth in SEQ ID NOs: 2, 20, 93, and 74 are provided in FIGS. 1-4 and in the Sequence Listing.

"Percent sequence identity" refers to the degree of sequence identity between any given reference sequence, e.g., SEQ ID NO: 2, and a candidate cold tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. Amino acid sequences of polypeptides having greater than 45% sequence identity to the polypeptide set forth in SEQ ID NO: 2 are provided in FIG. 1 and in the Sequence Listing. Examples of such polypeptides include Ceres CLONE ID no.1915941 (SEQ ID NO: 8), Ceres ANNOT ID no.1461830 (SEQ ID NO: 10), Ceres CLONE ID no.1080942 (SEQ ID NO: 15), and Ceres CLONE ID no.1073190 (SEQ ID NO: 17).

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 20. Amino acid sequences of polypeptides having greater than 45% sequence identity to the polypeptide set forth in SEQ ID NO: 20 are provided in FIG. 2 and in the Sequence Listing. Examples of such polypeptides include Ceres CLONE ID no.1842825 (SEQ ID NO: 22), Ceres ANNOT ID no.1482536 (SEQ ID NO: 28), Ceres CLONE ID no.463157 (SEQ ID NO: 32), Ceres CLONE ID no.1674443 (SEQ ID NO:40), GI ID no.1163 10719 (SEQ ID NO: 44), Ceres CLONE ID no.907473 (SEQ ID NO: 58), and Ceres CLONE ID no.1755065 (SEQ ID NO: 71).

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 93. Amino acid sequences of polypeptides having greater than 45% sequence identity to the polypeptide set forth in SEQ ID NO: 93 are provided in FIG. 3 and in the Sequence Listing. Examples of such polypeptides include Ceres CLONE ID no.473040 (SEQ ID NO: 79), Ceres CLONE ID no.922223 (SEQ ID NO: 81), GI ID no.125528967(SEQ ID NO: 82), GI ID no.125573200 (SEQ ID NO: 83), Ceres ANNOT ID no.1527409 (SEQ ID NO: 85), GI ID no.92871098 (SEQ ID NO: 86), Ceres CLONE ID no.1831117 (SEQ ID NO: 88), and Ceres ANNOT ID no.857222 (SEQ ID NO: 90).

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 93. Amino acid sequences of polypeptides having greater than 45% sequence identity to the polypeptide set forth in SEQ ID NO: 93 are provided in FIG. 4 and in the Sequence Listing. Examples of such polypeptides include Ceres CLONE ID no.1831117 (SEQ ID NO: 95), Ceres CLONE ID no.1844076 (SEQ ID NO: 98), Ceres CLONE ID no.473040 (SEQ ID NO: 104), Ceres CLONE ID no.922223 (SEQ ID NO: 106), and GI ID no.125528967 (SEQ ID NO: 107).

In some cases, a cold tolerance-modulating tasiRNA acts upon an ARF amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 116. Amino acid sequences of polypeptides having greater than 45% sequence identity to the polypeptide set forth in SEQ ID NO: 116 are provided in FIG. 5 and in the Sequence Listing. Examples of such polypeptides include LOCUS ID no.AT5G62000 (SEQ ID NO: 112), Ceres ANNOT ID no.1527370 (SEQ ID NO: 114), GI ID no.623 19853 (SEQ ID NO: 117), GI ID no.62319903 (SEQ ID NO:118), GI ID no.47716275 (SEQ ID NO: 119), GI ID no.125534572 (SEQ ID NO:120), GI ID no.26251300 (SEQ ID NO:121), GI ID no.115441981 (SEQ ID NO:123), GI ID no.23893346 (SEQ ID NO:124), GI ID no.115485689 (SEQ ID NO:125), GI ID no.108864435 (SEQ ID NO:126), GI ID no.50511471 (SEQ ID NO:127), LOCUS ID no.At2g33860 (SEQ ID NO:128), GI ID no.2245390 (SEQ ID NO:131), GI ID no.3228517 (SEQ ID NO:132), Ceres CLONE ID no.827306 (SEQ ID NO: 134), Ceres CLONE ID no.1598488 (SEQ ID NO: 136), GI ID no.125553314 (SEQ ID NO: 138), and Ceres CLONE ID no.462443 (SEQ ID NO: 143).

E. Other Sequences

It should be appreciated that a cold tolerance-modulating polypeptide can include additional amino acids that are not involved in cold tolerance modulation, and thus such a polypeptide can be longer than would otherwise be the case. For example, a cold tolerance-modulating polypeptide can include a purification tag, a chloroplast transit peptide, a mitochondrial transit peptide, an amyloplast transit peptide, or a leader sequence added to the amino or carboxy terminus. In some embodiments, a cold tolerance-modulating polypeptide includes an amino acid sequence that functions as a reporter, e.g., a green fluorescent protein or yellow fluorescent protein.

III. NUCLEIC ACIDS

Nucleic acids described herein include nucleic acids that are effective to modulate cold tolerance levels when transcribed in a plant or plant cell. Such nucleic acids include, without limitation, those that encode a cold tolerance-modulating polypeptide and those that can be used to inhibit expression of a cold tolerance-modulating polypeptide via a nucleic acid based method.

A. Cold Tolerance-Modulating Nucleic Acids

Nucleic acids encoding cold tolerance-modulating polypeptides are described herein. Examples of such nucleic acids include SEQ ID NOs: 3, 5, 7, 9, 11, 14, 16, 18, 19, 21, 23, 25, 27, 31, 33, 35, 37, 39, 41, 55, 57, 70, 75, 78, 80, 84, 87, 89, 91, 92, 94, 97, 99, 103, 105, 109, 113, 115, 129, 133, 135, 140, and 142, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 3, 5, 7, 9, 11, 14, 16, 18, 19, 21, 23, 25, 27, 31, 33, 35, 37, 39, 41, 55, 57, 70, 75, 78, 80, 84, 87, 89, 91, 92, 94, 97, 99, 103, 105, 109, 113, 115, 129, 133, 135, 140, and 142.

A cold tolerance-modulating nucleic acid can comprise the nucleotide sequence set forth in SEQ ID NO: 1. Alternatively, a cold tolerance-modulating nucleic acid can be a variant of the nucleic acid having the nucleotide sequence set forth in SEQ ID NO: 1. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1.

A cold tolerance-modulating nucleic acid can comprise the nucleotide sequence set forth in SEQ ID NO: 19. Alternatively, a cold tolerance-modulating nucleic acid can be a variant of the nucleic acid having the nucleotide sequence set forth in SEQ ID NO: 19. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 19.

A cold tolerance-modulating nucleic acid can comprise the nucleotide sequence set forth in SEQ ID NO: 92. Alternatively, a cold tolerance-modulating nucleic acid can be a variant of the nucleic acid having the nucleotide sequence set forth in SEQ ID NO: 92. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 92.

A cold tolerance-modulating nucleic acid can comprise the nucleotide sequence set forth in SEQ ID NO: 97. Alternatively, a cold tolerance-modulating nucleic acid can be a variant of the nucleic acid having the nucleotide sequence set forth in SEQ ID NO: 97. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 97.

A cold tolerance-modulating nucleic acid can comprise the nucleotide sequence set forth in SEQ ID NO: 111. Alternatively, a cold tolerance-modulating nucleic acid can be a variant of the nucleic acid having the nucleotide sequence set forth in SEQ ID NO: 111. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 111.

A cold tolerance-modulating sequence can be at least a fragment of a nucleotide sequence such as Ceres ANNOT ID no.1473961 (SEQ ID NO: 116) or homologs thereof. For example, the cold tolerance-modulating nucleotide may be a tasiRNA. Such cold tolerance-modulating nucleotide sequences can act upon a protein that comprises an auxin response factor motif. This motif is present in SEQ ID NO: 112, which sets forth the amino acid sequence of an *Arabidopsis* clone, identified herein as LOCUS ID no.AT5G62000 (SEQ ID NO: 112), that is predicted to encode an polypeptide comprising an auxin response factor motif. In certain embodiments, the protein comprising an auxin response factor motif is an ARF protein. The ARFs are key regulators of auxin-modulated gene expression. There are multiple ARF proteins, some of which activate, while others repress transcription. ARF proteins bind to auxin-responsive cis-acting promoter elements (AuxREs) using an N-terminal DNA-binding domain. It is thought that Aux/IAA proteins activate transcription by modifying ARF activity through the C-terminal protein-protein interaction domains found in both Aux/IAA and ARF proteins.

A cold tolerance-modulating sequence can be at least a fragment of a nucleotide sequence such as Ceres ANNOT ID no.1473961 (SEQ ID NO: 116) or homologs thereof. For example, the cold tolerance-modulating nucleotide may be a tasiRNA. Such cold tolerance-modulating nucleotide sequences can act upon a protein that comprises a B3 DNA binding domain. This domain is present in SEQ ID NO: 112, which sets forth the amino acid sequence of an *Arabidopsis* clone, identified herein as LOCUS ID no.AT5G62000 (SEQ ID NO: 112), that is predicted to encode an polypeptide comprising an B3 DNA binding domain. In certain embodiments, the protein comprising a B3 DNA binding domain is an ARF protein.

In some embodiments, a cold tolerance-modulating sequence is a tasiRNA sequence or a homolog thereof, such tasiRNA sequence being encoded by a nucleic acid sequence that comprises a domain having 80% or greater sequence identity to nucleic acid residues 305 to about 346 of SEQ ID NO: 111, residues 21 to about 62 of SEQ ID NO: 66, residues 20 to about 61 of SEQ ID NO: 67, residues 21 to about 62 of SEQ ID NO: 72, residues 21 to about 62 of SEQ ID NO: 73, residues 77 to about 118 of SEQ ID NO: 144, residues 292 to about 313 of SEQ ID NO: 145, residues 37 to about 78 of SEQ ID NO: 146, residues 56 to about 97 of SEQ ID NO: 147, residues 37 to about 78 of SEQ ID NO: 148, residues 45 to about 86 of SEQ ID NO: 149, residues 46 to about 98 of SEQ ID NO: 150, residues 476 to about 497 of SEQ ID NO: 151, residues 21 to about 62 of SEQ ID NO: 152, residues 21 to about 62 of SEQ ID NO: 153, residues 21 to about 62 of SEQ ID NO: 154, residues 21 to about 62 of SEQ ID NO: 155, or residues 21 to about 62 of SEQ ID NO: 156.

In some embodiments, a cold tolerance-modulating sequence is a nucleotide sequence or a homolog thereof, such as a tasiRNA sequence, wherein said nucleotide is encoded by a nucleic acid sequence that also comprises an miR390 recognition sequence having 80% or greater sequence identity to nucleic acid residues 109 to about 129 of SEQ ID NO: 66, residues 114 to about 135 of SEQ ID NO: 67, residues 119 to about 139 of SEQ ID NO: 72, residues 108 to about 128 of SEQ ID NO: 73, residues 234 to about 254 of SEQ ID NO: 144, residues 135 to about 176 of SEQ ID NO: 145, residues 173 to about 189 of SEQ ID NO: 147, residues 154 to about 170 of SEQ ID NO: 148, residues 134 to about 157 of SEQ ID NO: 149, residues 154 to about 198 of SEQ ID NO: 150, residues 319 to about 360 of SEQ ID NO: 151, residues 121 to about 141 of SEQ ID NO: 152, residues 120 to about 140 of SEQ ID NO: 153, residues 121 to about 141 of SEQ ID NO: 154, residues 121 to about 141 of SEQ ID NO: 155, residues 121 to about 141 of SEQ ID NO: 156, or residues 462 to about 483 of SEQ ID NO: 111. miR390 recognition sequences may guide in-phase processing of transcription (Allen et al. 2005).

In embodiments of the invention, a cold tolerance-modulating nucleotide, such as Ceres ANNOT ID no.1473961 (SEQ ID NO: 116) or a homolog thereof, can act upon an polypeptide that comprises a B3 DNA binding domain having 80% or greater sequence identity to amino acid residues 163 to 268 of SEQ ID NO: 112, residues 157 to 262 of SEQ ID NO: 114, residues 157 to 262 of SEQ ID NO: 116, residues 163 to 268 of SEQ ID NO: 117, residues 163 to 268 of SEQ ID NO: 118, residues 158 to 263 of SEQ ID NO: 119, residues 148 to 253 of SEQ ID NO: 120, residues 147 to 252 of SEQ ID NO: 121, residues 123 to 228 of SEQ ID NO: 122, residues 128 to 233 of SEQ ID NO: 123, residues 131 to 236 of SEQ ID NO: 124, residues 147 to 252 of SEQ ID NO: 125, residues 148 to 253 of SEQ ID NO: 126, residues 141 to 246 of SEQ ID NO: 127, residues 158 to 263 of SEQ ID NO: 128, residues 142 to 247 of SEQ ID NO: 130, residues 158 to 263 of SEQ ID NO: 131, residues 158 to 263 of SEQ ID NO: 132, residues 126 to 231 of SEQ ID NO: 134, residues 129 to 234 of SEQ ID NO: 136, residues 114 to 219 of SEQ ID NO: 137, residues 141 to 246 of SEQ ID NO: 138, residues 176 to 281 of SEQ ID NO: 139, residues 152 to 257 of SEQ ID NO: 141, or residues 121 to 225 of SEQ ID NO: 143.

In embodiments of the invention, a cold tolerance-modulating tasiRNA sequence such as Ceres ANNOT ID no.1473961 (SEQ ID NO: 116) can act upon an ARF polypeptide that comprises an auxin response factor motif having 80% or greater sequence identity to amino acid residues 290 to 372 of SEQ ID NO: 112, residues 284 to 366 of SEQ ID NO: 114, residues 284 to 366 of SEQ ID NO: 116, residues 290 to 372 of SEQ ID NO: 117, residues 290 to 372 of SEQ ID NO: 118, residues 285 to 367 of SEQ ID NO: 119, residues 275 to 357 of SEQ ID NO: 120, residues 274 to 356 of SEQ ID NO: 121, residues 250 to 331 of SEQ ID NO: 122, residues 255 to 336 of SEQ ID NO: 123, residues 258 to 340 of SEQ ID NO: 124, residues 274 to 356 of SEQ ID NO: 125, residues 275 to 357 of SEQ ID NO: 126, residues 268 to 349 of SEQ ID NO: 127, residues 285 to 367 of SEQ ID NO: 128, residues 269 to 351 of SEQ ID NO: 130, residues 285 to 367 of SEQ ID NO: 131, residues 285 to 367 of SEQ ID NO: 132, residues 253 to 334 of SEQ ID NO: 134, residues 256 to 337 of SEQ ID NO: 136, residues 241 to 322 of SEQ ID NO: 137, residues 268 to 349 of SEQ ID NO: 138, residues 302 to 384 of SEQ ID NO: 139, residues 279 to 361 of SEQ ID NO: 141, or residues 247 to 332 of SEQ ID NO: 143.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Cold Tolerance-Modulating Polypeptide A nucleic acid encoding one of the cold tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular cold tolerance-modulating polypeptide; i.e., for many amino acids, there is more than one nucleotide triplet that serves as the codon for the amino acid. Thus, codons in the coding sequence for a given cold tolerance-modulating polypeptide can be modified such that optimal expression in a particular plant species is obtained, using appropriate codon bias tables for that species.

In some cases, expression of a cold tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, Nature Reviews Drug Discovery 3: 318-329 (2004); and *Nature Reviews RNA interference collection,* October 2005 at nature.com/reviews/focus/mai. Typically, at least a fragment of a nucleic acid encoding cold tolerance-modulating polypeptides and/or its complement is expressed. A fragment is typically at least 20 nucleotides long, as needed for the methods noted below. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding cold tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA,* 92(13):6175-6179 (1995); de Feyter and Gaudron, Methods in Molecular Biology, Vol. 74, Chapter 43, "Expressing Ribozymes in Plants", Edited by Turner, P.C., Humana Press Inc., Totowa, NJ. RNA endoribonucleases which have been described, such as the one that occurs naturally in *Tetrahymena thermophila,* can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a cold tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the cold tolerance-modulating polypeptide. In other embodiments, one strand of the stem portion of a double stranded RNA comprises a sequence that is similar or identical to the sequence of an intron, or a fragment thereof, in the pre-mRNA encoding a cold tolerance-modulating polypeptide, and the other strand of the stem portion comprises a sequence that is similar or identical to the sequence that is complementary to the sequence of the intron, or a fragment thereof, in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

microRNA (miRNA) and tasiRNA, which are non-protein coding RNAs, can also be used to inhibit the expression of a gene. The gene targeted for inhibition may be an endogenous plant gene, a viral gene, a bacterial gene, a fungal gene, or an insect gene. miRNAs and tasiRNAs are regulatory agents consisting of about 19 to 25 ribonucleotides. miRNA are highly efficient at inhibiting the expression of endogenous genes and/or can guide in-phase processing of tasiRNA primary transcripts. tasiRNAs similarly inhibit gene expression by interacting with target mRNAs and guide cleavage by the same mechanism as do plant miRNAs, but differ from miRNAs in that they arise from double-stranded RNA, which may require RNA-dependent RNA polymerases.

For example, a tasiRNA can act upon an auxin responsive protein (ARF) (e.g., ARF3 or ARF4). In particular, inhibition of the expression of an ARF encoding gene (e.g., ARF3 or ARF4) may be obtained by interference by expression of a nucleic acid sequence encoding a tasiRNA. Transcription of a tasiRNA encoding nucleic acid sequence can be under the control of a promoter, such as, but not limited to, those promoters and regulatory regions described herein, or under promotional control of a tasiRNA coding sequence's own promoter. For such interference, the expression cassette is designed to express an RNA molecule that is modeled on an endogenous tasiRNA encoding sequence. The tasiRNA encoding sequence encodes an RNA that forms a hairpin structure containing a nucleotide sequence that is complementary to another endogenous gene (target sequence). For suppression of ARF protein expression, the nucleotide sequence is selected from an ARF transcript sequence and contains about 19 to 25 nucleotides of said ARF protein sequence in sense orientation and about 19 to 25 nucleotides of a corresponding antisense sequence that is complementary to the sense sequence. tasiRNA molecules are highly efficient at inhibiting the expression of endogenous genes. In *Arabidopsis*, a nuclear DCL enzyme is believed to be required for mature miRNA formation (Xie et al. (2004) PLOS Biol., 2:642-652, which is incorporated by reference herein). Inhibition of gene expression by miRNAs and tasiRNAs and methods for inhibition are known to those of skill in the art. See, for example, Javier, et al., (2003) Nature 425:257-263; Bartel (2004) Cell, 116:281-297; Kim (2005) Nature Rev. Mol. Cell Biol., 6:376-385; and Allen et al. (2005) Cell, 121:207-221, all of which are incorporated by reference herein.

Constructs containing regulatory regions operably linked to nucleic acid molecules in sense orientation can also be used to inhibit the expression of a gene. The transcription product can be similar or identical to the sense coding sequence, or a fragment thereof, of a cold tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide, or a fragment of such sequences. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.,* 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-0-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.,* 7:187-195; Hyrup et al., *Bioorgan. Med. Chem.,* 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate cold tolerance levels. A recombinant nucleic acid construct can comprise a nucleic acid encoding a cold tolerance-modulating polypeptide as described herein, operably linked to a regulatory region suitable for expressing the cold tolerance-modulating polypeptide in the plant or cell. Thus, a nucleic acid can comprise a coding sequence that encodes any of the cold tolerance-modulating polypeptides as set forth in SEQ ID NOs: 2, 20, 93, 74, or a homologs thereof. Examples of nucleic acids encoding cold tolerance-modulating polypeptides are set forth in SEQ ID NOs: 1, 19, 92, 97, or 111, and in FIGS. 1-4 and in the Sequence Listing. The cold tolerance-modulating polypeptide encoded by a recombinant nucleic acid can be a native cold tolerance-modulating polypeptide, or can be heterologous to the cell. In some cases, the recombinant construct contains a nucleic acid that inhibits expression of a cold tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, 13-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

D. Regulatory regions

The choice of regulatory regions to be included in a recombinant construct depends upon several factors, including, but not limited to, efficiency, selectability, inducibility, desired expression level, and cell-or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell,* 1:855-866 (1989); Bustos et al., *Plant Cell,* 1:839-854 (1989); Green et al., *EMBO J.,* 7:4035-4044 (1988); Meier et al., *Plant Cell,* 3:309-316 (1991); and Zhang et al., *Plant Physiology,* 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

ii. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of Agrobacterium tumefaciens, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

iii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672 , PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

iv. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean a' subunit of f3-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Other maturing endosperm promoters include the YP0092, PT0676, and PT0708 promoters.

v. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

vi. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis viviparous*-1 (see, GenBank No. U93215); *Arabidopsis atmycl* (see, Urao (1996) *Plant Mol. Biol.,* 32:571-57; Conceicao (1994) *Plant,* 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics,* 142: 1009-1020); maize Cat3 (see, GenBank No. L05934; Abler (1993) *Plant Mol. Biol.,* 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vii. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp 1) promoter (*Plant Cell Rep* (2001) 20:647-654), YP0097, YP0107, YP0088, YP0143, YP0156, PT0650, PT0695, PT0723, PT0838, PT0879, and PT0740.

viii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cablR promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcbl*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

ix. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, Plant Cell, 3 (10) :1051-1061 (1991)), the Commelina yellow mottle virus (CoYMV) promoter (Medberry et al., *Plant Cell,* 4(2):185-192 (1992)), and the rice tungro bacilliform virus (RTBV) promoter (Dai et al., *Proc. Natl. Acad. Sci. USA,* 101(2):687-692 (2004)).

x. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

xi. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a cold tolerance-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided, as long as the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous cold tolerance-modulating polypeptide whose expression has not previously been confirmed in particular recipient cells.

Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a cold tolerance-modulating polypeptide or nucleic acid. Physical and biochemical methods can be used to identify expression levels. These include Southern analysis or PCR amplification for detection of a polynucleotide; Northern blots, 51 RNAse protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of cold tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a cold tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may *include members of the genus Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (eucalyptus), *Triticosecale* (*Triticum*-wheat X rye) and bamboo.

Suitable species also include *Helianthus annuus* (sunflower), *Carthamus tinctorius* (safflower), *Jatropha curcas* (*Jatropha*), *Ricinus communis* (castor), *Elaeis guineensis* (palm), *Linum usitatissimum* (flax), and *Brassicajuncea.*

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium.*

Suitable species also include *Parthenium argentatum* (guayule), *Hevea* spp. (rubber), *Mentha spicata* (mint), *Mentha piperita* (mint), *Bixa orellana,* and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus,* and *Ricinus;* and the monocot genera *Elaeis, Festuca, Hordeum, Lolium, Oryza, Panicum, Pennisetum, Phleum, Poa, Saccharum, Secale, Sorghum, Triticosecale, Triticum,* and *Zea.* In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), Br*assica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp. *X Miscanthus* sp.).

D. Transgenic Plant Phenotypes

In some embodiments, a plant in which expression of a cold tolerance-modulating polypeptide is modulated can have increased levels of cold tolerance and/or biomass in vegetative tissues. Cold tolerance can be measured by means well know to those of skill in the art, including, but not limited to, seedling survival, decreased photosynthesis and membrane damage (measured by electrolyte leakage), seedling area, yield, and or biomass. For example, a cold tolerance-modulating polypeptide or nucleic acid described herein can be expressed in a transgenic plant, resulting in increased levels of cold tolerance and/or biomass. The cold tolerance level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, 100 or more than 100 percent, as compared to the cold tolerance level in a corresponding control plant that does not express the transgene. In some embodiments, a plant in which expression of a cold tolerance-modulating polypeptide or polynucleotide is modulated can have increased levels of biomass. The biomass level can be increased by at least 2 percent, e.g., 2, 3, 4, 5, 10, 15, 20, 25, 30, 35, 40, 50, 60, 70, 80, 90, 100, or more than 100 percent, as compared to the biomass level in a corresponding control plant that does not express the transgene. In some embodiments, differences can be measured for a plant in which expression of a cold tolerance-modulating polypeptide is modulated can be exposed to cold for one or more periods of time that may vary depending on climatic conditions. For example, for periods of about ½ hour, 1 hour, 3 hours, 6 hours, 12 hours, 1 day, 3 days, 5 days, 10 days, 1 month, 3 months, 6 months, 12 months, or the entire lifespan of such a plant.

Increases in cold tolerance in such plants can provide improved nutritional quantity and content in geographic locales where cold affects plants. Increases in cold tolerance in such plants can be useful in situations where plant parts such as, but not limited to, seeds, tubers, stems, leaves or roots are harvested for human or animal consumption.

Decrease in cold tolerance in such plants can be useful for species or varieties of plants that benefit from cold exposure. For example, cold sensitive plants might be able to undergo vernalization more easily. Decreases in cold tolerance in such plants can be useful in situations where plant parts such as, but not limited to, seeds, tubers, stems, leaves or roots are harvested for human or animal consumption.

Typically, a difference in the level of cold tolerance in a transgenic plant or cell relative to a control plant or cell is considered statistically significant at $p<0.05$ with an appropriate parametric or non-parametric statistic, e.g., Chi-square test, Student's t-test, Mann-Whitney test, or F-test. In some embodiments, a difference in the level of cold tolerance is statistically significant at $p<0.01$, $p<0.005$, or $p<0.001$. A statistically significant difference in, for example, the level of cold tolerance in a transgenic plant compared to the amount in cells of a control plant indicates that the recombinant nucleic acid present in the transgenic plant results in altered cold tolerance levels.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNAse protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. PLANT BREEDING

Genetic polymorphisms are discrete allelic sequence differences in a population. Typically, an allele that is present at 1% or greater is considered to be a genetic polymorphism. The discovery that polypeptides disclosed herein can modulate cold tolerance content is useful in plant breeding, because genetic polymorphisms exhibiting a degree of linkage with loci for such polypeptides are more likely to be correlated with variation in a cold tolerance trait. For example, genetic polymorphisms linked to the loci for such polypeptides are more likely to be useful in marker-assisted breeding programs to create lines having a desired modulation in the cold tolerance trait.

Thus, one aspect of the invention includes methods of identifying whether one or more genetic polymorphisms are associated with variation in a cold tolerance trait. Such methods involve determining whether genetic polymorphisms in a given population exhibit linkage with the locus for one of the polypeptides depicted in FIGS. 1 to 4 and/or functional homologs thereof, such as, but not limited to those identified in the Sequence Listing of this application. The correlation is measured between variation in the cold tolerance trait in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in the cold tolerance trait, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol.82, "*Arabidopsis* Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), The Maize Handbook, c. 1994 by Springer-Verlag New York, Inc.: New York, NY, USA; Berlin Germany; Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the cold tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, other biofuel molecules, and/or sugar-derived co-products per kilogram of plant material, relative to control plants. Such processing efficiencies are believed to be derived from the chemical composition of the plant material. By providing higher yields at an equivalent or even decreased cost of production relative to control plants that do not have increased levels of cold tolerance, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. EXAMPLES

Example 1—Transgenic *Arabidopsis* plants

The following symbols are used in the Examples with respect to *Arabidopsis* transformation: T1: first generation transformant; T2: second generation, progeny of self-pollinated T1 plants; T3: third generation, progeny of self-pollinated T2 plants; T4: fourth generation, progeny of self-pollinated T3 plants. Independent transformations are referred to as events.

The following is a list of nucleic acids that were isolated from *Arabidopsis thaliana* plants, Clone 2273, Clone 924103, and Clone 13209. The nucleic acids designated Clone 6639 and Clone 924103 were isolated from the species *Triticum aestivum*.

Each isolated nucleic acid described above was cloned into a Ti plasmid vector containing a phosphinothricin acetyltransferase gene which confers Finale™ resistance to transformed plants. A Ti plasmid vector useful for these constructs is CRS 338. Unless otherwise indicated, each Ceres Clone and/or Seedline derived from a Clone is in the sense orientation relative to either the 35S promoter in a Ti plasmid. Wild-type *Arabidopsis thaliana* ecotype Wassilewskija (Ws) plants were transformed separately with each construct. The transformations were performed essentially as described in Bechtold et al., C.R. Acad. Sci. Paris, 316:1194-1199 (1993).

Wild-type *Arabidopsis* Wassilewskija (Ws) plants were transformed with a Ti plasmid containing Clone 924103 in the sense orientation relative to the 326F promoter. The Ti plasmid vector used for this construct, CRS814, contains the Ceres-constructed, plant selectable marker gene phosphinothricin acetyltransferase (PAT) which confers herbicide resistance to transformed plants.

Wild-type *Arabidopsis* Wassilewskija (Ws) plants were transformed with a Ti plasmid containing clone 2273 in the sense orientation relative to the 32449 promoter.

Wild-type *Arabidopsis* Wassilewskija (Ws) plants were transformed with a Ti plasmid containing clone 13209 in the sense orientation relative to the 32449 promoter. The Ti plasmid vector used for this construct, CRS311, contains the Ceres-constructed, plant selectable marker gene phosphinothricin acetyltransferase (PAT) which confers herbicide resistance to transformed plants Transgenic *Arabidopsis* lines containing Clone 2273, Clone 6639, Clone 924103, or Clone 13209 were designated ME00327, ME04315, ME17294, or ME00572 respectively. The presence of each vector containing a nucleic acid described above in the respective transgenic *Arabidopsis* line transformed with the vector was confirmed by Finale™ resistance, PCR amplification from green leaf tissue extract, and/or sequencing of PCR products. As controls, wild-type *Arabidopsis* ecotype Ws plants were transformed with the empty vector—SR0059.

Example 2—Screening for Cold Tolerance in Transgenic Plants

How plants respond to stress in the environment dictates their ability to survive and reproduce. There are probably many mechanisms by which plants regulate the temperatures under which they will germinate (Lu and Hills, 2003). A number of polynucleotides that result in stress tolerance when over-expressed have been identified in model species such as *Arabidopsis.*

Over-expression of these polynucleotides could be useful for increasing low temperature, chilling or cold tolerance in crops. Assays described here focus on low temperature, chilling or cold tolerance in seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these polynucleotides, the result could be very valuable in agriculture in many crops and environments and make a significant contribution to sustainable farming. Furthermore, low temperature, chilling or cold tolerance may be modulated by expressing these polynucleotides under the control of a low temperature, chilling or cold inducible promoter.

1. Cold Growth Superpool Screen

Plates of solidified agar MS medium are prepared for the screen as follows. One liter of medium is prepared by mixing 2.15 g of MS basal salt mixture (from Phytotech M524) and 7 g of agar (from EM Science, 1.01614.1000) in water, and adjusting the pH to 5.7 with a 10N KOH solution. After autoclaving, 45 ml of media are transferred under sterile conditions per 100 mm square×15 mm deep plate.

Individual superpool and control seeds are sterilized in a 30% bleach solution for 5 minutes. Seeds are then rinsed repeatedly with sterile water to eliminate all bleach solution. Seeds are plated using a COPAS™ robot (Union Biometrica, Holliston, Massachusetts) at a density of 72 seeds per plate. The plates are wrapped with vent tape and transferred to a dark 4° C. refrigerator for 3 days to promote uniform germination. The plates are then placed horizontally in a Conviron growth chamber set at 22'C, 16:8 hour light:dark cycle, 70% humidity with fluorescent lamps emitting a light intensity of −100 μEinsteins. Normal growth is allowed to occur for 3-5 days. At end of 3-5 days of growth, images of the plates are scanned using an Epson perfection 4870 scanner. Then, cold-growth treatment is applied for 1-3 weeks. Accordingly, plates are transferred in a horizontal position to an 8'C. Conviron chamber under constant light at −100 μEinsteins. After a defined number of days of cold-growth treatment, for example 7 or 14, the plates are scanned again. The WinRhizo software program (Regent Instruments Inc., Canada) is used to determine the area for each seedling from the scanned images.

Individual seedlings that perform better in the cold growth screen are identified by visual inspection for those showing obvious morphological differences and by statistical analysis of the seedling area data. DNA from these candidate seedlings is extracted and the transgene amplified using PCR. The PCR product is sequenced to determine the identity of the transgene and consequently the ME line from which the candidate is derived.

2. Cold Growth Assay

The cold growth assay is used to validate candidate misexpression (ME) lines obtained from screens for enhanced growth under cold conditions. This procedure allows a high-throughput methodology for assessing transgenic *Arabidopsis* candidates that have germinated at normal temperature (22° C.) and light (−100 to 200 μEinsteins) in a walk-in growth chamber on agar solidified MS medium before transfer to cold temperature. It relies on the ability to discriminate between seedlings that have become significantly larger during cold growth than controls by imaging the seedlings when they are transferred to the cold and then periodically thereafter under cold growth conditions.

Plate preparation for the cold growth assay and the growth conditions are the same as those described for the cold growth screen as described above. Seeds from independent transformation events for each ME line are bleach sterilized and then plated at a density of 40 seeds per plate (30 seeds from the event and 10 wild-type control seeds). After cold-growth treatment, the seedlings are then FINALE® treated to identify the plants carrying the ME vector.

Cold growth is characterized by statistical analysis as follows. The control population is the internal non-transgenic segregants for that particular event. When there are not enough internal non-transgenic segregants for an event, a pool of all non-transgenic segregants from all events associated with that ME line is used (i.e. when non-transgenics are less than five for the event or the event appears to be homozygous). Pooling is only done for events associated with the same ME line and within an experiment (an experiment is the set of plates with a common sow date). Thus in the final analysis, the pooled control population may be different for generations T2 and T3.

The WinRhizo software program (Regent Instruments Inc., Canada) is used to determine the area for each seedling. The change in area is calculated for a defined number of days of treatment. A one-tailed t-test is used to compare change in area and the mean size of the transgenic seedlings within an event to the internal non-transgenic segregants. Significance is assessed at an a-value of 0.05.

3. Cold Flux Assay

The cold flux growth assay is used to validate candidate misexpression (ME) lines obtained from screens for enhanced growth under fluctuating cold conditions. This procedure allows a high-throughput methodology for assessing transgenic *Arabidopsis* candidates that have germinated at normal temperature (22° C.) and light (−100 to 200 μEinsteins) in a walk-in growth chamber on agar solidified MS medium before transfer to cold temperature. It relies on the ability to discriminate between seedlings that have become significantly larger during growth under fluctuating cold conditions than controls by imaging the seedlings when they are transferred to the cold and then periodically thereafter under cold growth conditions.

Plate preparation for the cold growth assay and the growth conditions are the same as those described for the cold growth screen as described above. Seeds from independent transformation events for each ME line are bleach sterilized and then plated at a density of 61 seeds per plate (including both seeds from the event and wild-type control seeds). After cold flux-growth treatment, the seedlings are then FINALE®-treated to identify the plants carrying the ME vector.

Normal growth is allowed to occur for 3-5 days. At end of 3-5 days of growth, images of the plates are scanned using an Epson perfection 4870 scanner. After 3-5 days growth in normal conditions, the plates are transferred in a horizontal position to an 8° C. Conviron under constant light at −100 μEinsteins. All transfers take place in the morning. Growth is allowed at 8° C. for 3-4 days. After 3-4 days growth at 8° C., plates are transferred to 1° C. Percival under constant light at −70 μEinsteins. Growth is allowed at 1° C. for 3-4 days. 8° C./1° C. cycling is repeated for a total of 14 days. The plates are imaged using CF imager and Winrhizo scanner. Individual seedlings are selected which are significantly larger and/or exhibit increased photosynthetic efficiency (Fv/Fm). Plates are visually observed as well. DNA from these candidate seedlings is extracted and the transgene amplified using PCR. The PCR product is sequenced to determine the identity of the transgene and consequently the ME line from which the candidate is derived. These seedlings are then grown for progeny seed.

Cold flux growth is characterized by statistical analysis as follows. The control population is the internal non-transgenic segregants for that particular event. When there are not enough internal non-transgenic segregants for an event, a pool of all non-transgenic segregants from all events associated with that ME line is used (i.e. when non-transgenics are less than five for the event or the event appears to be homozygous). Pooling is only done for events associated with the same ME line and within an experiment (an experiment is the set of plates with a common sow date). Thus in the final analysis, the pooled control population may be different for generations T2 and T3.

The WinRhizo software program (Regent Instruments Inc., Canada) is used to determine the area for each seedling. The change in area is calculated for a defined number of days of treatment. A one-tailed t-test is used to compare change in area and the mean size of the transgenic seedlings within an event to the internal non-transgenic segregants. Significance is assessed at an a-value of 0.05.

Example 3—Results for ME00327 Events (SEQ ID NO: 2)

Ectopic expression of clone 2273 (from *Arabidopsis thaliana*) under the control of the 32449 promoter in the ME00327 plants results in larger seedlings after 14 days fluctuation between 8° C. and 1° C.

The seedling area of transgenic plants within a seed line was compared to that of non-transgenic segregants within the same seed line after 14 days of growth at fluctuating temperatures of 8°° C. and 1° C. Six events of ME00327 were analyzed as described in the cold flux assay (Example 2). Events -04 and -06 were significant in at least two generations at $p<0.05$ using a one-tailed t-test assuming unequal variance (Table 1). The transgenic plants were visibly larger than the controls.

Event -04 segregated 3:1 (R:S) for Finale™ resistance in the $T_2$ generation. Event -06 appears to segregate for two inserts (15:1) in the $T_2$ generation.

TABLE 1 t-test comparison of seedling area between transgenic seedlings and control non-transgenic segregants after 14 days fluctuation between 8° C. and 1° C.

| | Event- | Transgenic | | | Control Non-Transgenics[a] | | | t-test |
|---|---|---|---|---|---|---|---|---|
| Events | Gen | Avg | SE | N | Avg | SE | N | p-value |
| ME00327-04 | -04-T2 | 0.0383 | 0.0014 | 16 | 0.0297 | 0.0011 | 14 | 2.58E−05 |
| ME00327-04-02 | -04-T3 | 0.0490 | 0.0023 | 27 | 0.0410 | 0.0019 | 32 | 4.48E−03 |
| ME00327-04-03 | -04-T3 | 0.0522 | 0.0018 | 32 | 0.0378 | 0.0020 | 26 | 9.46E−07 |
| ME00327-04-04 | -04-T3 | 0.0497 | 0.0020 | 35 | 0.0364 | 0.0022 | 25 | 1.38E−05 |
| ME00327-06[c] | -06-T2 | 0.0314 | 0.0011 | 29 | 0.0272 | 0.0009 | 39 | 1.98E−03 |
| ME00327-06[bc] | -06-T2 | 0.0392 | 0.0012 | 54 | 0.0346 | 0.0008 | 194 | 8.17E−04 |
| ME00327-06-01 | -06-T3 | 0.0296 | 0.0015 | 41 | 0.0232 | 0.0016 | 17 | 2.47E−03 |
| ME00327-06-03 | -06-T3 | 0.0356 | 0.0015 | 42 | 0.0290 | 0.0019 | 15 | 4.44E−03 |

[a]Transgenic seedlings were compared to internal non-transgenic segregants within an event unless otherwise indicated.
[b]These events were sown twice. The first time was to identify ME00327 as a Hit. They were repeated the second time with the next generation to identify ME00327 as a Lead.
[c]These events did not segregate non-transgenic seedlings and were compared to pooled non-transgenics for the line.

Plants from Events -04 and -06 which are hemizygous or homozygous for clone 2273 do not show any negative phenotypes under standard conditions. Events -04 and -06 of ME00327 were tested for negative phenotypes compared to the empty vector control SR00559. The results showed no detectable reduction in germination rate, the plants appeared wild-type in all instances, and no statistical differences in days to flowering, rosette area 7 days post-bolting, or fertility (silique number and seed fill).

Example 4—Results for ME04315 Events (SEQ ID NO: 20)

Candidate ME04315 was identified by superpool screen described above in Example 2. Ectopic expression of Clone 6639 under the control of the 35S promoter in ME04315 plants results in early germination at 8° C. resulting in larger seedlings after 10 days at 8° C.

The seedling area of transgenic plants within a seed line was compared to that of non-transgenic segregants within the same seed line after 10 days of growth at 8° C. Nine events of ME04315 were analyzed as described in the Cold Growth Assay described in Example 2 and showed significant tolerance under cold conditions in two generations. Three Events, -02, -03 and -06, were significant in both generations at $p<0.05$ using a one-tailed t-test assuming unequal variance (Table 2). '-99' signifies that seeds were pooled from several plants. Events -02 and -06 were from the T3 generation because T2 seed was not available. Subsequently, next generation seeds for three of the events (T3 or T4 as needed) were evaluated under cold germination conditions.

The transgenic plants were visibly larger and lighter in color than the controls. Under cold conditions, seedlings typically become darker, presumably due to the accumulation of anthocyanin. The lighter color exhibited by ME04315 seedlings suggests a decrease in this stress response. ME04315 plants grown under standard conditions in soil did not appear different in color than controls.

Event -03 segregated 3:1 (R:S) for Finale™ resistance in the T2 generation. Seed collected from individual, hemizygous plants was not available for Events -02 and -06. However, the T3 generation seeds that were pooled from several T2 plants segregated approximately 2:1 in a manner consistent with a single insert for Event -06 (only transgenic plants were pooled). Pooled T3 generation seeds for Event -02 segregated 1:3.

TABLE 2

T-test comparison of seedling area between transgenic seedlings and control non-transgenic segregants after 10 days at 8° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME04315-02-99[b] | 02-T3 | 0.0071 | 0.0013 | 10 | 0.0049 | 0.0007 | 24 | 7.50E−02 |
| ME04315-02-99 | 02-T3 | 0.0046 | 0.0007 | 16 | 0.0036 | 0.0002 | 50 | 7.92E−02 |
| ME04315-02-99-02[a] | 02-T4 | 0.0070 | 0.0002 | 61 | 0.0047 | 0.0002 | 213 | 6.66E−16 |
| ME04315-02-99-03 | 02-T4 | 0.0072 | 0.0002 | 45 | 0.0057 | 0.0007 | 3 | 2.08E−02 |
| ME04315-03[b] | 03-T2 | 0.0026 | 0.0002 | 18 | 0.0017 | 0.0003 | 7 | 0.0070 |
| ME04315-03 | 03-T2 | 0.0017 | 0.0001 | 35 | 0.0016 | 0.0001 | 19 | 0.2221 |
| ME04315-03-02 | 03-T3 | 0.0078 | 0.0005 | 12 | 0.0045 | 0.0011 | 7 | 6.69E−03 |
| ME04315-03-03 | 03-T3 | 0.0063 | 0.0003 | 45 | 0.0053 | 0.0004 | 24 | 0.0153 |
| ME04315-06-99[b] | 06-T3 | 0.0034 | 0.0006 | 16 | 0.0023 | 0.0003 | 14 | 0.0499 |
| ME04315-06-99 | 06-T3 | 0.0029 | 0.0002 | 42 | 0.0021 | 0.0001 | 28 | 9.52E−04 |
| ME04315-06-99-02[a] | 06-T4 | 0.0072 | 0.0002 | 61 | 0.0047 | 0.0002 | 213 | 3.33E−16 |

[a]Transgenic seedlings were compared to non-transgenic segregants within a seed line except for the T4 generation of Events -02 and -06. Since these seed lines were homozygous, they were compared to pooled non-transgenic segregants from another T4 generation event that was grown in the same flat as the T4 generation of Events -02 and -06.
[b]These events were sown twice. The first time was to identify ME04315 as a hit. They were repeated the second time with two generations to identify ME04315 as a Lead.

Plants from Events -02, -03 and -06 which are hemizygous or homozygous for Clone 6639 do not show any negative phenotypes under long-day conditions. The physical appearance of eight of the nine T1 plants was identical to the controls. Event -06 was smaller and had fewer rosette leaves.

Events -02, -03 and -06 of ME04315 exhibited no statistically significant negative phenotypes compared to empty vector control SR00559. There was no detectable reduction in germination rate, the plants appeared wild-type in all instances, and there was no observable or statistical differences between experimentals and controls for days to flowering, rosette area 7 days post-bolting or fertility (silique number and seed fill).

Example 5—Results for ME17294 Events (SEQ ID NO:93) 5' Truncated

Nine events of ME 17294 (Clone 924103 from *Triticum aestivum*) were analyzed as described in the cold germination assay (Example 2). In this study, the seedling area (a measure of germination timing and cotyledon expansion) of transgenic plants within a seed line was compared to that of non-transgenic segregants within the same seed line, except for the T3 generation of both events. These seed lines were homozygous for the transgene. For these seed lines, we used pooled non-transgenic segregants from another T3 generation event of ME 17294 that were collected from plants grown in the same flat as the T3 generation of Events -08 and -09.

The two events, -08 and -09, were significant in two generations at $p<0.05$ using a one-tailed t-test assuming unequal variance (Table 3). The transgenic plants are visibly larger.

Events -08 and -09 segregated 3:1 (R:S) for Finale™ resistance in the T2 generation. No T1 phenotypes were reported for this line.

TABLE 3 t-test comparison of seedling area between transgenic seedlings and control non-transgenic segregants after 10 days at 8° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME17294-08[b] | 08-T2 | 0.0032 | 0.0003 | 24 | 0.0022 | 0.0002 | 9 | 2.57E−03 |
| ME17294-08 | 08-T2 | 0.0021 | 0.0001 | 41 | 0.0018 | 0.0001 | 10 | 4.52E−03 |
| ME17294-08-02[a] | 08-T3 | 0.0083 | 0.0003 | 48 | 0.0064 | 0.0002 | 234 | 3.05E−08 |
| ME17294-08-04 | 08-T3 | 0.0075 | 0.0003 | 54 | 0.0064 | 0.0002 | 234 | 9.19E−04 |
| ME17294-09[b] | 09-T2 | 0.0058 | 0.0003 | 22 | 0.0035 | 0.0002 | 9 | 1.02E−06 |
| ME17294-09 | 09-T2 | 0.0039 | 0.0002 | 41 | 0.0029 | 0.0002 | 16 | 4.59E−04 |

TABLE 3-continued t-test comparison of seedling area between transgenic seedlings and control non-transgenic segregants after 10 days at 8° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME17294-09-01[a] | 09-T3 | 0.0073 | 0.0003 | 46 | 0.0064 | 0.0002 | 234 | 5.53E−03 |
| ME17294-09-04[a] | 09-T3 | 0.0087 | 0.0003 | 63 | 0.0064 | 0.0002 | 234 | −9.10E−11 |

[a]Transgenic seedlings were compared to internal non-transgenic segregants within a seed line except for the $T_3$ generation of Events -08 and -09. Since these seed lines were homozygous, they were compared to pooled non-transgenic segregants from another $T_3$ generation event that was grown in the same flat as the $T_3$ generation of Events -08 and -09.
[b]These events were sown twice. The first time was to identify ME17294 as a Hit. They were repeated the second time with two generations to identify ME 17294 as a Lead.

Plants from Events -08 and -09 which are hemizygous or homozygous for clone 924103 do not show any negative phenotypes under standard conditions. Events -08 and -09 of ME 17294 exhibited no statistically significant negative phenotypes compared to empty vector control SR00559. There was no detectable reduction in germination rate, the plants appeared wild-type in all instances, and there were no statistical differences between experimentals and controls for days to flowering, rosette area 7 days post-bolting, or fertility (silique number and seed fill).

Example 6—Results for ME00572 Events (SEQ ID NO: 111) tasiRNA

Clone 13209, in ME00572 plants, is a trans-acting small interfering RNA (tasiRNA) that interacts with ARFs (Auxin Response Factors). A megapool containing superpools 9-12 was screened for seedlings that grew more vigorously than controls after transfer to fluctuating cold conditions according to Example 2. Seven candidates were chosen from this megapool. ME00572 was represented two times in this set.

Four events of ME00572 showed significant tolerance under cold fluctuating conditions in at least two generations. The seedling area of transgenic plants within a seed line was compared to that of non-transgenic segregants within the same seed line after 14 days of growth at fluctuating temperatures of 8° C. and 1° C. Five events of ME00572 were analyzed as described in the Cold Flux Assay described in Example 2. Events -01, -03, -04 and -05 were significant in at least two generations at $p<0.05$ using a one-tailed t-test assuming unequal variance (Table 4). The transgenic plants were visibly larger than the controls.

Events -01 and -05 segregated 3:1 (R:S) for Finale™ resistance in the T2 generation. Event -04 segregated 3:1 in the T3 generation. Event -03 segregated 1:1 in the T2 generation.

TABLE 4 t-test comparison of seedling area between transgenic seedlings and control non-transgenic segregants after 14 days fluctuation between 8° C. and 1° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME00572-01 | -01-T2 | 0.0338 | 0.0293 | 26 | 0.0233 | 0.0010 | 4 | 0.155617 |
| ME00572-01[b] | -01-T2 | 0.0541 | 0.0021 | 45 | 0.0442 | 0.0030 | 13 | 4.92E−03 |
| ME00572-01-01 | -01-T3 | 0.0347 | 0.0017 | 40 | 0.0246 | 0.0014 | 14 | 1.53E−05 |
| ME00572-01-02[c] | -01-T3 | 0.0331 | 0.0013 | 59 | 0.0267 | 0.0005 | 294 | 2.35E−06 |
| ME00572-01-03[c] | -01-T3 | 0.0360 | 0.0010 | 59 | 0.0267 | 0.0005 | 294 | −9.39E−11 |
| ME00572-01-04 | -01-T3 | 0.0329 | 0.0013 | 46 | 0.0233 | 0.0018 | 14 | 3.19E−05 |
| ME00572-03 | -03-T2 | 0.0312 | 0.0016 | 11 | 0.0223 | 0.0013 | 19 | 9.71E−05 |
| ME00572-03[b] | -03-T2 | 0.0383 | 0.0024 | 24 | 0.0341 | 0.0023 | 25 | 1.04E−01 |
| ME00572-03-01 | -03-T3 | 0.0328 | 0.0014 | 30 | 0.0236 | 0.0008 | 28 | 1.42E−07 |
| ME00572-03-02 | -03-T3 | 0.0311 | 0.0010 | 26 | 0.0261 | 0.0015 | 33 | 3.81E−03 |
| ME00572-03-03 | -03-T3 | 0.0352 | 0.0011 | 28 | 0.0252 | 0.0009 | 32 | 1.39E−09 |
| ME00572-03-04 | -03-T3 | 0.0331 | 0.0019 | 23 | 0.0260 | 0.0014 | 35 | 1.97E−03 |
| ME00572-04-99 | -04-T3 | 0.0235 | 0.0009 | 23 | 0.0158 | 0.0020 | 7 | 6.98E−04 |
| ME00572-04-99[b] | -04-T3 | 0.0336 | 0.0012 | 31 | 0.0255 | 0.0010 | 29 | 2.01E−06 |
| ME00572-04-99-01[c] | -04-T4 | 0.0388 | 0.0014 | 57 | 0.0267 | 0.0005 | 294 | −9.39E−11 |
| ME00572-04-99-02 | -04-T4 | 0.0345 | 0.0011 | 41 | 0.0253 | 0.0018 | 19 | 3.93E−05 |
| ME00572-04-99-03[c] | -04-T4 | 0.0433 | 0.0012 | 60 | 0.0267 | 0.0005 | 294 | −3.33E−16 |
| ME00572-04-99-04 | -04-T4 | 0.0315 | 0.0010 | 44 | 0.0239 | 0.0012 | 16 | 3.22E−06 |
| ME00572-05 | -05-T2 | 0.0362 | 0.0020 | 19 | 0.0219 | 0.0020 | 10 | 1.13E−05 |
| ME00572-05-01[c] | -05-T3 | 0.0337 | 0.0011 | 57 | 0.0267 | 0.0005 | 294 | 6.21E−09 |
| ME00572-05-02 | -05-T3 | 0.0320 | 0.0014 | 39 | 0.0232 | 0.0020 | 17 | 3.59E−04 |
| ME00572-05-03[c] | -05-T3 | 0.0379 | 0.0011 | 59 | 0.0267 | 0.0005 | 294 | −9.39E−11 |
| ME00572-05-04 | -05-T3 | 0.0344 | 0.0020 | 37 | 0.0268 | 0.0022 | 19 | 7.26E−03 |

[a]Transgenic seedlings were compared to internal non-transgenic segregants within an event unless otherwise indicated.
[b]These events were sown twice. The first time was to identify ME00572 as a Hit. They were repeated the second time with the next generation to identify ME00572 as a Lead.
[c]These events did not segregate non-transgenic seedlings and were compared to pooled non-transgenics for the line Plants from Events -01, -03, -04 and -05 which are hemizygous or homozygous for clone 13209 do not show any negative phenotypes under standard conditions. Events -01, -03, -04 and -05 of ME00572 were tested for negative phenotypes compared to the empty vector control SR00559. There was no detectable reduction in germination rate, the plants appeared wild-type in all instances, and there was no statistical differences between experimentals and controls for days to flowering, rosette area 7 days post-bolting, and fertility (silique number and seed fill).

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., Proc. Natl. Acad. Sci. USA, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of 10-5 and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO: 2, 20, 74, 93, and 116, are shown in FIGS. 1-5, respectively. Additional exemplary homologs are correlated to certain Figures in the Sequence Listing.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 2.

The procedure above was repeated and an HMM was generated for each group of sequences shown in FIGS. 2, 3, 4, and 5 using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A plant cell comprising an exogenous nucleic acid, said exogenous nucleic acid comprising a heterologous regulatory region operably linked to a nucleotide sequence encoding a polypeptide, wherein said polypeptide comprises an amino acid sequence that has 98% or greater sequence identity to the amino acid sequence of SEQ ID NO: 93, and wherein a plant produced from said plant cell has an increased level of cold tolerance as compared to the corresponding level of cold tolerance of a control plant that does not comprise said nucleic acid.

2. The plant cell of claim 1, wherein the polypeptide comprises an amino acid sequence that has 99% or greater sequence identity to the amino acid sequence of SEQ ID NO: 93.

3. The plant cell according to claim 1, wherein the polypeptide comprises the amino acid sequence of SEQ ID NO: 93.

4. A transgenic plant comprising the plant cell of claim 1.

5. The transgenic plant of claim 4, wherein said polypeptide comprises an amino acid sequence that has 99% or greater sequence identity to the amino acid sequence of SEQ ID NO: 93.

6. The transgenic plant of claim 4, wherein said plant is a member of a species selected from the group consisting of sorghum, miscanthus, energycane, poplar, corn, soybean, canola, wheat, cotton, rice, sunflower, alfalfa, sugarbeet, and pearl millet.

7. A seed product comprising embryonic tissue from the transgenic plant according to claim 4, wherein the embryonic tissue comprises the exogenous nucleic acid.

8. The transgenic plant of claim 4, wherein said polypeptide comprises the amino acid sequence of SEQ ID NO: 93.

9. A seed producing the transgenic plant of claim 4.

* * * * *